(12) United States Patent
Wager

(10) Patent No.: US 7,812,040 B2
(45) Date of Patent: Oct. 12, 2010

(54) HISTAMINE-3 RECEPTOR ANTAGONISTS

(75) Inventor: Travis T Wager, New London, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/917,501

(22) PCT Filed: Jun. 12, 2006

(86) PCT No.: PCT/IB2006/001685

§ 371 (c)(1),
(2), (4) Date: Jun. 11, 2008

(87) PCT Pub. No.: WO2006/136924

PCT Pub. Date: Dec. 28, 2006

(65) Prior Publication Data

US 2009/0131433 A1    May 21, 2009

Related U.S. Application Data

(60) Provisional application No. 60/693,273, filed on Jun. 22, 2005.

(51) Int. Cl.
A61K 31/4245 (2006.01)
A61K 31/423 (2006.01)
A61K 31/4155 (2006.01)
A61K 31/40 (2006.01)
C07D 271/08 (2006.01)
C07D 263/58 (2006.01)
C07D 231/14 (2006.01)
C07D 207/04 (2006.01)

(52) U.S. Cl. .................. 514/364; 514/375; 514/406; 514/408; 548/125; 548/221; 548/374.1; 548/578

(58) Field of Classification Search ............. 514/235.5, 514/255.04, 428; 548/569; 544/141
See application file for complete search history.

(56) References Cited

U.S. PATENT DOCUMENTS

2005/0171181 A1   8/2005  Wager et al. ................ 514/408

FOREIGN PATENT DOCUMENTS

WO   WO 02072570      9/2002
WO   WO 2004101546   11/2004

Primary Examiner—Kamal A Saeed
Assistant Examiner—Kristin Bianchi
(74) Attorney, Agent, or Firm—Jennifer A. Kispert; Robert T. Ronau

(57) ABSTRACT

This invention is directed to a compound of the formula Ia or Ib, as defined herein, or a pharmaceutically acceptable salt thereof; a pharmaceutical composition containing a compound of formula I, a method of treatment of a disorder or condition that may be treated by antagonizing histamine H3 receptors, the method comprising administering to a mammal in need of such treatment a compound of formula I as described above, and a method of treatment of a disorder or condition selected from the group consisting of depression, mood disorders, schizophrenia, anxiety disorders, Alzheimer's disease, attention-deficit disorder (ADD), attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper and hypo motility and acidic secretion of the gastro-intestinal tract, the method comprising administering to a mammal in need of such treatment a compound of formula I as described above.

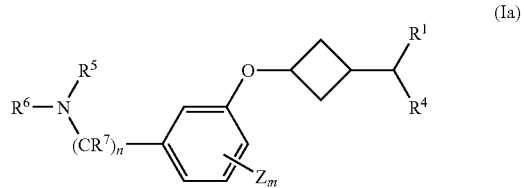

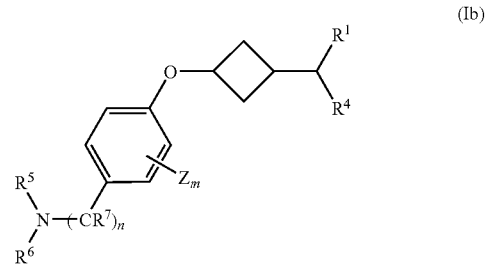

20 Claims, No Drawings

HISTAMINE-3 RECEPTOR ANTAGONISTS

The present application represents the national stage (35 USC 371) of international application PCT/IB2006/001685, and claims priority under 35 USC 119 to U.S. provisional application 60/693,273.

BACKGROUND OF THE INVENTION

This invention is directed to compounds of formula I described herein, to a pharmaceutical composition comprising such compounds, and to methods of treatment of disorders or conditions that may be treated by antagonizing histamine-3 (H3) receptors using such compounds. The histamine-3 (H3) receptor antagonists of the invention are useful for treating anxiety disorders, including, for example, generalized anxiety disorder, panic disorder, PTSD, and social anxiety disorder; mood adjustment disorders, including depressed mood, mixed anxiety and depressed mood, disturbance of conduct, and mixed disturbance of conduct and depressed mood; age-associated learning and mental disorders, including Alzheimer's disease; attention adjustment disorders, such as attention-deficit disorders, or other cognitive disorders due to general medical conditions; attention-deficit hyperactivity disorder; psychotic disorders including schizoaffective disorders and schizophrenia; sleep disorders, including narcolepsy and enuresis; obesity; dizziness, epilepsy, and motion sickness. The H3 receptor antagonists of the invention are also useful for treating, for example, allergy, allergy-induced airway (e.g., upper airway) responses, congestion (e.g., nasal congestion), hypotension, cardiovascular disease, diseases of the GI tract, hyper and hypo motility and acidic secretion of the gastrointestinal tract, sleeping disorders (e.g., hypersomnia, somnolence, and narcolepsy), disturbances of the central nervous system, attention deficit hyperactivity disorder (ADHD), hypo and hyperactivity of the central nervous system (for example, agitation and depression), and other CNS disorders (such as schizophrenia and migraine).

Histamine is a well-known mediator in hypersensitive reactions (e.g. allergies, hay fever, and asthma) that are commonly treated with antagonists of histamine or "antihistamines." It has also been established that histamine receptors exist in at least two distinct types, referred to as H1 and H2 receptors.

A third histamine receptor (H3 receptor) is believed to play a role in neurotransmission in the central nervous system, where the H3 receptor is thought to be disposed presynaptically on histaminergic nerve endings (*Nature*, 302, S32-837 (1983)). The existence of the H3 receptor has been confirmed by the development of selective H3 receptor agonists and antagonists (*Nature*, 327, 117-123 (1987)) and has subsequently been shown to regulate the release of the neurotransmitters in both the central nervous system and peripheral organs, particularly the lungs, cardiovascular system and gastrointestinal tract.

A number of diseases or conditions may be treated with histamine-3 receptor ligands wherein the H3 ligand may be an antagonist, agonist or partial agonist, see: (Imamura et al., *Circ. Res.*, (1996) 78, 475-481); (Imamura et. al., *Circ. Res.*, (1996) 78, 863-869); (Lin et al., *Brain Res.*, (1990) 523, 325-330); (Monti et al., *Neuropsychopharmacology* (1996) 15, 31 35); (Sakai, et al., *Life Sci.* (1991) 48, 2397-2404); (Mazurkiewiez-Kwilecki and Nsonwah, *Can. J. Physiol. Pharmacol.* (1989) 67, 75-78); (Panula, P. et al., *Neuroscience* (1998) 44, 465-481); (Wada et al., *Trends in Neuroscience* (1991) 14,415); (Monti et al., *Eur. J. Pharmacol.* (1991) 205, 283); (Mazurkiewicz-Kwilecki and Nsonwah, *Can. J. Physiol. Pharmacol.* (1989) 67, 75-78); (Haas et al., *Behav. Brain Res.* (1995) 66, 41-44); (De Almeida and Izquierdo, *Arch. Int. Pharmacodyn.* (1986) 283, 193-198); (Kamei et al., *Psychopharmacology* (1990) 102, 312-318); (Kamei and Sakata, *Japan. J. Pharmacol.* (1991) 57, 437-482); (Schwartz et al., *Psychopharmacology*; The fourth Generation of Progress, Bloom and Kupfer (eds.), Raven Press, New York, (1995) 3 97); (Shaywitz et al., *Psychopharmacology* (1984) 82, 73-77); (Dumery and Blozovski, *Exp. Brain Res.* (1987) 67, 61-69); (Tedford et al., *J. Pharmacol. Exp. Ther.* (1995) 275, 598-604); (Tedford et al., Soc. Neurosci. Abstr. (1996) 22, 22); (Yokoyama et al., *Eur. J. Pharmacol.* (1993) 234, 129); (Yokoyama and linuma, *CNS Drugs* (1996) 5, 321); (Onodera et al., *Prog. Neurobiol.* (1994) 42, 685); (Leurs and Timmerman, *Prog. Drug Res.* (1992) 39,127); (The Histamine H3 Receptor, Leurs and Timmerman (ed.), Elsevier Science, Amsterdam, The Netherlands (1998); (Leurs et al., *Trends in Pharm. Sci.* (1998) 19, 177-183); (Phillips et al., *Annual Reports in Medicinal Chemistry* (1998) 33, 31-40); (Matsubara et al., *Eur. J. Pharmacol.* (1992) 224, 145); (Rouleau et al., *J. Pharmacol. Exp. Ther.* (1997) 281, 1085); (Adam Szelag, "Role of histamine H3-receptors in the proliferation of neoplastic cells in vitro", *Med. Sci. Monit.*, 4(5): 747-755, (1998)); (Fitzsimons, C., H. Duran, F. Labombarda, B. Molinari and E. Rivera, "Histamine receptors signalling in epidermal tumor cell lines with H-ras gene alterations", *Inflammation Res.*, 47 (Suppl. 1): S50-S51, (1998)); (R. Leurs, R. C. Vollinga and H. Timmerman, "The medicinal chemistry and therapeutic potentials of ligand of the histamine H3 receptor", *Progress in Drug Research* 45: 170-165, (1995)); (R. Levi and N. C. E. Smith, "Histamine H3-receptors: A new frontier in myocardial ischemia", *J. Pharm. Exp. Ther.*, 292: 825-830, (2000)); (Hatta, E., K Yasuda and R. Levi, "Activation of histamine H3 receptors inhibits carrier-mediated norepinephrine release in a human model of protracted myocardial ischemia", *J. Pharm. Exp. Ther.*, 283: 494-500, (1997); (H. Yokoyama and K. Iinuma, "Histamine and Seizures: Implications for the treatment of epilepsy", *CNS Drugs*, 5(5); 321-330, (1995)); (K. Hurukami, H. Yokoyama, K. Onodera, K. Iinuma and T. Watanabe, AQ-0 145, "A newly developed histamine H3 antagonist, decreased seizure susceptibility of electrically induced convulsions in mice", *Meth. Find. Exp. Clin. Pharmacol.*, 17(C): 70-73, (1995); (Delaunois A., Gustin P., Garbarg M., and Ansay M., "Modulation of acetylcholine, capsaicin and substance P effects by histamine H3 receptors in isolated perfused rabbit lungs", *European Journal of Pharmacology* 277(2-3):243-50, (1995)); and (Dimitriadou, et al., "Functional relationship between mast cells and C-sensitive nerve fibres evidenced by histamine H3-receptor modulation in rat lung and spleen", *Clinical Science* 87(2):151-63, (1994). Such diseases or conditions include cardiovascular disorders such as acute myocardial infarction; memory processes, dementia and cognition disorders such as Alzheimer's disease and attention-deficit hyperactivity disorder; neurological disorders such as Parkinson's disease, schizophrenia, depression, epilepsy, and seizures or convulsions; cancer such as cutaneous carcinoma," medullary thyroid carcinoma and melanoma; respiratory disorders such as asthma; sleep disorders such as narcolepsy; vestibular dysfunction such as Meniere's disease; gastrointestinal disorders, inflammation, migraine, motion sickness, obesity, pain, and septic shock.

H3 receptor antagonists have also been previously described in, for example, WO 03/050099, WO 02/0769252, and WO 02/12224. The histamine H3 receptor (H3R) regulates the release of histamine and other neurotransmitters, including serotonin and acetylcholine. H3R is relatively neuron specific and inhibits the release of certain monoamines such as histamine. Selective antagonism of H3R receptors raises brain histamine levels and inhibits such activities as food consumption while minimizing non-specific peripheral consequences. Antagonists of the receptor increase synthesis and release of cerebral histamine and other monoamines. By this mechanism, they induce a prolonged wakefulness, improved cognitive function, reduction in food intake and normalization of vestibular reflexes. Accordingly, the receptor is an important target for new therapeutics in Alzheimer disease, mood and attention adjustments, including attention deficit hyperactive disorder (ADHD), cognitive deficiencies, obesity, dizziness, schizophrenia, epilepsy, sleeping disorders, narcolepsy and motion sickness, and various forms of anxiety.

The majority of histamine H3 receptor antagonists to date resemble histamine in possessing an imidazole ring that may be substituted, as described, for example, in WO96/38142. Non-imidazole neuroactive compounds such as beta histamines (Arrang, *Eur. J. Pharm.* 1985, 111:72-84) demonstrated some histamine H3 receptor activity but with poor potency. EP 978512 and EP 0982300A2 disclose non-imidazole alkyamines as histamine H3 receptor antagonists. WO 02/12224 (Ortho McNeil Pharmaceuticals) describes non-imidazole bicyclic derivatives as histamine H3 receptor ligands. Other receptor antagonists have been described in WO02/32893 and WO02/06233.

This invention is directed to histamine-3 (H3) receptor antagonists of the invention useful for treating the conditions listed in the preceding paragraphs. The compounds of this invention are highly selective for the H3 receptor (vs. other histamine receptors), and possess remarkable drug disposition properties (pharmacokinetics). In particular, the compounds of this invention selectively distinguish H3R from the other receptor subtypes H1R, H2R. In view of the increased level of interest in histamine H3 receptor agonists, inverse agonists and antagonists in the art, novel compounds that interact with the histamine H3 receptor would be a highly desirable contribution to the art. The present invention provides such a contribution to the art being based on the finding that a novel class of biaryl amines has a high and specific affinity to the histamine H3 receptor.

SUMMARY OF THE INVENTION

This invention is directed to a compound of the formula Ia or Ib

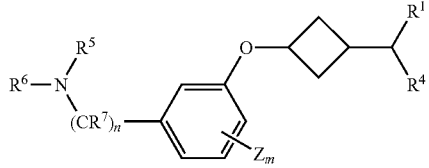

Ia

-continued

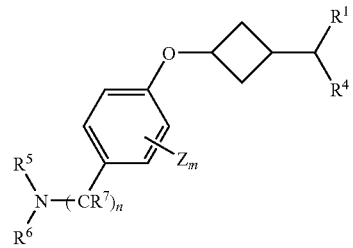

Ib or a pharmaceutically acceptable salt thereof, or cis isomer, or trans isomer, or a mixture of cis and trans isomer, wherein:

$R^1$ is selected from the group consisting of $OR^4$, and $NR^2R^3$;

$R^2$ and $R^3$ are each independently selected from the group consisting of hydrogen;

$C_1$-$C_8$ alkyl optionally substituted with 1 to 4 halogens;

$C_1$-$C_4$ alkyl group optionally substituted with a substituent selected from the group consisting of OH, one to four $C_1$-$C_4$ alkyl, $C_3$-$C_7$ cycloalkyl, $C_1$-$C_4$ dialkylamino, $C_6$-$C_{14}$ aryl optionally substituted with a halogen or $C_6$-$C_{10}$ aryloxy optionally substituted with one to two halogens, and 5-10-membered heteroaryl optionally substituted with a $C_6$-$C_{10}$ aryl group and optionally substituted with one to three $C_1$-$C_4$ alkyl groups;

$C_3$-$C_7$ cycloalkyl;

$C_6$-$C_{14}$ aryl;

3-8-membered heterocycloalkyl optionally substituted with one or more $C_1$-$C_4$ alkyl-carbonyl group;

$C_6$-$C_{10}$ arylsulfonyl optionally substituted with one or more $C_1$-$C_2$ alkyl;

5-10-membered heteroaryl; and $C_6$-$C_{14}$ aryl-$C_0$-$C_4$ alkylene-O—$C_0$-$C_4$ alkyl, wherein each CO—$C_4$ alkyl and each $C_0$-$C_4$ alkylene is optionally substituted with one to four $C_1$-$C_4$ alkyl;

—C(=O)$R^{3'}$, —S(O)$_2R^{3'}$; wherein $R^{3'}$ is selected from the group consisting of hydrogen, ($C_1$-$C_4$)alkyl, ($C_1$-$C_4$)alkenyl, aryl, heteroaryl, ($C_3$-$C_7$)cycloalkyl, ($C_3$-$C_7$)cycloheteroalky, and wherein each hydrogen in $R^{3'}$ may independently optionally be substituted with halo, ($C_1$-$C_4$)alkyl, ($C_2$-$C_4$)alkenyl, and —S(O)$_2CH_3$;

wherein $R^3$ can be further selected from the group consisting of $C_6$-$C_{14}$ arylcarbonyl-$C_6$-$C_{14}$ aryl; $C_6$-$C_{14}$ arylcarbonyl-3-8-membered heterocycloalkyl; $C_3$-$C_8$ cycloalkylcarbonyl-$C_6$-$C_{14}$ aryl; $C_3$-$C_8$ cycloalkylcarbonyl-3-8-membered heterocycloalkyl; 3-8-membered heterocycloalkylcarbonyl-$C_6$-$C_{14}$ aryl; and 3-8-membered heterocycloalkylcarbonyl-3-8-membered heterocycloalkyl;

or $R^3$ and $R^2$ together with the nitrogen of the $NR^2R^3$ group form a first 5-, 6-, or 7-membered aliphatic ring, wherein one of the carbons in the first 5-, 6-, or 7-membered aliphatic ring is optionally replaced by O, S, $NR^{2'}$, or CO, and the first 5-, 6-, or 7-membered aliphatic ring is optionally fused to a $C_6$-$C_{10}$ arylene and is optionally substituted at a ring carbon with a substituent selected from the group consisting of 5-10-membered heteroaryl optionally substituted with one or more halogens and optionally substituted with one or more $C_1$-$C_2$ alkyl, $C_1$-$C_4$ alkoxy optionally substituted with one or more $C_1$-$C_2$ alkoxy and optionally substituted with one or more $C_1$-$C_4$ dialkylaminocarbonyl, and one or two $C_1$-$C_4$ alkyl optionally and independently substituted with one or more $C_1$-$C_2$ alkoxy;

wherein $R^{2'}$ is hydrogen;

$C_1$-$C_8$ alkyl optionally substituted with 1 to 4 halogens;

5-10-membered heteroaryl optionally substituted with a substituent selected from the group consisting of halogen, $C_1$-$C_4$ alkyl, $C_1$-$C_2$ alkoxy, $C_6$-$C_{10}$ aryl, $C_1$-$C_4$ alkylaminocarbonyl, and cyano;

$C_1$-$C_4$ alkyl group optionally substituted with a substituent selected from the group consisting of $C_1$-$C_2$ alkoxycarbonyl, 5-10-membered heteroaryl optionally substituted with one or more $C_1$-$C_2$ alkyl, one to four $C_1$-$C_4$ alkyl, $C_3$-$C_7$ cycloalkyl, and $C_6$-$C_{14}$ aryl;

$C_6$-$C_{10}$ aryl optionally substituted with one or two $C_1$-$C_2$ alkyl; $C_1$-$C_4$ alkylcarbonyl;

or $C_6$-$C_{14}$ aryl-$C_0$-$C_4$ alkylene-O—$C_0$-$C_4$ alkyl, wherein each $C_0$-$C_4$ alkyl and each $C_0$-$C_4$ alkylene is optionally substituted with one to four $C_1$-$C_4$ alkyl; $C_1$-$C_4$ alkylsulfonyl;

$R^4$ is hydrogen or methyl;

$R^5$ and $R^6$ are each independently selected from the group consisting of hydrogen; $C_1$-$C_4$ alkyl group optionally substituted with a substituent selected from the group consisting of OH, $C_1$-$C_3$ alkyl, $C_1$-$C_3$ alkoxy;

or $R^5$ and $R^6$ together with the nitrogen form a 3-7-membered cyclic amine optionally substituted with one or more $C_1$-$C_4$ alkyl;

$R^7$ is independently hydrogen or methyl;

n is 1, 2, or 3;

m is 1, 2, or 3;

Z is independently selected from the group consisting of hydrogen, halogen, $C_1$-$C_4$ alkyl, $C_1$-$C_4$ alkoxy, and —C(H)=CH$_2$; or wherein, when m is 2 and both Z's are —C(H)=CH$_2$, both Z's together with 2 adjacent carbons of the phenyl ring of formula I form a 6 membered aromatic ring fused to said phenyl ring.

This invention is also directed to:

a pharmaceutical composition for treating, for example, a disorder or condition that may be treated by antagonizing histamine-3 receptors, the composition comprising a compound of formula I as described above, and optionally a pharmaceutically acceptable carrier;

a method of treatment of a disorder or condition that may be treated by antagonizing histamine-3 receptors, the method comprising administering to a mammal in need of such treatment a compound of formula I as described above; and a pharmaceutical composition for treating, for example, a disorder or condition selected from the group consisting of depression, mood disorders, schizophrenia, anxiety disorders, Alzheimer's disease, attention-deficit disorder (ADD), attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper and hypo motility and acidic secretion of the gastro-intestinal tract, the composition comprising a compound of formula I as described above, and optionally a pharmaceutically acceptable carrier.

This invention is also directed to a method of treatment of a disorder or condition selected from the group consisting of the disorders or conditions listed in the preceding paragraph, the method comprising administering to a mammal in need of such treatment a compound of formula I as described above.

The histamine-3 (H3) receptor antagonists of the invention are useful for treating, in particular, ADD, ADHD, obesity, anxiety disorders and respiratory diseases. Respiratory diseases that may be treated by the present invention include adult respiratory distress syndrome, acute respiratory distress syndrome, bronchitis, chronic bronchitis, chronic obstructive pulmonary disease, cystic fibrosis, asthma, emphysema, rhinitis and chronic sinusitis.

The pharmaceutical composition and method of this invention may also be used for preventing a relapse in a disorder or condition described in the previous paragraphs. Preventing such relapse is accomplished by administering to a mammal in need of such prevention a compound of formula I as described above.

The disclosed compounds may also be used as part of a combination therapy, including their administration as separate entities or combined in a single delivery system, which employs an effective dose of a histamine H3 antagonist compound of general formula I and an effective dose of a histamine H1 antagonist, such as cetirizine (Zyrtec™), for the treatment of allergic rhinitis, nasal congestion and allergic congestion.

The disclosed compounds may also be used as part of a combination therapy, including their administration as separate entities or combined in a single delivery system, which employs an effective dose of a histamine H3 antagonist compound of general formula I and an effective dose of a neurotransmitter reuptake blocker. Examples of neurotransmitter reuptake blockers will include the serotonin-selective reuptake inhibitors (SSRI's) like sertraline (Zoloft™), fluoxetine (Prozac™), and paroxetine (Paxil™), or non-selective serotonin, dopamine or norepinephrine reuptake inhibitors for treating depression and mood disorders.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

"Antagonizing histamine-3 (H3) receptors," as used herein, refers to acting as a histamine-3 receptor antagonist.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pre-gelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is 0.1 to 200 mg of the active ingredient per unit dose which could be administered, for example, 1 to 4 times per day.

Aerosol formulations for treatment of the conditions referred to above (e.g., attention deficit hyperactivity disorder) in the average human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

In connection with the use of an active compound of this invention with a histamine H1 antagonist, preferably cetirizine, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 95% by weight of the total composition, i.e., in amounts which are sufficient to provide the desired unit dosage and a histamine H1 antagonist, preferably cetirizine, is present in such dosage forms at concentration levels ranging from about 0.5% to about 95% by weight of the total composition, i.e., in amounts which are sufficient to provide the desired unit dosage.

A proposed daily dose of an active compound of this invention in the combination formulation (a formulation containing an active compound of this invention and a histamine H1 antagonist) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a histamine H1 antagonist, preferably cetirizine, in the combination formulation for oral, parenteral or buccal administration to the average adult human for the treatment of the conditions referred to above is from about 0.1 mg to about 2000 mg, preferably from about 1 mg to about 200 mg of the histamine H1 antagonist per unit dose which could be administered, for example, 1 to 4 times per day.

A preferred dose ratio of cetirizine to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 µg to about 100 mg of the active compound of this invention, preferably from about 1 µg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a histamine H1 antagonist, preferably cetirizine, preferably from about 1 mg to about 200 mg of cetirizine. Administration may be several times daily, for example 2, 3, 4 or 8 times, giving for example, 1, 2 or 3 doses each time.

As previously indicated, a histamine H1 antagonist, preferably cetirizine, in combination with compounds of formula I are readily adapted to therapeutic use as antidepressant agents. In general, these antidepressant compositions containing a histamine H1 antagonist, preferably cetirizine, and a compound of formula I are normally administered in dosages ranging from about 0.01 mg to about 100 mg per kg of body weight per day of a histamine H1 antagonist, preferably cetirizine, preferably from about 0.1 mg. to about 10 mg per kg of body weight per day of cetirizine; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

In connection with the use of an active compound of this invention with a neurotransmitter re-uptake blocker, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 95% by weight of the total composition, i.e., in amounts which are sufficient to provide the desired unit dosage and a neurotransmitter re-uptake blocker, preferably sertraline, is present in such dosage forms at concentration levels ranging from about 0.5% to about 95% by weight of the total composition, i.e., in amounts which are sufficient to provide the desired unit dosage.

A proposed daily dose of an active compound of this invention in the combination formulation (a formulation containing an active compound of this invention and a SSRI re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a neurotransmitter re-uptake blocker, preferably sertraline, in the combination formulation for oral, parenteral or buccal administration to the average adult human for the treatment of the conditions referred to above is from about 0.1 mg to about 2000 mg, preferably from about 1 mg to about 200 mg of the neurotransmitter re-uptake blocker per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 µg to about 100 mg of the active compound of this invention, preferably from about 1 µg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a neurotransmitter re-uptake blocker, preferably sertraline, preferably from about 1 mg to about 200 mg of sertraline. Administration may be several times daily, for example 2, 3, 4 or 8 times, giving for example, 1, 2 or 3 doses each time.

As previously indicated, a neurotransmitter re-uptake blocker, preferably sertraline, in combination with compounds of formula I are readily adapted to therapeutic use as antidepressant agents. In general, these antidepressant compositions containing a neurotransmitter re-uptake blocker, preferably sertraline, and a compound of formula I are normally administered in dosages ranging from about 0.01 mg to about 100 mg per kg of body weight per day of a neurotransmitter re-uptake blocker, preferably sertraline, preferably from about 0.1 mg. to about 10 mg per kg of body weight per day of sertraline; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

Anxiety disorders include, for example, generalized anxiety disorder, panic disorder, PTSD, and social anxiety disorder. Mood adjustment disorders include, for example, depressed mood, mixed anxiety and depressed mood, disturbance of conduct, and mixed disturbance of conduct and depressed mood. Attention adjustment disorders include, for example, in addition to ADHD, attention-deficit disorders or other cognitive disorders due to general medical conditions. Psychotic disorders include, for example, schizoaffective disorders and schizophrenia; sleep disorders include, for example, narcolepsy and enuresis.

Examples of the disorders or conditions which may be treated by the compound, composition and method of this invention are also as follows: depression, including, for example, depression in cancer patients, depression in Parkinson's patients, post-myocardial Infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, including manic depressive illness with mixed episodes and manic depressive illness with depressive episodes, seasonal affective disorder, bipolar depression BP I, bipolar depression BP II, or major depression with dysthymia; dysthymia; phobias, including, for example, agoraphobia, social phobia or simple phobias; eating disorders, including, for example, anorexia nervosa or bulimia nervosa; chemical dependencies, including, for example, addictions to alcohol, cocaine, amphetamine and other psychostimulants, morphine, heroin and other opioid agonists, phenobarbital and other barbiturates, nicotine, diazepam, benzodiazepines and other psychoactive substances; Parkinson's diseases, including, for example, dementia in Parkinson's disease, neuroleptic-induced parkinsonism or tardive dyskinesias; headache, including, for example, headache associated with vascular disorders; withdrawal syndrome; age-associated learning and mental disorders; apathy; bipolar disorder; chronic fatigue syndrome; chronic or acute stress; conduct disorder; cyclothymic disorder; somatoform disorders such as somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; post-traumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders including Tourette's disease.

As an example, the mammal in need of the treatment or prevention may be a human. As another example, the mammal in need of the treatment or prevention may be a mammal other than a human.

A compound of formula I that is basic in nature is capable of forming a wide variety of different salts with various inorganic and organic acids. The acid addition salts are readily prepared by treating the base compounds with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid salts of the active compound used in formulating the pharmaceutical composition of this invention that are basic in nature are those which form non-toxic acid addition salts, i.e., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogenphosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, methylbenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate and pamoate [i.e., 1,1'-methylene-bis-(2-hydroxy-3-naphthoate)] salts.

The most preferred embodiment of the present invention includes the following compounds of formula I:

Dimethyl-[4-(3-pyrrolidin-1-ylmethyl-cyclobutoxy)-benzyl]-amine;
Dimethyl-[4-(3-pyrrolidin-1-ylmethyl-cyclobutoxy)-benzyl]-amine;
4-[3-(4-Pyrrolidin-1-ylmethyl-phenoxy)-cyclobutylmethyl]-morpholine;
4-[3-(3-Methoxy-4-pyrrolidin-1-ylmethyl-phenoxy)-cyclobutylmethyl]-morpholine;
4-[3-(3,5-Dimethyl-4-pyrrolidin-1-ylmethyl-phenoxy)-cyclobutylmethyl]-morpholine;
4-[3-(3-Chloro-4-pyrrolidin-1-ylmethyl-phenoxy)-cyclobutylmethyl]-morpholine;
4-[3-(2-Chloro-4-pyrrolidin-1-ylmethyl-phenoxy)-cyclobutylmethyl]-morpholine;
4-[3-(2-Isopropyl-5-methyl-4-pyrrolidin-1-ylmethyl-phenoxy)-cyclobutylmethyl]-morpholine;
4-[3-(3-Methyl-4-pyrrolidin-1-ylmethyl-phenoxy)-cyclobutylmethyl]-morpholine;
4-[3-(2-Chloro-3-pyrrolidin-1-ylmethyl-phenoxy)-cyclobutylmethyl]-morpholine;
4-[3-(2-Methyl-4-pyrrolidin-1-ylmethyl-phenoxy)-cyclobutylmethyl]-morpholine;
4-{3-[3-Chloro-4-((S)-1-pyrrolidin-1-yl-ethyl)-phenoxy]-cyclobutylmethyl}-morpholine;
4-{3-[3-Chloro-4-((R)-2-methyl-pyrrolidin-1-ylmethyl)-phenoxy]-cyclobutylmethyl}-morpholine;
Cyclobutanecarboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2-cyclopropyl-N-methyl-acetamide;
3,5-Dimethyl-isoxazole-4-carboxylic acid [3-(2-chloro-3-pyrrolidin-1-ylmethyl-phenoxy)-cyclobutylmethyl]-methyl-amide;
1-Ethyl-1-H-pyrazole-4-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-isonicotinamide;
N-[3-(3-Chloro-4-pyrrolidin-1-ylmethyl-phenoxy)-cyclobutylmethyl]-3,4,N-trimethyl-benzamide; and
N-{3-[3-Chloro-4-((S)-2-methyl-pyrrolidin-1-ylmethyl)-phenoxy]-cyclobutylmethyl}-N-methyl-benzamide.

More preferred embodiments of the present invention also include the foregoing compounds:

[3-(2,5-Dichloro-4-pyrrolidin-1-ylmethyl-phenoxy)-cyclobutylmethyl]-methyl-amine;
3,5-Dimethyl-isoxazole-4-carboxylic acid [3-(2-chloro-3-pyrrolidin-1-ylmethyl-phenoxy)-cyclobutylmethyl]-amide;
C-[3-(2-Chloro-3-pyrrolidin-1-ylmethyl-phenoxy)-cyclobutyl]-methylamine;
1-Methyl-cyclopropanecarboxylic acid [3-(2-chloro-3-pyrrolidin-1-ylmethyl-phenoxy)-cyclobutylmethyl]-amide;
1-Methyl-cyclopropanecarboxylic acid [3-(3-chloro-5-fluoro-4-pyrrolidin-1-ylmethyl-phenoxy)-cyclobutylmethyl]-methyl-amide;
1-Methyl-cyclopropanecarboxylic acid [3-(3,5-difluoro-4-pyrrolidin-1-ylmethyl-phenoxy)-cyclobutylmethyl]-methyl-amide;
[3-(3,5-Difluoro-4-pyrrolidin-1-ylmethyl-phenoxy)-cyclobutylmethyl]-methyl-amine;

3,5-Dimethyl-isoxazole-4-carboxylic acid [3-(3-chloro-5-fluoro-4-pyrrolidin-1-ylmethyl-phenoxy)-cyclobutylmethyl]-methyl-amide;

[3-(3-Chloro-5-fluoro-4-pyrrolidin-1-ylmethyl-phenoxy)-cyclobutylmethyl]-methyl-amine;

3,5-Dimethyl-isoxazole-4-carboxylic acid [3-(2-methoxy-3-pyrrolidin-1-ylmethyl-phenoxy)-cyclobutylmethyl]-methyl-amide;

[3-(2-Methoxy-3-pyrrolidin-1-ylmethyl-phenoxy)-cyclobutylmethyl]-methyl-carbamic acid tert-butyl ester;

6-Methyl-pyridine-2-carboxylic acid {3-[3-chloro-4-((S)-2-methyl-pyrrolidin-1-ylmethyl)-phenoxy]-cyclobutylmethyl}-methyl-amide;

N-{3-[3-Chloro-4-((S)-2-methyl-pyrrolidin-1-ylmethyl)-phenoxy]-cyclobutylmethyl}-3,N-dimethyl-butyramide;

N-[3-(3-Chloro-4-pyrrolidin-1-ylmethyl-phenoxy)-cyclobutylmethyl]-N-methyl-C-phenyl-methanesulfonamide;

1-[3-(3-Chloro-4-pyrrolidin-1-ylmethyl-phenoxy)-cyclobutylmethyl]-3-(4-fluoro-phenyl)-1-methyl-urea;

N-[3-(3-Chloro-4-pyrrolidin-1-ylmethyl-phenoxy)-cyclobutylmethyl]-N-methyl-propionamide;

N-[3-(3-Chloro-4-pyrrolidin-1-ylmethyl-phenoxy)-cyclobutylmethyl]-2,4,N-trimethyl-benzamide;

2,6-Dimethyl-pyrimidine-4-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-N-methyl-2-pyridin-4-yl-acetamide;

3,5-Dimethyl-isoxazole-4-carboxylic acid [3-(3-chloro-4-pyrrolidin-1-ylmethyl-phenoxy)-cyclobutylmethyl]-methyl-amide;

Cyclopropanecarboxylic acid [3-(3-chloro-4-pyrrolidin-1-ylmethyl-phenoxy)-cyclobutylmethyl]-methyl-amide;

1-Methyl-cyclopropanecarboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2-fluoro-N-methyl-benzamide;

1-[3-(3-Chloro-4-pyrrolidin-1-ylmethyl-phenoxy)-cyclobutylmethyl]-3-(3-methoxy-phenyl)-1-methyl-urea;

N-[3-(3-Chloro-4-pyrrolidin-1-ylmethyl-phenoxy)-cyclobutylmethyl]-N-methyl-nicotinamide;

3-(4-Chloro-phenyl)-1-[3-(3-chloro-4-pyrrolidin-1-ylmethyl-phenoxy)-cyclobutylmethyl]-1-methyl-urea;

3-(2-Chloro-phenyl)-1-[3-(3-chloro-4-pyrrolidin-1-ylmethyl-phenoxy)-cyclobutylmethyl]-1-methyl-urea;

1-[3-(3-Chloro-4-pyrrolidin-1-ylmethyl-phenoxy)-cyclobutylmethyl]-1-methyl-3-phenyl-urea;

1-[3-(3-Chloro-4-pyrrolidin-1-ylmethyl-phenoxy)-cyclobutylmethyl]-3-(3-fluoro-phenyl)-1-methyl-urea;

4-Methyl-oxazole-5-carboxylic acid [3-(3-chloro-4-pyrrolidin-1-ylmethyl-phenoxy)-cyclobutylmethyl]-methyl-amide;

Pyridine-2-carboxylic acid [3-(3-chloro-4-pyrrolidin-1-ylmethyl-phenoxy)-cyclobutylmethyl]-methyl-amide;

1-[3-(3-Chloro-4-pyrrolidin-1-ylmethyl-phenoxy)-cyclobutylmethyl]-1-methyl-3-p-tolyl-urea;

5-Ethyl-isoxazole-3-carboxylic acid [3-(3-chloro-4-pyrrolidin-1-ylmethyl-phenoxy)-cyclobutylmethyl]-methyl-amide;

3-(3-Acetyl-phenyl)-1-[3-(3-chloro-4-pyrrolidin-1-ylmethyl-phenoxy)-cyclobutylmethyl]-1-methyl-urea;

2-Ethyl-5-methyl-2H-pyrazole-3-carboxylic acid [3-(3-chloro-4-pyrrolidin-1-ylmethyl-phenoxy)-cyclobutylmethyl]-methyl-amide;

5-Isopropyl-isoxazole-3-carboxylic acid [3-(3-chloro-4-pyrrolidin-1-ylmethyl-phenoxy)-cyclobutylmethyl]-methyl-amide;

1-[3-(3-Chloro-4-pyrrolidin-1-ylmethyl-phenoxy)-cyclobutylmethyl]-3-(4-methoxy-2-methyl-phenyl)-1-methyl-urea;

N-[3-(3-Chloro-4-pyrrolidin-1-ylmethyl-phenoxy)-cyclobutylmethyl]-4,N-dimethyl-benzamide;

1-[3-(3-Chloro-4-pyrrolidin-1-ylmethyl-phenoxy)-cyclobutylmethyl]-3-(3,5-dimethyl-phenyl)-1-methyl-urea;

3-(5-Chloro-2-methyl-phenyl)-1-[3-(3-chloro-4-pyrrolidin-1-ylmethyl-phenoxy)-cyclobutylmethyl]-1-methyl-urea;

1-[3-(3-Chloro-4-pyrrolidin-1-ylmethyl-phenoxy)-cyclobutylmethyl]-3-(2,6-dimethyl-phenyl)-1-methyl-urea;

N-[3-(3-Chloro-4-pyrrolidin-1-ylmethyl-phenoxy)-cyclobutylmethyl]-3,5-difluoro-N-methyl-benzamide;

N-[3-(3-Chloro-4-pyrrolidin-1-ylmethyl-phenoxy)-cyclobutylmethyl]-2,3-difluoro-N-methyl-benzamide;

1-[3-(3-Chloro-4-pyrrolidin-1-ylmethyl-phenoxy)-cyclobutylmethyl]-3-(2-methoxy-5-methyl-phenyl)-1-methyl-urea;

N-[3-(3-Chloro-4-pyrrolidin-1-ylmethyl-phenoxy)-cyclobutylmethyl]-2,5,N-trimethyl-benzamide;

N-[3-(3-Chloro-4-pyrrolidin-1-ylmethyl-phenoxy)-cyclobutylmethyl]-2-(2-fluoro-phenyl)-N-methyl-acetamide;

N-[3-(3-Chloro-4-pyrrolidin-1-ylmethyl-phenoxy)-cyclobutylmethyl]-2,4-difluoro-N-methyl-benzamide;

1-[3-(3-Chloro-4-pyrrolidin-1-ylmethyl-phenoxy)-cyclobutylmethyl]-3-(2-methoxy-phenyl)-1-methyl-urea;

4-Methyl-furazan-3-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2-(3-fluoro-phenyl)-N-methyl-acetamide;

3-Isopropyl-isoxazole-5-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2,4,N-trimethyl-benzenesulfonamide;

3-(4-Chloro-2-methyl-phenyl)-1-[3-(3-chloro-4-pyrrolidin-1-ylmethyl-phenoxy)-cyclobutylmethyl]-1-methyl-urea;

5-Cyclopropyl-isoxazole-3-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-N-methyl-benzamide;

N-[3-(3-Chloro-4-pyrrolidin-1-ylmethyl-phenoxy)-cyclobutylmethyl]-2-methoxy-N-methyl-nicotinamide;

N-[3-(3-Chloro-4-pyrrolidin-1-ylmethyl-phenoxy)-cyclobutylmethyl]-3,N-dimethyl-butyramide;

5-Cyclopropyl-oxazole-4-carboxylic acid [3-(3-chloro-4-pyrrolidin-1-ylmethyl-phenoxy)-cyclobutylmethyl]-methyl-amide;

2-Ethyl-4-methyl-oxazole-5-carboxylic acid [3-(3-chloro-4-pyrrolidin-1-ylmethyl-phenoxy)-cyclobutylmethyl]-methyl-amide;

1,5-Dimethyl-1H-pyrazole-3-carboxylic acid [3-(3-chloro-4-pyrrolidin-1-ylmethyl-phenoxy)-cyclobutylmethyl]-methyl-amide;

6-Methyl-pyridine-2-carboxylic acid [3-(3-chloro-4-pyrrolidin-1-ylmethyl-phenoxy)-cyclobutylmethyl]-methyl-amide;

1-isopropyl-1H-pyrazole-4-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2,N-dimethyl-nicotinamide;

3-(3-Chloro-phenyl)-1-[3-(3-chloro-4-pyrrolidin-1-ylmethyl-phenoxy)-cyclobutylmethyl]-1-methyl-urea;
N-[3-(3-Chloro-4-pyrrolidin-1-ylmethyl-phenoxy)-cyclobutylmethyl]-3-fluoro-N-methyl-benzamide;
1-[3-(3-Chloro-4-pyrrolidin-1-ylmethyl-phenoxy)-cyclobutylmethyl]-3-(4-methoxy-phenyl)-1-methyl-urea;
1-[3-(3-Chloro-4-pyrrolidin-1-ylmethyl-phenoxy)-cyclobutylmethyl]-3-(2,4-difluoro-phenyl)-1-methyl-urea;
Propane-2-sulfonic acid [3-(3-chloro-4-pyrrolidin-1-ylmethyl-phenoxy)-cyclobutylmethyl]-methyl-amide;
4-Chloro-N-[3-(3-chloro-4-pyrrolidin-1-ylmethyl-phenoxy)-cyclobutylmethyl]-N-methyl-benzamide;
1-[3-(3-Chloro-4-pyrrolidin-1-ylmethyl-phenoxy)-cyclobutylmethyl]-3-(3,4-dimethyl-phenyl)-1-methyl-urea;
1-[3-(3-Chloro-4-pyrrolidin-1-ylmethyl-phenoxy)-cyclobutylmethyl]-3-(2-ethyl-phenyl)-1-methyl-urea;
Pyridine-3-sulfonic acid [3-(3-chloro-4-pyrrolidin-1-ylmethyl-phenoxy)-cyclobutylmethyl]-methyl-amide;
1-[3-(3-Chloro-4-pyrrolidin-1-ylmethyl-phenoxy)-cyclobutylmethyl]-1-methyl-3-o-tolyl-urea;
3-(3-Chloro-4-methyl-phenyl)-1-[3-(3-chloro-4-pyrrolidin-1-ylmethyl-phenoxy)-cyclobutylmethyl]-1-methyl-urea;
1-{[3-(3-Chloro-4-pyrrolidin-1-ylmethyl-phenoxy)-cyclobutyl]methyl}-1-methyl-3-(2-trifluoromethyl-phenyl)-urea;
1-[(3-(3-Chloro-4-pyrrolidin-1-ylmethyl-phenoxy)-cyclobutylmethyl]-3-ethyl-1-methyl-urea;
3-Ethyl-5-methyl-isoxazole-4-carboxylic acid [3-(3-chloro-4-pyrrolidin-1-ylmethyl-phenoxy)-cyclobutylmethyl]-methyl-amide;
3-Chloro-N-[3-(3-chloro-4-pyrrolidin-1-ylmethyl-phenoxy)-cyclobutylmethyl]-N-methyl-benzamide;
5-Cyclopropyl-2H-pyrazole-3-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-4-fluoro-N-methyl-benzamide;
3-(3-Chloro-2-methyl-phenyl)-1-[3-(3-chloro-4-pyrrolidin-1-ylmethyl-phenoxy)-cyclobutylmethyl]-1-methyl-urea;
N-[3-(3-Chloro-4-pyrrolidin-1-ylmethyl-phenoxy)-cyclobutylmethyl]-3,4-difluoro-N-methyl-benzamide;
1-[3-(3-Chloro-4-pyrrolidin-1-ylmethyl-phenoxy)-cyclobutylmethyl]-1-methyl-3-m-tolyl-urea;
1-[3-(3-Chloro-4-pyrrolidin-1-ylmethyl-phenoxy)-cyclobutylmethyl]-3-(2,5-dimethyl-phenyl)-1-methyl-urea;
3-(2-Chloro-6-methyl-phenyl)-1-[3-(3-chloro-4-pyrrolidin-1-ylmethyl-phenoxy)-cyclobutylmethyl]-1-methyl-urea;
N-[3-(3-Chloro-4-pyrrolidin-1-ylmethyl-phenoxy)-cyclobutylmethyl]-N-methyl-acetamide;
5-Ethyl-2-methyl-2H-pyrazole-3-carboxylic acid [3-(3-chloro-4-pyrrolidin-1-ylmethyl-phenoxy)-cyclobutylmethyl]-methyl-amide;
5-Methyl-isoxazole-3-carboxylic acid [3-(3-chloro-4-pyrrolidin-1-ylmethyl-phenoxy)-cyclobutylmethyl]-methyl-amide;
Prop-2-ene-1-sulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2-methoxy-N-methyl-acetamide;
N-[3-(3-Chloro-4-pyrrolidin-1-ylmethyl-phenoxy)-cyclobutylmethyl]-6,N-dimethyl-nicotinamide;
1-[3-(3-Chloro-4-pyrrolidin-1-ylmethyl-phenoxy)-cyclobutylmethyl]-3-isopropyl-1-methyl-urea;
N-[3-(3-Chloro-4-pyrrolidin-1-ylmethyl-phenoxy)-cyclobutylmethyl]-N-methyl-isobutyramide;
Cyclobutanecarboxylic acid [3-(3-chloro-4-pyrrolidin-1-ylmethyl-phenoxy)-cyclobutylmethyl]-methyl-amide;
3-Ethyl-isoxazole-5-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2,5-difluoro-N-methyl-benzamide;
1-{[3-(3-Chloro-4-pyrrolidin-1-ylmethyl-phenoxy)-cyclobutyl]methyl}-1-methyl-3-(4-trifluoromethyl-phenyl)-urea;
3-(5-Chloro-2-methoxy-phenyl)-1-[3-(3-chloro-4-pyrrolidin-1-ylmethyl-phenoxy)-cyclobutylmethyl]-1-methyl-urea;
3-Benzyl-1-[3-(3-chloro-4-pyrrolidin-1-ylmethyl-phenoxy)-cyclobutylmethyl]-1-methyl-urea;
Pyrazine-2-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2,4-difluoro-N-methyl-benzenesulfonamide;
1-[3-(2-Chloro-3-pyrrolidin-1-ylmethyl-phenoxy)-cyclobutylmethyl]-3-isopropyl-1-methyl-urea;
4-Chloro-N-[3-(2-chloro-3-pyrrolidin-1-ylmethyl-phenoxy)-cyclobutylmethyl]-N-methyl-benzamide;
N-[3-(2-Chloro-3-pyrrolidin-1-ylmethyl-phenoxy)-cyclobutylmethyl]-3,4-difluoro-N-methyl-benzamide;
3-Benzyl-1-[3-(2-chloro-3-pyrrolidin-1-ylmethyl-phenoxy)-cyclobutylmethyl]-1-methyl-urea;
3,5-Dimethyl-isoxazole-4-sulfonic acid [3-(2-chloro-3-pyrrolidin-1-ylmethyl-phenoxy)-cyclobutylmethyl]-methyl-amide;
1-Methyl-cyclopropanecarboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2,4-difluoro-N-methyl-benzamide;
N-[3-(2-Chloro-3-pyrrolidin-1-ylmethyl-phenoxy)-cyclobutylmethyl]-2,5-difluoro-N-methyl-benzamide;
3-Chloro-N-[3-(2-chloro-3-pyrrolidin-1-ylmethyl-phenoxy)-cyclobutylmethyl]-2,N-dimethyl-benzenesulfonamide;
5-Ethyl-isoxazole-3-carboxylic acid [3-(2-chloro-3-pyrrolidin-1-ylmethyl-phenoxy)-cyclobutylmethyl]-methyl-amide;
3,5-Dimethyl-isoxazole-4-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-3,5-difluoro-N-methyl-benzamide;
N-[3-(2-Chloro-3-pyrrolidin-1-ylmethyl-phenoxy)-cyclobutylmethyl]-N-methyl-2-pyridin-2-yl-acetamide;
3-tert-Butyl-1-[3-(2-chloro-3-pyrrolidin-1-ylmethyl-phenoxy)-cyclobutylmethyl]-1-methyl-urea;
N-[3-(2-Chloro-3-pyrrolidin-1-ylmethyl-phenoxy)-cyclobutylmethyl]-2,N-dimethyl-nicotinamide;
1-[3-(2-Chloro-3-pyrrolidin-1-ylmethyl-phenoxy)-cyclobutylmethyl]-3-(2-fluoro-phenyl)-1-methyl-urea;
N-[3-(2-Chloro-3-pyrrolidin-1-ylmethyl-phenoxy)-cyclobutylmethyl]-6,N-dimethyl-nicotinamide;
Propane-1-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2-fluoro-N-methyl-benzamide;
N-[3-(2-Chloro-3-pyrrolidin-1-ylmethyl-phenoxy)-cyclobutylmethyl]-N-methyl-benzamide;
1-[3-(2-Chloro-3-pyrrolidin-1-ylmethyl-phenoxy)-cyclobutylmethyl]-3-(4-methoxy-phenyl)-1-methyl-urea;
3-(5-Chloro-2-methyl-phenyl)-1-[3-(2-chloro-3-pyrrolidin-1-ylmethyl-phenoxy)-cyclobutylmethyl]-1-methyl-urea;

Thiophene-3-sulfonic acid [3-(2-chloro-3-pyrrolidin-1-ylmethyl-phenoxy)-cyclobutylmethyl]-methyl-amide;
4-Methyl-pentanoic acid [3-(2-chloro-3-pyrrolidin-1-ylmethyl-phenoxy)-cyclobutylmethyl]-methyl-amide;
4-Chloro-N-[3-(2-chloro-3-pyrrolidin-1-ylmethyl-phenoxy)-cyclobutylmethyl]-N-methyl-benzenesulfonamide;
(S)—N-[3-(2-Chloro-3-pyrrolidin-1-ylmethyl-phenoxy)-cyclobutylmethyl]-2-hydroxy-N-methyl-2-phenyl-acetamide;
1,5-Dimethyl-1H-pyrazole-3-carboxylic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-1-methyl-3-m-tolyl-urea;
N-[3-(2-Chloro-3-pyrrolidin-1-ylmethyl-phenoxy)-cyclobutylmethyl]-2,3-difluoro-N-methyl-benzamide;
4-Methyl-oxazole-5-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-4-fluoro-N-methyl-benzenesulfonamide;
2-Chloro-N-[3-(2-chloro-3-pyrrolidin-1-ylmethyl-phenoxy)-cyclobutylmethyl]-N-methyl-benzenesulfonamide;
1-[3-(2-Chloro-3-pyrrolidin-1-ylmethyl-phenoxy)-cyclobutylmethyl]-3-ethyl-1-methyl-urea;
1-Isopropyl-1H-pyrazole-4-carboxylic acid [3-(2-chloro-3-pyrrolidin-1-ylmethyl-phenoxy)-cyclobutylmethyl]-methyl-amide;
3-(3-Acetyl-phenyl)-1-[3-(2-chloro-3-pyrrolidin-1-ylmethyl-phenoxy)-cyclobutylmethyl]-1-methyl-urea;
5-Methyl-isoxazole-3-carboxylic acid [3-(2-chloro-3-pyrrolidin-1-ylmethyl-phenoxy)-cyclobutylmethyl]-methyl-amide;
2-Ethyl-4-methyl-oxazole-5-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-3-fluoro-N-methyl-benzamide;
N-[3-(2-Chloro-3-pyrrolidin-1-ylmethyl-phenoxy)-cyclobutylmethyl]-N-methyl-2-pyridin-4-yl-acetamide;
5-Ethyl-2-methyl-2H-pyrazole-3-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-N-methyl-2-pyrazol-1-yl-acetamide;
Cyclopropanecarboxylic acid [3-(2-chloro-3-pyrrolidin-1-ylmethyl-phenoxy)-cyclobutylmethyl]-methyl-amide;
3-Chloro-N-[3-(2-chloro-3-pyrrolidin-1-ylmethyl-phenoxy)-cyclobutylmethyl]-N-methyl-benzenesulfonamide;
1-[3-(2-Chloro-3-pyrrolidin-1-ylmethyl-phenoxy)-cyclobutylmethyl]-3-(2-ethyl-phenyl)-1-methyl-urea;
N-[3-(2-Chloro-3-pyrrolidin-1-ylmethyl-phenoxy)-cyclobutylmethyl]-2-(2-fluoro-phenyl)-N-methyl-acetamide;
N-[3-(2-Chloro-3-pyrrolidin-1-ylmethyl-phenoxy)-cyclobutylmethyl]-N-methyl-C-phenyl-methanesulfonamide;
N-[3-(2-Chloro-3-pyrrolidin-1-ylmethyl-phenoxy)-cyclobutylmethyl]-4-fluoro-N-methyl-benzamide;
N-[3-(2-Chloro-3-pyrrolidin-1-ylmethyl-phenoxy)-cyclobutylmethyl]-N-methyl-benzenesulfonamide;
1-{[3-(2-Chloro-3-pyrrolidin-1-ylmethyl-phenoxy)-cyclobutyl]methyl}-1-methyl-3-(2-trifluoromethyl-phenyl)-urea;
N-[3-(2-Chloro-3-pyrrolidin-1-ylmethyl-phenoxy)-cyclobutylmethyl]-2-cyclopentyl-N-methyl-acetamide;
N-[3-(2-Chloro-3-pyrrolidin-1-ylmethyl-phenoxy)-cyclobutylmethyl]-N-methyl-acetamide;
N-[3-(2-Chloro-3-pyrrolidin-1-ylmethyl-phenoxy)-cyclobutylmethyl]-N-methyl-isonicotinamide;
Cyclopentanecarboxylic acid [3-(2-chloro-3-pyrrolidin-1-ylmethyl-phenoxy)-cyclobutylmethyl]-methyl-amide;
Benzo[1,2,5]thiadiazole-4-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-3,4-difluoro-N-methyl-benzenesulfonamide;
1-[3-(2-Chloro-3-pyrrolidin-1-ylmethyl-phenoxy)-cyclobutylmethyl]-1-methyl-3-o-tolyl-urea;
3-Chloro-N-[3-(2-chloro-3-pyrrolidin-1-ylmethyl-phenoxy)-cyclobutylmethyl]-N-methyl-benzamide;
5-Cyclopropyl-2H-pyrazole-3-carboxylic acid [3-(2-chloro-3-pyrrolidin-1-ylmethylphenoxy)-cyclobutylmethyl]-methyl-amide;
3-(4-Chloro-phenyl)-1-[3-(2-chloro-3-pyrrolidin-1-ylmethyl-phenoxy)-cyclobutylmethyl]-1-methyl-urea;
Piperidine-1-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-N-methyl-2-(3-methyl-pyrazol-1-yl)-acetamide;
1-[3-(2-Chloro-3-pyrrolidin-1-ylmethyl-phenoxy)-cyclobutylmethyl]-1-methyl-3-p-tolyl-urea;
N-[3-(2-Chloro-3-pyrrolidin-1-ylmethyl-phenoxy)-cyclobutylmethyl]-4,4,4-trifluoro-N-methyl-butyramide;
Morpholine-4-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2-(3,5-dimethyl-isoxazol-4-yl)-N-methyl-acetamide;
N-[3-(2-Chloro-3-pyrrolidin-1-ylmethyl-phenoxy)-cyclobutylmethyl]-3,N-dimethyl-butyramide;
Tetrahydro-pyran-4-carboxylic acid [3-(2-chloro-3-pyrrolidin-1-ylmethyl-phenoxy)-cyclobutylmethyl]-methyl-amide;
3-(3-Chloro-2-methyl-phenyl)-1-[3-(2-chloro-3-pyrrolidin-1-ylmethyl-phenoxy)-cyclobutylmethyl]-1-methyl-urea;
Propane-2-sulfonic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-3-(2-methoxy-phenyl)-1-methyl-urea;
3-(2-Chloro-phenyl)-1-[3-(2-chloro-3-pyrrolidin-1-ylmethyl-phenoxy)-cyclobutylmethyl]-1-methyl-urea;
1-[3-(2-Chloro-3-pyrrolidin-1-ylmethyl-phenoxy)-cyclobutylmethyl]-3-(2,5-dimethyl-phenyl)-1-methyl-urea;
4-Methyl-furazan-3-carboxylic acid [3-(2-chloro-3-pyrrolidin-1-ylmethyl-phenoxy)-cyclobutylmethyl]-methyl-amide;
N-({trans-3-[3-(2-chloro-pyrrolidiylmethyl)phenoxy]cyclobutyl}methyl)-N,N',N'-trimethylsulfamide;
N-[3-(2-Chloro-3-pyrrolidin-1-ylmethyl-phenoxy)-cyclobutylmethyl]-2,4-dimethoxy-N-methyl-benzenesulfonamide;
2,5-Dimethyl-thiophene-3-sulfonic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-1-methyl-3-phenyl-urea;
N-[3-(2-Chloro-3-pyrrolidin-1-ylmethyl-phenoxy)-cyclobutylmethyl]-N-methyl-isobutyramide;
1-[3-(2-Chloro-3-pyrrolidin-1-ylmethyl-phenoxy)-cyclobutylmethyl]-3-(2,4-difluoro-phenyl)-1-methyl-urea;
6-Methyl-pyridine-2-carboxylic acid [3-(2-chloro-3-pyrrolidin-1-ylmethyl-phenoxy)-cyclobutylmethyl]-methyl-amide;

3-(3-Chloro-phenyl)-1-[3-(2-chloro-3-pyrrolidin-1-ylm-ethyl-phenoxy)-cyclobutylmethyl]-1-methyl-urea;
N-[3-(2-Chloro-3-pyrrolidin-1-ylmethyl-phenoxy)-cyclobutylmethyl]-N-methyl-nicotinamide;
N-[3-(2-Chloro-3-pyrrolidin-1-ylmethyl-phenoxy)-cyclobutylmethyl]-2-(3-fluoro-phenyl)-N-methyl-acetamide;
1-[3-(2-Chloro-3-pyrrolidin-1-ylmethyl-phenoxy)-cyclobutylmethyl]-3-(3-methoxy-phenyl)-1-methyl-urea;
N-[3-(2-Chloro-3-pyrrolidin-1-ylmethyl-phenoxy)-cyclobutylmethyl]-2,5,N-trimethyl-benzamide;
N-[3-(2-Chloro-3-pyrrolidin-1-ylmethyl-phenoxy)-cyclobutylmethyl]-2-cyclopropyl-N-methyl-acetamide;
N-[3-(2-Chloro-3-pyrrolidin-1-ylmethyl-phenoxy)-cyclobutylmethyl]-N-methyl-propionamide;
N-[3-(2-Chloro-3-pyrrolidin-1-ylmethyl-phenoxy)-cyclobutylmethyl]-2-methoxy-N-methyl-nicotinamide;
N-[3-(2-Chloro-3-pyrrolidin-1-ylmethyl-phenoxy)-cyclobutylmethyl]-2,6-difluoro-N-methyl-benzamide;
1-{[3-(2-Chloro-3-pyrrolidin-1-ylmethyl-phenoxy)-cyclobutyl]methyl}-1-methyl-3-(3-trifluoromethyl-phenyl)-urea;
N-[3-(2-Chloro-3-pyrrolidin-1-ylmethyl-phenoxy)-cyclobutylmethyl]-2-methoxy-N-methyl-acetamide;
N-[3-(2-Chloro-3-pyrrolidin-1-ylmethyl-phenoxy)-cyclobutylmethyl]-3-methoxy-N-methyl-propionamide;
N-[3-(2-Chloro-3-pyrrolidin-1-ylmethyl-phenoxy)-cyclobutylmethyl]-2,3,N-trimethyl-benzamide;
N-[3-(2-Chloro-3-pyrrolidin-1-ylmethyl-phenoxy)-cyclobutylmethyl]-N-methyl-2-pyridin-3-yl-acetamide;
N-[3-(2-Chloro-3-pyrrolidin-1-ylmethyl-phenoxy)-cyclobutylmethyl]-3-fluoro-N-methyl-benzenesulfonamide;
N-[3-(2-Chloro-3-pyrrolidin-1-ylmethyl-phenoxy)-cyclobutylmethyl]-2,2,N-trimethyl-propionamide;
1-Ethyl-1H-pyrazole-4-carboxylic acid [3-(2-chloro-3-pyrrolidin-1-ylmethyl-phenoxy)-cyclobutylmethyl]-methyl-amide;
Pyridine-2-carboxylic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-3-(2,6-dimethyl-phenyl)-1-methyl-urea;
N-[3-(2-Chloro-3-pyrrolidin-1-ylmethyl-phenoxy)-cyclobutylmethyl]-3,3,N-trimethyl-butyramide;
4-[3-(2-Fluoro-4-pyrrolidin-1-ylmethyl-phenoxy)-cyclobutylmethyl]-morpholine;
4-{3-[2-Fluoro-4-(2-pyrrolidin-1-yl-ethyl)-phenoxy]-cyclobutylmethyl}-morpholine;
Pyridine-3-sulfonic acid [3-(4-pyrrolidin-1-ylmethyl-phenoxy)-cyclobutylmethyl]-amide;
2,5-Dimethyl-2H-pyrazole-3-carboxylic acid [3-(4-pyrrolidin-1-ylmethyl-phenoxy)-cyclobutylmethyl]-amide;
N-[3-(4-Pyrrolidin-1-ylmethyl-phenoxy)-cyclobutylmethyl]-isonicotinamide;
2-Methyl-2H-pyrazole-3-carboxylic acid [3-(4-pyrrolidin-1-ylmethyl-phenoxy)-cyclobutylmethyl]-amide;
6-Methyl-N-[3-(4-pyrrolidin-1-ylmethyl-phenoxy)-cyclobutylmethyl]-nicotinamide;
C-Phenyl-N-[3-(4-pyrrolidin-1-ylmethyl-phenoxy)-cyclobutylmethyl]-methanesulfonamide;
Ethanesulfonic acid [3-(4-pyrrolidin-1-ylmethyl-phenoxy)-cyclobutylmethyl]-amide;
4-{3-[4-(1-Pyrrolidin-1-yl-ethyl)-phenoxy]-cyclobutylmethyl}-morpholine;
4-[3-(2,5-Dimethoxy-4-pyrrolidin-1-ylmethyl-phenoxy)-cyclobutylmethyl]-morpholine;
4-[3-(2,6-Dimethyl-4-pyrrolidin-1-ylmethyl-phenoxy)-cyclobutylmethyl]-morpholine;
4-{3-[3-Chloro-4-(1-pyrrolidin-1-yl-ethyl)-phenoxy]-cyclobutylmethyl}-morpholine;
4-[3-(4-Pyrrolidin-1-ylmethyl-naphthalen-1-yloxy)-cyclobutylmethyl]-morpholine;
4-[3-(2-Ethoxy-4-pyrrolidin-1-ylmethyl-phenoxy)-cyclobutylmethyl]-morpholine;
4-[3-(2-Chloro-6-methoxy-4-pyrrolidin-1-ylmethyl-phenoxy)-cyclobutylmethyl]-morpholine;
4-[3-(3-Pyrrolidin-1-ylmethyl-phenoxy)-cyclobutylmethyl]-morpholine;
4-[3-(2-Methoxy-4-pyrrolidin-1-ylmethyl-phenoxy)-cyclobutylmethyl]-morpholine;
3,4-Difluoro-N-methyl-N-[3-(4-pyrrolidin-1-ylmethyl-phenoxy)-cyclobutylmethyl]-benzenesulfonamide;
Pyridine-3-sulfonic acid methyl-[3-(4-pyrrolidin-1-ylmethyl-phenoxy)-cyclobutylmethyl]-amide;
2-Methoxy-N-methyl-N-[3-(4-pyrrolidin-1-ylmethyl-phenoxy)-cyclobutylmethyl]-acetamide;
2,5-Dimethyl-2H-pyrazole-3-carboxylic acid methyl-[3-(4-pyrrolidin-1-ylmethyl-phenoxy)-cyclobutylmethyl]-amide; and
1-Methanesulfonyl-4-[3-(4-pyrrolidin-1-ylmethyl-phenoxy)-cyclobutylmethyl]-piperazine.

Other preferred compounds of formula I in accordance with the present invention are the following:
Ethanesulfonic acid methyl-[3-(4-pyrrolidin-1-ylmethyl-phenoxy)-cyclobutylmethyl]-amide;
1,3,5-Trimethyl-1H-pyrazole-4-sulfonic acid methyl-[3-(4-pyrrolidin-1-ylmethyl-phenoxy)-cyclobutylmethyl]-amide;
N-Methyl-2-pyridin-3-yl-N-[3-(4-pyrrolidin-1-ylmethyl-phenoxy)-cyclobutylmethyl]-acetamide;
N-Methyl-N-[3-(4-pyrrolidin-1-ylmethyl-phenoxy)-cyclobutylmethyl]-nicotinamide;
2-Chloro-4-fluoro-N-methyl-N-[3-(4-pyrrolidin-1-ylmethyl-phenoxy)-cyclobutylmethyl]-benzenesulfonamide;
3-Methoxy-N-methyl-N-[3-(4-pyrrolidin-1-ylmethyl-phenoxy)-cyclobutylmethyl]-propionamide;
2,N-Dimethyl-N-[3-(4-pyrrolidin-1-ylmethyl-phenoxy)-cyclobutylmethyl]-nicotinamide;
2-Methyl-2H-pyrazole-3-carboxylic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-isobutyramide;
5-Ethyl-isoxazole-3-carboxylic acid methyl-[3-(4-pyrrolidin-1-ylmethyl-phenoxy)-cyclobutylmethyl]-amide;
2-Cyclopentyl-N-methyl-N-[3-(4-pyrrolidin-1-ylmethyl-phenoxy)-cyclobutylmethyl]-acetamide;
N-Methyl-N-[3-(4-pyrrolidin-1-ylmethyl-phenoxy)-cyclobutylmethyl]-methanesulfonamide;
4-Acetyl-N-methyl-N-[3-(4-pyrrolidin-1-ylmethyl-phenoxy)-cyclobutylmethyl]-benzenesulfonamide;
6,N-Dimethyl-N-[3-(4-pyrrolidin-1-ylmethyl-phenoxy)-cyclobutylmethyl]-nicotinamide;
6-Methyl-pyridine-2-carboxylic acid methyl-[3-(4-pyrrolidin-1-ylmethyl-phenoxy)-cyclobutylmethyl]-amide;
Pyridine-2-carboxylic acid methyl-[3-(4-pyrrolidin-1-ylmethyl-phenoxy)-cyclobutylmethyl]-amide;
Tetrahydro-pyran-4-carboxylic acid methyl-[3-(4-pyrrolidin-1-ylmethyl-phenoxy)-cyclobutylmethyl]-amide;
N-Methyl-2-pyridin-4-yl-N-[3-(4-pyrrolidin-1-ylmethyl-phenoxy)-cyclobutylmethyl]-acetamide;
3,N-Dimethyl-N-[3-(4-pyrrolidin-1-ylmethyl-phenoxy)-cyclobutylmethyl]-butyramide;
Propane-2-sulfonic acid methyl-[3-(4-pyrrolidin-1-ylmethyl-phenoxy)-cyclobutylmethyl]-amide;

4-Chloro-N-methyl-N-[3-(4-pyrrolidin-1-ylmethyl-phenoxy)-cyclobutylmethyl]-benzenesulfonamide;
3-Methyl-1H-pyrazole-4-carboxylic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-propionamide;
N-Methyl-2-pyridin-2-yl-N-[3-(4-pyrrolidin-1-ylmethyl-phenoxy)-cyclobutylmethyl]-acetamide;
N-Methyl-C-phenyl-N-[3-(4-pyrrolidin-1-ylmethyl-phenoxy)-cyclobutylmethyl]-methanesulfonamide;
2,2,2-Trifluoro-ethanesulfonic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-acetamide;
Piperidine-1-sulfonic acid methyl-[3-(4-pyrrolidin-1-ylmethyl-phenoxy)-cyclobutylmethyl]-amide;
Pyrrolidine-1-sulfonic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-isonicotinamide;
Pyrazine-2-carboxylic acid methyl-[3-(4-pyrrolidin-1-ylmethyl-phenoxy)-cyclobutylmethyl]-amide;
4-[3-(2,6-Dimethoxy-4-pyrrolidin-1-ylmethyl-phenoxy)-cyclobutylmethyl]-morpholine;
4-[3-(2-Methoxy-5-pyrrolidin-1-ylmethyl-phenoxy)-cyclobutylmethyl]-morpholine;
4-[3-(4-Methoxy-3-pyrrolidin-1-ylmethyl-phenoxy)-cyclobutylmethyl]-morpholine;
4-{3-[3-Chloro-4-((R)-1-pyrrolidin-1-yl-ethyl)-phenoxy]-cyclobutylmethyl}-morpholine;
4-[3-(3-Methyl-5-pyrrolidin-1-ylmethyl-phenoxy)-cyclobutylmethyl]-morpholine;
N-[3-(4-Pyrrolidin-1-ylmethyl-phenoxy)-cyclobutylmethyl]-nicotinamide;
2-Pyridin-4-yl-N-[3-(4-pyrrolidin-1-ylmethyl-phenoxy)-cyclobutylmethyl]-acetamide;
3-Methyl-N-[3-(4-pyrrolidin-1-ylmethyl-phenoxy)-cyclobutylmethyl]-butyramide;
2-Methoxy-N-[3-(4-pyrrolidin-1-ylmethyl-phenoxy)-cyclobutylmethyl]-acetamide;
N-[3-(4-Pyrrolidin-1-ylmethyl-phenoxy)-cyclobutylmethyl]-acetamide;
N-[3-(4-Pyrrolidin-1-ylmethyl-phenoxy)-cyclobutylmethyl]-isobutyramide;
N-[3-(4-Pyrrolidin-1-ylmethyl-phenoxy)-cyclobutylmethyl]-propionamide;
N-[3-(4-Pyrrolidin-1-ylmethyl-phenoxy)-cyclobutylmethyl]-methanesulfonamide;
2-Cyclopentyl-N-[3-(4-pyrrolidin-1-ylmethyl-phenoxy)-cyclobutylmethyl]-acetamide;
3-Methoxy-N-[3-(4-pyrrolidin-1-ylmethyl-phenoxy)-cyclobutylmethyl]-propionamide;
2-Pyridin-2-yl-N-[3-(4-pyrrolidin-1-ylmethyl-phenoxy)-cyclobutylmethyl]-acetamide;
Piperidine-1-sulfonic acid [3-(4-pyrrolidin-1-ylmethyl-phenoxy)-cyclobutylmethyl]-amide;
N-[3-(2-Chloro-3-pyrrolidin-1-ylmethyl-phenoxy)-cyclobutylmethyl]-2,6-difluoro-N-methyl-benzenesulfonamide;
N-[3-(2-Chloro-3-pyrrolidin-1-ylmethyl-phenoxy)-cyclobutylmethyl]-4,N-dimethyl-benzamide;
1-[3-(2-Chloro-3-pyrrolidin-1-ylmethyl-phenoxy)-cyclobutylmethyl]-3-(3-fluoro-phenyl)-1-methyl-urea;
2-Oxo-2,3-dihydro-benzooxazole-6-sulfonic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-3-(3,5-dimethyl-phenyl)-1-methyl-urea;
4-Methyl-thiophene-2-sulfonic acid [3-(2-chloro-3-pyrrolidin-1-ylmethyl-phenoxy)-cyclobutylmethyl]-methyl-amide;
3-(5-Chloro-2-methoxy-phenyl)-1-[3-(2-chloro-3-pyrrolidin-1-ylmethyl-phenoxy)-cyclobutylmethyl]-1-methyl-urea;
2-Ethyl-5-methyl-2H-pyrazole-3-carboxylic acid [3-(2-chloro-3-pyrrolidin-1-ylmethyl-phenoxy)-cyclobutylmethyl]-methyl-amide;
4-Acetyl-N-[3-(2-chloro-3-pyrrolidin-1-ylmethyl-phenoxy)-cyclobutylmethyl]-N-methyl-benzenesulfonamide;
Pyrrolidine-1-sulfonic acid [3-(2-chloro-3-pyrrolidin-1-ylmethyl-phenoxy)-cyclobutylmethyl]-methyl-amide;
Cyclohexanecarboxylic acid [3-(2-chloro-3-pyrrolidin-1-ylmethyl-phenoxy)-cyclobutylmethyl]-methyl-amide;
2-Chloro-N-[3-(2-chloro-3-pyrrolidin-1-ylmethyl-phenoxy)-cyclobutylmethyl]-N-methyl-benzamide;
4-tert-Butyl-N-[3-(2-chloro-3-pyrrolidin-1-ylmethyl-phenoxy)-cyclobutylmethyl]-N-methyl-benzenesulfonamide;
3-Chloro-N-[3-(2-chloro-3-pyrrolidin-1-ylmethyl-phenoxy)-cyclobutylmethyl]-4-fluoro-N-methyl-benzenesulfonamide;
2,3-Dihydro-benzo[1,4]dioxine-6-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-5-fluoro-2,N-dimethyl-benzenesulfonamide;
Furazan-3-carboxylic acid [3-(2-chloro-3-pyrrolidin-1-ylmethyl-phenoxy)-cyclobutylmethyl]-methyl-amide;
2,6-Dimethyl-pyrimidine-4-carboxylic acid [3-(2-chloro-3-pyrrolidin-1-ylmethyl-phenoxy)-cyclobutylmethyl]-methyl-amide;
5-Chloro-thiophene-2-sulfonic acid [3-(2-chloro-3-pyrrolidin-1-ylmethyl-phenoxy)-cyclobutylmethyl]-methyl-amide;
4-Chloro-N-[3-(2-chloro-3-pyrrolidin-1-ylmethyl-phenoxy)-cyclobutylmethyl]-2,5,N-trimethyl-benzenesulfonamide;
5-Isopropyl-isoxazole-3-carboxylic acid [3-(2-chloro-3-pyrrolidin-1-ylmethyl-phenoxy)-cyclobutylmethyl]-methyl-amide;
3-(2-Chloro-6-methyl-phenyl)-1-[3-(2-chloro-3-pyrrolidin-1-ylmethyl-phenoxy)-cyclobutylmethyl]-1-methyl-urea;
N-[3-(2-Chloro-3-pyrrolidin-1-ylmethyl-phenoxy)-cyclobutylmethyl]-4-ethyl-N-methyl-benzenesulfonamide;
N-[3-(2-Chloro-3-pyrrolidin-1-ylmethyl-phenoxy)-cyclobutylmethyl]-3,N-dimethyl-benzenesulfonamide;
N-[3-(2-Chloro-3-pyrrolidin-1-ylmethyl-phenoxy)-cyclobutylmethyl]-2-methoxy-5,N-dimethyl-benzenesulfonamide;
1-[3-(2-Chloro-3-pyrrolidin-1-ylmethyl-phenoxy)-cyclobutylmethyl]-3-(2-methoxy-5-methyl-phenyl)-1-methyl-urea;
N-[3-(2-Chloro-3-pyrrolidin-1-ylmethyl-phenoxy)-cyclobutylmethyl]-4,N-dimethyl-benzenesulfonamide;
Prop-2-ene-1-sulfonic acid [3-(2-chloro-3-pyrrolidin-1-ylmethyl-phenoxy)-cyclobutylmethyl]-methyl-amide;
Thiophene-2-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2,5-dimethoxy-N-methyl-benzenesulfonamide;
(E)-2-Phenyl-ethenesulfonic acid [3-(2-chloro-3-pyrrolidin-1-ylmethyl-phenoxy)-cyclobutylmethyl]-methyl-amide;
2-{[3-(2-Chloro-3-pyrrolidin-1-ylmethyl-phenoxy)-cyclobutylmethyl]-methyl-sulfamoyl}-benzoic acid methyl ester;

1,3,5-Trimethyl-1H-pyrazole-4-sulfonic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2-(3,5-dimethyl-pyrazol-1-yl)-N-methyl-acetamide;

1-[3-(2-Chloro-3-pyrrolidin-1-ylmethyl-phenoxy)-cyclobutylmethyl]-3-(3,4-dimethyl-phenyl)-1-methyl-urea;

1-{[3-(2-Chloro-3-pyrrolidin-1-ylmethyl-phenoxy)-cyclobutyl]methyl}-1-methyl-3-(4-trifluoromethyl-phenyl)-urea;

Pyridine-3-sulfonic acid [3-(2-chloro-3-pyrrolidin-1-ylmethyl-phenoxy)-cyclobutylmethyl]-methyl-amide;

5-Methyl-thiophene-2-sulfonic acid [3-(2-chloro-3-pyrrolidin-1-ylmethyl-phenoxy)-cyclobutylmethyl]-methyl-amide;

5-Methyl-pyrazine-2-carboxylic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2,4,N-trimethyl-benzamide;

N-(4-{[3-(2-Chloro-3-pyrrolidin-1-ylmethyl-phenoxy)-cyclobutylmethyl]-methyl-sulfamoyl}-phenyl)-acetamide;

N-[3-(2-Chloro-3-pyrrolidin-1-ylmethyl-phenoxy)-cyclobutylmethyl]-N-methyl-methanesulfonamide;

N-[3-(2-Chloro-3-pyrrolidin-1-ylmethyl-phenoxy)-cyclobutylmethyl]-3,4-dimethoxy-N-methyl-benzenesulfonamide;

N-[3-(2-Chloro-3-pyrrolidin-1-ylmethyl-phenoxy)-cyclobutylmethyl]-2,4,N-trimethyl-benzenesulfonamide;

N-[3-(2-Chloro-3-pyrrolidin-1-ylmethyl-phenoxy)-cyclobutylmethyl]-N-methyl-4-trifluoromethyl-benzenesulfonamide;

5-Chloro-N-[3-(2-chloro-3-pyrrolidin-1-ylmethyl-phenoxy)-cyclobutylmethyl]-2-methoxy-N-methyl-benzenesulfonamide;

3-(3-Chloro-4-methyl-phenyl)-1-[3-(2-chloro-3-pyrrolidin-1-ylmethyl-phenoxy)-cyclobutylmethyl]-1-methyl-urea;

Quinoline-8-sulfonic acid [3-(2-chloro-3-pyrrolidin-1-ylmethyl-phenoxy)-cyclobutylmethyl]-methyl-amide;

Ethanesulfonic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2,4,5-trifluoro-N-methyl-benzenesulfonamide;

N-[3-(2-Chloro-3-pyrrolidin-1-ylmethyl-phenoxy)-cyclobutylmethyl]-N-methyl-2-trifluoromethyl-benzenesulfonamide;

Benzo[b]thiophene-2-sulfonic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2-fluoro-N-methyl-benzenesulfonamide;

N-[3-(2-Chloro-3-pyrrolidin-1-ylmethyl-phenoxy)-cyclobutylmethyl]-4-methoxy-N-methyl-benzenesulfonamide;

1-[3-(2-Chloro-3-pyrrolidin-1-ylmethyl-phenoxy)-cyclobutylmethyl]-3-(4-fluoro-phenyl)-1-methyl-urea;

Naphthalene-1-sulfonic acid [3-(2-chloro-3-pyrrolidin-1-ylmethyl-phenoxy)-cyclobutylmethyl]-methyl-amide;

N-(3-{[3-(2-Chloro-3-pyrrolidin-1-ylmethyl-phenoxy)-cyclobutylmethyl]-methyl-sulfamoyl}-phenyl)-acetamide;

5-Ethyl-thiophene-2-sulfonic acid [3-(2-chloro-3-pyrrolidin-1-ylmethyl-phenoxy)-cyclobutylmethyl]-methyl-amide;

3-(4-Chloro-2-methyl-phenyl)-1-[3-(2-chloro-3-pyrrolidin-1-ylmethyl-phenoxy)-cyclobutylmethyl]-1-methyl-urea;

Naphthalene-2-sulfonic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-3,4,N-trimethyl-benzamide;

5-Chloro-1,3-dimethyl-1H-pyrazole-4-sulfonic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2,5,N-trimethyl-benzenesulfonamide;

3-Methyl-thiophene-2-sulfonic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-N-methyl-3-trifluoromethyl-benzenesulfonamide;

Pyrazine-2-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-N-methyl-2-pyridin-2-yl-acetamide;

5-Methyl-pyrazine-2-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2,5-dimethoxy-N-methyl-benzenesulfonamide;

N-[3-(3-Chloro-4-pyrrolidin-1-ylmethyl-phenoxy)-cyclobutylmethyl]-2,4-difluoro-N-methyl-benzenesulfonamide;

Cyclohexanecarboxylic acid [3-(3-chloro-4-pyrrolidin-1-ylmethyl-phenoxy)-cyclobutylmethyl]-methyl-amide;

Cyclopentanecarboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2-cyclopropyl-N-methyl-acetamide;

N-(3-{[3-(3-Chloro-4-pyrrolidin-1-ylmethyl-phenoxy)-cyclobutylmethyl]-methyl-sulfamoyl}-phenyl)-acetamide;

N-[3-(3-Chloro-4-pyrrolidin-1-ylmethyl-phenoxy)-cyclobutylmethyl]-3,4-dimethoxy-N-methyl-benzenesulfonamide;

N-[3-(3-Chloro-4-pyrrolidin-1-ylmethyl-phenoxy)-cyclobutylmethyl]-2-(3,5-dimethyl-pyrazol-1-yl)-N-methyl-acetamide;

3-Chloro-N-[3-(3-chloro-4-pyrrolidin-1-ylmethyl-phenoxy)-cyclobutylmethyl]-2,N-dimethyl-benzenesulfonamide;

N-[3-(3-Chloro-4-pyrrolidin-1-ylmethyl-phenoxy)-cyclobutylmethyl]-2,5,N-trimethyl-benzenesulfonamide;

(S)—N-[3-(3-Chloro-4-pyrrolidin-1-ylmethyl-phenoxy)-cyclobutylmethyl]-2-hydroxy-N-methyl-2-phenyl-acetamide;

Naphthalene-1-sulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2,6-difluoro-N-methyl-benzenesulfonamide;

Piperidine-1-sulfonic acid [3-(3-chloro-4-pyrrolidin-1-ylmethyl-phenoxy)-cyclobutylmethyl]-methyl-amide;

3,5-Dimethyl-isoxazole-4-sulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-3-methoxy-N-methyl-propionamide;

N-[3-(3-Chloro-4-pyrrolidin-1-ylmethyl-phenoxy)-cyclobutylmethyl]-N-methyl-methanesulfonamide;

4-Chloro-N-[3-(3-chloro-4-pyrrolidin-1-ylmethyl-phenoxy)-cyclobutylmethyl]-2,5,N-trimethyl-benzenesulfonamide;

2-Methoxy-pyrimidine-5-carboxylic acid [3-(3-chloro-4-pyrrolidin-1-ylmethyl-phenoxy)-cyclobutylmethyl]-methyl-amide;

1-[3-(3-Chloro-4-pyrrolidin-1-ylmethyl-phenoxy)-cyclobutylmethyl]-3-(2-fluoro-phenyl)-1-methyl-urea;

N-[3-(3-Chloro-4-pyrrolidin-1-ylmethyl-phenoxy)-cyclobutylmethyl]-2,4-dimethoxy-N-methyl-benzenesulfonamide;

N-[3-(3-Chloro-4-pyrrolidin-1-ylmethyl-phenoxy)-cyclobutylmethyl]-3,3,N-trimethyl-butyramide;

1,3,5-Trimethyl-1H-pyrazole-4-sulfonic acid [3-(3-chloro-4-pyrrolidin-1-ylmethyl-phenoxy)-cyclobutylmethyl]-methyl-amide;

Morpholine-4-sulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-4-methoxy-N-methyl-benzenesulfonamide;

N-[3-(3-Chloro-4-pyrrolidin-1-ylmethyl-phenoxy)-cyclobutylmethyl]-2,4,5-trifluoro-N-methyl-benzenesulfonamide;

3-tert-Butyl-1-[3-(3-chloro-4-pyrrolidin-1-ylmethyl-phenoxy)-cyclobutylmethyl]-1-methyl-urea;

2,3-Dihydro-benzo[1,4]dioxine-6-sulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-N-methyl-benzenesulfonamide;

2-Oxo-2,3-dihydro-benzooxazole-6-sulfonic acid [3-(3-chloro-4-pyrrolidin-1-ylmethyl-phenoxy)-cyclobutylmethyl]-methyl-amide;

2-Chloro-N-[3-(3-chloro-4-pyrrolidin-1-ylmethyl-phenoxy)-cyclobutylmethyl]-N-methyl-benzenesulfonamide;

N-[3-(3-Chloro-4-pyrrolidin-1-ylmethyl-phenoxy)-cyclobutylmethyl]-5-fluoro-2,N-dimethyl-benzenesulfonamide;

2-{[3-(3-Chloro-4-pyrrolidin-1-ylmethyl-phenoxy)-cyclobutylmethyl]-methyl-sulfamoyl}-benzoic acid methyl ester;

4-tert-Butyl-N-[3-(3-chloro-4-pyrrolidin-1-ylmethyl-phenoxy)-cyclobutylmethyl]-N-methyl-benzenesulfonamide;

N-[3-(3-Chloro-4-pyrrolidin-1-ylmethyl-phenoxy)-cyclobutylmethyl]-N-methyl-2-(3-methyl-pyrazol-1-yl)-acetamide;

N-[3-(3-Chloro-4-pyrrolidin-1-ylmethyl-phenoxy)-cyclobutylmethyl]-2-methoxy-5,N-dimethyl-benzenesulfonamide;

Ethanesulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-3,4-difluoro-N-methyl-benzenesulfonamide;

N-[3-(3-Chloro-4-pyrrolidin-1-ylmethyl-phenoxy)-cyclobutylmethyl]-N-methyl-2-(4-methyl-furazan-3-yl)-acetamide;

N-[3-(3-Chloro-4-pyrrolidin-1-ylmethyl-phenoxy)-cyclobutylmethyl]-4,4,4-trifluoro-N-methyl-butyramide;

N-[3-(3-Chloro-4-pyrrolidin-1-ylmethyl-phenoxy)-cyclobutylmethyl]-N-methyl-2-trifluoromethyl-benzenesulfonamide;

2,5-Dimethyl-thiophene-3-sulfonic acid [3-(3-chloro-4-pyrrolidin-1-ylmethyl-phenoxy)-cyclobutylmethyl]-methyl-amide;

Benzo[1,2,5]thiadiazole-4-sulfonic acid [3-(3-chloro-4-pyrrolidin-1-ylmethyl-phenoxy)-cyclobutylmethyl]-methyl-amide;

Quinoline-8-sulfonic acid [3-(3-chloro-4-pyrrolidin-1-ylmethyl-phenoxy)-cyclobutylmethyl]-methyl-amide;

4-Acetyl-N-[3-(3-chloro-4-pyrrolidin-1-ylmethyl-phenoxy)-cyclobutylmethyl]-N-methyl-benzenesulfonamide;

Furazan-3-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-N-methyl-3-trifluoromethyl-benzenesulfonamide;

Pyrrolidine-1-sulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-N-methyl-2-pyridin-3-yl-acetamide;

(E)-2-Phenyl-ethenesulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2,2,N-trimethyl-propionamide;

N-[3-(3-Chloro-4-pyrrolidin-1-ylmethyl-phenoxy)-cyclobutylmethyl]-2-cyclopentyl-N-methyl-acetamide;

N-[3-(3-Chloro-4-pyrrolidin-1-ylmethyl-phenoxy)-cyclobutylmethyl]-2-(3,5-dimethyl-isoxazol-4-yl)-N-methyl-acetamide;

N-[3-(3-Chloro-4-pyrrolidin-1-ylmethyl-phenoxy)-cyclobutylmethyl]-3-fluoro-N-methyl-benzenesulfonamide;

Tetrahydro-pyran-4-carboxylic acid [3-(3-chloro-4-pyrrolidin-1-ylmethyl-phenoxy)-cyclobutylmethyl]-methyl-amide;

2-Chloro-N-[3-(3-chloro-4-pyrrolidin-1-ylmethyl-phenoxy)-cyclobutylmethyl]-4-fluoro-N-methyl-benzenesulfonamide;

N-[3-(3-Chloro-4-pyrrolidin-1-ylmethyl-phenoxy)-cyclobutylmethyl]-N-methyl-2-pyrazol-1-yl-acetamide;

N-(4-{[3-(3-Chloro-4-pyrrolidin-1-ylmethyl-phenoxy)-cyclobutylmethyl]-methyl-sulfamoyl}-phenyl)-acetamide;

4-Methyl-pentanoic acid [3-(3-chloro-4-pyrrolidin-1-ylmethyl-phenoxy)-cyclobutylmethyl]-methyl-amide;

5-Chloro-N-[3-(3-chloro-4-pyrrolidin-1-ylmethyl-phenoxy)-cyclobutylmethyl]-2-methoxy-N-methyl-benzenesulfonamide;

1-{[3-(3-Chloro-4-pyrrolidin-1-ylmethyl-phenoxy)-cyclobutyl]methyl}-1-methyl-3-(3-trifluoromethyl-phenyl)-urea;

4-[3-(3-Chloro-5-pyrrolidin-1-ylmethyl-phenoxy)-cyclobutylmethyl]-morpholine;

Tetrahydro-pyran-4-carboxylic acid [3-(2-methoxy-3-pyrrolidin-1-ylmethyl-phenoxy)-cyclobutylmethyl]-methyl-amide;

Tetrahydro-pyran-4-carboxylic acid [3-(3-chloro-5-fluoro-4-pyrrolidin-1-ylmethyl-phenoxy)-cyclobutylmethyl]-methyl-amide;

3,5-Dimethyl-isoxazole-4-carboxylic acid [3-(3,5-difluoro-4-pyrrolidin-1-ylmethyl-phenoxy)-cyclobutylmethyl]-methyl-amide;

1-Methyl-cyclopropanecarboxylic acid [3-(2-fluoro-3-pyrrolidin-1-ylmethyl-phenoxy)-cyclobutylmethyl]-methyl-amide;

Tetrahydro-pyran-4-carboxylic acid [3-(2-fluoro-3-pyrrolidin-1-ylmethyl-phenoxy)-cyclobutylmethyl]-methyl-amide;

3,5-Dimethyl-isoxazole-4-carboxylic acid [3-(2-fluoro-3-pyrrolidin-1-ylmethyl-phenoxy)-cyclobutylmethyl]-methyl-amide;

Tetrahydro-pyran-4-carboxylic acid [3-(3,5-difluoro-4-pyrrolidin-1-ylmethyl-phenoxy)-cyclobutylmethyl]-methyl-amide;

[3-(2-Fluoro-3-pyrrolidin-1-ylmethyl-phenoxy)-cyclobutylmethyl]-methyl-amine;

Tetrahydro-pyran-4-carboxylic acid [3-(2-chloro-3-pyrrolidin-1-ylmethyl-phenoxy)-cyclobutylmethyl]-amide;

Tetrahydro-pyran-4-carboxylic acid [3-(2,5-dichloro-4-pyrrolidin-1-ylmethyl-phenoxy)-cyclobutylmethyl]-methyl-amide;

3,5-Dimethyl-isoxazole-4-carboxylic acid [3-(2,5-dichloro-4-pyrrolidin-1-ylmethyl-phenoxy)-cyclobutylmethyl]-methyl-amide;

1-Methyl-cyclopropanecarboxylic acid [3-(2,5-dichloro-4-pyrrolidin-1-ylmethyl-phenoxy)-cyclobutylmethyl]-methyl-amide;

[3-(2,4-Dichloro-3-pyrrolidin-1-ylmethyl-phenoxy)-cyclobutylmethyl]-methyl-amine;

Tetrahydro-pyran-4-carboxylic acid [3-(2,4-dichloro-3-pyrrolidin-1-ylmethyl-phenoxy)-cyclobutylmethyl]-methyl-amide; and Cyclobutanecarboxylic acid [3-(2,4-dichloro-3-pyrrolidin-1-ylmethyl-phenoxy)-cyclobutylmethyl]-methyl-amide.

DETAILED DESCRIPTION OF THE INVENTION

The compound of formula I according to the invention may be prepared by the general procedure shown in Scheme 1.

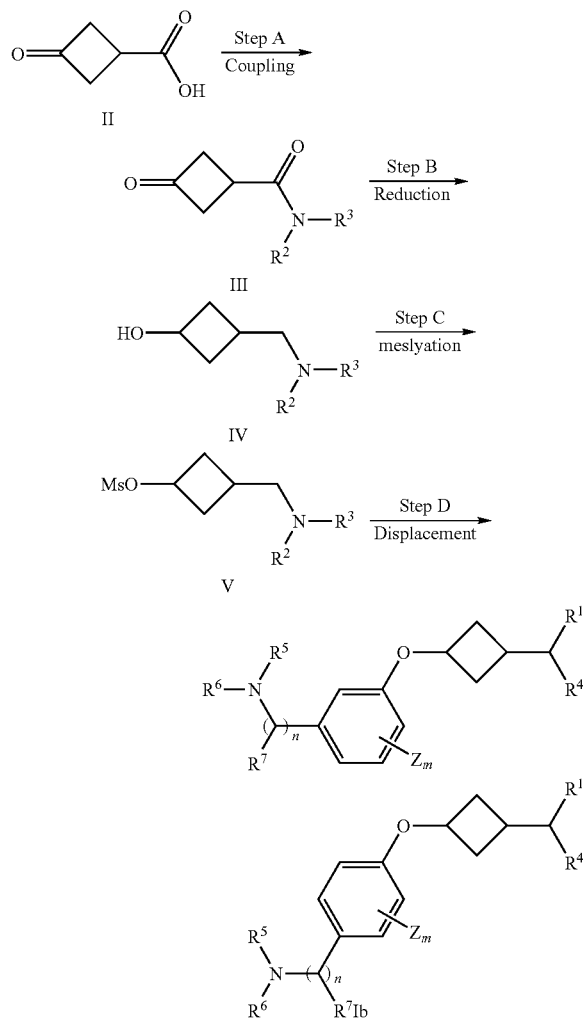

In Scheme 1, compounds of the formula I are prepared as follows.

Step A:

Intermediate of the formula II may be reacted with a primary or secondary amines of general formula $HNR^2R^3$, where $R^2$ and $R^3$ are as defined in the specification, in the presence of a coupling reagent such as dicyclohexyl carbodiimide, carbonyl diimidazole, tripropylphosphonic anhydride, alkyl chloroformate, bis(2-oxo-3-oxazolidinyl)phosphinic chloride, benzotriazol-1-yloxy-tris(dimethylamino)phosphonium hexafluorophosphate, or any other such standard literature reagents in the presence of a trialkyl amine base, such as triethyl amine or diisopropylethyl amine, wherein tripropylphosphonic anhydride and triethylamine are a preferred combination in a reaction inert solvent, where ethyl acetate, from −78° C. to 40° C., where room temperature was preferred to afford the N-acylated compounds of the formula III.

Step B:

The amides of an intermediate of the general formula III is reduced with an appropriate reduction reagent such as, but not limited to, lithium aluminum hydride, or sodium borohydride and aluminum trichloride in diglyme, where lithium aluminum hydride is preferred. The reaction is normally effected in an aprotic solvent, such as tetrahydrofuran, or diethyl ether at a reaction temperature from about 0 C to the reflux temperature of the solvent employed, yielding a compound of the general formula IV.

Step C:

Reaction of alcohol of the formula IV with a sulfonyl chloride, where methanesulfonyl chloride is preferred, in the presence of a base, where preferred bases are pyridine, and triethyl amine in a reaction-inert-solvent, where preferred solvent is methylene chloride at a reaction temperature from about 0 C to rt gives a compound of the general formula V.

Step D:

Intermediates of the general formula V may then be reacted with a phenol of the general formula VI or VII. This can be accomplished, for example, using a procedure referred to as Mitsunobu displacement condition which is a method well known to those skilled in the art. This method may be conducted by reaction of intermediates of the general formula V in the presence of diethyazodicarboxylate (DEAD) or diisopropylazodicarboxylate (DIAD) and triphenylphosphine with a phenol of the general formula (VI) or (VII) in a reaction inert solvent, where preferred solvent is THF at a reaction temperature of 0 C to the reflux temperature of the solvent to yield compounds of the general formula I. Alternative microwave conditions can be employed in this Mitsunobu displacement reaction, where preferred microwave conditions are at a temperature about 100-120 C for less than 30 min. The preferred method of displacement is by reaction of compounds of the general formula VI or VII in DMSO in the presence of a base, such as, but not limited to potassium tert-butoxide in an inert atmosphere at a temperature of about 100° C. for about 15 minutes, and then a solution of intermediate of the general formula V and tetrabutyl ammonium bromide (TBAB) in DMSO are added, and the reaction mixture is stirred at a temperature of about 100° C. to give a compound of the general formula I.

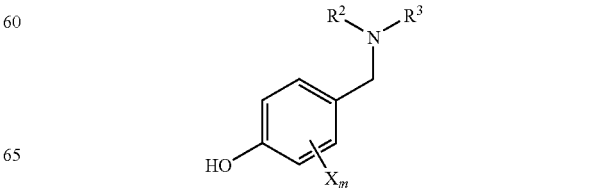

-continued

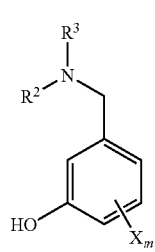

VII oxazolidinyl)phosphinic chloride, benzotriazol-1-yloxy-tris(dimethylamino)phosphonium hexafluorophosphate, or any other such standard literature reagents in the presence of a trialkyl amine base, such as triethyl amine or diisopropylethyl amine, wherein tripropylphosphonic anhydride and triethylamine are a preferred combination in a reaction inert solvent, where ethyl acetate, from −78° C. to 40° C., where room temperature is preferred to afford the N-acylated compounds of the formula (VIII).

Step F:

The amides of an intermediate of the general formula (VIII) is reduced with an appropriate reduction reagent such as, but not limited to, lithium aluminum hydride, or sodium

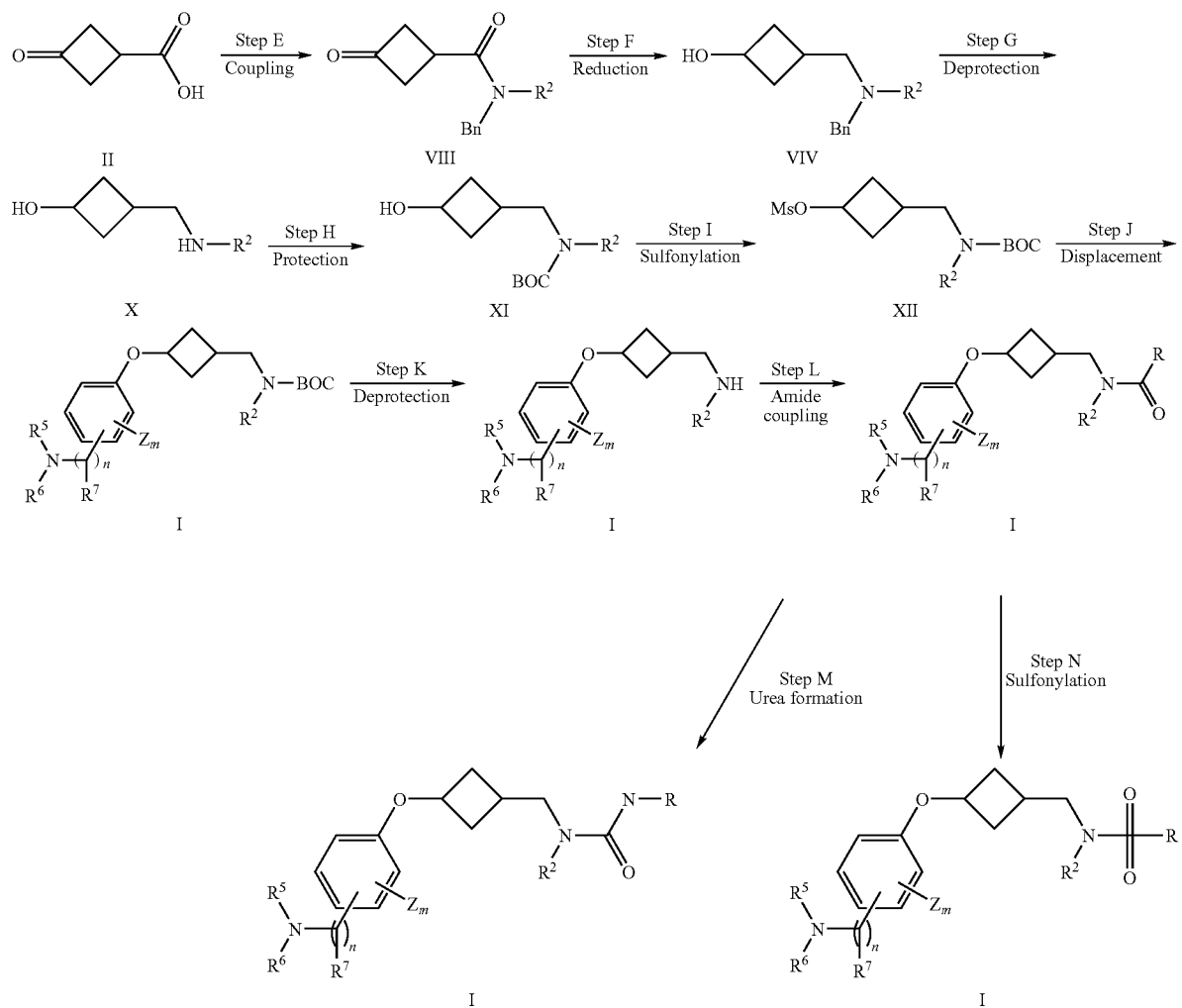

In Scheme 2, compounds of the formula (I) are prepared as follows.

Step E:

Intermediate of the formula (II) may be reacted with a benzyl amine or secondary alkyl benzyl amine of general formula $HNR^2Bn$, where $R^2$ are as defined in the specification, in the presence of a coupling reagent such as dicyclohexyl carbodiimide, carbonyl diimidazole, tripropylphosphonic anhydride, alkyl chloroformate, bis(2-oxo-3- borohydride and aluminum trichloride in diglyme, where lithium aluminum hydride is preferred. The reaction is normally effected in an aprotic solvent, such as tetrahydrofuran, or diethyl ether at a reaction temperature from about 0 C to the reflux temperature of the solvent employed, yielding a compound of the general formula (VIV).

Step G:

Intermediate of the general formula (VIV) may be deprotected using hydrogenation conditions which are well know to those skilled in the art (e.g. T. W Greene; P. G. Wuts, Protective Groups in Organic Synthesis, 3$^{rd}$ edition, John Wiley&Sons Inc. New York, 1999). The preferred method of removal of the protecting group is by reaction of compound of the general formula (VIV) under standard hydrogenation conditions, preferable using 5% palladium on carbon or Pearlman's catalyst (20% palladium hydroxide on carbon), where palladium on carbon is preferred in the presence of hydrogen, at a pressure of around 45 psi in ethyl alcohol yields a compound of the general formula (X).

Step H:

Protection of compounds of the general formula (X) can be accomplished by methods known in the art (e.g. T. W Greene; P. G. Wuts, Protective Groups in Organic Synthesis, 3$^{rd}$ edition, John Wiley&Sons Inc. New York, 1999). Reaction of compounds of the general formula (X) with di-tert-butyl dicarbonate in the presence of a amine base, where triethylamine is preferred in a reaction inert solvent, such as, dichloromethane or 1,2-dichloroethane, where dichloromethane is preferred at a reaction temperature from about 0 C to rt gives a compounds of the general formula (XI).

Step I:

Reaction of alcohol of the formula (XI) with a sulfonyl chloride, where methanesulfonyl chloride is preferred, in the presence of a base, where preferred bases are pyridine, and triethyl amine in a reaction-inert-solvent, where preferred solvent is methylene chloride at a reaction temperature from about 0 C to rt gives a compound of the general formula (XII).

Step J:

Intermediates of the general formula (XIII) may then be reacted with a phenol of the general formula (VI) or (VII). This can be accomplished, for example, using a procedure referred to as Mitsunobu displacement condition which is a method well known to those skilled in the art. This method may be conducted by reaction of intermediates of the general formula (XIII) in the presence of diethyazodicarboxylate (DEAD) or diisopropylazodicarboxylate (DIAD) and triphenylphosphine with a phenol of the general formula (VI) or (VII) in a reaction inert solvent, where preferred solvent is THF at a reaction temperature of 0 C to the reflux temperature of the solvent to yield compounds of the general formula I. Alternative microwave conditions can be employed in this Mitsunobu displacement reaction, where preferred microwave conditions are at a temperature about 100-120 C for less than 30 min. The preferred method of displacement is by reaction of compounds of the general formula (VI) or (VII) in DMSO in the presence of a base, such as, but not limited to potassium tert-butoxide in an inert atmosphere at a temperature of about 100° C. for about 15 minutes, and then a solution of intermediate of the general formula (XIII) and tetrabutyl ammonium bromide (TBAB) in DMSO are added, and the reaction mixture is stirred at a temperature of about 100° C. to give a compound of the general formula (I).

Step K:

Removal of the BOC protecting group of the compound of formula (I) can be accomplished using conditions described in the literature. The preferred method of protecting group removal is by reaction of compounds of the formula I in a reaction inert solvent, where methylene chloride is preferred with an acid where preferred acids are TFA, and aqueous HCl at a reaction temperature from about 0 C to the reflux temperature of the solvent employed, where about rt is preferred to give a new compound of the formula (I).

Step L:

Compounds of the general formula (I) with NRH can be acylated under standard acid coupling condition, which appear in the literature. This can be accomplished by reaction of a compounds of the general formula (I) having NRH in the presence of a trialkyl base, such as triethylamine or diisopropylethylamine, sodium hydride, with a carbonyl donor, such as an acid chloride, an acid anhydride, or an activated carboxylic derivative prepared from a carboxylic acid and an activating reagent such as a polymer-supported coupling agent, or, alternatively, dicylohexylcarbondiimide, 1,1-carbonyldiimdazole, tripropylphosphonic anhydride, an alkyl chloroformate, bis-(2-oxo-3-oxazolidinyl)phosphinic chloride, or benzotriazol-1-yloxy-tris(dimethylamino)phosphonium hexafluorophosphate, wherein tripropylphosphonic anhydride and triethylamine are a preferred combination in ethyl acetate, from −78° C. to 40° C., where room temperature is preferred to afford the N-acylated compounds of the formula (I). Alternative compounds of the general formula (I) with NHR can by coupled by reaction of a compound of the general formula (I) in DMF in the presence of a carboxylic acid, BOP and an amine base, where diisopropylethylamine is preferred. The mixture is stirred at rt and then heat to about 45° C. for 24 hours to give a compound of the general formula (I).

Step M:

Compounds of the general formula (I) having NRH can be converted to the urea using standard condition. For example reaction of (I) having NHR in a reaction inert solvent where preferred solvent is methylene chloride with an isocyanate at a reaction temperature from about rt to the reflux temperature of the solvent employed gives a urea compound of the formula (I).

Step N:

Compounds of the formula (I) have NHR can be converted to the sulfonamide by reaction of compounds of the general formula (I) in a reaction inert solvent where preferred solvent is methylene chloride, in the presence of and amine base, where triethylamine is preferred, and in the presence of a sulfonyl chloride at a reaction temperature of about 0 C to rt, where rt is preferred, gives an sulfonamide of the general formula (I).

In the examples below the following terms are intended to have the following, general meaning:

DIPEA: diisopropylethylamine
DMF: dimethylformamide
$MgSO_4$: magnesium sulfate
DMA: dimethyl acetamide
LRMS: low resolution mass spectrometry
° C.: degrees Celsius
calcd; calculated
d; day(s); doublet (spectral)
DCE: 1,2-dichloroethane
EtOAc: ethyl acetate
g: grams
hr; hours
Hz: hertz
J: coupling constant (in NMR)
L: liter(s)
LAH: lithium aluminum hydride
MHz: megahertz
Min: minute(s)
m/z mass to charge ratio (in mass spectrometry)
obsd: observed
PPTs: pyridinium p-toluenesulfonate:
TsO: p-toluenesulfonate
Rf: retention factor (in chromatography)
Rt: retention time (in chromatography)
rt: room temperature
s: singlet (NMR), second(s)
t: triplet TFA: trifluoroacetic acid
TFAA: trifluoroacetic anhydride
THF: tetrahydrofuran
TLC: thin layer chromatography
Ts: tosyl, p-toluenesulfonyl
TsOH: p-toluenesulfonic acid Solvents were purchased and used without purification. Yields were calculated for material judged homogenous by thin layer chromatography and NMR. Thin layer chromatography was performed on Merck Kieselgel 60 F 254 plates eluting with the solvents indicated, visualized by a 254 nm UV lamp, and stained with either an aqueous $KMnO_4$ solution or an ethanolic solution of 12-molybdophosphoric acid. Flash column chromatography was performed with using either pre-packed Biotage□ or ISCO□ columns using the size indicated. Nuclear magnetic resonance (NMR) spectra were acquired on a Unity 400 or 500 at 400 MHz or 500 MHz for $^1H$, respectively, and 100 MHz or 125 MHz for $^{13}C$ NMR, respectively. Chemical shifts for proton $^1H$ NMR spectra are reported in parts per million relative to the singlet of $CDCl_3$ at 7.24 ppm. Chemical shifts for $^{13}C$ NMR spectra are reported in parts per million downfield relative to the center line of the triplet of CDCl at 77.0 ppm. Mass spectra analyses were performed on a APCI Gilson 215, micromass ZMD (50% Acetonitrile/50% water) spectrometer. Examples and intermediates are listed as can be but not limited to mixtures of isomers, or diastereomers. Specific nomenclature was generated using AutoNom.

Reactions under microwave conditions were done using 5 mL round bottom vials, fitted with septa. The vials containing the reactants were inserted into the reaction chamber of a CEM™ microwave apparatus (maximum power of 300 W) from Personal Chemistry Inc., and heated to the appropriate temperature for a the prescribed period of time.

HPLC was performed according to the following methods:

General Procedure A: To the respective amines (0.1 mmol, 2 equiv) weighed into a 2-dram vial dissolved in 0.4 mL of DCE as added the aldehyde intermediate 6 (11.4 mg, equiv) as a solution dissolved in 0.4 ml of DCE and acetic acid (0.006 ml, 0.1 mmol, 2 equiv). The reaction was shaken at room temperature for 5 hr, and then $Na(OAc)_3BH$ (~32 mg, 0.15 mmol, 3 equiv) was added neat in one portion. The resulting reaction mixture was shaken at room temperature over night. LRMS analysis of crude reaction mixture indicated product formation. The reactions were quenched by partitioning the samples between 2.5 ml of methylene chloride and 1.5 ml of aqueous NaOH (1 M), vortexed and the organics were extracted and load onto Silicycle SCX SPE cartridge (6-ml). Repeat extraction 2×. Change vials and elute with 5 ml of MeOH. Switch to tared vials and elute with 7.5 ml of 1 N TEA in MeOH. The solvents were removed under reduced pressure and the residual was purified by HPLC using method indicated.

General Procedure B: To the respective amines salts (0.1 mmol, 2 equiv) weighed into a 2-dram vial was dissolved in 0.1 mL of DCE. The aldehyde intermediate VIII (13.2 mg, 0.05 mmol, 1 equiv) was added as a solution dissolved in 0.5 ml of DCE and a solution of triethylamine (0.014 ml, 0.1 mmol, 2 equiv, in 0.1 mL of DCE). The reaction was shaken at room temperature overnight, and then Na(OAc)3BH (~21 mg, 0.1 mmol, 2 equiv) was added neat in one portion. The resulting reaction mixture was shaken at room temperature for ~3 hours. LRMS analysis of crude reaction mixture indicated product formation. The reactions were quenched by partitioning the samples between 2.5 ml of methylene chloride and 1.5 ml of aqueous NaOH (1 M), vortexed and the organics were extracted and load onto Silicycle SCX SPE cartridge (6-ml). Repeat extraction 2×. Change vials and elute with 5 ml of MeOH. Switch to tared vials and elute with 7.5 ml of 1 N TEA in MeOH. The solvents were removed under reduced pressure and the residual was purified by HPLC using method indicated.

Purification Method A: Preparative conditions (Waters 600 & Waters 2767 Sample Manager); Column: Waters Xterra PrepMS $C_{18}$, 5 μm, 30×100 mm steel column, part # 186001120, solvent A—0.1% Trifluoroacetic acid/water; solvent B—Acetonitrile; volume of injection: 1100 μL; time 0.0, 100% solvent A, 0% solvent B, flow 20; time 2.0, 100% solvent A, 0% solvent B, flow 20; time 12.0, 0% solvent A, 100% solvent B, flow 20; time 14.0, 0% solvent A, 100% solvent B, flow 20; time 14.1, 100% solvent A, 0% solvent B, flow 20; time 19,100% solvent A, 0% solvent B, flow 20.

Mass spectral (micromassZO) conditions; Capillary (kV): 3.0; Cone (V): 20; Extractor (V): 3.0; RF Lens (V): 0.5; Source temp. (° C.): 120; Desolvation temp. (° C.): 360; Desolvation gas flow (L/hr): 450; Cone gas flow (L/hr): 150; LM Resolution: 15; HM Resolution: 15; Ion Energy: 0.2; Multiplier: 550.

Splitter; Acurate by LC Packings, 1/10,000; Upchurch needle valve setting: 14; Make up pump (Waters 515) Flow (ml/min.): 1. PDA (Waters 996) Settings; Start/End wavelength (nm): 200/600; Resolution: 1.2; Sample Rate: 1; Channels: TIC, 254 nm and 220 nm.

The following intermediates may be prepared by the procedures described above:

Intermediate 1

4-(Pyrrolidin-1-ylmethyl)phenol (2). $NaB(OAc)_3H$ (43.4 g, 0.21 mol) was added in portions during 30 min to a mixture of pyrrolidine (17 mL, 0.21 mol) and 4-hydroxybenzaldehyde 1 (20 g, 0.16 mol) in $CH_2Cl_2$ (200 mL) under vigorous stirring and cooling with an ice bath in an atmosphere of argon. The mixture was stirred for 3 h and cooled. Then 10 N NaOH (20.5 mL) and water (300 mL) were added. The organic layer was separated, the aqueous one was extracted with chloroform (3×200 mL). The organic fractions were evaporated. The residue was dissolved in water, concentrated HCl (15 mL) was added, and the mixture was extracted with ether (3×200 mL). The organic fractions were discarded. The aqueous layer was alkalized with 10 N NaOH (16 mL) and extracted with $CH_2Cl_2$ (3×200 mL). The combined extracts were washed with brine, dried with $Na_2SO_4$, and evaporated. The title compound (16.6 g, 57%) was obtained as yellow crystals. 1H NMR-data (DMSO-d6): 9.18 (br.s, 1H, OH); 7.00 (d, 2H, Ph, J=8.6 Hz); 6.68 (d, 2H, Ph, J=8.6 Hz); 3.43 (s, 2H, $CH_2$); 2.33-2.42 (m, 4H); 1.62-1.71 (m, 4H).

Intermediate 2

N-Benzyl-N-methyl-3-oxocyclobutanecarboxamide (4). Acid, 3-oxocyclobutanecarboxylic acid (12.7 g, 0.11 mol), N-benzylmethylamine (15.7 mL, 0.12 mol), and triethylamine (48 mL, 0.33 mol) were dissolved in DMF (100 mL). BOP (49 g, 11 mol) was added at 0° C. under stirring in argon. The mixture was stirred at 20° C. for 20 h, evaporated, and the residue was dried at 0.5 mmHg. The residue was purified by chromatography (silica gel, 63-100 μm, 750 mL, $CCl_4$→$CHCl_3$, $CHCl_3$/MeOH 100:0→95:5). The title compound (15.5 g, 64%) was obtained as a colorless oil. 1H NMR-data (DMSO-d6): 7.20 (m, 5H, Ph); 4.62 s, 4.55 s (2H, $CH_2$); 3.46-3.62 (m, 1H); 3.28 (m, 4H,); 2.85 s, 2.94 s (3H, $NCH_3$).

Intermediate 3 cis-3-{[Benzyl(methyl)amino]methyl}cyclobutanol (5). $LiAlH_4$ (5.4 g, 0.14 mol) was added to a solution of intermediate 2, N-Benzyl-N-methyl-3-oxocyclobutanecarboxamide (15.5 g, 0.07 mol) in absolute THF (100 mL) under stirring in argon. The mixture was refluxed under stirring for 2 h and cooled. Then 10 N NaOH (14 mL) and water (5 mL) were added. The organic layer was decanted, and the aqueous one was extracted with THF (2×50 mL). The organic layers were evaporated to afford the title compound (8.6 g, 59%) as a colorless oil. 1H NMR-data (DMSO-d6): 7.19-7.33 (m, 5H, Ph); 4.85 (d, 1H, OH, J=6.6); 3.83-3.94 (m, 1H); 3.40 (s, 2H, CH$_2$); 2.24-2.34 (m, 4H); 2.07 (s, 3H, NCH$_3$); 1.81-1.92 (m, 1H); 1.34-1.44 (m, 2H).

Intermediate 4 cis-3-[(Methylamino)methyl]cyclobutanol (6). 5% Pd/C (1 g) was added to a solution of intermediate 3, cis-3-{[Benzyl(methyl)amino]methyl}cyclobutanol (8.6 g, 0.042 mol) in MeOH (100 mL). The mixture was stirred in a flow of hydrogen for 48 h and filtered through Celite. The solid was washed on the filter with MeOH (2×50 mL). The filtrate was evaporated. Obtained crude intermediate 4 (5.3 g, ~100%) was used in the next stage without additional purification. 1H NMR-data (DMSO-d6): 4.87-5.49 (br.s, 2H, NH, OH); 3.86-3.96 (m, 1H); 2.73 (d, 2H, CH$_2$, J=7.1); 2.39 (s, 3H, NCH$_3$); 2.24-2.34 (m, 2H); 1.85-1.97 (m, 1H); 1.46-1.57 (m, 2H).

Intermediate 5 tert-Butyl [(cis-3-Hydroxycyclobutyl)methyl]methylcarbamate (7). (Boc)$_2$O (10.5 g, 0.048 mol) was added to a solution of intermediate 4, cis-3-[(Methylamino)methyl]cyclo-butanol (5.3 g, 0.046 mol) and Et$_3$N (13.3 mL, 0.09 mol) in 50 mL absolute THF under stirring. The mixture was stirred at room temperature for 3 h and coevaporated with CCl$_4$. The residue was purified by chromatography (silica gel, 63-100μμ, 300 mL, CCl$_4$→CHCl$_3$, CHCl$_3$/MeOH 100:0→80:20) to give the title compound (6.75 g, 70%) as a colorless oil. 1H NMR-data (DMSO-d6): 4.92 (d, 1H, OH, J=6.6); 3.80-3.92 (m, 1H); 3.15 (d, 2H, CH$_2$, J=6.8); 2.74 (s, 3H, NCH$_3$); 2.17-2.26 (m, 2H); 1.78-1.89 (m, 1H); 1.44-1.55 (m, 2H); 1.38 (s, 9H, Boc).

Intermediate 6 cis-3-{[(tert-Butoxycarbonyl)(methyl)amino]methyl}cyclobutyl Methanesulfonate (8). Intermediate 5, tert-Butyl [(cis-3-hydroxycyclobutyl)methyl]methylcarbamate (6.75 g, 31 mmol) and triethylamine (10.9 mL, 75 mmol) were dissolved in CH$_2$Cl$_2$ (50 mL). MsCl (2.9 mL, 38 mmol) was added dropwise under stirring and cooling with an ice bath in argon. The temperature was brought to ambient within 1 h. Water (100 mL) was added, and the layers were separated. The organic one was washed with water, brine, dried with Na$_2$SO$_4$, and evaporated. Compound 9 (9 g, 31 mmol, ~100%) was obtained as a yellow oil. This crude product was used for the next stage without additional purification. 1H NMR-data (DMSO-d6): 4.76-4.88 (m, 1H); 3.23 (d, 2H, CH$_2$, J=6.6); 3.12 (s, 3H, MS); 2.76 (s, 3H, NCH$_3$); 2.38-2.48 (m, 2H); 2.00-2.12 (m, 1H); 1.86-97 (m, 2H); 1.38 (s, 9H, Boc).

EXAMPLE 1 tert-Butyl Methyl({trans-3-[4-(pyrrolidin-1-ylmethyl)phenoxy]cyclobutyl}methyl)-carbamate (9). A solution on intermediate 1,4-(pyrrolidin-1-ylmethyl)phenol (5.5 g, 62 mmol) and potassium tert-butoxide (3.5 g, 31 mmol) in DMSO (100 mL) was heated to 100° C. under vigorous stirring in a flow of argon. The mixture was stirred at this temperature for 15 min. A solution of compound 8 (4.5 g, 15.5 mmol) in DMSO (100 mL) and tetrabutylammonium bromide (1.5 g, 9 mmol) were added. The mixture was stirred at 100° C. for 1 h and cooled. The residue was dissolved in EtOAc (200 mL). The solution was washed with water (300 mL), 1 N NaOH (2×100 mL), brine, dried with Na$_2$SO$_4$, and evaporated. The residue was purified by chromatography (silica gel, 63/100 μm, 60 g, CHCl$_3$/hexane 20:80→100:0, CHCl$_3$/MeOH 100:0→80:20 to furnish the title compound (5.56 g, 96%). 1H NMR-data (DMSO-d6): 7.17 (d, 2H, Ph, J=8.6); 6.73 (d, 2H, Ph, J=8.6); 4.68-4.85 (m, 1H); 3.47 (s, 2H, CH$_2$); 3.33 (d, 2H, CH$_2$, J=7.8); 2.78 (s, 3H, NCH$_3$); 2.50-2.60 (m, 1H); 2.33-2.44 (m, 4H); 2.00-2.27 (m, 4H); 1.62-1.71 (m, 4H); 1.38 (s, 9H, Boc).

EXAMPLE 2

Methyl({trans-3-[4-(pyrrolidin-1-ylmethyl)phenoxy]cyclobutyl}methyl)amine (10). Trifluoroacetic acid (8.6 mL, 111 mmol) was added to a solution of compound 9 (5.56 g, 15 mmol) in dichloromethane (50 mL). The reaction mass was stirred at room temperature for 24 h and evaporated in vacuo. The residue was diluted with water (50 mL), and the obtained solution was extracted with CH$_2$Cl$_2$. The organic layer was discarded. The aqueous one was alkalized with 10 N NaOH to pH 12 and extracted with CHCl$_3$ (3×100 mL). The combined extracts were dried and evaporated to afford the title compound (3 g, 74%) as a yellow oil. LCMS-data: M+H 275.2, 276.2 (calc. 274.4). 1H NMR-data (DMSO-d6): 7.16 (d, 2H, Ph, J=8.6); 6.72 (d, 2H, Ph, J=8.6); 4.65-4.78 (m, 1H); 3.46 (s, 2H, CH$_2$); 2.56 (d, 2H, CH$_2$, J=7.6); 2.34-2.41 (m, 4H); 2.28 (s, 3H, NCH$_3$); 2.00-2.30 (m, 5H); 1.60-1.71 (m, 4H).

General Procedure C: Amide Coupling

A 0.5 M DMF solution (250 uL) of the carboxylic acid in anhydrous DMF was treated with 250 uL of a 0.5 M DMF solution of BOP and then with 40 uL of anhydrous diisopropylethylamine. To the resulting mixture was added 200 uL of a 0.5 M DMF solution of the starting amine. The mixture was agitated at 25° C. for 10 minutes and then at 45° C. for 24 hours. The mixture was treated with 2 mL of methanol. The mixture was applied to an ion exchange column (4.5 grams of Dowex H$^+$ form cation exchange resin in methanol) and the column was eluted with methanol (4×5 mL) to remove neutral impurities. The product was then eluted with a 30% solution of dimethylamine in methanol (2×5 mL). The methanol was removed from the product by evaporation. The product was purified by HPLC (Preparative Purification Method A). Product purity and identity were confirmed by LCMS analysis (Analytical Purification Method B).

General Procedure S: Sulfonamide Coupling

A 0.5 M CH$_2$Cl$_2$ solution (200 uL) of the amine was treated with 45 uL of triethylamine. The resulting solution was treated with 300 uL of a 0.5 M CH$_2$Cl$_2$ solution of the sulfonyl chloride. The mixture was agitated for 24 hours at room temperature. It was treated with 2 mL of methanol and applied to an ion exchange column (4.5 g of Dowex cation exchange resin in the pyridinium form in methanol). The column was eluted with methanol (4×5 mL) to remove neutral impurities. It was then eluted with 30% dimethylamine in methanol to elute the product. The solvent was removed from the product by evaporation. The product was further purified by HPLC (Preparative Purification Method A). Purity and identity were confirmed by LCMS (Analytical Purification Method B).

General Procedure U: Urea Formation from an Isocyanate and an Amine

A 0.5 M CH$_2$Cl$_2$ solution of amine (200 uL) was treated with 200 uL of a 0.5 M solution of the isocyanate. The mixture was agitated for 24 hours. It was treated with 2 mL of methanol and applied to an ion exchange column (4.5 g of Dowex cation exchange resin in the pyridinium form in methanol). The column was eluted with methanol (4×5 mL) to remove neutral impurities. It was then eluted with 30% dimethylamine in methanol to elute the product. The solvent was removed from the product by evaporation. The product was further purified by HPLC (Preparative Purification Method A). Purity and identity were confirmed by LCMS (Analytical Purification Method B).

Preparative Purification Method A: HPLC Purification

The compound was dissolved in 1.5 mL of 5:1 acetonitrile/water. It was injected onto a Luna C18 5 um 20×250 mm column. The column was eluted over 18.5 minutes with an acetonitrile/water gradient containing 0.1% trifluoroacetic acid.

Analytical Purification Method B: Analytical LCMS

The compound was injected onto Betasil C18 10 uM 150× 4.6 mm HPLC column and eluted at 2.5 mL/min. A linear gradient was used of 100% solvent A to 100% solvent B over 4 minutes followed by 3 minutes of 100% solvent B. Solvent A is 0.1% TFA in 5:95 acetonitrile/water. Solvent B is 0.1% TFA in acetonitrile. Purity was established using an Evaporative Light Scatter Detector (ELSD). Identity was established by APCI positive ion mass spectroscopy.

EXAMPLE 3

N-Methyl-2-pyridin-3-yl-N-[3-(4-pyrrolidin-1-ylmethyl-phenoxy)-cyclobutylmethyl]-acetamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 58.6 mg, HPLC purity ELSD=100%, retention time (min)=2.185; LRMS m/z Calcd for $C_{24}H_{31}N_3O_2$, 393.5; obsd LRMS APCI (M+1) m/z 394.

EXAMPLE 4

N-Methyl-N-[3-(4-pyrrolidin-1-ylmethyl-phenoxy)-cyclobutylmethyl]-nicotinamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 58 mg, HPLC purity ELSD=100%, retention time (min)=2.213; LRMS m/z Calcd for $C_{23}H_{29}N_3O_2$, 379.5; obsd LRMS APCI (M+1) m/z 380.

EXAMPLE 5

3-Methoxy-N-methyl-N-[3-(4-pyrrolidin-1-ylmethyl-phenoxy)-cyclobutylmethyl]-propionamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 44.3 mg, HPLC purity ELSD=100%, retention time (min)=2.52; LRMS m/z Calcd for $C_{21}H_{32}N_2O_3$, 360.5; obsd LRMS APCI (M+1) m/z 361.

EXAMPLE 6

2,N-Dimethyl-N-[3-(4-pyrrolidin-1-ylmethyl-phenoxy)-cyclobutylmethyl]-nicotinamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 58.7 mg, HPLC purity ELSD=100%, retention time (min)=2.2; LRMS m/z Calcd for $C_{24}H_{31}N_3O_2$, 393.5; obsd LRMS APCI (M+1) m/z 394.

EXAMPLE 7

2-Methyl-2H-pyrazole-3-carboxylic acid methyl-[3-(4-pyrrolidin-1-ylmethyl-phenoxy)-cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 66 mg, HPLC purity ELSD=100%, retention time (min)=2.553; LRMS m/z Calcd for '$C_{22}H_{30}N_4O_2$, 382.5; obsd LRMS APCI (M+1) m/z 383.

EXAMPLE 8

N-Methyl-N-[3-(4-pyrrolidin-1-ylmethyl-phenoxy)-cyclobutylmethyl]-isobutyramide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 60 mg, HPLC purity ELSD=100%, retention time (min)=2.745; LRMS m/z Calcd for $C_{21}H_{32}N_2O_2$, 344.5; obsd LRMS APCI (M+1) m/z 345.

EXAMPLE 9

2,5-Dimethyl-2H-pyrazole-3-carboxylic acid methyl-[3-(4-pyrrolidin-1-ylmethylphenoxy)-cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 76.7 mg, HPLC purity ELSD=100%, retention time (min)=2.61; LRMS m/z Calcd for $C_{23}H_{32}N_4O_2$, 396.5; obsd LRMS APCI (M+1) m/z 397.

EXAMPLE 10

5-Ethyl-isoxazole-3-carboxylic acid methyl-[3-(4-pyrrolidin-1-ylmethyl-phenoxy)cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 71 mg, HPLC purity ELSD=100%, retention time (min)=2.951; LRMS m/z Calcd for $C_{23}H_{31}N_3O_3$, 397.5; obsd LRMS APCI (M+1) m/z 398.

EXAMPLE 11

2-Cyclopentyl-N-methyl-N-[3-(4-pyrrolidin-1-ylmethyl-phenoxy)-cyclobutylmethyl]acetamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 64.2 mg, HPLC purity ELSD=100%, retention time (min)=3.137; LRMS m/z Calcd for $C_{24}H_{36}N_2O_2$, 384.6; obsd LRMS APCI (M+1) m/z 385.

EXAMPLE 12

6,N-Dimethyl-N-[3-(4-pyrrolidin-1-ylmethyl-phenoxy)-cyclobutylmethyl]-nicotinamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 67 mg, HPLC purity ELSD=100%, retention time (min)=2.195; LRMS m/z Calcd for C24H31N3O2, 393.5; obsd LRMS APCI (M+1) m/z 394.

EXAMPLE 13

6-Methyl-pyridine-2-carboxylic acid methyl-[3-(4-pyrrolidin-1-ylmethyl-phenoxy)cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 43.6 mg, HPLC purity ELSD=100%, retention time (min)=2.431; LRMS m/z Calcd for C24H31N3O2, 393.5; obsd LRMS APCI (M+1) m/z 394.

EXAMPLE 14

Pyridine-2-carboxylic acid methyl-[3-(4-pyrrolidin-1-ylmethyl-phenoxy)-cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 57.9 mg, HPLC purity ELSD=100%, retention time (min)=2.486; LRMS m/z Calcd for C23H29N3O2, 379.5; obsd LRMS APCI (M+1) m/z 380.

EXAMPLE 15

2-Methoxy-N-methyl-N-[3-(4-pyrrolidin-1-ylmethyl-phenoxy)-cyclobutylmethyl]-acetamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 66.5 mg, HPLC purity ELSD=100%, retention time (min)=2.426; LRMS m/z Calcd for C20H30N2O3, 346.5; obsd LRMS APCI (M+1) m/z 347.

EXAMPLE 16

Tetrahydro-pyran-4-carboxylic acid methyl-[3-(4-pyrrolidin-1-ylmethyl-phenoxy)-cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 44.7 mg, HPLC purity ELSD=99.7%, retention time (min)=2.549; LRMS m/z Calcd for C23H34N2O3, 386.5; obsd LRMS APCI (M+1) m/z 387.

EXAMPLE 17

N-Methyl-2-pyridin-4-yl-N-[3-(4-pyrrolidin-1-ylmethyl-phenoxy)-cyclobutylmethyl]-acetamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 55.2 mg, HPLC purity ELSD=100%, retention time (min)=2.189; LRMS m/z Calcd for C24H31N3O2, 393.5; obsd LRMS APCI (M+1) m/z 394.

EXAMPLE 18

3,N-Dimethyl-N-[3-(4-pyrrolidin-1-ylmethyl-phenoxy)-cyclobutylmethyl]-butyramide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 42.5 mg, HPLC purity ELSD=100%, retention time (min)=2.921; LRMS m/z Calcd for C22H34N2O2, 358.5; obsd LRMS APCI (M+1) m/z 359.

EXAMPLE 19

3-Methyl-1H-pyrazole-4-carboxylic acid methyl-[3-(4-pyrrolidin-1-ylmethyl-phenoxy)-cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 43.2 mg, HPLC purity ELSD=100%, retention time (min)=2.394; LRMS m/z Calcd for C22H30N4O2, 382.5; obsd LRMS APCI (M+1) m/z 383.

EXAMPLE 20

N-Methyl-N-[3-(4-pyrrolidin-1-ylmethyl-phenoxy)-cyclobutylmethyl]-propionamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 54.4 mg, HPLC purity ELSD=100%, retention time (min)=2.603; LRMS m/z Calcd for C20H30N2O2, 330.5; obsd LRMS APCI (M+1) m/z 331.

EXAMPLE 21

N-Methyl-2-pyridin-2-yl-N-[3-(4-pyrrolidin-1-ylmethyl-phenoxy)-cyclobutylmethyl]-acetamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 55.6 mg, HPLC purity ELSD=100%, retention time (min)=2.185; LRMS m/z Calcd for 'C24H31N3O2, 393.5; obsd LRMS APCI (M+1) m/z 394.

EXAMPLE 22

N-Methyl-N-[3-(4-pyrrolidin-1-ylmethyl-phenoxy)-cyclobutylmethyl]-acetamide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 58.9 mg, HPLC purity ELSD=100%, retention time (min)=2.437; LRMS m/z Calcd for C19H28N2O2, 316.4; obsd LRMS APCI (M+1) m/z 317.

EXAMPLE 23

N-Methyl-N-[3-(4-pyrrolidin-1-ylmethyl-phenoxy)-cyclobutylmethyl]-isonicotin-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 61.2 mg, HPLC purity ELSD=100%, retention time (min)=2.199; LRMS m/z Calcd for C23H29N3O2, 379.5; obsd LRMS APCI (M+1) m/z 380.

EXAMPLE 24

Pyrazine-2-carboxylic acid methyl-[3-(4-pyrrolidin-1-ylmethyl-phenoxy)-cyclobutylmethyl]-amide. Reaction was conducted using the conditions described in General Procedure C: Amide Coupling, using Example 2 as the starting amine and the appropriate acid. The product was purified by HPLC (Preparative Purification Method A) yielding the title compound as the TFA salt, 49.7 mg, HPLC purity ELSD=100%, retention time (min)=2.474; LRMS m/z Calcd for C22H28N4O2, 380.5; obsd LRMS APCI (M+1) m/z 381.

EXAMPLE 25

Ethanesulfonic acid methyl-[3-(4-pyrrolidin-1-ylmethyl-phenoxy)-cyclobutylmethyl]-amide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 57.7 mg, HPLC purity ELSD=100%, retention time (min)=2.771; LRMS m/z Calcd for C19H30N2O3S, 366.5; obsd LRMS APCI (M+1) m/z 367.

EXAMPLE 26

1,3,5-Trimethyl-1H-pyrazole-4-sulfonic acid methyl-[3-(4-pyrrolidin-1-ylmethylphenoxy)-cyclobutylmethyl]-amide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 9.8 mg, HPLC purity ELSD=100%, retention time (min)=2.896; LRMS m/z Calcd for C23H34N4O3S, 446.6; obsd LRMS APCI (M+1) m/z 447.

EXAMPLE 27

2-Chloro-4-fluoro-N-methyl-N-[3-(4-pyrrolidin-1-ylmethyl-phenoxy)-cyclobutylmethyl]-benzenesulfonamide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 39.6 mg, HPLC purity ELSD=100%, retention time (min)=3.402; LRMS m/z Calcd for C23H28ClFN2O3S, 467.0; obsd LRMS APCI (M+1) m/z 467.

EXAMPLE 28

N-Methyl-N-[3-(4-pyrrolidin-1-ylmethyl-phenoxy)-cyclobutylmethyl]methanesulfonamide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 30.2 mg, HPLC purity ELSD=100%, retention time (min)=2.667; LRMS m/z Calcd for C18H28N2O3S, 352.4; obsd LRMS APCI (M+1) m/z 353.

EXAMPLE 29

4-Acetyl-N-methyl-N-[3-(4-pyrrolidin-1-ylmethyl-phenoxy)-cyclobutylmethyl]benzene-sulfonamide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 33.5 mg, HPLC purity ELSD=99%, retention time (min)=3.141; LRMS m/z Calcd for C25H32N2O4S, 456.6; obsd LRMS APCI (M+1) m/z 457.

EXAMPLE 30

Pyridine-3-sulfonic acid methyl-[3-(4-pyrrolidin-1-ylmethyl-phenoxy)-cyclobutylmethyl]-amide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 39.4 mg, HPLC purity ELSD=100%, retention time (min)=2.785; LRMS m/z Calcd for C22H29N3O3S, 415.5; obsd LRMS APCI (M+1) m/z 416.

EXAMPLE 31

3,4-Difluoro-N-methyl-N-[3-(4-pyrrolidin-1-ylmethyl-phenoxy)-cyclobutylmethyl]-benzenesulfonamide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 14 mg, HPLC purity ELSD=100%, retention time (min)=3.417; LRMS m/z Calcd for C23H28F2N2O3S, 450.5; obsd LRMS APCI (M+1) m/z 451.

EXAMPLE 32

Propane-2-sulfonic acid methyl-[3-(4-pyrrolidin-1-ylmethyl-phenoxy)-cyclobutylmethyl]-amide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 27.2 mg, HPLC purity ELSD=95.9, retention time (min)=2.943; LRMS m/z Calcd for C20H32N2O3S, 380.5; obsd LRMS APCI (M+1) m/z 381.

EXAMPLE 33

4-Chloro-N-methyl-N-[3-(4-pyrrolidin-1-ylmethyl-phenoxy)-cyclobutylmethyl]-benzene-sulfonamide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 12.4 mg, HPLC purity ELSD=100, retention time (min)=3.503; LRMS m/z Calcd for C23H29ClN2O3S, 449.0; obsd LRMS APCI (M+1) m/z 449.

EXAMPLE 34

N-Methyl-C-phenyl-N-[3-(4-pyrrolidin-1-ylmethyl-phenoxy)-cyclobutylmethyl]-methanesulfonamide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 46.9 mg, HPLC purity ELSD=99.6, retention time (min)=3.194; LRMS m/z Calcd for C24H32N2O3S, 428.6; obsd LRMS APCI (M+1) m/z 429.

EXAMPLE 35

2,2,2-Trifluoro-ethanesulfonic acid methyl-[3-(4-pyrrolidin-1-ylmethyl-phenoxy)-cyclobutylmethyl]-amide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 20.2 mg, HPLC purity ELSD=97, retention time (min)=3.117; LRMS m/z Calcd for C19H27F3N2O3S, 420.4; obsd LRMS APCI (M+1) m/z 421.

EXAMPLE 36

Piperidine-1-sulfonic acid methyl-[3-(4-pyrrolidin-1-ylmethyl-phenoxy)-cyclobutylmethyl]-amide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 13.8 mg, HPLC purity ELSD=100, retention time (min)=3.308; LRMS m/z Calcd for C22H35N3O3S, 421.6; obsd LRMS APCI (M+1) m/z 422.

EXAMPLE 37

Pyrrolidine-1-sulfonic acid methyl-[3-(4-pyrrolidin-1-ylmethyl-phenoxy)-cyclobutylmethyl]-amide. Reaction was conducted using the conditions described in General Procedure S: Sulfonamide Coupling, using Example 2 as the starting amine and the appropriate sulfonyl chloride. The product was purified by HPLC (Preparative Purification Method A) yielding the title compound as the TFA salt, 12.4 mg, HPLC purity ELSD=97.7, retention time (min)=3.086; LRMS m/z Calcd for C21H33N3O3S, 407.5; obsd LRMS APCI (M+1) m/z 408.

Intermediate
({trans-3-[4-(Pyrrolidin-1-ylmethyl)phenoxy]cyclobutyl}methyl)amine

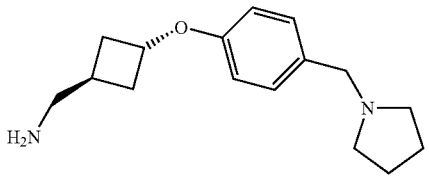

Intermediate 7
N-Benzyl-3-oxocyclobutanecarboxamide (4). Acid, 3-oxocyclobutanecarboxylic acid (10 g, 0.087 mol), benzylamine (10.5 mL, 0.96 mol), and triethylamine (38 mL, 0.26 mol) were dissolved in DMF (100 mL). BOP (38.7 g, 0.087 mol) was added at 0° C. under stirring in argon. The mixture was stirred at 20° C. for 20 h, evaporated, and the residue was dried at 0.5 mmHg. The residue was purified by chromatography (silica gel, 63-100 μm, 1 L, CCl$_4$→CHCl$_3$, CHCl$_3$/MeOH 100:0→95:5). The title compound (7.12 g, 40%) was obtained as a colorless oil. 1H NMR-data (DMSO-d6): 8.62 (br.s, 1H, NH); 7.21-7.36 (m, 5H, Ph); 4.32 (d, 2H, CH$_2$, J=6.1 Hz); 3.10-3.28 (m, 5H).

Intermediate 8
cis-3-[(Benzylamino)methyl]cyclobutanol (5). LiAlH$_4$ (2.7 g, 0.07 mol) was added to a solution of intermediate 7, N-Benzyl-3-oxocyclobutanecarboxamide (7.12 g, 0.035 mol) in absolute THF (100 mL) under stirring in argon. The mixture was refluxed under stirring for 2 h and cooled. Then 10 N NaOH (2 mL) and water (1 mL) were added. The organic layer was decanted, and the aqueous one was extracted with THF (2×50 mL). The organic layers were evaporated to afford the title compound (3.9 g, 58%) as a colorless oil. 1H NMR-data (DMSO-d6): 7.00-7.49 (m, 6H, NH, Ph); 4.80 (br.s, 1H, OH); 3.81-3.95 (m, 1H); 3.67 (s, 2H, CH$_2$); 2.48 (d, 2H, CH$_2$, J=6.8 Hz); 2.19-2.30 (m, 2H); 1.70-1.84 (m, 1H); 1.35-1.50 (m, 2H).

Intermediate 9
cis-3-(Aminomethyl)cyclobutanol (6). 5% Pd/C (1.6 g) was added to a solution of intermediate 8, cis-3-[(Benzylamino)methyl]cyclobutanol (3.9 g, 0.02 mol) in MeOH (50 mL). The mixture was stirred in a flow of hydrogen for 48 h and filtered through Celite. The solid was washed on the filter with MeOH (2×50 mL). The filtrate was evaporated. Obtained crude product cis-3-(aminomethyl)cyclobutanol (1.95 g, ~195%) was used for the next stage without additional purification.

Intermediate 10
tert-Butyl [(cis-3-Hydroxycyclobutyl)methyl]carbamate (7). (Boc)$_2$O (4.42 g, 0.02 mol) was added to a solution of intermediate 9, cis-3-(aminomethyl)cyclobutanol (1.95 g, 0.019 mol) and Et$_3$N (5.6 mL, 0.039 mol) in 20 mL absolute THF under stirring. The mixture was stirred at room temperature for 30 min, evaporated, and coevaporated with CCl$_4$. The residue was recrystallized form ether to give the title compound (3 g, 77%) as yellow crystals. $^1$H NMR-data (DMSO-d6): 6.61-6.87 (m, 1H, NH); 4.85 (br.s, 1H, OH); 3.77-3.92 (m, 1H); 2.90 (t, 2H, CH$_2$, J=6.1 Hz); 2.10-2.22 (m, 2H); 1.67-1.80 (m, 1H); 1.21-1.51 (m, 11H, CH$_2$, Boc).

Intermediate 11
cis-3-{[(tert-Butoxycarbonyl)amino]methyl}cyclobutyl Methanesulfonate (8). Inter-mediate 10, tert-butyl [(cis-3-hydroxycyclobutyl)methyl]carbamate (3 g, 15 mmol) and triethylamine (5.2 mL, 36 mmol) were dissolved in CH$_2$Cl$_2$ (50 mL). MsCl (1.4 mL, 18 mmol) was added dropwise under stirring and cooling with an ice bath in argon. The temperature was brought to ambient within 1 h. Water (50 mL) was added, and the layers were separated. The organic one was washed with water, brine, dried with Na$_2$SO$_4$, and evaporated. The title compound (3.5 g, 85%) was obtained as a yellow oil. This crude product was used for the next stage without additional purification. 1H NMR-data (DMSO-d6): 6.74-7.00 (m, 1H, NH); 4.73-4.86 (m, 1H); 3.10 (s, 3H, MS); 2.97 (t, 2H, CH$_2$, J=5.7 Hz); 2.32-2.42 (m, 2H); 1.80-2.43 (m, 3H); 1.38 (s, 9H, Boc).

EXAMPLE 38 tert-Butyl ({trans-3-[4-(Pyrrolidin-1-ylmethyl)phenoxy]cyclobutyl}methyl)carbamate (9). A solution on intermediate 2,4-(pyrrolidin-1-ylmethyl)phenol (4.5 g, 25 mmol) and potassium tert-butoxide (2.85 g, 25 mmol) in DMSO (100 mL) was heated to 100° C. under vigorous stirring in a flow of argon. The mixture was stirred at this temperature for 15 min.

A solution intermediate 11, cis-3-{[(tert-butoxycarbonyl)amino]methyl}cyclobutyl methanesulfonate (3.5 g, 13 mmol) in DMSO (100 mL) and tetrabutylammonium bromide (1.23 g, 3.8 mmol) were added. The mixture was stirred at 100° C. for 1 h and cooled. The residue was dissolved in EtOAc (150 mL). The solution was washed with water (300 mL), 1 N NaOH (2×100 mL), brine, dried with $Na_2SO_4$, and evaporated. The residue was purified by chromatography (silica gel, 63/100 μm, 60 g, $CHCl_3$/hexane 20:80→100:0, $CHCl_3$/MeOH 100:0→80:20 to furnish the title compound (2.16 g, 47%). LCMS-data: M+H 361.2, 362.2, M-Boc+H 261.2, 262.2 (calc. 360.5). 1H NMR-data (DMSO-d6): 7.17 (d, 2H, Ph, J=8.6 Hz); 6.86-7.00 (m, 1H, NH); 6.72 (d, 2H, Ph, J=8.6 Hz); 4.65-4.76 (m, 1H); 3.47 (s, 3H, $CH_2$); 3.00 (t, 2H, $CH_2$, J=6.3 Hz); 2.30-2.44 (m, 5H); 2.18-2.28 (m, 2H); 2.00-2.13 (m, 2H); 1.60-1.72 (m, 4H); 1.4 (s, 9H, Boc).

EXAMPLE 39

({trans-3-[4-(Pyrrolidin-1-ylmethyl)phenoxy]cyclobutyl}methyl)amine (10). Trifluoro-acetic acid (3.5 mL, 49 mmol) was added to a solution of Example 38, tert-butyl ({trans-3-[4-(pyrrolidin-1-ylmethyl)phenoxy]cyclobutyl}methyl)carbamate (2.16 g, 6 mmol) in dichloromethane (20 mL). The reaction mass was stirred at room temperature for 2 h and evaporated in vacuo. The residue was diluted with water (50 mL), and the obtained solution was extracted with $CH_2Cl_2$. The organic layer was discarded. The aqueous one was alkalized with 10 N NaOH to pH 12 and extracted with $CHCl_3$ (3×50 mL). The combined extracts were dried and evaporated to afford the title compound (1.4 g, 91%) as a yellow oil. LCMS-data: M+H 261.2, 262.2 (calc 260.38). 1H NMR-data (DMSO-d6): 7.17 (d, 2H, Ph, J=8.6 Hz); 6.72 (d, 2H, Ph, J=8.6 Hz); 4.65-4.76 (m, 1H); 3.47 (s, 3H, $CH_2$); 2.63 (d, 2H, $CH_2$, J=6.6 Hz); 2.32-2.42 (m, 4H); 2.18-2.28 (m, 3H); 2.00-2.13 (m, 2H); 1.60-1.72 (m, 4H).

Intermediate 12

2-Chloro-3-hydroxybenzaldehyde. Chlorine was bubbled through a solution of m-hydroxybenzaldehyde (CAS 100-83-4) (100 g, 820 mmol) in glacial acetic acid (440 g) at 15° C. until the increase in weight was 56 g. The mixture was stirred at room temperature for 12 h. Then the colorless crystals (~70 g) were separated by filtration, dryed in vacuo and recrystallized from $Et_2O$/hexane mixture (1:1) to give the title compound (51.5 g, 40%, 330 mmol) as colorless crystals. GC/MS data: 155 (M–H)⁺ (calculated for $C_7H_5ClO_2$ 156.6); ¹H NMR data (DMSO-d6): 10.63 (s, 1H, COH); 10.34 (s, 1H, OH); 7.25-7.33 (m, 3H, Ph).

Intermediate 13

2-Chloro-3-pyrrolidin-1-ylmethyl-phenol. Pyrrolidine (71.3 mL, 855 mmol) was added to a solution of intermediate 12, 2-chloro-3-hydroxybenzaldehyde (103 g, 658 mmol) in dichloromethane (1 L). The reaction mixture was cooled on ice bath, and sodium triacetoxyborohydride (209.3 g, 987 mmol) was added in portions under stirring. The reaction mixture was stirred for 12 h at room temperature. Water (500 mL) and concentrated HCl were added to attain pH~2. The organic layer was separated. The aqueous one was extracted with $CH_2Cl_2$ (2×400 mL), then with EtOAc (400 mL). The organic layers were discarded. The aqueous fraction was alkalized with $K_2CO_3$ to pH~10, and the product was extracted with $CHCl_3$ (3×500 mL). The organic layer was dried with $Na_2SO_4$ and evaporated in vacuo. The obtained crystals were separated by filtration from $Et_2O$/hexane mixture (1:1) and coevaporated with dioxane to give the title compound (76 g, 55%, 359 mmol). LCMS data: 214 and 212 (M+H)⁺ (calculated for $C_{11}H_{14}ClNO$ 211.7); ¹H NMR data (DMSO-d6): 9.96 (br.s, 1H, OH); 7.08 (t, 1H, J=7.8 Hz, Ar—H); 6.91 (dd, 1H, $J_1$=1.7 Hz, $J_2$=7.3 Hz, Ar—H); 6.86 (dd, 1H, $J_1$=1.7 Hz, $J_2$=8.0 Hz, Ar—H); 3.64 (s, 2H, $\underline{CH_2}$Ar); 2.43-2.52 (m, 4H+DMSO); 1.65-1.74 (m, 4H).

Intermediate 2

N-Benzyl-N-methyl-3-oxocyclobutanecarboxamide. CDI (40 g, 0.25 mol) was added to a solution of 3-oxo-cyclobutanecarboxylic acid (23 g, 0.2 mol) in THF (100 ml) at 0° C. under stirring, the mixture was stirred at RT for 1 h. N-methylbenzylamine (32 ml, 0.25 mol) was added to the mixture and the mixture was stirred at RT for 3 h and evaporated. The residue was purified by chromatography (silica gel, 63-100 μm, 500 g, $CHCl_3$/MeOH 100:0→95:5). The title compound (27.9 g, 64%) was obtained as a colorless oil. ¹H NMR data (DMSO-d6): 7.20 (m, 5H, Ph); 4.62 s, 4.55 s (2H, $CH_2$); 3.46-3.62 (m, 1H); 3.28 (m, 4H,); 2.85 s, 2.94 s (3H, $NCH_3$).

Intermediate 3 cis-3-{[Benzyl(methyl)amino]methyl}cyclobutanol. A solution of intermediate 2, N-benzyl-N-methyl-3-oxocyclobutanecarboxamide (27.9 g, 0.128 mol) in absolute THF (40 mL) was added to a suspension of $LiAlH_4$ (9.75 g, 0.257 mol) in absolute THF (200 ml) under stirring in argon. The mixture was refluxed under stirring for 1 h and cooled. Then 10 N NaOH (25 mL) and water (25 mL) were added. The organic layer was decanted, and the aqueous one was extracted with THF (2×50 mL). The organic layers were evaporated. The residue was purified by chromatography (silica gel, 63-100 μm, 300 g, $CHCl_3$/MeOH 100:0→90:10). The title compound (25 g, 95%) was obtained as a colorless oil. ¹H NMR-data (DMSO-d6): 7.19-7.33 (m, 5H, Ph); 4.85 (d, 1H, OH, J=6.6 Hz); 3.83-3.94 (m, 1H); 3.40 (s, 2H, $CH_2$); 2.24-2.34 (m, 4H); 2.07 (s, 3H, $NCH_3$); 1.81-1.92 (m, 1H); 1.34-1.44 (m, 2H).

Intermediate 4 cis-3-[(Methylamino)methyl]cyclobutanol. 5% Pd/C (5 g) was added to a solution of intermediate 3, cis-3-{[benzyl(methyl)amino]methyl}cyclobutanol (25 g, 0.121 mol) in MeOH (200 mL). The mixture was stirred in a flow of $H_2$ for 24 h and filtered through Celite. The solid was washed on the filter with MeOH (2×50 mL). The filtrate was evaporated. Obtained crude title product (14 g, ~100%) was used for the next stage without additional purification. ¹H NMR-data (DMSO-d6): 4.87-5.49 (br.s, 2H, NH, OH); 3.86-3.96 (m, 1H); 2.73 (d, 2H, $CH_2$, J=7.1 Hz); 2.39 (s, 3H, $NCH_3$); 2.24-2.34 (m, 2H); 1.85-1.97 (m, 1H); 1.46-1.57 (m, 2H).

Intermediate 5 tert-Butyl [(cis-3-Hydroxycyclobutyl)methyl]methylcarbamate. $(Boc)_2O$ (28 g, 0.13 mol) was added to a solution of intermediate 4, cis-3-[(methylamino)methyl]cyclobutanol (14 g, 0.12 mol) and $Et_3N$ (35 mL, 0.24 mol) in 150 mL absolute THF under stirring. The mixture was stirred at room temperature for 1 h and evaporated. The residue was purified by chromatography (silica gel, 63-100μ, 300 g, $CHCl_3$/MeOH 100:0→95:5) to give the title compound (22.6 g, 87%) as a colorless oil. ¹H NMR-data (DMSO-d6): 4.92 (d, 1H, OH, J=6.6 Hz); 3.80-3.92 (m, 1H); 3.15 (d, 2H, $CH_2$, J=6.8 Hz); 2.74 (s, 3H, $NCH_3$); 2.17-2.26 (m, 2H); 1.78-1.89 (m, 1H); 1.44-1.55 (m, 2H); 1.38 (s, 9H, Boc).

Intermediate 6 cis-3-{[(tert-Butoxycarbonyl)(methyl)amino]methyl}cyclobutyl Methanesulfonate. Intermediate 5, tert-Butyl [(cis-3-hydroxycyclobutyl)methyl]methylcarbamate (22.6 g, 105 mmol) and triethylamine (36 mL, 250 mmol) were dissolved in $CH_2Cl_2$ (50 mL). MsCl (9.75 mL, 126 mmol) was added dropwise at –20° C. under stirring in argon. The temperature was brought to ambient within 1 h. Water (100 mL) was added, and the layers were separated. The organic one was washed with water, brine, dried with Na$_2$SO$_4$, and evaporated. The title compound (29 g, 96%) was obtained as a yellow oil. This crude product was used for the next stage without additional purification. $^1$H NMR-data (DMSO-d6): 4.76-4.88 (m, 1H); 3.23 (d, 2H, CH$_2$, J=6.6 Hz); 3.12 (s, 3H, MS); 2.76 (s, 3H, NCH$_3$); 2.38-2.48 (m, 2H); 2.00-2.12 (m, 1H); 1.86-97 (m, 2H); 1.38 (s, 9H, Boc).

EXAMPLE 40 tert-Butyl Methyl({trans-3-[2-chloro-3-(pyrrolidin-1-yl-methyl)phenoxy]cyclobutyl}-methyl) carbamate. A mixture of intermediate 6, cis-3-{[(tert-Butoxycarbonyl)(methyl)amino]-methyl}cyclobutyl methanesulfonate (15.93 g, 54.3 mmol), intermediate 13, 2-chloro-3-pyrrolidin-1-ylmethyl-phenol (23 g, 0.108 mol) and Cs$_2$CO$_3$ (35.2 g, 108 mmol) in DMSO (200 mL) was heated at 90-95° C. for 2 h under vigorous stirring in a flow of argon, then cooled. Water (200 ml) and ether (200 ml) were added, and the layers were separated. The water layer was extracted with ether (2×300 ml), the combined organic layers were washed with water (300 mL), brine, dried with Na$_2$SO$_4$, and evaporated. The residue was purified by chromatography (silica gel, 63/100 μm, 500 g, CHCl$_3$/hexane 20:80→100:0, CHCl$_3$/MeOH 100:0→80:20 to furnish the title compound (14.6 g, 65%). LC/MS data: 409.2, 411.2, 412.1 (M+H) (calculated for C$_{22}$H$_{33}$ClN$_2$O$_3$ 408.97). $^1$H NMR-data (DMSO-d6): 7.21 (t, 1H, J=7.8 Hz, Ar); 7.05 (brd, 1H, J=7.1 Hz, Ar); 6.78 (brd, 1H, J=7.1 Hz, Ar); 4.82-4.89 (m, 1H); 3.66 (s, 2H, CH$_2$); 3.33 (d, 2H, J=8.0 Hz, CH$_2$); 2.78 (s, 3H, NCH$_3$); 2.52-2.62 (m, 1H); 2.43-2.50 (m, 4H); 2.11-2.30 (m, 4H); 1.65-1.73 (m, 4H); 1.41 (s, 9H, Boc).

EXAMPLE 41

Methyl({trans-3-[2-chloro-3-(pyrrolidin-1-ylmethyl)phenoxy]cyclobutyl}methyl)amine. 4M HCl in dioxane (65 ml) was added to a solution of example 40, tert-Butyl Methyl ({trans-3-[2-chloro-3-(pyrrolidin-1-ylmethyl)phenoxy]cyclobutyl}methyl) carbamate (24.7 g, 60.4 mmol) in 100 ml of dioxane. The mixture was stirred for 20 h and evaporated to dryness. The residue was recrystallized from MeOH-i-PrOH. The crystals were separated by filtration and dryed, then CHCl$_3$ (100 mL) and saturated K$_2$CO$_3$ (100 ml) were added under stirring. The layers were separated; the water solution was extracted with CHCl$_3$ (3×100 mL). The combined extracts were dried (Na$_2$SO$_4$) and evaporated; the residue was dried in vacuo. The title compound (14.2 g, 76%) was obtained as a yellow oil. LC/MS data: 309.1, 311.1 (M+H) (calculated for C$_{17}$H$_{25}$ClN$_2$O 308.85). $^1$H NMR-data (DMSO-d6): 7.20 (t, 1H, J=8.07 Hz, Ar); 7.04 (brd, 1H, J=7.0 Hz, Ar); 6.78 (brd, 1H, J=7.0 Hz); 4.77-4.86 (m, 1H), 3.65 (s, 2H, CH$_2$); 2.57 (d, 2H, J=7.4 Hz, CH$_2$); 2.43-2.52 (m, 4H); 2.31-2.43 (m, 1H); 2.298 (s, 3H, NCH$_3$); 2.20-2.27 (m, 2H); 2.10-2.19 (m, 2H); 1.64-1.73 (m, 4H).

EXAMPLE 42

N-[3-(2-Chloro-3-pyrrolidin-1-ylmethyl-phenoxy)-cyclobutylmethyl]-3,3,N-trimethyl-butyramide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 51 mg; HPLC purity ELSD=100%, retention time (min)=1.719; LRMS m/z Calcd for C23H35ClN2O2, 407.0; obsd LRMS APCI (M+1) m/z 407.

EXAMPLE 43

Pyridine-2-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 49 mg; HPLC purity ELSD=98.9%, retention time (min)=1.398; LRMS m/z Calcd for C23H28ClN3O2, 413.9; obsd LRMS APCI (M+1) m/z 414.

EXAMPLE 44

1-Ethyl-1H-pyrazole-4-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 8 mg; HPLC purity ELSD=95.0651%, retention time (min)=1.505; LRMS m/z Calcd for C23H31ClN4O2, 431.0; obsd LRMS APCI (M+1) m/z 431.

EXAMPLE 45

N-[3-(2-Chloro-3-pyrrolidin-1-ylmethyl-phenoxy)-cyclobutylmethyl]-4,N-dimethyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 42 mg; HPLC purity ELSD=100%, retention time (min)=1.721; LRMS m/z Calcd for 'C25H31ClN2O2, 427.0; obsd LRMS APCI (M+1) m/z 427.

EXAMPLE 46

N-[3-(2-Chloro-3-pyrrolidin-1-ylmethyl-phenoxy)-cyclobutylmethyl]-2,2,N-trimethyl-propionamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 47 mg; HPLC purity ELSD=99.6558%, retention time (min)=1.661; LRMS m/z Calcd for 'C22H33ClN2O2, 393.0; obsd LRMS APCI (M+1) m/z 393.

EXAMPLE 47

N-[3-(2-Chloro-3-pyrrolidin-1-ylmethyl-phenoxy)-cyclobutylmethyl]-N-methyl-2-pyridin-3-yl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 44 mg; HPLC purity ELSD=99.2499%, retention time (min)=1.219; LRMS m/z Calcd for C24H30ClN3O2, 428.0; obsd LRMS APCI (M+1) m/z 428.

EXAMPLE 48

N-[3-(2-Chloro-3-pyrrolidin-1-ylmethyl-phenoxy)-cyclobutylmethyl]-2,3,N-trimethyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 16 mg; HPLC purity ELSD=99.5%, retention time (min)=1.784; LRMS m/z Calcd for C26H33ClN2O2, 441.0; obsd LRMS APCI (M+1) m/z 441.

EXAMPLE 49

N-[3-(2-Chloro-3-pyrrolidin-1-ylmethyl-phenoxy)-cyclobutylmethyl]-3-methoxy-N-methyl-propionamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 48 mg; HPLC purity ELSD=100%, retention time (min)=1.439; LRMS m/z Calcd for C21H31ClN2O3, 394.9; obsd LRMS APCI (M+1) m/z 395.

EXAMPLE 50

N-[3-(2-Chloro-3-pyrrolidin-1-ylmethyl-phenoxy)-cyclobutylmethyl]-2-methoxy-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 40 mg; HPLC purity ELSD=99.5%, retention time (min)=1.375; LRMS m/z Calcd for C20H29ClN2O3, 380.9; obsd LRMS APCI (M+1) m/z 381.

EXAMPLE 51

Cyclobutanecarboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 53 mg; HPLC purity ELSD=100%, retention time (min)=1.613; LRMS m/z Calcd for C22H31ClN2O2, 391.0; obsd LRMS APCI (M+1) m/z 391.

EXAMPLE 52

N-[3-(2-Chloro-3-pyrrolidin-1-ylmethyl-phenoxy)-cyclobutylmethyl]-2,6-difluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 22 mg; HPLC purity ELSD=81.8%, retention time (min)=1.701; LRMS m/z Calcd for C24H27ClF2N2O2, 448.9; obsd LRMS APCI (M+1) m/z 449.

EXAMPLE 53

N-[3-(2-Chloro-3-pyrrolidin-1-ylmethyl-phenoxy)-cyclobutylmethyl]-2-methoxy-N-methyl-nicotinamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 15 mg; HPLC purity ELSD=99.1%, retention time (min)=1.549; LRMS m/z Calcd for C24H30ClN3O3, 444.0; obsd LRMS APCI (M+1) m/z 444.

EXAMPLE 54

N-[3-(2-Chloro-3-pyrrolidin-1-ylmethyl-phenoxy)-cyclobutylmethyl]-N-methyl-propionamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 39 mg; HPLC purity ELSD=99.6%, retention time (min)=1.486; LRMS m/z Calcd for C20H29ClN2O2, 364.9; obsd LRMS APCI (M+1) m/z 365.

EXAMPLE 55

N-[3-(2-Chloro-3-pyrrolidin-1-ylmethyl-phenoxy)-cyclobutylmethyl]-2-cyclo-propyl-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 51 mg; HPLC purity ELSD=100%, retention time (min)=1.587; LRMS m/z Calcd for C22H31ClN2O2, 391.0; obsd LRMS APCI (M+1) m/z 391.

EXAMPLE 56

2-Ethyl-5-methyl-2H-pyrazole-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 39 mg; HPLC purity ELSD=99.9%, retention time (min) =1.533; LRMS m/z Calcd for C24H33ClN4O2, 445.0; obsd LRMS APCI (M+1) m/z 445.

EXAMPLE 57

N-[3-(2-Chloro-3-pyrrolidin-1-ylmethyl-phenoxy)-cyclobutylmethyl]-2,5,N-trimethyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 18 mg; HPLC purity ELSD=99.7%, retention time (min)=1.775; LRMS m/z Calcd for C26H33ClN2O2, 441.0; obsd LRMS APCI (M+1) m/z 441.

EXAMPLE 58

N-[3-(2-Chloro-3-pyrrolidin-1-ylmethyl-phenoxy)-cyclobutylmethyl]-2-(3-fluoro-phenyl)-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 55 mg; HPLC purity ELSD=100%, retention time (min)=1.697; LRMS m/z Calcd for C25H30ClFN2O2, 445.0; obsd LRMS APCI (M+1) m/z 445.

EXAMPLE 59

N-[3-(2-Chloro-3-pyrrolidin-1-ylmethyl-phenoxy)-cyclobutylmethyl]-N-methyl nicotin-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 55 mg; HPLC purity ELSD=99.9%, retention time (min)=1.224; LRMS m/z Calcd for C23H28ClN3O2, 413.9; obsd LRMS APCI (M+1) m/z 414.

EXAMPLE 60

Cyclohexanecarboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 44 mg; HPLC purity ELSD=100%, retention time (min)=1.762; LRMS m/z Calcd for C24H35ClN2O2, 419.0; obsd LRMS APCI (M+1) m/z 419.

EXAMPLE 61

6-Methyl-pyridine-2-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 43 mg; HPLC purity ELSD=100%, retention time (min)=1.375; LRMS m/z Calcd for C24H30ClN3O2, 428.0; obsd LRMS APCI (M+1) m/z 428.

EXAMPLE 62

2-Chloro-N-[3-(2-chloro-3-pyrrolidin-1-ylmethyl-phenoxy)-cyclobutylmethyl]-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 52 mg; HPLC purity ELSD=81.9%, retention time (min)=1.731; LRMS m/z Calcd for C24H28Cl2N2O2, 447.4; obsd LRMS APCI (M+1) m/z 447.

EXAMPLE 63

N-[3-(2-Chloro-3-pyrrolidin-1-ylmethyl-phenoxy)-cyclobutylmethyl]-N-methyl-isobutyramide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 55 mg; HPLC purity ELSD=99.79%, retention time (min)=1.55; LRMS m/z Calcd for C21H31ClN2O2, 378.9; obsd LRMS APCI (M+1) m/z 379.

EXAMPLE 64

4-Methyl-furazan-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 35 mg; HPLC purity ELSD=96.0%, retention time (min)=1.663; LRMS m/z Calcd for C21H27ClN4O3, 418.9; obsd LRMS APCI (M+1) m/z 419.

EXAMPLE 65

Furazan-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 25 mg; HPLC purity ELSD=92.8%, retention time (min)=1.505; LRMS m/z Calcd for C20H25ClN4O3, 404.9; obsd LRMS APCI (M+1) m/z 405.

EXAMPLE 66

2,6-Dimethyl-pyrimidine-4-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 9 mg; HPLC purity ELSD=99.2%, retention time (min)=1.453; LRMS m/z Calcd for C24H31ClN4O2, 443.0; obsd LRMS APCI (M+1) m/z 443.

EXAMPLE 67

Tetrahydro-pyran-4-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 12 mg; HPLC purity ELSD=99.4%, retention time (min)=1.468; LRMS m/z Calcd for C23H33ClN2O3, 421.0; obsd LRMS APCI (M+1) m/z 421.

EXAMPLE 68

N-[3-(2-Chloro-3-pyrrolidin-1-ylmethyl-phenoxy)-cyclobutylmethyl]-3,N-dimethyl-butyramide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 30 mg; HPLC purity ELSD=100%, retention time (min)=1.666; LRMS m/z Calcd for C22H33ClN2O2, 393.0; obsd LRMS APCI (M+1) m/z 393.

EXAMPLE 69

N-[3-(2-Chloro-3-pyrrolidin-1-ylmethyl-phenoxy)-cyclobutylmethyl]-2-(3,5-dimethyl-isoxazol-4-yl)-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 44 mg; HPLC purity ELSD=97.4%, retention time (min)=1.528; LRMS m/z Calcd for C24H32ClN3O3, 446.0; obsd LRMS APCI (M+1) m/z 446.

EXAMPLE 70

5-Isopropyl-isoxazole-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 8 mg; HPLC purity ELSD=100%, retention time (min)=1.777; LRMS m/z Calcd for C24H32ClN3O3, 446.0; obsd LRMS APCI (M+1) m/z 446.

EXAMPLE 71

N-[3-(2-Chloro-3-pyrrolidin-1-ylmethyl-phenoxy)-cyclobutylmethyl]-4,4,4-trifluoro-N-methyl-butyramide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 24 mg; HPLC purity ELSD=100%, retention time (min)=1.652; LRMS m/z Calcd for C21H28ClF3N2O2, 432.9; obsd LRMS APCI (M+1) m/z 433.

EXAMPLE 72

N-[3-(2-Chloro-3-pyrrolidin-1-ylmethyl-phenoxy)-cyclobutylmethyl]-N-methyl-2-(3-methyl-pyrazol-1-yl)-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 51 mg; HPLC purity ELSD=100%, retention time (min)=1.414; LRMS m/z Calcd for C23H31ClN4O2, 431.0; obsd LRMS APCI (M+1) m/z 431.

EXAMPLE 73

5-Cyclopropyl-2H-pyrazole-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 13 mg; HPLC purity ELSD=97.6%, retention time (min)=1.542; LRMS m/z Calcd for C24H31ClN4O2, 443.0; obsd LRMS APCI (M+1) m/z 443.

EXAMPLE 74

3-Chloro-N-[3-(2-chloro-3-pyrrolidin-1-ylmethyl-phenoxy)-cyclobutylmethyl]-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 40 mg; HPLC purity ELSD=100%, retention time (min)=1.741; LRMS m/z Calcd for C24H28Cl2N2O2, 447.4; obsd LRMS APCI (M+1) m/z 447.

EXAMPLE 75

Cyclopentanecarboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 43 mg; HPLC purity ELSD=100%, retention time (min)=1.692; LRMS m/z Calcd for C23H33ClN2O2, 405.0; obsd LRMS APCI (M+1) m/z 405.

EXAMPLE 76

N-[3-(2-Chloro-3-pyrrolidin-1-ylmethyl-phenoxy)-cyclobutylmethyl]-N-methyl-isonicotinamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 53 mg; HPLC purity ELSD=99.6527%, retention time (min)=1.19; LRMS m/z Calcd for C23H28ClN3O2, 413.9; obsd LRMS APCI (M+1) m/z 414.

EXAMPLE 77

N-[3-(2-Chloro-3-pyrrolidin-1-ylmethyl-phenoxy)-cyclobutylmethyl]-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 54 mg; HPLC purity ELSD=100%, retention time (min)=1.387; LRMS m/z Calcd for C19H27ClN2O2, 350.9; obsd LRMS APCI (M+1) m/z 351.

EXAMPLE 78

N-[3-(2-Chloro-3-pyrrolidin-1-ylmethyl-phenoxy)-cyclobutylmethyl]-2-(3,5-dimethyl-pyrazol-1-yl)-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 62 mg; HPLC purity ELSD=100%, retention time (min)=1.35; LRMS m/z Calcd for C24H33ClN4O2, 445.0; obsd LRMS APCI (M+1) m/z 445.

EXAMPLE 79

N-[3-(2-Chloro-3-pyrrolidin-1-ylmethyl-phenoxy)-cyclobutylmethyl]-2-cyclopentyl-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 43 mg; HPLC purity ELSD=100%, retention time (min)=1.787; LRMS m/z Calcd for C24H35ClN2O2, 419.0; obsd LRMS APCI (M+1) m/z 419.

EXAMPLE 80

5-Methyl-pyrazine-2-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 55 mg; HPLC purity ELSD=100%, retention time (min)=1.465; LRMS m/z Calcd for C23H29ClN4O2, 429.0; obsd LRMS APCI (M+1) m/z 429.

EXAMPLE 81

N-[3-(2-Chloro-3-pyrrolidin-1-ylmethyl-phenoxy)-cyclobutylmethyl]-2,4,N-trimethyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 41 mg; HPLC purity ELSD=100%, retention time (min)=1.735; LRMS m/z Calcd for C26H33ClN2O2, 441.0; obsd LRMS APCI (M+1) m/z 441.

EXAMPLE 82

N-[3-(2-Chloro-3-pyrrolidin-1-ylmethyl-phenoxy)-cyclobutylmethyl]-4-fluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 38 mg; HPLC purity ELSD=100%, retention time (min)=1.659; LRMS m/z Calcd for C24H28ClFN2O2, 430.9; obsd LRMS APCI (M+1) m/z 431.

EXAMPLE 83

N-[3-(2-Chloro-3-pyrrolidin-1-ylmethyl-phenoxy)-cyclobutylmethyl]-2-(2-fluoro-phenyl)-N-methyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 34 mg; HPLC purity ELSD=100%, retention time (min)=1.715; LRMS m/z Calcd for C25H30ClFN2O2, 445.0; obsd LRMS APCI (M+1) m/z 445.

EXAMPLE 84

Cyclopropanecarboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 35 mg; HPLC purity ELSD=99.4001%, retention time (min)=1.526; LRMS m/z Calcd for C21H29ClN2O2, 376.9; obsd LRMS APCI (M+1) m/z 377.

EXAMPLE 85

N-[3-(2-Chloro-3-pyrrolidin-1-ylmethyl-phenoxy)-cyclobutylmethyl]-N-methyl-2-pyrazol-1-yl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 43 mg; HPLC purity ELSD=99.7396%, retention time (min)=1.402; LRMS m/z Calcd for C22H29ClN4O2, 417.0; obsd LRMS APCI (M+1) m/z 417.

EXAMPLE 86

5-Ethyl-2-methyl-2H-pyrazole-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 40 mg; HPLC purity ELSD=99.6142%, retention time (min)= 1.597; LRMS m/z Calcd for C24H33ClN4O2, 445.0; obsd LRMS APCI (M+1) m/z 445.

EXAMPLE 87

N-[3-(2-Chloro-3-pyrrolidin-1-ylmethyl-phenoxy)-cyclobutylmethyl]-N-methyl-2-pyridin-4-yl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 47 mg; HPLC purity ELSD=98.7375%, retention time (min)=1.202; LRMS m/z Calcd for C24H30ClN3O2, 428.0; obsd LRMS APCI (M+1) m/z 428.

EXAMPLE 88

N-[3-(2-Chloro-3-pyrrolidin-1-ylmethyl-phenoxy)-cyclobutylmethyl]-3-fluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 36 mg; HPLC purity ELSD=100%, retention time (min)=1.668; LRMS m/z Calcd for C24H28ClFN2O2, 430.9; obsd LRMS APCI (M+1) m/z 431.

EXAMPLE 89

2-Ethyl-4-methyl-oxazole-5-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 10 mg; HPLC purity ELSD=95.1532%, retention time (min)= 1.626; LRMS m/z Calcd for C24H32ClN3O3, 446.0; obsd LRMS APCI (M+1) m/z 446.

EXAMPLE 90

5-Methyl-isoxazole-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 48 mg; HPLC purity ELSD=99.7325%, retention time (min)=1.562; LRMS m/z Calcd for C22H28ClN3O3, 417.9; obsd LRMS APCI (M+1) m/z 418.

EXAMPLE 91

1-Isopropyl-1H-pyrazole-4-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 10 mg; HPLC purity ELSD=99.2448%, retention time (min)=1.574 LRMS m/z Calcd for C24H33ClN4O2, 445.0; obsd LRMS APCI (M+1) m/z 445.

EXAMPLE 92

4-Methyl-oxazole-5-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 33 mg; HPLC purity ELSD=97.0001%, retention time (min)=1.486; LRMS m/z Calcd for C22H28ClN3O3, 417.9; obsd LRMS APCI (M+1) m/z 418.

EXAMPLE 93

N-[3-(2-Chloro-3-pyrrolidin-1-ylmethyl-phenoxy)-cyclobutylmethyl]-2,3-difluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 14 mg; HPLC purity ELSD=100%, retention time (min)=1.705; LRMS m/z Calcd for C24H27ClF2N2O2, 448.9; obsd LRMS APCI (M+1) m/z 449.

EXAMPLE 94

1,5-Dimethyl-1H-pyrazole-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 32 mg; HPLC purity ELSD=99.7582%, retention time (min)= 1.513; LRMS m/z Calcd for C23H31ClN4O2, 431.0; obsd LRMS APCI (M+1) m/z 431.

EXAMPLE 95

(S)—N-[3-(2-Chloro-3-pyrrolidin-1-ylmethyl-phenoxy)-cyclobutylmethyl]-2-hydroxy-N-methyl-2-phenyl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 28 mg; HPLC purity ELSD=95.9267%, retention time (min)=1.59; LRMS m/z Calcd for C25H31ClN2O3, 443.0; obsd LRMS APCI (M+1) m/z 443.

EXAMPLE 96

4-Methyl-pentanoic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 47 mg; HPLC purity ELSD=99.3948%, retention time (min)=1.744; LRMS m/z Calcd for C23H35ClN2O2, 407.0; obsd LRMS APCI (M+1) m/z 407.

EXAMPLE 97

N-[3-(2-Chloro-3-pyrrolidin-1-ylmethyl-phenoxy)-cyclobutylmethyl]-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 54 mg; HPLC purity ELSD=99.6082%, retention time (min)=1.617; LRMS m/z Calcd for C24H29ClN2O2, 413.0; obsd LRMS APCI (M+1) m/z 413.

EXAMPLE 98

N-[3-(2-Chloro-3-pyrrolidin-1-ylmethyl-phenoxy)-cyclobutylmethyl]-2-fluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 40 mg; HPLC purity ELSD=100%, retention time (min)=1.664; LRMS m/z Calcd for C24H28ClFN2O2, 430.9; obsd LRMS APCI (M+1) m/z 431.

EXAMPLE 99

N-[3-(2-Chloro-3-pyrrolidin-1-ylmethyl-phenoxy)-cyclobutylmethyl]-6,N-dimethyl-nicotinamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 10 mg; HPLC purity ELSD=100%, retention time (min)=1.242; LRMS m/z Calcd for C24H30ClN3O2, 428.0; obsd LRMS APCI (M+1) m/z 428.

EXAMPLE 100

N-[3-(2-Chloro-3-pyrrolidin-1-ylmethyl-phenoxy)-cyclobutylmethyl]-2,N-dimethyl-nicotinamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 47 mg; HPLC purity ELSD=100%, retention time (min)=1.218; LRMS m/z Calcd for C24H30ClN3O2, 428.0; obsd LRMS APCI (M+1) m/z 428.

EXAMPLE 101

N-[3-(2-Chloro-3-pyrrolidin-1-ylmethyl-phenoxy)-cyclobutylmethyl]-N-methyl-2-pyridin-2-yl-acetamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 50 mg; HPLC purity ELSD=99.4058%, retention time (min)=1.224; LRMS m/z Calcd for C24H30ClN3O2, 428.0; obsd LRMS APCI (M+1) m/z 428.

EXAMPLE 102

N-[3-(2-Chloro-3-pyrrolidin-1-ylmethyl-phenoxy)-cyclobutylmethyl]-3,5-difluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 11 mg; HPLC purity ELSD=99.4652%, retention time (min)=1.715; LRMS m/z Calcd for C24H27ClF2N2O2, 448.9; obsd LRMS APCI (M+1) m/z 449.

EXAMPLE 103

3,5-Dimethyl-isoxazole-4-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 28 mg; HPLC purity ELSD=99.5436%, retention time (min)=1.49; LRMS m/z Calcd for C23H30ClN3O3, 432.0; obsd LRMS APCI (M+1) m/z 432.

EXAMPLE 104

5-Ethyl-isoxazole-3-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 48 mg; HPLC purity ELSD=100%, retention time (min)=1.679; LRMS m/z Calcd for C23H30ClN3O3, 432.0; obsd LRMS APCI (M+1) m/z 432.

EXAMPLE 105

N-[3-(2-Chloro-3-pyrrolidin-1-ylmethyl-phenoxy)-cyclobutylmethyl]-2,5-difluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 9 mg; HPLC purity ELSD=100%, retention time (min)=1.708; LRMS m/z Calcd for C24H27ClF2N2O2, 448.9; obsd LRMS APCI (M+1) m/z 449.

EXAMPLE 106

N-[3-(2-Chloro-3-pyrrolidin-1-ylmethyl-phenoxy)-cyclobutylmethyl]-2,4-difluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 8 mg; HPLC purity ELSD=100%, retention time (min)=1.709; LRMS m/z Calcd for C24H27ClF2N2O2, 448.9; obsd LRMS APCI (M+1) m/z 449.

EXAMPLE 107

1-Methyl-cyclopropanecarboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 53 mg; HPLC purity ELSD=100%, retention time (min)=1.561; LRMS m/z Calcd for C22H31ClN2O2, 391.0; obsd LRMS APCI (M+1) m/z 391.

EXAMPLE 108

N-[3-(2-Chloro-3-pyrrolidin-1-ylmethyl-phenoxy)-cyclobutylmethyl]-3,4,N-trimethyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 20 mg; HPLC purity ELSD=100%, retention time (min)=1.778; LRMS m/z Calcd for C26H33ClN2O2, 441.0; obsd LRMS APCI (M+1) m/z 441.

EXAMPLE 109

N-[3-(2-Chloro-3-pyrrolidin-1-ylmethyl-phenoxy)-cyclobutylmethyl]-3,4-difluoro-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 10 mg; HPLC purity ELSD=100%, retention time (min)=1.712; LRMS m/z Calcd for C24H27ClF2N2O2, 448.9; obsd LRMS APCI (M+1) m/z 449.

EXAMPLE 110

4-Chloro-N-[3-(2-chloro-3-pyrrolidin-1-ylmethyl-phenoxy)-cyclobutylmethyl]-N-methyl-benzamide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 32 mg; HPLC purity ELSD=100%, retention time (min)=1.749; LRMS m/z Calcd for C24H28Cl2N2O2, 447.4; obsd LRMS APCI (M+1) m/z 447.

EXAMPLE 111

Pyrazine-2-carboxylic acid [3-(2-chloro-3-pyrrolidin-1-ylmethyl-phenoxy)-cyclobutylmethyl]-methyl-amide. Reaction was conducted using the conditions described in General Procedure C: Amide Coupling, using Example 41 as the starting amine and the appropriate acid. The product was purified by HPLC (Preparative Purification Method A) yielding the title compound as the TFA salt, 38 mg; HPLC purity ELSD=99.6%, retention time (min)=1.417; LRMS m/z Calcd for C22H27ClN4O2, 414.9; obsd LRMS APCI (M+1) m/z 415.

EXAMPLE 112

N-[3-(2-Chloro-3-pyrrolidin-1-ylmethyl-phenoxy)-cyclobutylmethyl]-2,6-difluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 27 mg, HPLC purity ELSD=100%, retention time (min)=1.814; LRMS m/z Calcd for C23H27ClF2N2O3S, 485.0; obsd LRMS APCI (M+1) m/z 485.

EXAMPLE 113

N-[3-(2-Chloro-3-pyrrolidin-1-ylmethyl-phenoxy)-cyclobutylmethyl]-3-fluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 26 mg, HPLC purity ELSD=100%, retention time (min)=, retention time (min)=1.835; LRMS m/z Calcd for C23H28ClFN2O3S, 467.0; obsd LRMS APCI (M+1) m/z 467.

EXAMPLE 114

2-Oxo-2,3-dihydro-benzooxazole-6-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 24 mg, HPLC purity ELSD=100%, retention time (min)=1.642; LRMS m/z Calcd for C24H28ClN3O5S, 506.0; obsd LRMS APCI (M+1) m/z 506.

EXAMPLE 115

4-Methyl-thiophene-2-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 15 mg, HPLC purity ELSD=100%, retention time (min)=1.874; LRMS m/z Calcd for C22H29ClN2O3 S2, 469.1; obsd LRMS APCI (M+1) m/z 469.

EXAMPLE 116

4-Acetyl-N-[3-(2-chloro-3-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 32 mg, HPLC purity ELSD=97.6%, retention time (min)=1.773; LRMS m/z Calcd for C25H31ClN2O4S, 491.0; obsd LRMS APCI (M+1) m/z 491.

EXAMPLE 117

Pyrrolidine-1-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 21 mg, HPLC purity ELSD=100%, retention time (min)=1.689; LRMS m/z Calcd for C21H32ClN3O3S, 442.0; obsd LRMS APCI (M+1) m/z 442.

EXAMPLE 118

4-tert-Butyl-N-[3-(2-chloro-3-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 45 mg, HPLC purity ELSD=99.8%, retention time (min)=2.043; LRMS m/z Calcd for C27H37ClN2O3S, 505.1; obsd LRMS APCI (M+1) m/z 505.

EXAMPLE 119

3-Chloro-N-[3-(2-chloro-3-pyrrolidin-1-ylmethyl-phenoxy)-cyclobutylmethyl]-4-fluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 49 mg, HPLC purity ELSD=100%, retention time (min)=1.913; LRMS m/z Calcd for C23H27Cl2FN2O3S, 501.4; obsd LRMS APCI (M+1) m/z 501.

EXAMPLE 120

2,5-Dimethyl-thiophene-3-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 20 mg, HPLC purity ELSD=99.6%, retention time (min)=1.91; LRMS m/z Calcd for C23H31ClN2O3S2, 483.1; obsd LRMS APCI (M+1) m/z 483.

EXAMPLE 121

N-[3-(2-Chloro-3-pyrrolidin-1-ylmethyl-phenoxy)-cyclobutylmethyl]-2,4-dimethoxy-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 24 mg, HPLC purity ELSD=99.5%, retention time (min)=1.797; LRMS m/z Calcd for C25H33ClN2O5S, 509.1; obsd LRMS APCI (M+1) m/z 509.

EXAMPLE 123

2,3-Dihydro-benzo[1,4]dioxine-6-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 33 mg, HPLC purity ELSD=100%, retention time (min)=1.818; LRMS m/z Calcd for C25H31ClN2O5S, 507.0; obsd LRMS APCI (M+1) m/z 507.

EXAMPLE 124

N-[3-(2-Chloro-3-pyrrolidin-1-ylmethyl-phenoxy)-cyclobutylmethyl]-5-fluoro-2,N-dimethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 46 mg, HPLC purity ELSD=99.8%, retention time (min)=1.87; LRMS m/z Calcd for C24H30ClFN2O3S, 481.0; obsd LRMS APCI (M+1) m/z 481.

EXAMPLE 125

Propane-2-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 10 mg, HPLC purity ELSD=100%, retention time (min)=1.645; LRMS m/z Calcd for C20H31ClN2O3S, 415.0; obsd LRMS APCI (M+1) m/z 415.

EXAMPLE 126

5-Chloro-thiophene-2-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 26 mg, HPLC purity ELSD=100%, retention time (min)=1.935; LRMS m/z Calcd for C21H26Cl2N2O3S2, 489.5; obsd LRMS APCI (M+1) m/z 489.

EXAMPLE 127

4-Chloro-N-[3-(2-chloro-3-pyrrolidin-1-ylmethyl-phenoxy)-cyclobutylmethyl]-2,5,N-trimethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 53 mg, HPLC purity ELSD=98.7%, retention time (min)=2.056; LRMS m/z Calcd for C25H32Cl2N2O3S, 511.5; obsd LRMS APCI (M+1) m/z 511.

EXAMPLE 128

Morpholine-4-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 23 mg, HPLC purity ELSD=100%, retention time (min)=1.572; LRMS m/z Calcd for C21H32ClN3O4S, 458.0; obsd LRMS APCI (M+1) m/z 458

EXAMPLE 129

N-[3-(2-Chloro-3-pyrrolidin-1-ylmethyl-phenoxy)-cyclobutylmethyl]-4-ethyl-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 40 mg, HPLC purity ELSD=98.7%, retention time (min)=1.938; LRMS m/z Calcd for C25H33ClN2O3S, 477.1; obsd LRMS APCI (M+1) m/z 477.

EXAMPLE 130

N-[3-(2-Chloro-3-pyrrolidin-1-ylmethyl-phenoxy)-cyclobutylmethyl]-3,N-dimethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 37 mg, HPLC purity ELSD=100%, retention time (min)=1.855; LRMS m/z Calcd for C24H31ClN2O3S, 463.0; obsd LRMS APCI (M+1) m/z 463.

EXAMPLE 131

N-[3-(2-Chloro-3-pyrrolidin-1-ylmethyl-phenoxy)-cyclobutylmethyl]-2-methoxy-5,N-dimethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 35 mg, HPLC purity ELSD=100%, retention time (min)=1.841; LRMS m/z Calcd for C25H33ClN2O4S, 493.1; obsd LRMS APCI (M+1) m/z 493.

EXAMPLE 132

Piperidine-1-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulfonyl chloride. The product was purified by HPLC (Preparative Purification Method A) yielding the title compound as the TFA salt, 17 mg, HPLC purity ELSD=100%, retention time (min)=1.809; LRMS m/z Calcd for C22H34ClN3O3S, 456.0; obsd LRMS APCI (M+1) m/z 456.

EXAMPLE 133

N-[3-(2-Chloro-3-pyrrolidin-1-ylmethyl-phenoxy)-cyclobutylmethyl]-4,N-dimethyl-benzenesulfonamide. Reaction was conducted using the conditions described in General Procedure S: Sulfonamide Coupling, using Example 41 as the starting amine and the appropriate sulfonyl chloride. The product was purified by HPLC (Preparative Purification Method A) yielding the title compound as the TFA salt, 24 mg, HPLC purity ELSD=99.4%, retention time (min)=1.877; LRMS m/z Calcd for C24H31ClN2O3S, 463.0; obsd LRMS APCI (M+1) m/z 463.

EXAMPLE 134

Prop-2-ene-1-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulfonyl chloride. The product was purified by HPLC (Preparative Purification Method A) yielding the title compound as the TFA salt, 15 mg, HPLC purity ELSD=100%, retention time (min)=1.625; LRMS m/z Calcd for C20H29ClN2O3S, 413.0; obsd LRMS APCI (M+1) m/z 413.

EXAMPLE 135

Thiophene-2-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulfonyl chloride. The product was purified by HPLC (Preparative Purification Method A) yielding the title compound as the TFA salt, 7 mg, HPLC purity ELSD=100%, retention time (min)=1.809; LRMS m/z Calcd for C21H27ClN2O3S2, 455.0; obsd LRMS APCI (M+1) m/z 455.

EXAMPLE 136

N-[3-(2-Chloro-3-pyrrolidin-1-ylmethyl-phenoxy)-cyclobutylmethyl]-2,5-dimethoxy-N-methyl-benzenesulfonamide. Reaction was conducted using the conditions described in General Procedure S: Sulfonamide Coupling, using Example 41 as the starting amine and the appropriate sulfonyl chloride. The product was purified by HPLC (Preparative Purification Method A) yielding the title compound as the TFA salt, 41 mg, HPLC purity ELSD=99.7%, retention time (min)=1.795; LRMS m/z Calcd for C25H33ClN2O5S, 509.1; obsd LRMS APCI (M+1) m/z 509.

EXAMPLE 137

(E)-2-Phenyl-ethenesulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulfonyl chloride. The product was purified by HPLC (Preparative Purification Method A) yielding the title compound as the TFA salt, 25 mg, HPLC purity ELSD=97.5%, retention time (min)=1.89; LRMS m/z Calcd for C25H31ClN2O3S, 475.1; obsd LRMS APCI (M+1) m/z 475.

EXAMPLE 138

2-{[3-(2-Chloro-3-pyrrolidin-1-ylmethyl-phenoxy)-cyclobutylmethyl]-methyl-sulfamoyl}-benzoic acid methyl ester Reaction was conducted using the conditions described in General Procedure S: Sulfonamide Coupling, using Example 41 as the starting amine and the appropriate sulfonyl chloride. The product was purified by HPLC (Preparative Purification Method A) yielding the title compound as the TFA salt, 8 mg, HPLC purity ELSD=100%, retention time (min)=1.791; LRMS m/z Calcd for C25H31ClN2O5S, 507.0; obsd LRMS APCI (M+1) m/z 507.

EXAMPLE 139

N-[3-(2-Chloro-3-pyrrolidin-1-ylmethyl-phenoxy)-cyclobutylmethyl]-3,4-difluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 44 mg, HPLC purity ELSD=100%, retention time (min)=1.852; LRMS m/z Calcd for C23H27ClF2N2O3S, 485.0; obsd LRMS APCI (M+1) m/z 485.

EXAMPLE 140

Benzo[1,2,5]thiadiazole-4-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 31 mg, HPLC purity ELSD=100%, retention time (min)=1.783; LRMS m/z Calcd for C23H27ClN4O3S2, 507.1; obsd LRMS APCI (M+1) m/z 507.

EXAMPLE 141

1,3,5-Trimethyl-1H-pyrazole-4-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 31 mg, HPLC purity ELSD=100%, retention time (min)=1.646; LRMS m/z Calcd for C23H33ClN4O3S, 481.1; obsd LRMS APCI (M+1) m/z 481.

EXAMPLE 142

Pyridine-3-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 12 mg, HPLC purity ELSD=99.3%, retention time (min)=1.605; LRMS m/z Calcd for C22H28ClN3O3S, 450.0; obsd LRMS APCI (M+1) m/z 450.

EXAMPLE 143

5-Methyl-thiophene-2-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 16 mg, HPLC purity ELSD=100%, retention time (min)=1.871; LRMS m/z Calcd for C22H29ClN2O3S2, 469.1; obsd LRMS APCI (M+1) m/z 469.

EXAMPLE 144

N-[3-(2-Chloro-3-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 23 mg, HPLC purity ELSD=100%, retention time (min)=1.803; LRMS m/z Calcd for C23H29ClN2O3S, 449.0; obsd LRMS APCI (M+1) m/z 449.

EXAMPLE 145

N-[3-(2-Chloro-3-pyrrolidin-1-ylmethyl-phenoxy)-cyclobutylmethyl]-N-methyl-C-phenyl-methanesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 48 mg, HPLC purity ELSD=99.5%, retention time (min)=1.778; LRMS m/z Calcd for C24H31ClN2O3S, 463.0; obsd LRMS APCI (M+1) m/z 463.

EXAMPLE 146

N-(4-{[3-(2-Chloro-3-pyrrolidin-1-ylmethyl-phenoxy)-cyclobutylmethyl]-methyl-sulfamoyl}-phenyl)-acetamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 51 mg, HPLC purity ELSD=99.6%, retention time (min)=1.631; LRMS m/z Calcd for C25H32ClN3O4S, 506.1; obsd LRMS APCI (M+1) m/z 506.

EXAMPLE 147

N-[3-(2-Chloro-3-pyrrolidin-1-ylmethyl-phenoxy)-cyclobutylmethyl]-N-methyl-methanesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 28 mg, HPLC purity ELSD=99.3%, retention time (min)=1.472; LRMS m/z Calcd for C18H27ClN2O3S, 386.9; obsd LRMS APCI (M+1) m/z 387.

EXAMPLE 148

3-Chloro-N-[3-(2-chloro-3-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 31 mg, HPLC purity ELSD=99.9%, retention time (min)=1.901; LRMS m/z Calcd for C23H28Cl2N2O3S, 483.5; obsd LRMS APCI (M+1) m/z 483.

EXAMPLE 149

N-[3-(2-Chloro-3-pyrrolidin-1-ylmethyl-phenoxy)-cyclobutylmethyl]-3,4-dimethoxy-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 25 mg, HPLC purity ELSD=100%, retention time (min)=1.765; LRMS m/z Calcd for C25H33ClN2O5S, 509.1; obsd LRMS APCI (M+1) m/z 509.

EXAMPLE 150

N-[3-(2-Chloro-3-pyrrolidin-1-ylmethyl-phenoxy)-cyclobutylmethyl]-2,4,N-trimethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 19 mg, HPLC purity ELSD=100%, retention time (min)=1.927; LRMS m/z Calcd for C25H33ClN2O3S, 477.1; obsd LRMS APCI (M+1) m/z 477.

EXAMPLE 151

N-[3-(2-Chloro-3-pyrrolidin-1-ylmethyl-phenoxy)-cyclobutylmethyl]-N-methyl-4-trifluoromethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 19 mg, HPLC purity ELSD=100%, retention time (min)=1.972; LRMS m/z Calcd for C24H28ClF3N2O3S, 517.0; obsd LRMS APCI (M+1) m/z 517.

EXAMPLE 152

5-Chloro-N-[3-(2-chloro-3-pyrrolidin-1-ylmethyl-phenoxy)-cyclobutylmethyl]-2-methoxy-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 25 mg, HPLC purity ELSD=100%, retention time (min)=1.897; LRMS m/z Calcd for C24H30Cl2N2O4S, 513.5; obsd LRMS APCI (M+1) m/z 513.

EXAMPLE 153

2-Chloro-N-[3-(2-chloro-3-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 49 mg, HPLC purity ELSD=99.9%, retention time (min)=1.838; LRMS m/z Calcd for C23H28Cl2N2O3S, 483.5; obsd LRMS APCI (M+1) m/z 483.

EXAMPLE 154

Quinoline-8-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 52 mg, HPLC purity ELSD=100%, retention time (min)=1.769; LRMS m/z Calcd for C26H30ClN3O3S, 500.1; obsd LRMS APCI (M+1) m/z 500.

EXAMPLE 155

N-[3-(2-Chloro-3-pyrrolidin-1-ylmethyl-phenoxy)-cyclobutylmethyl]-4-fluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 42 mg, HPLC purity ELSD=99.8%, retention time (min)=1.797; LRMS m/z Calcd for C23H28ClFN2O3S, 467.0; obsd LRMS APCI (M+1) m/z 467.

EXAMPLE 156

Ethanesulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 40 mg, HPLC purity ELSD=99.5%, retention time (min)=1.534; LRMS m/z Calcd for C19H29ClN2O3S, 401.0; obsd LRMS APCI (M+1) m/z 401.

EXAMPLE 157

N-[3-(2-Chloro-3-pyrrolidin-1-ylmethyl-phenoxy)-cyclobutylmethyl]-2,4,5-trifluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 19 mg, HPLC purity ELSD=100%, retention time (min)=1.891; LRMS m/z Calcd for C23H26ClF3N2O3S, 503.0; obsd LRMS APCI (M+1) m/z 503.

EXAMPLE 158

N-[3-(2-Chloro-3-pyrrolidin-1-ylmethyl-phenoxy)-cyclobutylmethyl]-N-methyl-2-trifluoromethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 26 mg, HPLC purity ELSD=100%, retention time (min)=1.894; LRMS m/z Calcd for C24H28ClF3N2O3S, 517.0; obsd LRMS APCI (M+1) m/z 517.

EXAMPLE 159

Benzo[b]thiophene-2-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 19 mg, HPLC purity ELSD=100%, retention time (min)=1.994; LRMS m/z Calcd for C25H29ClN2O3S2, 505.1; obsd LRMS APCI (M+1) m/z 505.

EXAMPLE 160

4-Chloro-N-[3-(2-chloro-3-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 22 mg, HPLC purity ELSD=100%, retention time (min)=1.92; LRMS m/z Calcd for C23H28Cl2N2O3S, 483.5; obsd LRMS APCI (M+1) m/z 483.

EXAMPLE 161

N-[3-(2-Chloro-3-pyrrolidin-1-ylmethyl-phenoxy)-cyclobutylmethyl]-2-fluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 26 mg, HPLC purity ELSD=100%, retention time (min)=1.809; LRMS m/z Calcd for C23H28ClFN2O3S, 467.0; obsd LRMS APCI (M+1) m/z 467.

EXAMPLE 162

Thiophene-3-sulfonic acid [3-(2-chloro-3-pyrrolidin-1-yl-methyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 19 mg, HPLC purity ELSD=99.7%, retention time (min)=1.758; LRMS m/z Calcd for C21H27ClN2O3S2, 455.0; obsd LRMS APCI (M+1) m/z 455.

EXAMPLE 163

N-[3-(2-Chloro-3-pyrrolidin-1-ylmethyl-phenoxy)-cyclobutylmethyl]-4-methoxy-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 27 mg, HPLC purity ELSD=100%, retention time (min)=1.825; LRMS m/z Calcd for C24H31ClN2O4S, 479.0; obsd LRMS APCI (M+1) m/z 479.

EXAMPLE 164

Propane-1-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 43 mg, HPLC purity ELSD=98.7%, retention time (min)=1.626; LRMS m/z Calcd for C20H31ClN2O3S, 415.0; obsd LRMS APCI (M+1) m/z 415.

EXAMPLE 165

Naphthalene-1-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 26 mg, HPLC purity ELSD=100%, retention time (min)=1.945; LRMS m/z Calcd for C27H31ClN2O3S, 499.1; obsd LRMS APCI (M+1) m/z 499.

EXAMPLE 166

N-(3-{[3-(2-Chloro-3-pyrrolidin-1-ylmethyl-phenoxy)-cyclobutylmethyl]-methyl-sulfamoyl}-phenyl)-acetamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 21 mg, HPLC purity ELSD=99.2%, retention time (min)=1.65; LRMS m/z Calcd for C25H32ClN3O4S, 506.1; obsd LRMS APCI (M+1) m/z 506.

EXAMPLE 167

5-Ethyl-thiophene-2-sulfonic acid [3-(2-chloro-3-pyrrolidin-1-ylmethyl-phenoxy)-cyclo-butylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 14 mg, HPLC purity ELSD=100% retention time (min)=1.953; LRMS m/z Calcd for C23H31ClN2O3S2, 483.1; obsd LRMS APCI (M+1) m/z 483.

EXAMPLE 168

Naphthalene-2-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 18 mg, HPLC purity ELSD=99.2%, retention time (min)=; 1.996 LRMS m/z Calcd for C27H31ClN2O3S, 499.1; obsd LRMS APCI (M+1) m/z 499.

EXAMPLE 169

3-Chloro-N-[3-(2-chloro-3-pyrrolidin-1-ylmethyl-phenoxy)-cyclobutylmethyl]-2,N-dimethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 26 mg, HPLC purity ELSD=100%, retention time (min)=1.968; LRMS m/z Calcd for C24H30Cl2N2O3S, 497.5; obsd LRMS APCI (M+1) m/z 497.

EXAMPLE 170

3,5-Dimethyl-isoxazole-4-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 49 mg, HPLC purity ELSD=98.8%, retention time (min)=1.738; LRMS m/z Calcd for C22H30ClN3O4S, 468.0; obsd LRMS APCI (M+1) m/z 468.

EXAMPLE 171

5-Chloro-1,3-dimethyl-1H-pyrazole-4-sulfonic acid [3-(2-chloro-3-pyrrolidin-1-ylmethyl-phenoxy)-cyclobutylmethyl]-methyl-amide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 15 mg, HPLC purity

EXAMPLE 172

N-[3-(2-Chloro-3-pyrrolidin-1-ylmethyl-phenoxy)-cyclobutylmethyl]-2,5,N-trimethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 27 mg, HPLC purity ELSD=100%, retention time (min)=1.922; LRMS m/z Calcd for C25H33ClN2O3S, 477.1; obsd LRMS APCI (M+1) m/z 477.

EXAMPLE 173

N-[3-(2-Chloro-3-pyrrolidin-1-ylmethyl-phenoxy)-cyclobutylmethyl]-2,4-difluoro-N-methyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 32 mg, HPLC purity ELSD=96.3%, 1.852; LRMS m/z Calcd for C23H27ClF2N2O3S, 485.0; obsd LRMS APCI (M+1) m/z 485.

EXAMPLE 174

3-Methyl-thiophene-2-sulfonic acid [3-(2-chloro-3-pyrrolidin-1-ylmethyl-phenoxy)-cyclobutylmethyl]-methylamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 18 mg, HPLC purity ELSD=100%, retention time (min)=1.838; LRMS m/z Calcd for C22H29ClN2O3S2, 469.1; obsd LRMS APCI (M+1) m/z 469.

EXAMPLE 175

N-[3-(2-Chloro-3-pyrrolidin-1-ylmethyl-phenoxy)-cyclobutylmethyl]-N-methyl-3-trifluoromethyl-benzenesulfonamide. Reaction was conducted using the conditions described in General Procedure S: Sulfonamide Coupling, using Example 41 as the starting amine and the appropriate sulonyl chloride. The product was purified by HPLC (Preparative Purification Method A) yielding the title compound as the TFA salt, 8 mg, HPLC purity ELSD=48%, 100, retention time (min)=1.928; LRMS m/z Calcd for C24H28ClF3N2O3S, 517.0; obsd LRMS APCI (M+1) m/z 517.

EXAMPLE 176

1-[3-(2-Chloro-3-pyrrolidin-1-ylmethyl-phenoxy)-cyclobutylmethyl]-3-(2,6-dimethyl-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 46 mg, HPLC purity ELSD=98.7%, retention time (min)=1.636; LRMS m/z Calcd for C26H34ClN3O2, 456; obsd LRMS APCI (M+1) m/z 456.

EXAMPLE 177

1-[3-(2-Chloro-3-pyrrolidin-1-ylmethyl-phenoxy)-cyclobutylmethyl]-3-(3-fluoro-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 36 mg, HPLC purity ELSD=99.2%, retention time (min)=1.693; LRMS m/z Calcd for C24H29ClFN3O2, 446; obsd LRMS APCI (M+1) m/z 446.

EXAMPLE 178

1-{[3-(2-Chloro-3-pyrrolidin-1-ylmethyl-phenoxy)-cyclobutyl]methyl}-1-methyl-3-(3-trifluoromethyl-phenyl)-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 34 mg, HPLC purity ELSD=99.6%, retention time (min)=1.829; LRMS m/z Calcd for C25H29ClF3N3O2, 496; obsd LRMS APCI (M+1) m/z 496.

EXAMPLE 179

1-[3-(2-Chloro-3-pyrrolidin-1-ylmethyl-phenoxy)-cyclobutylmethyl]-3-(3,5-dimethyl-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 45 mg, HPLC purity ELSD=99.1%, retention time (min)=1.759; LRMS m/z Calcd for C26H34ClN3O2, 456; obsd LRMS APCI (M+1) m/z 456.

EXAMPLE 180

3-(5-Chloro-2-methoxy-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 37 mg, HPLC purity ELSD=99.4%, retention time (min)=1.852; LRMS m/z Calcd for C25H31Cl2N3O3, 492; obsd LRMS APCI (M+1) m/z 492.

EXAMPLE 181

1-[3-(2-Chloro-3-pyrrolidin-1-ylmethyl-phenoxy)-cyclobutylmethyl]-3-(3-methoxy-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 37 mg, HPLC purity ELSD=99%, retention time (min)=1.652; LRMS m/z Calcd for C25H32ClN3O3, 458; obsd LRMS APCI (M+1) m/z 458.

EXAMPLE 182

3-(3-Chloro-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 47 mg, HPLC purity ELSD=99.1%, retention time (min)=1.748; LRMS m/z Calcd for C24H29Cl2N3O2, 462; obsd LRMS APCI (M+1) m/z 462.

EXAMPLE 183

1-[3-(2-Chloro-3-pyrrolidin-1-ylmethyl-phenoxy)-cyclobutylmethyl]-3-(2,4-difluoro-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 41 mg, HPLC purity ELSD=98.6%, retention time (min)=1.636; LRMS m/z Calcd for C24H28ClF2N3O2, 464; obsd LRMS APCI (M+1) m/z 464.

EXAMPLE 184

1-[3-(2-Chloro-3-pyrrolidin-1-ylmethyl-phenoxy)-cyclobutylmethyl]-1-methyl-3-phenyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 46 mg, HPLC purity ELSD=98.6%, retention time (min)= 1.611; LRMS m/z Calcd for C24H30ClN3O2, 428; obsd LRMS APCI (M+1) m/z 428.

EXAMPLE 185

1-[3-(2-Chloro-3-pyrrolidin-1-ylmethyl-phenoxy)-cyclobutylmethyl]-3-(2,5-dimethyl-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 41 mg, HPLC purity ELSD=97%, retention time (min)=1.713; LRMS m/z Calcd for C26H34ClN3O2, 456; obsd LRMS APCI (M+1) m/z 456.

EXAMPLE 186

3-(2-Chloro-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 44 mg, HPLC purity ELSD=97.1%, retention time (min)=1.737; LRMS m/z Calcd for C24H29Cl2N3O2, 462; obsd LRMS APCI (M+1) m/z 462.

EXAMPLE 187

1-[3-(2-Chloro-3-pyrrolidin-1-ylmethyl-phenoxy)-cyclobutylmethyl]-3-(2-methoxy-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 45 mg, HPLC purity ELSD=98.8%, retention time (min)=1.695; LRMS m/z Calcd for C25H32ClN3O3, 458; obsd LRMS APCI (M+1) m/z 458.

EXAMPLE 188

3-(3-Chloro-2-methyl-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 45 mg, HPLC purity ELSD=96.8%, retention time (min)=1.727; LRMS m/z Calcd for C25H31Cl2N3O2, 476; obsd LRMS APCI (M+1) m/z 476.

EXAMPLE 189

3-(2-Chloro-6-methyl-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 46 mg, HPLC purity ELSD=97.4%, retention time (min)=1.652; LRMS m/z Calcd for C25H31Cl2N3O2, 476; obsd LRMS APCI (M+1) m/z 476.

EXAMPLE 190

1-[3-(2-Chloro-3-pyrrolidin-1-ylmethyl-phenoxy)-cyclobutylmethyl]-1-methyl-3-p-tolyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 59 mg, HPLC purity ELSD=99.1%, retention time (min)= 1.677; LRMS m/z Calcd for C25H32ClN3O2, 442; obsd LRMS APCI (M+1) m/z 442.

EXAMPLE 191

1-[3-(2-Chloro-3-pyrrolidin-1-ylmethyl-phenoxy)-cyclobutylmethyl]-3-(2-methoxy-5-methyl-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 46 mg, HPLC purity ELSD=99.6%, retention time (min)=1.759; LRMS m/z Calcd for C26H34ClN3O3, 472; obsd LRMS APCI (M+1) m/z 472.

EXAMPLE 192

1-[3-(2-Chloro-3-pyrrolidin-1-ylmethyl-phenoxy)-cyclobutylmethyl]-3-(4-methoxy-2-methyl-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 46 mg, HPLC purity ELSD=98.3%, retention time (min)=1.607; LRMS m/z Calcd for C26H34ClN3O3, 472; obsd LRMS APCI (M+1) m/z 472.

EXAMPLE 193

3-(4-Chloro-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 46 mg, HPLC purity ELSD=99.1%, retention time (min)=1.733; LRMS m/z Calcd for C24H29Cl2N3O2, 462; obsd LRMS APCI (M+1) m/z 462.

EXAMPLE 194

1-[3-(2-Chloro-3-pyrrolidin-1-ylmethyl-phenoxy)-cyclobutylmethyl]-1-methyl-3-o-tolyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 62 mg, HPLC purity ELSD=96.8%, retention time (min)= 1.604; LRMS m/z Calcd for C25H32ClN3O2, 442; obsd LRMS APCI (M+1) m/z 442.

EXAMPLE 195

1-[3-(2-Chloro-3-pyrrolidin-1-ylmethyl-phenoxy)-cyclobutylmethyl]-3-(3,4-dimethyl-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 45 mg, HPLC purity ELSD=98.9%, retention time (min)=1.726; LRMS m/z Calcd for C26H34ClN3O2, 456; obsd LRMS APCI (M+1) m/z 456.

EXAMPLE 196

1-{[3-(2-Chloro-3-pyrrolidin-1-ylmethyl-phenoxy)-cyclobutyl]methyl}-1-methyl-3-(4-trifluoromethyl-phenyl)-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 49 mg, HPLC purity ELSD=99.8%, retention time (min)=1.793; LRMS m/z Calcd for C25H29ClF3N3O2, 496; obsd LRMS APCI (M+1) m/z 496.

EXAMPLE 197

1-{[3-(2-Chloro-3-pyrrolidin-1-ylmethyl-phenoxy)-cyclobutyl]methyl}-1-methyl-3-(2-trifluoromethyl-phenyl)-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 36 mg, HPLC purity ELSD=90%, retention time (min)=1.738; LRMS m/z Calcd for C25H29ClF3N3O2, 496; obsd LRMS APCI (M+1) m/z 496.

EXAMPLE 198

1-[3-(2-Chloro-3-pyrrolidin-1-ylmethyl-phenoxy)-cyclobutylmethyl]-3-(2-ethyl-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 40 mg, HPLC purity ELSD=96.2%, retention time (min)=1.693; LRMS m/z Calcd for C26H34ClN3O2, 456; obsd LRMS APCI (M+1) m/z 456.

EXAMPLE 199

3-(3-Chloro-4-methyl-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 39 mg, HPLC purity ELSD=99.6%, retention time (min)=1.815; LRMS m/z Calcd for C25H31Cl2N3O2, 476; obsd LRMS APCI (M+1) m/z 476.

EXAMPLE 200

3-(3-Acetyl-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 49 mg, HPLC purity ELSD=99.2%, retention time (min)=1.589; LRMS m/z Calcd for C26H32ClN3O3, 470; obsd LRMS APCI (M+1) m/z 470.

EXAMPLE 201

1-[3-(2-Chloro-3-pyrrolidin-1-ylmethyl-phenoxy)-cyclobutylmethyl]-3-ethyl-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 39 mg, HPLC purity ELSD=100%, retention time (min)= 1.441; LRMS m/z Calcd for C20H30ClN3O2, 380; obsd LRMS APCI (M+1) m/z 380.

EXAMPLE 202

1-[3-(2-Chloro-3-pyrrolidin-1-ylmethyl-phenoxy)-cyclobutylmethyl]-1-methyl-3-m-tolyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 62 mg, HPLC purity ELSD=98.9%, retention time

EXAMPLE 203

3-(5-Chloro-2-methyl-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 39 mg, HPLC purity ELSD=97%, retention time (min)=1.765; LRMS m/z Calcd for C25H31Cl2N3O2, 476; obsd LRMS APCI (M+1) m/z 476.

EXAMPLE 204

1-[3-(2-Chloro-3-pyrrolidin-1-ylmethyl-phenoxy)-cyclobutylmethyl]-3-(4-methoxy-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 47 mg, HPLC purity ELSD=98.9%, retention time (min)=1.604; LRMS m/z Calcd for C25H32ClN3O3, 458; obsd LRMS APCI (M+1) m/z 458.

EXAMPLE 205

1-[3-(2-Chloro-3-pyrrolidin-1-ylmethyl-phenoxy)-cyclobutylmethyl]-3-(4-fluoro-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 46 mg, HPLC purity ELSD=99.1%, retention time (min)=1.623; LRMS m/z Calcd for C24H29ClFN3O2, 446; obsd LRMS APCI (M+1) m/z 446.

EXAMPLE 206

1-[3-(2-Chloro-3-pyrrolidin-1-ylmethyl-phenoxy)-cyclobutylmethyl]-3-(2-fluoro-phenyl)-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 67 mg, HPLC purity ELSD=98.2%, retention time (min)=1.543; LRMS m/z Calcd for C24H29ClFN3O2, 446; obsd LRMS APCI (M+1) m/z 446.

EXAMPLE 207

3-tert-Butyl-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 60 mg, HPLC purity ELSD=99.4%, retention time (min)= 1.612; LRMS m/z Calcd for C22H34ClN3O2, 408; obsd LRMS APCI (M+1) m/z 408.

EXAMPLE 208

3-(4-Chloro-2-methyl-phenyl)-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 51 mg, HPLC purity ELSD=97.5%, retention time (min)=1.722; LRMS m/z Calcd for C25H31Cl2N3O2, 476; obsd LRMS APCI (M+1) m/z 476.

EXAMPLE 209

3-Benzyl-1-[3-(2-chloro-3-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 44 mg, HPLC purity ELSD=99.8%, retention time (min)= 1.615; LRMS m/z Calcd for C25H32ClN3O2, 442; obsd LRMS APCI (M+1) m/z 442.

EXAMPLE 210

1-[3-(2-Chloro-3-pyrrolidin-1-ylmethyl-phenoxy)-cyclobutylmethyl]-3-isopropyl-1-methyl-urea. Reaction was conducted using the conditions described in General Procedure U: Urea Formation from an Isocyanate and an Amine, using Example 41 as the starting amine and the appropriate isocyanate. The product was purified by HPLC (Preparative Purification Method A) yielding the title compound as the TFA salt, 55 mg, HPLC purity ELSD=100%, retention time (min)=1.48; LRMS m/z Calcd for C21H32ClN3O2, 394; obsd LRMS APCI (M+1) m/z 394.

Methyl({trans-3-[3-chloro-4-(pyrrolidin-1-ylmethyl)phenoxy]cyclobutyl}methyl)amine

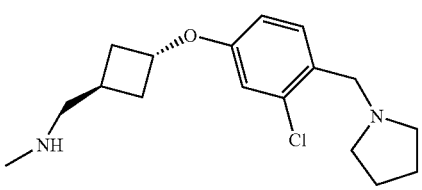

Scheme of the Synthesis

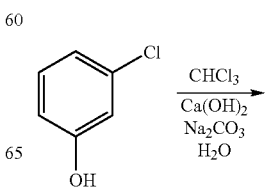

-continued

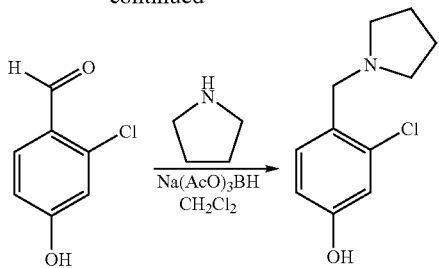

Intermediate 14

2-Chloro-4-hydroxybenzaldehyde. 3-Chlorophenol (CAS 108-43-0) (49.2 g, 0.380 mol), calcium hydroxide (122.0 g), and sodium carbonate (139.4 g) were suspended in water (872 mL). Chloroform (90.6 g, 0.760 mol) was added for 80 min, and the mixture was refluxed under vigorous stirring for 3 h. The reaction mixture was cooled on ice bath. Concentrated HCl (385 mL) and chloroform (300 mL) were added. The aqueous layer was discarded. The organic one was dried with anhydrous $Na_2SO_4$ (50 g) and evaporated in vacuo. The residue was purified by chromatography (silica gel 63-100 μm, 600 g, $CCl_4 \rightarrow CHCl_3 \rightarrow CHCl_3/EtOAc$ 93:7). Fractions containing the product were combined, evaporated, and coevaporated with dioxane to give the title compound (9.77 g, 0.062 mol, 16%) as a white powder. $^1$H NMR data (DMSO-d6): 11.06 (s, 1H, CO$\underline{H}$); 10.14 (s, 1H, OH); 7.75 (d, 1H, J=8.5 Hz, Ar—H); 6.92 (d, 1H, J=2 Hz, Ar—H); 6.85 (d.d., 1H, $J_1$=8.5 Hz, $J_2$=2 Hz, Ar—H).

Intermediate 15

3-Chloro-4-pyrrolidin-1-ylmethyl-phenol. Pyrrolidine (22.0 mL, 0.255 mol) was added to a suspension of intermediate 14, 2-chloro-4-hydroxybenzaldehyde (30.8 g, 0.196 mol) in dichloromethane (620 mL). The reaction mixture was cooled with an ice bath. Sodium triacetoxyborohydride (65.8 g, 0.295 mol) was added in portions under stirring. The reaction mixture was stirred for 12 h at room temperature. Water (600 mL) and dichloromethane (600 mL) were added. The reaction mixture was acidified with concentrated HCl to pH~2. The organic layer was separated. The aqueous one was subjected to extraction with EtOAc (2×500 mL), and the extracts were discarded. The aqueous fraction was alkalized with a saturated solution of potassium carbonate to pH 9-10. The product was extracted with $CHCl_3$ (3×500 mL). The organic layer was dried with anhydrous $Na_2SO_4$ (50 g). The solvent was evaporated in vacuo. The obtained oil was refluxed in $Et_2O$ (400 mL) for 1 h. Then hexane (200 mL) was added, and the mixture was cooled. The formed residue was separated by filtration and dried. $^1$H NMR spectrum showed the presence of acetic acid (2.3% w/w). The residue was dissolved in a mixture of $Et_2O$ (100 mL) and $CH_2Cl_2$ (100 mL), and a solution of NaOH (0.4 g) in water (4 mL) was added. The product was extracted form the organic layer. The extract was dried with anhydrous $Na_2SO_4$ (50 g), evaporated, and coevaporated with dioxane. The title compound (23.5 g, 0.11 mol, 56%) was obtained as a pale-yellow powder. LC/MS data: 212.0 and 214.0 (M+H)$^+$ (calculated for $C_{22}H_{14}ClNO$ 211.7). $^1$H NMR data (DMSO-d6): 9.73 (br.s., 1H, OH); 7.24 (d, 1H, J=8.3 Hz, Ar—H); 6.78 (d, 1H, J=2.4 Hz, Ar—H); 6.70 (d.d., 1H, $J_1$=8.3 Hz, $J_2$=2.4 Hz, Ar—H); 3.54 (s, 2H, $\underline{CH_2}$Ar); 2.40-2.47 (m, 4H); 1.63-1.70 (m, 4H).

EXAMPLE 211 tert-Butyl Methyl({trans-3-[3-chloro-4-(pyrrolidin-1-ylmethyl)phenoxy]cyclobutyl}-methyl) carbamate. A mixture of intermediate 6, cis-3-{[(tert-Butoxycarbonyl)(methyl) amino]methyl}cyclobutyl methanesulfonate (15 g, 51 mmol), intermediate 15, 3-chloro-4-pyrrolidin-1-ylmethyl-phenol (21.7 g, 0.102 mol) and $Cs_2CO_3$ (33.3 g, 102 mmol) in DMSO (200 mL) was heated to 90° C. for 2 h under vigorous stirring in a flow of argon and cooled. Water (200 ml) was added, and the layers were separated. The water layer was extracted with ether (3×300 ml), the combined organic layers were washed with water (300 mL), brine, dried with $Na_2SO_4$, and evaporated. The residue was purified by chromatography (silica gel, 63/100 μm, 500 g, $CHCl_3$/hexane 20:80→100:0, $CHCl_3$/MeOH 100:0→80:20 to furnish the title compound (13.14 g, 63%). LC/MS data: 409.1, 411.1, 412.1 (M+H) (calculated for $C_{22}H_{33}ClN_2O_3$ 408.97). $^1$H NMR-data (DMSO-d6): 7.35 (d, 1H, J=8.5 Hz, Ar); 6.84 (d, 1H, J=2.2 Hz, Ar); 6.77 (dd, 1H, J1=2.2 Hz, J2=8.5 Hz, Ar); 4.75-4.86 (m, 1H); 3.62 (brs, 2H, $CH_2$); 3.33 (d, 2H, J=7.8 Hz, $CH_2$); 2.77 (brs, 3H, $NCH_3$); 2.40-2.60 (m, 5H); 2.02-2.28 (m, 4H); 1.62-1.75 (m, 4H); 1.41 (s, 9H, Boc).

EXAMPLE 212

Methyl({trans-3-[3-chloro-4-(pyrrolidin-1-ylmethyl)phenoxy]cyclobutyl}methyl)amine (101828-013). Trifluoroacetic acid (24 mL, 321 mmol) was added to a solution of example 211, tert-butyl methyl({trans-3-[3-chloro-4-(pyrrolidin-1-ylmethyl)phenoxy]cyclobutyl}methyl) carbamate (13.14 g, 32.1 mmol) in dichloromethane (200 mL). The reaction mixture was stirred at room temperature for 2 h and evaporated in vacuo. Water (50 ml), $CHCl_3$ (200 ml), and $K_2CO_3$ (50 ml) were added to the residue, the mixture was shaken and the layers were separated. The aqueous layer was extracted with $CHCl_3$ (3×100 mL). The combined extracts were dried and evaporated. The title compound (9.5 g, 96%) was obtained as a yellow oil. LC/MS data: 309.1, 311.1 (M+H) (calculated for $C_{17}H_{25}ClN_2O$ 308.85). $^1$H NMR-data (DMSO-d6): 7.32 (d, 1H, J=8.5 Hz, Ar); 6.83 (d, 1H, J=2.5 Hz, Ar); 6.76 (dd, 1H, J1=8.5 Hz, J2=2.5 Hz, Ar); 4.73-4.82 (m, 1H), 3.57 (s, 2H, $CH_2$); 2.56 (d, 2H, J=7.3 Hz, $CH_2$); 2.40-2.48 (m, 4H); 2.31-2.403 (m, 1H); 2.28 (s, 3H, $NCH_3$); 2.17-2.26 (m, 2H); 2.04-2.15 (m, 2H); 1.62-1.73 (m, 4H).

EXAMPLE 213

Pyrazine-2-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 43 mg; HPLC purity ELSD=100%, retention time (min)=1.218; LRMS m/z Calcd for C22H27ClN4O2, 414.9; obsd LRMS APCI (M+1) m/z 415.

EXAMPLE 214

N-[3-(3-Chloro-4-pyrrolidin-1-ylmethyl-phenoxy)-cyclobutylmethyl]-N-methyl-2-pyridin-2-yl-acetamide. Reaction was conducted using the conditions described in General Procedure C: Amide Coupling, using Example 212 as the starting amine and the appropriate acid. The product was purified by HPLC (Preparative Purification Method A) yield-

EXAMPLE 215

5-Methyl-pyrazine-2-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 44 mg; HPLC purity ELSD=100%, retention time (min)=1.255; LRMS m/z Calcd for C23H29ClN4O2, 429.0; obsd LRMS APCI (M+1) m/z 429.

EXAMPLE 216

1-Ethyl-1H-pyrazole-4-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 16 mg; HPLC purity ELSD=100%, retention time (min)=1.272; LRMS m/z Calcd for C23H31ClN4O2, 431.0; obsd LRMS APCI (M+1) m/z 431.

EXAMPLE 217

Cyclohexanecarboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 57 mg; HPLC purity ELSD=100%, retention time (min)=1.52; LRMS m/z Calcd for C24H35ClN2O2, 419.0; obsd LRMS APCI (M+1) m/z 419.

EXAMPLE 218

Cyclopentanecarboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 51 mg; HPLC purity ELSD=100%, retention time (min)=1.473; LRMS m/z Calcd for C23H33ClN2O2, 405.0; obsd LRMS APCI (M+1) m/z 405.

EXAMPLE 219

N-[3-(3-Chloro-4-pyrrolidin-1-ylmethyl-phenoxy)-cyclobutylmethyl]-2,5-difluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 12 mg; HPLC purity ELSD=100%, retention time (min)=1.512; LRMS m/z Calcd for C24H27ClF2N2O2, 448.9; obsd LRMS APCI (M+1) m/z 449.

EXAMPLE 220

3-Ethyl-isoxazole-5-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 8 mg; HPLC purity ELSD=100%, retention time (min)=1.446; LRMS m/z Calcd for C23H30ClN3O3, 432.0; obsd LRMS APCI (M+1) m/z 432.

EXAMPLE 221

Cyclobutanecarboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 61 mg; HPLC purity ELSD=100%, retention time (min)=1.398; LRMS m/z Calcd for C22H31ClN2O2, 391.0; obsd LRMS APCI (M+1) m/z 391.

EXAMPLE 222

N-[3-(3-Chloro-4-pyrrolidin-1-ylmethyl-phenoxy)-cyclobutylmethyl]-N-methyl-isobutyramide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 39 mg; HPLC purity ELSD=100%, retention time (min)=1.354; LRMS m/z Calcd for C21H31ClN2O2, 378.9; obsd LRMS APCI (M+1) m/z 379.

EXAMPLE 223

N-[3-(3-Chloro-4-pyrrolidin-1-ylmethyl-phenoxy)-cyclobutylmethyl]-6,N-dimethyl-nicotinamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 23 mg; HPLC purity ELSD=100%, retention time (min)=1.076; LRMS m/z Calcd for C24H30ClN3O2, 428.0; obsd LRMS APCI (M+1) m/z 428.

EXAMPLE 224

N-[3-(3-Chloro-4-pyrrolidin-1-ylmethyl-phenoxy)-cyclobutylmethyl]-2-methoxy-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 44 mg; HPLC purity ELSD=100%, retention time (min)=1.187; LRMS m/z Calcd for C20H29ClN2O3, 380.9; obsd LRMS APCI (M+1) m/z 381.

EXAMPLE 225

N-[3-(3-Chloro-4-pyrrolidin-1-ylmethyl-phenoxy)-cyclobutylmethyl]-2-cyclopropyl-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 58 mg; HPLC purity ELSD=99.6%, retention time (min)=1.355; LRMS m/z Calcd for C22H31ClN2O2, 391.0; obsd LRMS APCI (M+1) m/z 391.

EXAMPLE 226

N-[3-(3-Chloro-4-pyrrolidin-1-ylmethyl-phenoxy)-cyclobutylmethyl]-2-(3,5-dimethyl-pyrazol-1-yl)-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 55 mg; HPLC purity ELSD=100%, retention time (min)=1.179; LRMS m/z Calcd for C24H33ClN4O2, 445.0; obsd LRMS APCI (M+1) m/z 445.

EXAMPLE 227

5-Methyl-isoxazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 54 mg; HPLC purity ELSD=100%, retention time (min)=1.365; LRMS m/z Calcd for C22H28ClN3O3, 417.9; obsd LRMS APCI (M+1) m/z 418.

EXAMPLE 228

5-Ethyl-2-methyl-2H-pyrazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 44 mg; HPLC purity ELSD=100%, retention time (min)=1.37; LRMS m/z Calcd for C24H33ClN4O2, 445.0; obsd LRMS APCI (M+1) m/z 445.

EXAMPLE 229

N-[3-(3-Chloro-4-pyrrolidin-1-ylmethyl-phenoxy)-cyclobutylmethyl]-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 43 mg; HPLC purity ELSD=100%, retention time (min)=1.185; C19H27ClN2O2, 350.9; obsd LRMS APCI (M+1) m/z 351.

EXAMPLE 230

(S)—N-[3-(3-Chloro-4-pyrrolidin-1-ylmethyl-phenoxy)-cyclobutylmethyl]-2-hydroxy-N-methyl-2-phenyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 19 mg; HPLC purity ELSD=80.7%, retention time (min)=1.421; LRMS m/z Calcd for C25H31ClN2O3, 443.0; obsd LRMS APCI (M+1) m/z 443.

EXAMPLE 231

N-[3-(3-Chloro-4-pyrrolidin-1-ylmethyl-phenoxy)-cyclobutylmethyl]-3,4-difluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 15 mg; HPLC purity ELSD=100%, retention time (min)=1.51; LRMS m/z Calcd for C24H27ClF2N2O2, 448.9; obsd LRMS APCI (M+1) m/z 449.

EXAMPLE 232

N-[3-(3-Chloro-4-pyrrolidin-1-ylmethyl-phenoxy)-cyclobutylmethyl]-4-fluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 43 mg; HPLC purity ELSD=100%, retention time (min)=1.45; LRMS m/z Calcd for C24H28ClFN2O2, 430.9; obsd LRMS APCI (M+1) m/z 431.

EXAMPLE 233

5-Cyclopropyl-2H-pyrazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 21 mg; HPLC purity ELSD=100%, retention time (min)=1.339; LRMS m/z Calcd for C24H31ClN4O2, 443.0; obsd LRMS APCI (M+1) m/z 443.

EXAMPLE 234

3-Chloro-N-[3-(3-chloro-4-pyrrolidin-1-ylmethyl-phenoxy)-cyclobutylmethyl]-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 41 mg; HPLC purity ELSD=100%, retention time (min)=1.532; LRMS m/z Calcd for C24H28Cl2N2O2, 447.4; obsd LRMS APCI (M+1) m/z 447.

EXAMPLE 235

3-Ethyl-5-methyl-isoxazole-4-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 15 mg; HPLC purity ELSD=100%, retention time (min)= 1.382; LRMS m/z Calcd for C24H32ClN3O3, 446.0; obsd LRMS APCI (M+1) m/z 446.

EXAMPLE 236

N-[3-(3-Chloro-4-pyrrolidin-1-ylmethyl-phenoxy)-cyclobutylmethyl]-3-methoxy-N-methyl-propionamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 37 mg; HPLC purity ELSD=100%, retention time (min)=1.232; LRMS m/z Calcd for C21H31ClN2O3, 394.9; obsd LRMS APCI (M+1) m/z 395.

EXAMPLE 237

4-Chloro-N-[3-(3-chloro-4-pyrrolidin-1-ylmethyl-phenoxy)-cyclobutylmethyl]-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 40 mg; HPLC purity ELSD=100%, retention time (min)=1.538; LRMS m/z Calcd for C24H28Cl2N2O2, 447.4; obsd LRMS APCI (M+1) m/z 447.

EXAMPLE 238

2-Methoxy-pyrimidine-5-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 17 mg; HPLC purity ELSD=93.9%, retention time (min)=1.226; LRMS m/z Calcd for C23H29ClN4O3, 445.0; obsd LRMS APCI (M+1) m/z 445.

EXAMPLE 239

N-[3-(3-Chloro-4-pyrrolidin-1-ylmethyl-phenoxy)-cyclobutylmethyl]-3-fluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 60 mg; HPLC purity ELSD=100%, retention time (min)=1.443; LRMS m/z Calcd for C24H28ClFN2O2, 430.9; obsd LRMS APCI (M+1) m/z 431.

EXAMPLE 240

N-[3-(3-Chloro-4-pyrrolidin-1-ylmethyl-phenoxy)-cyclobutylmethyl]-2,N-dimethyl-nicotinamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 60 mg; HPLC purity ELSD=100%, retention time (min)=1.063; LRMS m/z Calcd for C24H30ClN3O2, 428.0; obsd LRMS APCI (M+1) m/z 428.

EXAMPLE 241

1-Isopropyl-1H-pyrazole-4-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 16 mg; HPLC purity ELSD=100%, retention time (min)=1.333; LRMS m/z Calcd for C24H33ClN4O2, 445.0; obsd LRMS APCI (M+1) m/z 445.

EXAMPLE 242

6-Methyl-pyridine-2-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 51 mg; HPLC purity ELSD=100%, retention time (min)=1.193; LRMS m/z Calcd for C24H30ClN3O2, 428.0; obsd LRMS APCI (M+1) m/z 428.

EXAMPLE 243

1,5-Dimethyl-1H-pyrazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 21 mg; HPLC purity ELSD=98.4%, retention time (min)= 1.311; LRMS m/z Calcd for C23H31ClN4O2, 431.0; obsd LRMS APCI (M+1) m/z 431.

EXAMPLE 244

2-Ethyl-4-methyl-oxazole-5-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 14 mg; HPLC purity ELSD=100%, retention time (min)=1.371; LRMS m/z Calcd for C24H32ClN3O3, 446.0; obsd LRMS APCI (M+1) m/z 446.

EXAMPLE 245

N-[3-(3-Chloro-4-pyrrolidin-1-ylmethyl-phenoxy)-cyclobutylmethyl]-3,3,N-trimethyl-butyramide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 56 mg; HPLC purity

EXAMPLE 246

5-Cyclopropyl-oxazole-4-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 14 mg; HPLC purity ELSD=95.5%, retention time (min)=1.4; LRMS m/z Calcd for C24H30ClN3O3, 444.0; obsd LRMS APCI (M+1) m/z 444.

ELSD=100%, retention time (min)=1.515; LRMS m/z Calcd for C23H35ClN2O2, 407.0; obsd LRMS APCI (M+1) m/z 407.

EXAMPLE 247

N-[3-(3-Chloro-4-pyrrolidin-1-ylmethyl-phenoxy)-cyclobutylmethyl]-3,N-dimethyl-butyramide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 40 mg; HPLC purity ELSD=100%, retention time (min)=1.447; LRMS m/z Calcd for C22H33ClN2O2, 393.0; obsd LRMS APCI (M+1) m/z 393.

EXAMPLE 248

N-[3-(3-Chloro-4-pyrrolidin-1-ylmethyl-phenoxy)-cyclobutylmethyl]-2-methoxy-N-methyl-nicotinamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 17 mg; HPLC purity ELSD=100%, retention time (min)=1.353; LRMS m/z Calcd for C24H30ClN3O3, 444.0; obsd LRMS APCI (M+1) m/z 444.

EXAMPLE 249

N-[3-(3-Chloro-4-pyrrolidin-1-ylmethyl-phenoxy)-cyclobutylmethyl]-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 64 mg; HPLC purity ELSD=100%, retention time (min)=1.408; LRMS m/z Calcd for C24H29ClN2O2, 413.0; obsd LRMS APCI (M+1) m/z 413.

EXAMPLE 250

5-Cyclopropyl-isoxazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 16 mg; HPLC purity ELSD=100%, retention time (min)=1.505; LRMS m/z Calcd for C24H30ClN3O3, 444.0; obsd LRMS APCI (M+1) m/z 444.

EXAMPLE 251

3-Isopropyl-isoxazole-5-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 13 mg; HPLC purity ELSD=100%, retention time (min)=1.519; LRMS m/z Calcd for C24H32ClN3O3, 446.0; obsd LRMS APCI (M+1) m/z 446.

EXAMPLE 252

N-[3-(3-Chloro-4-pyrrolidin-1-ylmethyl-phenoxy)-cyclobutylmethyl]-2-(3-fluoro-phenyl)-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 53 mg; HPLC purity ELSD=98.6%, retention time (min)=1.501; LRMS m/z Calcd for C25H30ClFN2O2, 445.0; obsd LRMS APCI (M+1) m/z 445.

EXAMPLE 253

4-Methyl-furazan-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 33 mg; HPLC purity ELSD=95.6%, retention time (min)=1.47; LRMS m/z Calcd for C21H27ClN4O3, 418.9; obsd LRMS APCI (M+1) m/z 419.

EXAMPLE 254

N-[3-(3-Chloro-4-pyrrolidin-1-ylmethyl-phenoxy)-cyclobutylmethyl]-2,4-difluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 12 mg; HPLC purity ELSD=100%, retention time (min)=1.512; LRMS m/z Calcd for C24H27ClF2N2O2, 448.9; obsd LRMS APCI (M+1) m/z 449.

EXAMPLE 255

N-[3-(3-Chloro-4-pyrrolidin-1-ylmethyl-phenoxy)-cyclobutylmethyl]-2-(2-fluoro-phenyl)-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 59 mg; HPLC purity ELSD=100%, retention time (min)=1.498; LRMS m/z Calcd for C25H30ClFN2O2, 445.0; obsd LRMS APCI (M+1) m/z 445.

EXAMPLE 256

N-[3-(3-Chloro-4-pyrrolidin-1-ylmethyl-phenoxy)-cyclobutylmethyl]-2,5,N-trimethyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 17 mg; HPLC purity ELSD=100%, retention time (min)=1.586; LRMS m/z Calcd for C26H33ClN2O2, 441.0; obsd LRMS APCI (M+1) m/z 441.

EXAMPLE 257

N-[3-(3-Chloro-4-pyrrolidin-1-ylmethyl-phenoxy)-cyclobutylmethyl]-2,3-difluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 14 mg; HPLC purity ELSD=100%, retention time (min)=1.519; LRMS m/z Calcd for C24H27ClF2N2O2, 448.9; obsd LRMS APCI (M+1) m/z 449.

EXAMPLE 258

N-[3-(3-Chloro-4-pyrrolidin-1-ylmethyl-phenoxy)-cyclobutylmethyl]-3,5-difluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 16 mg; HPLC purity ELSD=100%, retention time (min)=1.519; LRMS m/z Calcd for C24H27ClF2N2O2, 448.9; obsd LRMS APCI (M+1) m/z 449.

EXAMPLE 259

N-[3-(3-Chloro-4-pyrrolidin-1-ylmethyl-phenoxy)-cyclobutylmethyl]-4,N-dimethyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 46 mg; HPLC purity ELSD=100%, retention time (min)=1.487; LRMS m/z Calcd for C25H31ClN2O2, 427.0; obsd LRMS APCI (M+1) m/z 427.

EXAMPLE 260

N-[3-(3-Chloro-4-pyrrolidin-1-ylmethyl-phenoxy)-cyclobutylmethyl]-N-methyl-2-(3-methyl-pyrazol-1-yl)-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 48 mg; HPLC purity ELSD=100%, retention time (min)=1.211; LRMS m/z Calcd for C23H31ClN4O2, 431.0; obsd LRMS APCI (M+1) m/z 431.

EXAMPLE 261

N-[3-(3-Chloro-4-pyrrolidin-1-ylmethyl-phenoxy)-cyclobutylmethyl]-N-methyl-isonicotinamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 54 mg; HPLC purity ELSD=97.0%, retention time (min)=1.059; LRMS m/z Calcd for C23H28ClN3O2, 413.9; obsd LRMS APCI (M+1) m/z 414.

EXAMPLE 262

5-Isopropyl-isoxazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 15 mg; HPLC purity ELSD=100%, retention time (min)=1.565; LRMS m/z Calcd for C24H32ClN3O3, 446.0; obsd LRMS APCI (M+1) m/z 446.

EXAMPLE 263

263 N-[3-(3-Chloro-4-pyrrolidin-1-ylmethyl-phenoxy)-cyclobutylmethyl]-N-methyl-2-(4-methyl-furazan-3-yl)-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 10 mg; HPLC purity ELSD=100%, retention time (min)=1.394; LRMS m/z Calcd for C22H29ClN4O3, 432.9; obsd LRMS APCI (M+1) m/z 433.

EXAMPLE 264

N-[3-(3-Chloro-4-pyrrolidin-1-ylmethyl-phenoxy)-cyclobutylmethyl]-4,4,4-trifluoro-N-methyl-butyramide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 19 mg; HPLC purity ELSD=100%, retention time (min)=1.477; LRMS m/z Calcd for C21H28ClF3N2O2, 432.9; obsd LRMS APCI (M+1) m/z 433.

EXAMPLE 265

2-Ethyl-5-methyl-2H-pyrazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 17 mg; HPLC purity ELSD=100%, retention time (min)=1.353; LRMS m/z Calcd for C24H33ClN4O2, 445.0; obsd LRMS APCI (M+1) m/z 445.

EXAMPLE 266

5-Ethyl-isoxazole-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification

EXAMPLE 267

Pyridine-2-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 43 mg; HPLC purity ELSD=100%, retention time (min)=1.206; LRMS m/z Calcd for C23H28ClN3O2, 413.9; obsd LRMS APCI (M+1) m/z 414.

EXAMPLE 268

4-Methyl-oxazole-5-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 46 mg; HPLC purity ELSD=98.1%, retention time (min)=1.264; LRMS m/z Calcd for C22H28ClN3O3, 417.9; obsd LRMS APCI (M+1) m/z 418.

EXAMPLE 269

Furazan-3-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 36 mg; HPLC purity ELSD=89.4%, retention time (min)=1.321; LRMS m/z Calcd for C20H25ClN4O3, 404.9; obsd LRMS APCI (M+1) m/z 405.

EXAMPLE 270

N-[3-(3-Chloro-4-pyrrolidin-1-ylmethyl-phenoxy)-cyclobutylmethyl]-N-methyl-2-pyridin-3-yl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 42 mg; HPLC purity ELSD=91.8%, retention time (min)=1.076; LRMS m/z Calcd for C24H30ClN3O2, 428.0; obsd LRMS APCI (M+1) m/z 428.

EXAMPLE 271

N-[3-(3-Chloro-4-pyrrolidin-1-ylmethyl-phenoxy)-cyclobutylmethyl]-2,2,N-trimethyl-propionamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 58 mg; HPLC purity ELSD=100%, retention time (min)=1.463; LRMS m/z Calcd for C22H33ClN2O2, 393.0; obsd LRMS APCI (M+1) m/z 393.

EXAMPLE 272

N-[3-(3-Chloro-4-pyrrolidin-1-ylmethyl-phenoxy)-cyclobutylmethyl]-N-methyl-nicotinamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 50 mg; HPLC purity ELSD=100%, retention time (min)=1.073; LRMS m/z Calcd for C23H28ClN3O2, 413.9; obsd LRMS APCI (M+1) m/z 414.

EXAMPLE 273

N-[3-(3-Chloro-4-pyrrolidin-1-ylmethyl-phenoxy)-cyclobutylmethyl]-2-cyclopentyl-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 39 mg; HPLC purity ELSD=100%, retention time (min)=1.559; LRMS m/z Calcd for C24H35ClN2O2, 419.0; obsd LRMS APCI (M+1) m/z 419.

EXAMPLE 274

N-[3-(3-Chloro-4-pyrrolidin-1-ylmethyl-phenoxy)-cyclobutylmethyl]-2-(3,5-dimethyl-isoxazol-4-yl)-N-methyl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 44 mg; HPLC purity ELSD=91.9%, retention time (min)=1.322; LRMS m/z Calcd for C24H32ClN3O3, 446.0; obsd LRMS APCI (M+1) m/z 446.

EXAMPLE 275

N-[3-(3-Chloro-4-pyrrolidin-1-ylmethyl-phenoxy)-cyclobutylmethyl]-2-fluoro-N-methyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 56 mg; HPLC purity ELSD=100%, retention time (min)=1.45; LRMS m/z Calcd for C24H28ClFN2O2, 430.9; obsd LRMS APCI (M+1) m/z 431.

EXAMPLE 276

1-Methyl-cyclopropanecarboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 62 mg; HPLC purity ELSD=100%, retention time (min)=1.351; LRMS m/z Calcd for C22H31ClN2O2, 391.0; obsd LRMS APCI (M+1) m/z 391.

EXAMPLE 277

Tetrahydro-pyran-4-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 20 mg; HPLC purity ELSD=100%, retention time (min)=1.26; LRMS m/z Calcd for C23H33ClN2O3, 421.0; obsd LRMS APCI (M+1) m/z 421.

EXAMPLE 278

N-[3-(3-Chloro-4-pyrrolidin-1-ylmethyl-phenoxy)-cyclobutylmethyl]-N-methyl-2-pyrazol-1-yl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 46 mg; HPLC purity ELSD=100%, retention time (min)=1.199; LRMS m/z Calcd for C22H29ClN4O2, 417.0; obsd LRMS APCI (M+1) m/z 417.

EXAMPLE 279

Cyclopropanecarboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 43 mg; HPLC purity ELSD=100%, retention time (min)=1.31; LRMS m/z Calcd for C21H29ClN2O2, 376.9; obsd LRMS APCI (M+1) m/z 377.

EXAMPLE 280

3,5-Dimethyl-isoxazole-4-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 21 mg; HPLC purity ELSD=100%, retention time (min)=1.308; LRMS m/z Calcd for C23H30ClN3O3, 432.0; obsd LRMS APCI (M+1) m/z 432.

EXAMPLE 281

N-[3-(3-Chloro-4-pyrrolidin-1-ylmethyl-phenoxy)-cyclobutylmethyl]-N-methyl-2-pyridin-4-yl-acetamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 55 mg; HPLC purity ELSD=93.69 1.072; LRMS m/z Calcd for C24H30ClN3O2, 428.0; obsd LRMS APCI (M+1) m/z 428.

EXAMPLE 282

2,6-Dimethyl-pyrimidine-4-carboxylic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 18 mg; HPLC purity ELSD=100%, retention time (min)=1.228; LRMS m/z Calcd for C24H31ClN4O2, 443.0; obsd LRMS APCI (M+1) m/z 443.

EXAMPLE 283

N-[3-(3-Chloro-4-pyrrolidin-1-ylmethyl-phenoxy)-cyclobutylmethyl]-2,4,N-trimethyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 17 mg; HPLC purity ELSD=100%, retention time (min)=1.58; LRMS m/z Calcd for C26H33ClN2O2, 441.0; obsd LRMS APCI (M+1) m/z 441.

EXAMPLE 284

N-[3-(3-Chloro-4-pyrrolidin-1-ylmethyl-phenoxy)-cyclobutylmethyl]-N-methyl-propionamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 39 mg; HPLC purity ELSD=98.50 1.277; LRMS m/z Calcd for C20H29Cl N2O2, 364.9; obsd LRMS APCI (M+1) m/z 365.

EXAMPLE 285

4-Methyl-pentanoic acid [3-(3-chloro-4-pyrrolidin-1-ylmethyl-phenoxy)-cyclobutylmethyl]-methyl-amide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 52 mg; HPLC purity ELSD=100%, retention time (min)=1.532; LRMS m/z Calcd for C23H35ClN2O2, 407.0; obsd LRMS APCI (M+1) m/z 407.

EXAMPLE 286

N-[3-(3-Chloro-4-pyrrolidin-1-ylmethyl-phenoxy)-cyclobutylmethyl]-3,4,N-trimethyl-benzamide. Reaction was conducted using the conditions described in General Procedure C: Amide Coupling, using Example 212 as the starting amine and the appropriate acid. The product was purified by HPLC (Preparative Purification Method A) yielding the title compound as the TFA salt, 18 mg; HPLC purity ELSD=100%, retention time (min)=1.581; LRMS m/z Calcd for C26H33ClN2O2, 441.0; obsd LRMS APCI (M+1) m/z 441.

EXAMPLE 287

N-[3-(3-Chloro-4-pyrrolidin-1-ylmethyl-phenoxy)-cyclobutylmethyl]-2,5-dimethoxy-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 8 mg, HPLC purity ELSD=96.5%, retention time (min)=1.637; LRMS, m/z Calcd for $C_{25}H_{33}ClN_2O_5S$, 509.1; obsd LRMS APCI (M+1) m/z 509.

EXAMPLE 288

N-[3-(3-Chloro-4-pyrrolidin-1-ylmethyl-phenoxy)-cyclobutylmethyl]-2,4-difluoro-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 9 mg, HPLC purity ELSD=97.2%, retention time (min)=1.682; LRMS, m/z Calcd for $C_{23}H_{27}ClF_2N_2O_3S$, 485.0; obsd LRMS APCI (M+1) m/z 485.

EXAMPLE 289

Prop-2-ene-1-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 35 mg, HPLC purity ELSD=96.7%, retention time (min)=1.428; LRMS, m/z Calcd for $C_{20}H_{29}ClN_2O_3S$, 413.0; obsd LRMS APCI (M+1) m/z 413.

EXAMPLE 290

N-(3-{[3-(3-Chloro-4-pyrrolidin-1-ylmethyl-phenoxy)-cyclobutylmethyl]-methyl-sulfamoyl}-phenyl)-acetamide. Reaction was conducted using the conditions described in General Procedure S: Sulfonamide Coupling, using Example 212 as the starting amine and the appropriate sulfonyl chloride. The product was purified by HPLC (Preparative Purification Method A) yielding the title compound as the TFA salt, 38 mg, HPLC purity ELSD=100%, retention time (min)=1.441; LRMS, m/z Calcd for $C_{25}H_{32}ClN_3O_4S$, 506.1; obsd LRMS APCI (M+1) m/z 506.

EXAMPLE 291

N-[3-(3-Chloro-4-pyrrolidin-1-ylmethyl-phenoxy)-cyclobutylmethyl]-3,4-dimethoxy-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 7 mg, HPLC purity ELSD=94.4%, retention time (min)=1.594; LRMS, m/z Calcd for $C_{25}H_{33}ClN_2O_5S$, 509.1; obsd LRMS APCI (M+1) m/z 509.

EXAMPLE 292

3-Chloro-N-[3-(3-chloro-4-pyrrolidin-1-ylmethyl-phenoxy)-cyclobutylmethyl]-2,N-dimethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 46 mg, HPLC purity ELSD=100%, retention time (min)=1.774; LRMS, m/z Calcd for $C_{24}H_{30}Cl_2N_2O_3S$, 497.5; obsd LRMS APCI (M+1) m/z 497.

EXAMPLE 293

N-[3-(3-Chloro-4-pyrrolidin-1-ylmethyl-phenoxy)-cyclobutylmethyl]-2,5,N-trimethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 12 mg, HPLC purity ELSD=100%, retention time (min)=1.755; LRMS, m/z Calcd for $C_{25}H_{33}ClN_2O_3S$, 477.1; obsd LRMS APCI (M+1) m/z 477.

EXAMPLE 295

Naphthalene-1-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 12 mg, HPLC purity ELSD=100%, retention time (min)=1.765; LRMS, m/z Calcd for $C_{27}H_{31}ClN_2O_3S$, 499.1; obsd LRMS APCI (M+1) m/z 499.

EXAMPLE 296

N-[3-(3-Chloro-4-pyrrolidin-1-ylmethyl-phenoxy)-cyclobutylmethyl]-2,6-difluoro-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 9 mg, HPLC purity ELSD=96.0%, retention time (min)=1.642; LRMS, m/z Calcd for $C_{23}H_{27}ClF_2N_2O_3S$, 485.0; obsd LRMS APCI (M+1) m/z 485.

EXAMPLE 297

Piperidine-1-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 25 mg, HPLC purity ELSD=99.4%, retention time (min)=1.621; LRMS, m/z Calcd for $C_{22}H_{34}ClN_3O_3S$, 456.0; obsd LRMS APCI (M+1) m/z 456.

EXAMPLE 298

3,5-Dimethyl-isoxazole-4-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 10 mg, HPLC purity ELSD=97.0%, retention time (min)=1.578; LRMS, m/z Calcd for C22H30ClN3O4S, 468.0; obsd LRMS APCI (M+1) m/z 468.

EXAMPLE 299

N-[3-(3-Chloro-4-pyrrolidin-1-ylmethyl-phenoxy)-cyclobutylmethyl]-N-methyl-methanesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 35 mg, HPLC purity ELSD=99.1%, retention time (min)=1.283; C18H27ClN2O3S, 386.9; obsd LRMS APCI (M+1) m/z 387.

EXAMPLE 300

Pyridine-3-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulfonyl chloride. The product was purified by HPLC (Preparative Purification Method A) yielding the title compound as the TFA salt, 26 mg, HPLC purity ELSD=100%, retention time (min)=1.387; LRMS, m/z Calcd for C22H28ClN3O3S, 450.0; obsd LRMS APCI (M+1) m/z 450.

EXAMPLE 301

4-Chloro-N-[3-(3-chloro-4-pyrrolidin-1-ylmethyl-phenoxy)-cyclobutylmethyl]-2,5,N-trimethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 13 mg, HPLC purity ELSD=99.1%, retention time (min)=1.892; LRMS, m/z Calcd for C25H32Cl2N2O3S, 511.5; obsd LRMS APCI (M+1) m/z 511.

EXAMPLE 302

Propane-2-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulfonyl chloride. The product was purified by HPLC (Preparative Purification Method A) yielding the title compound as the TFA salt, 17 mg, HPLC purity ELSD=89.5%, retention time (min)=1.443; LRMS, m/z Calcd for C20H31ClN2O3S, 415.0; obsd LRMS APCI (M+1) m/z 415.

EXAMPLE 303

N-[3-(3-Chloro-4-pyrrolidin-1-ylmethyl-phenoxy)-cyclobutylmethyl]-2,4-dimethoxy-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 44 mg, HPLC purity ELSD=100%, retention time (min)=1.585; LRMS, m/z Calcd for C25H33ClN2O5S, 509.1; obsd LRMS APCI (M+1) m/z 509.

EXAMPLE 304

1,3,5-Trimethyl-1H-pyrazole-4-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulfonyl chloride. The product was purified by HPLC (Preparative Purification Method A) yielding the title compound as the TFA salt, 10 mg, HPLC purity ELSD=100%, retention time (min)=1.449; LRMS, m/z Calcd for C23H33ClN4O3S, 481.1; obsd LRMS APCI (M+1) m/z 481.

EXAMPLE 305

Morpholine-4-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 20 mg, HPLC purity ELSD=83.3%, retention time (min)=1.406; LRMS, m/z Calcd for C21H32ClN3O4S, 458.0; obsd LRMS APCI (M+1) m/z 458.

EXAMPLE 306

N-[3-(3-Chloro-4-pyrrolidin-1-ylmethyl-phenoxy)-cyclobutylmethyl]-4-methoxy-N-methyl-benzenesulfonamide. Reaction was conducted using the conditions described in General Procedure S: Sulfonamide Coupling, using Example 212 as the starting amine and the appropriate sulfonyl chloride. The product was purified by HPLC (Preparative Purification Method A) yielding the title compound as the TFA salt, 7 mg, HPLC purity ELSD=100%, retention time (min)=1.657; LRMS, m/z Calcd for C24H31ClN2O4S, 479.0; obsd LRMS APCI (M+1) m/z 479.

EXAMPLE 307

N-[3-(3-Chloro-4-pyrrolidin-1-ylmethyl-phenoxy)-cyclobutylmethyl]-2,4,5-trifluoro-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 8 mg, HPLC purity ELSD=100%, retention time (min)=1.726; LRMS, m/z Calcd for C23H26ClF3N2O3S, 503.0; obsd LRMS APCI (M+1) m/z 503.

EXAMPLE 308

N-[3-(3-Chloro-4-pyrrolidin-1-ylmethyl-phenoxy)-cyclobutylmethyl]-2,4,N-trimethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 34 mg, HPLC purity ELSD=100%, retention time (min)= 1.722; LRMS, m/z Calcd for C25H33ClN2O3S, 477.1; obsd LRMS APCI (M+1) m/z 477.

EXAMPLE 309

2,3-Dihydro-benzo[1,4]dioxine-6-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 9 mg, HPLC purity ELSD=96.1%, retention time (min)=1.645; LRMS, m/z Calcd for C25H31ClN2O5S, 507.0; obsd LRMS APCI (M+1) m/z 507.

EXAMPLE 310

N-[3-(3-Chloro-4-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 7 mg, HPLC purity ELSD=89.2%, retention time (min)=1.636; LRMS, m/z Calcd for C23H29ClN2O3S, 449.0; obsd LRMS APCI (M+1) m/z 449.

EXAMPLE 311

2-Oxo-2,3-dihydro-benzooxazole-6-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 29 mg, HPLC purity ELSD=100%, retention time (min)=1.447; LRMS, m/z Calcd for C24H28ClN3O5S, 506.0; obsd LRMS APCI (M+1) m/z 506.

EXAMPLE 312

2-Chloro-N-[3-(3-chloro-4-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 9 mg, HPLC purity ELSD=100%, retention time (min)= 1.689; LRMS, m/z Calcd for C23H28Cl2N2O3S, 483.5; obsd LRMS APCI (M+1) m/z 483.

EXAMPLE 313

N-[3-(3-Chloro-4-pyrrolidin-1-ylmethyl-phenoxy)-cyclobutylmethyl]-5-fluoro-2,N-dimethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 10 mg, HPLC purity ELSD=100%, retention time (min)=1.723; LRMS, m/z Calcd for C24H30ClFN2O3S, 481.0; obsd LRMS APCI (M+1) m/z 481.

EXAMPLE 314

2-{[3-(3-Chloro-4-pyrrolidin-1-ylmethyl-phenoxy)-cyclobutylmethyl]-methyl-sulfamoyl}-benzoic acid methyl ester Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 12 mg, HPLC purity ELSD=100%, retention time (min)=1.591; LRMS, m/z Calcd for C25H31ClN2O5S, 507.0; obsd LRMS APCI (M+1) m/z 507.

EXAMPLE 315

4-tert-Butyl-N-[3-(3-chloro-4-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 9 mg, HPLC purity ELSD=100%, retention time (min)= 1.935; LRMS, m/z Calcd for C27H37ClN2O3S, 505.1; obsd LRMS APCI (M+1) m/z 505.

EXAMPLE 316

N-[3-(3-Chloro-4-pyrrolidin-1-ylmethyl-phenoxy)-cyclobutylmethyl]-2-methoxy-5,N-dimethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 7 mg, HPLC purity ELSD=95.9%, retention time (min)=1.689; LRMS, m/z Calcd for C25H33ClN2O4S, 493.1; obsd LRMS APCI (M+1) m/z 493.

EXAMPLE 317

Ethanesulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 37 mg, HPLC purity ELSD=100%, retention time (min)=1.355; C19H29ClN2O3S, 401.0; obsd LRMS APCI (M+1) m/z 401.

EXAMPLE 318

N-[3-(3-Chloro-4-pyrrolidin-1-ylmethyl-phenoxy)-cyclobutylmethyl]-3,4-difluoro-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 8 mg, HPLC purity ELSD=100%, retention time (min)=1.72; LRMS, m/z Calcd for C23H27ClF2N2O3S, 485.0; obsd LRMS APCI (M+1) m/z 485.

EXAMPLE 319

N-[3-(3-Chloro-4-pyrrolidin-1-ylmethyl-phenoxy)-cyclobutylmethyl]-N-methyl-2-trifluoromethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 28 mg, HPLC purity ELSD=100%, retention time (min)=1.697; LRMS, m/z Calcd for $C_{24}H_{28}ClF_3N_2O_3S$, 517.0; obsd LRMS APCI (M+1) m/z 517.

EXAMPLE 320

2,5-Dimethyl-thiophene-3-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 15 mg, HPLC purity ELSD=100%, retention time (min)=1.748; LRMS, m/z Calcd for $C_{23}H_{31}ClN_2O_3S_2$ 483.1; obsd LRMS APCI (M+1) m/z 483.

EXAMPLE 321

Benzo[1,2,5]thiadiazole-4-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 11 mg, HPLC purity ELSD=100%, retention time (min)=1.618; LRMS, m/z Calcd for $C_{23}H_{27}ClN_4O_3S_2$ 507.1; obsd LRMS APCI (M+1) m/z 507.

EXAMPLE 322

Quinoline-8-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 39 mg, HPLC purity ELSD=100%, retention time (min)=1.554; LRMS, m/z Calcd for $C_{26}H_{30}ClN_3O_3S$, 500.1; obsd LRMS APCI (M+1) m/z 500.

EXAMPLE 323

4-Acetyl-N-[3-(3-chloro-4-pyrrolidin-1-ylmethyl-phenoxy)-cyclobutylmethyl]-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 12 mg, HPLC purity ELSD=98.8%, retention time (min)=1.585; LRMS, m/z Calcd for $C_{25}H_{31}ClN_2O_4S$, 491.0; obsd LRMS APCI (M+1) m/z 491.

EXAMPLE 324

N-[3-(3-Chloro-4-pyrrolidin-1-ylmethyl-phenoxy)-cyclobutylmethyl]-N-methyl-3-trifluoromethyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 11 mg, HPLC purity ELSD=98.9%, retention time (min)=1.788; LRMS, m/z Calcd for $C_{24}H_{28}ClF_3N_2O_3S$, 517.0; obsd LRMS APCI (M+1) m/z 517.

EXAMPLE 325

Pyrrolidine-1-sulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 30 mg, HPLC purity ELSD=100%, retention time (min)=1.499; LRMS, m/z Calcd for $C_{21}H_{32}ClN_3O_3S$, 442.0; obsd LRMS APCI (M+1) m/z 442.

EXAMPLE 326

(E)-2-Phenyl-ethenesulfonic acid [3-(3-chloro-4-pyrrolidin-1-ylmethyl-phenoxy)-cyclobutylmethyl]-methyl-amide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 10 mg, HPLC purity ELSD=95.8%, retention time (min)=1.722; LRMS, m/z Calcd for $C_{25}H_{31}ClN_2O_3S$, 475.1; obsd LRMS APCI (M+1) m/z 475.

EXAMPLE 327

N-[3-(3-Chloro-4-pyrrolidin-1-ylmethyl-phenoxy)-cyclobutylmethyl]-3-fluoro-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 7 mg, HPLC purity ELSD=100%, retention time (min)= 1.689; LRMS, m/z Calcd for $C_{23}H_{28}ClFN_2O_3S$, 467.0; obsd LRMS APCI (M+1) m/z 467.

EXAMPLE 328

2-Chloro-N-[3-(3-chloro-4-pyrrolidin-1-ylmethyl-phenoxy)-cyclobutylmethyl]-4-fluoro-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 13 mg, HPLC purity ELSD=100%, retention time (min)=1.706; LRMS, m/z Calcd for C23H27Cl2FN2O3S, 501.4; obsd LRMS APCI (M+1) m/z 501.

EXAMPLE 329

N-(4-{[3-(3-Chloro-4-pyrrolidin-1-ylmethyl-phenoxy)-cyclobutylmethyl]-methyl-sulfamoyl}-phenyl)-acetamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 13 mg, HPLC purity ELSD=100%, retention time (min)=1.456; LRMS, m/z Calcd for C25H32ClN3O4S, 506.1; obsd LRMS APCI (M+1) m/z 506.

EXAMPLE 330

N-[3-(3-Chloro-4-pyrrolidin-1-ylmethyl-phenoxy)-cyclobutylmethyl]-N-methyl-C-phenyl-methanesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, 39 mg, HPLC purity ELSD=93.4%, retention time (min)=1.583; LRMS, m/z Calcd for C24H31ClN2O3S, 463.0; obsd LRMS APCI (M+1) m/z 463.

EXAMPLE 331

5-Chloro-N-[3-(3-chloro-4-pyrrolidin-1-ylmethyl-phenoxy)-cyclobutylmethyl]-2-methoxy-N-methyl-benzenesulfonamide. Reaction was conducted using the conditions described in General Procedure S: Sulfonamide Coupling, using Example 212 as the starting amine and the appropriate sulonyl chloride. The product was purified by HPLC (Preparative Purification Method A) yielding the title compound as the TFA salt, mg, HPLC purity ELSD=100%, retention time (min)=1.72; LRMS, m/z Calcd for C24H30Cl2N2O4S, 513.5; obsd LRMS APCI (M+1) m/z 513.

EXAMPLE 332

3-Benzyl-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 37 mg, HPLC purity ELSD=100%, retention time (min)=1.661; LRMS m/z Calcd for C25H32ClN3O2, 442; obsd LRMS APCI (M+1) m/z 442.

EXAMPLE 333

3-(5-Chloro-2-methoxy-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 53 mg, HPLC purity ELSD=99.6%, retention time (min)=1.841; LRMS m/z Calcd for C25H31Cl2N3O3, 492; obsd LRMS APCI (M+1) m/z 492.

EXAMPLE 334

1-{[3-(3-Chloro-4-pyrrolidin-1-ylmethyl-phenoxy)-cyclobutyl]methyl}-1-methyl-3-(4-trifluoromethyl-phenyl)-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 37 mg, HPLC purity ELSD=99.8%, retention time (min)=1.851; LRMS m/z Calcd for C25H29ClF3N3O2, 496; obsd LRMS APCI (M+1) m/z 496.

EXAMPLE 335

1-[3-(3-Chloro-4-pyrrolidin-1-ylmethyl-phenoxy)-cyclobutylmethyl]-3-isopropyl-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 35 mg, HPLC purity ELSD=100%, retention time (min)=1.549; LRMS m/z Calcd for C21H32ClN3O2, 394; obsd LRMS APCI (M+1) m/z 394.

EXAMPLE 336

3-(2-Chloro-6-methyl-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 37 mg, HPLC purity ELSD=98.2%, retention time (min)=1.7; LRMS m/z Calcd for C25H31Cl2N3O2, 476; obsd LRMS APCI (M+1) m/z 476.

EXAMPLE 337

1-[3-(3-Chloro-4-pyrrolidin-1-ylmethyl-phenoxy)-cyclobutylmethyl]-3-(2,5-dimethyl-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 38 mg, HPLC purity ELSD=97.7%, retention time (min)=1.755; LRMS m/z Calcd for C26H34ClN3O2, 456; obsd LRMS APCI (M+1) m/z 456.

EXAMPLE 338

1-[3-(3-Chloro-4-pyrrolidin-1-ylmethyl-phenoxy)-cyclobutylmethyl]-1-methyl-3-m-tolyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=99.1%, retention time (min)=1.729; LRMS m/z Calcd for C25H32ClN3O2, 442; obsd LRMS APCI (M+1) m/z 442.

EXAMPLE 339

3-(3-Chloro-2-methyl-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 34 mg, HPLC purity ELSD=97.4%, retention time (min)=1.784; LRMS m/z Calcd for C25H31Cl2N3O2, 476; obsd LRMS APCI (M+1) m/z 476.

EXAMPLE 340

1-[3-(3-Chloro-4-pyrrolidin-1-ylmethyl-phenoxy)-cyclobutylmethyl]-3-ethyl-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 34 mg, HPLC purity ELSD=100%, retention time (min)=1.472; LRMS m/z Calcd for C20H30ClN3O2, 380; obsd LRMS APCI (M+1) m/z 380.

EXAMPLE 341

1-{[3-(3-Chloro-4-pyrrolidin-1-ylmethyl-phenoxy)-cyclobutyl]methyl}-1-methyl-3-(2-trifluoromethyl-phenyl)-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 36 mg, HPLC purity ELSD=91.6%, retention time (min)=1.769; LRMS m/z Calcd for C25H29ClF3N3O2, 496; obsd LRMS APCI (M+1) m/z 496.

EXAMPLE 342

3-(3-Chloro-4-methyl-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 48 mg, HPLC purity ELSD=99.2%, retention time (min)=1.843; LRMS m/z Calcd for C25H31Cl2N3O2, 476; obsd LRMS APCI (M+1) m/z 476.

EXAMPLE 343

1-[3-(3-Chloro-4-pyrrolidin-1-ylmethyl-phenoxy)-cyclobutylmethyl]-1-methyl-3-o-tolyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=97.3%, retention time (min)=1.673; LRMS m/z Calcd for C25H32ClN3O2, 442; obsd LRMS APCI (M+1) m/z 442.

EXAMPLE 344

1-[3-(3-Chloro-4-pyrrolidin-1-ylmethyl-phenoxy)-cyclobutylmethyl]-3-(2-ethyl-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 38 mg, HPLC purity ELSD=96.4%, retention time (min)=1.738; LRMS m/z Calcd for C26H34ClN3O2, 456; obsd LRMS APCI (M+1) m/z 456.

EXAMPLE 345

1-[3-(3-Chloro-4-pyrrolidin-1-ylmethyl-phenoxy)-cyclobutylmethyl]-3-(3,4-dimethyl-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=99.4%, retention time (min)=1.777; LRMS m/z Calcd for C26H34ClN3O2, 456; obsd LRMS APCI (M+1) m/z 456.

EXAMPLE 346

1-[3-(3-Chloro-4-pyrrolidin-1-ylmethyl-phenoxy)-cyclobutylmethyl]-3-(2,4-difluoro-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=98.9%, retention time (min)=1.662; LRMS m/z Calcd for C24H28ClF2N3O2, 464; obsd LRMS APCI (M+1) m/z 464.

EXAMPLE 347

1-[3-(3-Chloro-4-pyrrolidin-1-ylmethyl-phenoxy)-cyclobutylmethyl]-3-(4-methoxy-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 37 mg, HPLC purity ELSD=98.4%, retention time (min)=1.632; LRMS m/z Calcd for C25H32ClN3O3, 458; obsd LRMS APCI (M+1) m/z 458.

EXAMPLE 348

3-(3-Chloro-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 41 mg, HPLC purity ELSD=99.5%, retention time (min)=1.782; LRMS m/z Calcd for C24H29Cl2N3O2, 462; obsd LRMS APCI (M+1) m/z 462.

EXAMPLE 339

1-[3-(3-Chloro-4-pyrrolidin-1-ylmethyl-phenoxy)-cyclobutylmethyl]-3-(2-fluoro-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 35 mg, HPLC purity ELSD=98.3%, retention time (min)=1.664; LRMS m/z Calcd for C24H29ClFN3O2, 446; obsd LRMS APCI (M+1) m/z 446.

EXAMPLE 350

3-(4-Chloro-2-methyl-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 42 mg, HPLC purity ELSD=98.2%, retention time (min)=1.767; LRMS m/z Calcd for C25H31Cl2N3O2, 476; obsd LRMS APCI (M+1) m/z 476.

EXAMPLE 351

3-tert-Butyl-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 33 mg, HPLC purity ELSD=99.0%, retention time (min)=1.657; LRMS m/z Calcd for C22H34ClN3O2, 408; obsd LRMS APCI (M+1) m/z 408.

EXAMPLE 352

1-[3-(3-Chloro-4-pyrrolidin-1-ylmethyl-phenoxy)-cyclobutylmethyl]-3-(2-methoxy-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 37 mg, HPLC purity ELSD=98.7%, retention time (min)=1.732; LRMS m/z Calcd for C25H32ClN3O3, 458; obsd LRMS APCI (M+1) m/z 458.

EXAMPLE 353

1-[3-(3-Chloro-4-pyrrolidin-1-ylmethyl-phenoxy)-cyclobutylmethyl]-3-(2-methoxy-5-methyl-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 57 mg, HPLC purity ELSD=98.9%, retention time (min)=1.783; LRMS m/z Calcd for C26H34ClN3O3, 472; obsd LRMS APCI (M+1) m/z 472.

EXAMPLE 354

1-[3-(3-Chloro-4-pyrrolidin-1-ylmethyl-phenoxy)-cyclobutylmethyl]-3-(2,6-dimethyl-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 38 mg, HPLC purity ELSD=98.9%, retention time (min)=1.688; LRMS m/z Calcd for C26H34ClN3O2, 456; obsd LRMS APCI (M+1) m/z 456.

EXAMPLE 355

3-(5-Chloro-2-methyl-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 39 mg, HPLC purity ELSD=97.8%, retention time (min)=1.779; LRMS m/z Calcd for C25H31Cl2N3O2, 476; obsd LRMS APCI (M+1) m/z 476.

EXAMPLE 356

1-[3-(3-Chloro-4-pyrrolidin-1-ylmethyl-phenoxy)-cyclobutylmethyl]-3-(3,5-dimethyl-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 37 mg, HPLC purity ELSD=97.6%, retention time (min)=1.794; LRMS m/z Calcd for C26H34ClN3O2, 456; obsd LRMS APCI (M+1) m/z 456.

EXAMPLE 357

1-[3-(3-Chloro-4-pyrrolidin-1-ylmethyl-phenoxy)-cyclobutylmethyl]-3-(4-methoxy-2-methyl-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 39 mg, HPLC purity ELSD=98.4%, retention time (min)=1.659; LRMS m/z Calcd for C26H34ClN3O3, 472; obsd LRMS APCI (M+1) m/z 472.

EXAMPLE 358

3-(3-Acetyl-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 37 mg, HPLC purity ELSD=99.2%, retention time (min)=1.641; LRMS m/z Calcd for C26H32ClN3O3, 470; obsd LRMS APCI (M+1) m/z 470.

EXAMPLE 359

1-[3-(3-Chloro-4-pyrrolidin-1-ylmethyl-phenoxy)-cyclobutylmethyl]-1-methyl-3-p-tolyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=99.3%, retention time (min)=1.718; LRMS m/z Calcd for C25H32ClN3O2, 442; obsd LRMS APCI (M+1) m/z 442.

EXAMPLE 359

1-[3-(3-Chloro-4-pyrrolidin-1-ylmethyl-phenoxy)-cyclobutylmethyl]-3-(3-fluoro-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 38 mg, HPLC purity ELSD=99.3%, retention time (min)=1.705; LRMS m/z Calcd for C24H29ClFN3O2, 446; obsd LRMS APCI (M+1) m/z 446.

EXAMPLE 360

1-[3-(3-Chloro-4-pyrrolidin-1-ylmethyl-phenoxy)-cyclobutylmethyl]-1-methyl-3-phenyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=98.6%, retention time (min)=1.648; LRMS m/z Calcd for C24H30ClN3O2, 428; obsd LRMS APCI (M+1) m/z 428.

EXAMPLE 361

3-(2-Chloro-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 38 mg, HPLC purity ELSD=97.5%, retention time (min)=1.765; LRMS m/z Calcd for C24H29Cl2N3O2, 462; obsd LRMS APCI (M+1) m/z 462.

EXAMPLE 362

3-(4-Chloro-phenyl)-1-[3-(3-chloro-4-pyrrolidin-1-ylmethyl-phenoxy)-cyclobutylmethyl]-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=99.5%, retention time (min)=1.776; LRMS m/z Calcd for C24H29Cl2N3O2, 462; obsd LRMS APCI (M+1) m/z 462.

EXAMPLE 363

1-[3-(3-Chloro-4-pyrrolidin-1-ylmethyl-phenoxy)-cyclobutylmethyl]-3-(3-methoxy-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 41 mg, HPLC purity ELSD=98.9%, retention time (min)=1.661; LRMS m/z Calcd for C25H32ClN3O3, 458; obsd LRMS APCI (M+1) m/z 458.

EXAMPLE 364

1-[3-(3-Chloro-4-pyrrolidin-1-ylmethyl-phenoxy)-cyclobutylmethyl]-3-(4-fluoro-phenyl)-1-methyl-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 43 mg, HPLC purity ELSD=98.8%, retention time (min)=1.676; LRMS m/z Calcd for C24H29ClFN3O2, 446; obsd LRMS APCI (M+1) m/z 446.

EXAMPLE 365

1-{[3-(3-Chloro-4-pyrrolidin-1-ylmethyl-phenoxy)-cyclobutyl]methyl}-1-methyl-3-(3-trifluoromethyl-phenyl)-urea. Reaction was conducted using the conditions described in General Procedure U: Urea Formation from an Isocyanate and an Amine, using Example 212 as the starting amine and the appropriate isocyanate. The product was purified by HPLC (Preparative Purification Method A) yielding the title compound as the TFA salt, 40 mg, HPLC purity ELSD=99.7%, retention time (min)=1.843; LRMS m/z Calcd for C25H29ClF3N3O2, 496; obsd LRMS APCI (M+1) m/z 496.

Intermediate 16

3-Chloro-5-fluorophenol. A solution of 3-chloro-5-fluoroanisole (10 g, 62 mmol) in $CH_2Cl_2$ (50 mL) was cooled in a stream of argon to −70° C. under stirring. $BBr_3$ (11.8 mL, 124 mmol) was added dropwise under vigorous stirring at −70° C. in 15 min. The reaction mixture was heated to room temperature and alkalized with the saturated $NaHCO_3$ solution to pH ~6. The layers were separated, and the water layer was extracted with $CH_2Cl_2$ (2×50 mL). The combined organic layer was washed with brine, dried over $Na_2SO_4$ and evaporated in vacuo to give the title compound (8 g, 88%, 54.6 mmol) as a yellow oil. $^1H$ NMR data (dmso-d6): 10.36 (s, 1H, OH), 6.73-6.79 (m, 1H, H—Ar), 6.64-6.68 (m, 1H, H—Ar), 6.53-6.59 (m, 1H, H—Ar).

Intermediate 16

1-(tert-Butyldimethylsilyl)oxy-3-chloro-5-fluorobenzene. To a solution of 3-chloro-5-fluorophenol, intermediate 15 (8 g, 54.6 mmol) and imidazole (8.17 g, 120 mmol) in DMF (30 mL) was added TBDMSCI (9.05 g, 60 mmol) at 0° C., and the mixture was stirred at RT for 20 min. Water was added at 0° C., and aqueous layer was extracted with $Et_2O$. The organic layer was washed with brine, dried over $Na_2SO_4$ and evaporated in vacuo. The residue was purified by chromatography (silica gel 63-100μ, 400 mL, Hex→Hex/EtOAc 93:7) to furnish the title compound (13.1 g, 92%, 50 mmol) as a colorless oil. 1H NMR data (dmso-d6): 6.98-7.04 (m, 1H, H—Ar), 6.75-6.78 (m, 1H, H—Ar), 6.69-6.74 (m, 1H, H—Ar), 0.94 (s, 9H, t-Bu), 0.21 (s, 6H, $2CH_3$).

Intermediate 17

4-hydroxy-2-chloro-6-fluorobenzaldehyde. Sec-BuLi (1.3M solution in cyclohexane, 42.3 mL, 55 mmol) was added slowly at −78° C. to a solution of intermediate 16, 1-(tert-Butyldimethylsilyl)oxy-3-chloro-5-fluorobenzene (13.1 g, 50 mmol) and TMEDA (8.3 mL, 55 mmol) in THF (200 mL) and the mixture was stirred at the same temperature for 30 min. DMF (4.23 mL, 55 mmol) was added to the mixture at −78° C., and the mixture was stirred at the same temperature for 1.5 h. Then 10% aqueous HCl was added to attain pH~4-5 (200 mL), and the reaction mixture was stirred at RT for 12 h. Aqueous layer was extracted with EtOAc (200 mL). The organic layer was separated. The organic layer was washed with sat. NaHCO$_3$, then H$_2$O was added, HCl was added to attain pH~3-4, the organic layer was separated, washed with brine, dried with Na$_2$SO$_4$ and evaporated in vacuo to give the title compound (7.53 g, 86%, 43 mmol) as a white solid. 1H NMR data (dmso-d6): 11.51 (br.s, 1H, OH), 10.15 (s, 1H, CHO), 6.78-6.83 (m, 1H, H—Ar), 6.68 (dd, 1H, J$_1$=2.2 Hz, J$_2$=12.7 Hz, H—Ar).

Intermediate 18

3-chloro-5-fluoro-4-(pyrrolidin-1-ylmethyl)phenol. Pyrrolidine (4.65 mL, 56 mmol) was added to a solution of intermediate 17, 4-hydroxy-2-chloro-6-fluorobenzaldehyde (7.5 g, 43 mmol) in dichloromethane (100 mL). The reaction mixture was cooled on ice bath, and sodium triacetoxyborohydride (13.71 g, 65 mmol) was added in portions under stirring. The reaction mixture was intensively stirred for 24 h at RT. Water (100 mL) and concentrated HCl were added to attain pH~2. The organic layer was separated. The aqueous one was extracted with CH$_2$Cl$_2$ (2×100 mL), then with EtOAc (100 mL). The organic layers were discarded. The aqueous fraction was alkalized with K$_2$CO$_3$ to pH~10, the obtained crystals were separated by filtration, dried in vacuo, recrystallized from Et$_2$O/hexane mixture (1:1) to give the title compound (7 g, 71%, 30 mmol). LCMS data: 231 and 230 (M+H)$^+$ (calculated for C$_{11}$H$_{13}$ClFNO 229.7). $^1$H NMR data (DMSO-d6): 10.25 (br.s, 1H, OH), 6.66-6.70 (m, 1H, H—Ar), 6.54 (dd, 1H, J$_1$=2.2 Hz, J$_2$=11.3 Hz, H—Ar), 3.58 (d, 2H, J1=2.4 Hz, Ar—CH$_2$); 2.38-2.46 (m, 4H), 1.58-1.68 (m, 4H).

EXAMPLE 366 tert-butyl ({trans-3-[3-chloro-5-fluoro-4-(pyrrolidin-1-ylmethyl)phenoxy]cyclobutyl}-methyl)methylcarbamate. A mixture of intermediate 6, cis-3-{[(tert-butoxycarbonyl)(methyl)amino]methyl}cyclobutyl methanesulfonate (1.5 g, 5.2 mmol), intermediate 18, 3-chloro-5-fluoro-4-(pyrrolidin-1-ylmethyl)phenol (2.38 g, 10.4 mmol) and Cs$_2$CO$_3$ (3.38 g, 10.4 mmol) in DMSO (20 mL) was heated at 90-95° C. for 4 h under vigorous stirring in a flow of argon, then cooled. Water (40 ml) and EtOAc (40 ml) were added, and the layers were separated. The water layer was extracted with ether (20 ml), the combined organic layers were washed with 1N NaOH (3×25 mL), brine, dried with Na$_2$SO$_4$, and evaporated to give the title compound (1.8 g, 82%) as a yellow oil. LC/MS data: 427.6, 429.6, 430.5 (M+H) (calculated for C$_{22}$H$_{32}$CFIN$_2$O$_3$ 426.96). $^1$H NMR-data (DMSO-d6): 6.76 (br. s, 1H, Ar—H); 6.71 (dd, 1H, J1=2.2 Hz, J2=11.5 Hz, Ar—H); 4.79-4.92 (m, 1H); 3.65 (s, 2H); 3.32 (d, 2H, J=8.0 Hz); 2.78 (s, 3H, NCH$_3$); 2.38-2.62 (m, 5H+DMSO); 2.20-2.28 (m, 2H); 2.05-2.17 (m, 2H); 1.58-1.73 (m, 4H); 1.41 (s, 9H, Boc).

EXAMPLE 367

({trans-3-[3-Chloro-5-fluoro-4-(pyrrolidin-1-ylmethyl) phenoxy]cyclobutyl}methyl). 4M HCl in dioxane (5.3 ml) was added to a solution of example 366, tert-butyl ({trans-3-[3-chloro-5-fluoro-4-(pyrrolidin-1-ylmethyl)phenoxy] cyclobutyl}methyl)methylcarbamate (1.8 g, 4.2 mmol) in 2 ml of dioxane. The mixture was stirred for 20 h and evaporated to dryness. The residue was recrystallized from MeOH-Et$_2$O. The crystals were separated by filtration and dryed, then CH$_2$Cl$_2$ (30 mL) and saturated 10 N NaOH (pH 12) were added under stirring. The layers were separated; the water solution was extracted with CH$_2$Cl$_2$ (3×20 mL). The combined extracts were dried (Na$_2$SO$_4$) and evaporated; the residue was dried in vacuo to give the title compound (1.1 g, 80%) as a yellow oil. LC/MS data: 329.4, 327.4 (M+H), 368.5 (M+CH$_3$CN+H) (calculated for C$_{17}$H$_{24}$ClFN$_2$O 326.85). $^1$H NMR-data (DMSO-d6): 6.75-6.79 (m, 1H, Ar—H); 6.68 (dd, 1H, J1=2.2 Hz, J2=11.5 Hz, Ar—H); 4.72-4.89 (m, 1H), 3.54 (d, 2H, J=2.2 Hz); 2.57 (d, 2H, J=9.3 Hz); 2.41-2.47 (m, 4H); 2.31-2.41 (m, 1H); 2.30 (s, 3H, NCH$_3$); 2.20-2.28 (m, 2H); 2.03-2.15 (m, 2H); 1.58-1.67 (m, 4H).

EXAMPLE 368

N-({trans-3-[3-Chloro-5-fluoro-4-(pyrrolidin-1-ylmethyl)phenoxy]cyclobutyl}methyl)-N,1-dimethylcyclopropanecarboxamide hydrochloride. CDI (0.61 mmol) was added to a solution of 1-methylcyclopropanecarboxylic acid CAS 6914-76-7 (92 mg, 0.92 mmol, 1.5 eq) in THF (2 ml) at RT under stirring, the mixture was stirred at RT for 1 h. Then example 367 ({trans-3-[3-chloro-5-fluoro-4-(pyrrolidin-1-ylmethyl)phenoxy]cyclobutyl}methyl) (200 mg, 0.61 mmol) was added to the mixture and the solution was stirred at RT for 20 h and evaporated. The residue was purified by chromatography (silica gel, 63-100 μm, 3 g, hexane/CHCl$_3$ 20:80→0:100, then CHCl$_3$/MeOH 100:0→95:5). The residue was dissolved in ether (1 mL), 4N HCl/dioxane (0.20 mL) was added, and the reaction mixture was evaporated to dryness. The obtained crystals were washed with ether and dried in vacuo to yield the title compound (155 mg, 57%). LC/MS data: 411.1, 409.1 (M+H) (calculated for C$_{22}$H$_{30}$ClFN$_2$O$_2$ 408.95). $^1$H NMR-data (DMSO-d6): 10.28 (br.s, 1H, NH$^+$); 6.83-7.03 (m, 2H, Ar—H); 4.80-5.02 (m, 1H), 4.41 (s, 2H); 3.40-3.55 (m, 4H); 2.88-3.20 (m, 5H); 2.56-2.67 (m, 1H); 2.20-2.31 (m, 2H); 2.09-2.19 (m, 2H); 1.95-2.06 (m, 2H); 1.83-1.94 (m, 2H); 1.23 (s, 3H, CH$_3$); 0.74-0.83 (m, 2H), 0.53-0.59 (m, 2H).

EXAMPLE 369

N-({trans-3-[3-Chloro-5-fluoro-4-(pyrrolidin-1-ylmethyl)phenoxy]cyclobutyl}methyl)-N-methyltetrahydro-2H-pyran-4-carboxamide hydrochloride. CDI (0.61 mmol) was added to a solution of tetrahydropyran-4-yl-carboxylic acid CAS 5337-03-1 (120 mg, 0.92 mmol) in THF (2 ml) at RT under stirring, the mixture was stirred at RT for 1 h. Then example 367 ({trans-3-[3-chloro-5-fluoro-4-(pyrrolidin-1-ylmethyl)phenoxy]cyclobutyl}methyl) (200 mg, 0.61 mmol) was added to the mixture and the solution was stirred at RT for 20 h and evaporated. The residue was purified by chromatography (silica gel, 63-100 μm, 3 g, hexane/CHCl$_3$ 20:80→0:100, then CHCl$_3$/MeOH 100:0→95:5). The residue was dissolved in ether (1 mL), 4N HCl/dioxane (0.20 mL) was added, and the reaction mixture was evaporated to dryness. The obtained crystals were washed with ether and dried in vacuo to yield the title compound (160 mg, 55% yield). LC/MS data: 441.1, 439.1 (M+H) (calculated for C$_{23}$H$_{32}$ClFN$_2$O$_3$ 438.97).

¹H NMR-data (DMSO-d6): 10.35 (br.s, 1H, NH⁺); 6.84-7.04 (m, 2H, Ar—H); 4.78-5.10 (m, 1H), 4.41 (s, 2H); 3.85 (d, 2H, J=10.7 Hz); 3.31-3.53 (m, 6H); 3.07-3.20 (m, 2H); 3.03 (s, 2H); 2.76-2.93 (m, 2H); 2.53-2.65 (m, 1H); 2.14-2.30 (m, 2H); 2.07-2.18 (m, 2H); 1.95-2.05 (m, 2H); 1.81-1.93 (m, 2H); 1.46-1.67 (m, 4H).

EXAMPLE 370

N-({trans-3-[3-Chloro-5-fluoro-4-(pyrrolidin-1-ylmethyl)phenoxy]cyclobutyl}methyl)-N,3,5-trimethylisoxazole-4-carboxamide hydrochloride. CDI (0.61 mmol) was added to a solution of 3,5-dimethylisoxazole-4-carbonyl chloride (98 mg, 0.61 mmol) in THF (2 ml) at RT under stirring, the mixture was stirred at RT for 1 h. Then example 367 ({trans-3-[3-chloro-5-fluoro-4-(pyrrolidin-1-ylmethyl)phenoxy]cyclobutyl}methyl) (200 mg, 0.61 mmol) was added to the mixture and the solution was stirred at RT for 20 h and evaporated. The residue was purified by chromatography (silica gel, 63-100 μm, 3 g, hexane/CHCl₃ 20:80→0:100, then CHCl₃/MeOH 100:0→95:5). The residue was dissolved in ether (1 mL), 4N HCl/dioxane (0.20 mL) was added, and the reaction mixture was evaporated to dryness. The obtained crystals were washed with ether and dried in vacuo to yield the title compound (190 mg, 64% yield). LC/MS data: 452.1, 450.1 (M+H) (calculated for $C_{23}H_{29}ClFN_3O_3$ 449.96). ¹H NMR-data (DMSO-d6): 10.12 (br.s, 1H, NH⁺); 6.76-7.08 (m, 2H, Ar—H); 4.60-5.10 (m, 1H), 4.41 (s, 2H); 3.57-3.67 (m, 1H); 3.37-3.52 (m, 3H); 3.06-3.23 (m, 2H); 2.91 (s, 3H); 2.61-2.78 (m, 1H); 2.28-2.41 (m, 4H); 2.11-2.23 (m, 6H); 1.94-2.06 (m, 2H); 1.79-1.94 (m, 2H).

Intermediate 19

1-(tert-Butyldimethylsilyl)oxy-3,5-difluorobenzene. To a solution of 3,5-difluorophenol (CAS 2713-34-0) (9 g, 69.2 mmol) and imidazole (10.35 g, 152 mmol) in DMF (30 mL) was added TBDMSCl (11.47 g, 76 mmol) at 0° C., and the mixture was stirred at RT for 20 min. Water was added at 0° C., and aqueous layer was extracted with Et₂O. The organic layer was washed with brine, dried over Na₂SO₄ and evaporated in vacuo. The residue was purified by chromatography (silica gel 63-100μ, 400 mL, Hex→Hex/EtOAc 93:7) to furnish the title compound (15.3 g, 91%, 62.6 mmol) as a colorless oil. 1H NMR data (dmso-d6): 6.77-6.84 (m, 1H, H—Ar), 6.52-6.60 (m, 2H, H—Ar), 0.94 (s, 9H, t-Bu), 0.21 (s, 6H, 2CH₃).

Intermediate 20

4-hydroxy-2,6-difluorobenzaldehyde. Sec-BuLi (1.3M solution in cyclohexane, 53 mL, 69.3 mmol) was added slowly at −78° C. to a solution of intermediate 19, 1-(tert-butyldimethylsilyl)oxy-3,5-difluorobenzene (15.3 g, 62.6 mmol) and TMEDA (10.5 mL, 69.3 mmol) in THF (200 mL) and the mixture was stirred at the same temperature for 30 min. DMF (5.33 mL, 69.3 mmol) was added to the mixture at −78° C., and the mixture was stirred at the same temperature for 1.5 h. Then 10% aqueous HCl was added to attain pH~4-5 (200 mL), and then the reaction mixture was stirred at RT for 12 h. The aqueous layer was extracted with EtOAc (200 mL). The organic layer was separated. The organic layer was washed with sat. NaHCO₃, then H₂O was added, HCl was added to attain pH~3-4, the organic layer was separated, washed with brine, dried with Na₂SO₄ and evaporated in vacuo to give the title compound (9.7 g, 97%, 61.3 mmol) as a white solid. ¹H NMR data (dmso-d6): 11.54 (br.s, 1H, OH), 10.00 (s, 1H, CHO), 6.50-6.57 (m, 2H, H—Ar).

Intermediate 21

3,5-Difluoro-4-(pyrrolidin-1-ylmethyl)phenol. Pyrrolidine (6.6 mL, 80 mmol) was added to a solution of intermediate 20, 4-hydroxy-2,6-difluorobenzaldehyde (9.7 g, 61.3 mmol) in dichloromethane (100 mL). The reaction mixture was cooled on ice bath, and sodium triacetoxyborohydride (19.5 g, 925 mmol) was added in portions under stirring. The reaction mixture was intensively stirred for 24 h at RT. Water (100 mL) and concentrated HCl were added to attain pH~2. The organic layer was separated. The aqueous one was extracted with CH₂Cl₂ (2×100 mL), then with EtOAc (100 mL). The organic layers were discarded. The aqueous fraction was alkalized with K₂CO₃ to pH~10, the obtained crystals were separated by filtration, dried in vacuo, dissolved in small amount of water, HCl was added to attain pH~7, and water layer was extracted with CHCl₃ (2×100 mL). The organic layer was separated, washed with brine, dried with Na₂SO₄ and evaporated in vacuo to give the title compound (2.6 g, 20%, 12 mmol). LCMS data: 215 and 214 (M+H)⁺ (calculated for $C_{11}H_{13}F_2NO$ 213.23). ¹H NMR data (DMSO-d6): 10.26 (br.s, 1H, OH), 6.38-6.46 (m, 2H, H—Ar), 3.52 (s, 2H, Ar—CH₂); 2.35-2.44 (m, 4H), 1.58-1.68 (m, 4H).

EXAMPLE 371 tert-butyl ({trans-3-[3,5-difluoro-4-(pyrrolidin-1-ylmethyl)phenoxy]cyclobutyl}methyl)-methylcarbamate. A mixture of intermediate 6, cis-3-{[(tert-butoxycarbonyl)(methyl)-amino]methyl}cyclobutyl methanesulfonate (2 g, 6.9 mmol), intermediate 21, 3,5-difluoro-4-(pyrrolidin-1-ylmethyl)phenol (3.47 g, 13.8 mmol) and Cs₂CO₃ (4.5 g, 13.8 mmol) in DMSO (20 mL) was heated at 90-95° C. for 4 h under vigorous stirring in a flow of argon, then cooled. Water (40 ml) and EtOAc (40 ml) were added, and the layers were separated. The water layer was extracted with ether (20 ml), the combined organic layers were washed with 1N NaOH (3×25 mL), brine, dried with Na₂SO₄, and evaporated to give the title compound (2.8 g, 98%) as a yellow oil. LC/MS data: 411.6, 412.6 (M+H) (calculated for $C_{22}H_{32}F_2N_2O_3$ 410.51). ¹H NMR-data (DMSO-d6): 6.50-6.61 (m, 2H, Ar—H); 4.79-4.87 (m, 1H); 3.55 (s, 2H, CH₂); 3.32 (d, 2H, J=8.1 Hz, CH₂); 2.78 (s, 3H, NCH₃); 2.52-2.62 (m, 1H); 2.38-2.50 (m, 4H); 2.20-2.28 (m, 2H); 2.05-2.17 (m, 2H); 1.58-1.73 (m, 4H); 1.41 (s, 9H, Boc).

EXAMPLE 372

({trans-3-[3-5-difluoro-4-(pyrrolidin-1-ylmethyl)phenoxy]cyclobutyl}methyl)methylamine. 4M HCl in dioxane (8.05 ml) was added to a solution of example 371 tert-butyl ({trans-3-[3,5-difluoro-4-(pyrrolidin-1-ylmethyl)phenoxy]cyclobutyl}methyl)-methylcarbamate (2.8 g, 6.8 mmol) in 2 ml of dioxane. The mixture was stirred for 20 h and evaporated to dryness. The residue was recrystallized from MeOH-Et₂O. The crystals were separated by filtration and dryed, then CH₂Cl₂ (30 mL) and saturated 10N NaOH (pH 12) were added under stirring. The layers were separated, the water solution was extracted with CH₂Cl₂ (3×20 mL). The combined extracts were dried (Na₂SO₄) and evaporated; the residue was dried in vacuo to give the title compound (1.7 g, 81%) as a yellow oil. LC/MS data: 311.4, 312.4 (M+H), 352.5 (M+H+CH₃CN) (calculated for $C_{17}H_{24}F_2N_2O$ 310.39). ¹H NMR-data (DMSO-d6): 6.50-6.63 (m, 2H, Ar—H); 4.72-4.89 (m, 1H), 3.54 (s, 2H), 2.57 (d, 2H, J=7.4 Hz); 2.20-2.44 (m, 5H); 2.30 (s, 3H, NCH₃); 2.20-2.28 (m, 2H); 2.03-2.15 (m, 2H); 1.58-1.67 (m, 4H).

EXAMPLE 373

N-({trans-3-[3,5-Difluoro-4-(pyrrolidin-1-ylmethyl)phenoxy]cyclobutyl}methyl)-N,1-dimethylcyclopropanecarboxamide hydrochloride. CDI (111 mg) was added to a solution of 1-methylcyclopropanecarboxylic acid CAS 6914-76-7 (97 mg, 0.97 mmol) in THF (2 ml) at RT under stirring, the mixture was stirred at RT for 1 h. Example 372, ({trans-3-[3-5-difluoro-4-(pyrrolidin-1-ylmethyl)phenoxy]cyclobutyl}methyl)methylamine (200 mg, 0.64 mmol) was added to the mixture and the solution was stirred at RT for 20 h and evaporated. The residue was purified by chromatography (silica gel, 63-100 μm, 3 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness to give the title compound (210 mg, 76%). LC/MS data: 393.2 (M+H) (calculated for $C_{22}H_{30}F_2N_2O_2$ 392.49). $^1$H NMR-data (DMSO-d6): 10.44 (br.s, 1H, NH$^+$); 6.70-6.80 (m, 2H, Ar—H); 4.80-4.97 (m, 1H), 4.32 (s, 2H); 3.35-3.54 (m, 4H); 2.88-3.15 (m, 5H); 2.56-2.67 (m, 1H); 2.22-2.31 (m, 2H); 2.09-2.19 (m, 2H); 1.79-2.01 (m, 4H); 1.23 (s, 3H, CH$_3$); 0.74-0.83 (m, 2H), 0.53-0.59 (m, 2H).

EXAMPLE 374

N-({trans-3-[3,5-Difluoro-4-(pyrrolidin-1-ylmethyl)phenoxy]cyclobutyl}methyl)-N-methyltetrahydro-2H-pyran-4-carboxamide hydrochloride. CDI (111 mg) was added to a solution of tetrahydropyran-4-yl-carboxylic acid CAS 5337-03-1 (126 mg, 0.96 mmol) in THF (2 ml) at RT under stirring, the mixture was stirred at RT for 1 h. Example 372, ({trans-3-[3-5-difluoro-4-(pyrrolidin-1-ylmethyl)phenoxy]cyclobutyl}methyl)methylamine (200 mg, 0.64 mmol) was added to the mixture and the solution was stirred at RT for 20 h and evaporated. The residue was purified by chromatography (silica gel, 63-100 μm, 3 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness to give the title compound (140 mg, 47%). LC/MS data: 423.2 (M+H) (calculated for $C_{23}H_{32}F_2N_2O_3$ 422.52). $^1$H NMR-data (DMSO-d6): 10.44 (br.s, 1H, NH$^+$); 6.68-6.83 (m, 2H, Ar—H); 4.78-5.10 (m, 1H), 4.32 (s, 2H); 3.85 (d, 2H, J=11.2 Hz); 3.31-3.53 (m, 6H); 2.98-3.14 (m, 4H); 2.76-2.93 (m, 2H); 2.53-2.65 (m, 1H); 2.14-2.30 (m, 2H); 2.07-2.18 (m, 2H); 1.95-2.05 (m, 2H); 1.81-1.93 (m, 2H); 1.46-1.67 (m, 4H).

EXAMPLE 375

N-({trans-3-[3,5-Difluoro-4-(pyrrolidin-1-ylmethyl)phenoxy]cyclobutyl}methyl)-N,3,5-trimethylisoxazole-4-carboxamide hydrochloride. Example 372, ({trans-3-[3-5-difluoro-4-(pyrrolidin-1-ylmethyl)phenoxy]cyclobutyl}methyl)methylamine (200 mg, 0.64 mmol (200 mg, 0.7 mmol) and triethylamine (0.1 mL, 0.7 mmol) were dissolved in CH$_2$Cl$_2$ (2 mL). 3,5-Dimethylisoxazole-4-carbonyl chloride (109 mg, 0.7 mmol) was added dropwise under stirring. The mixture was stirred at RT for 3 h and sat. K$_2$CO$_3$ was added. The mixture was stirred at RT for 20 h, dried with Na$_2$SO$_4$, and evaporated. The residue was purified chromatographically (silica gel 40-63 μm, 3 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (103 mg, 0.64 mmol). LC/MS data: 434.1 (M+H) (calculated for $C_{23}H_{29}F_2N_3O_3$ 433.5). $^1$H NMR-data (DMSO-d6): 10.51 (br.s, 1H, NH$^+$); 6.63-6.82 (m, 2H, Ar—H); 4.54-5.19 (m, 1H), 4.31 (s, 2H); 3.57-3.67 (m, 1H); 3.37-3.52 (m, 3H); 2.97-3.13 (m, 2H); 2.91 (s, 3H); 2.61-2.78 (m, 1H); 2.28-2.41 (m, 4H); 2.11-2.23 (m, 6H); 1.94-2.06 (m, 2H); 1.79-1.94 (m, 2H).

Intermediate 22

2,6-Dichloro-3-hydroxybenzaldehyde. 50 g 60 mol % of 2-chloro-3-hydroxybenzaldehyde, 25 mol % of 2,6-dichloro-3-hydroxybenzaldehyde, and 15 mol % of 6-chloro-3-hydroxybenzaldehyde was dissolved in glacial acetic acid (500 mL). Chlorine was bubbled into the obtained solution under stirring at 15° C. until the weight increased by 20 g. The formed white crystals were separated by filtration, dried, and recrystallized from ether/hexane mixture. As a result, the title compound (6.8 g) was obtained. The filtrate containing acetic acid was evaporated to dryness. The residue was crystallized from ether/hexane mixture to give 11.5 g more of the title compound to give a total yield of 18.3 g (32%). GCMS data: 189, 190, 191, 192 (calculated for $C_7H_4Cl_2O_2$ 191.01). $^1$H NMR-data (DMSO-d6): 10.87 (s, 1H, OH), 10.33 (s, 1H, COH), 7.37 (d, 1H, J=9 Hz, ArH), 7.18 (d, 1H, J=9 Hz, ArH).

Intermediate 23

2,4-Dichloro-3-(pyrrolidin-1-ylmethyl)phenol. A solution of intermediate 22, 2,6-Dichloro-3-hydroxybenzaldehyde (5.00 g, 26.18 mmol) in 5 mL of dichloromethane was added to a mixture of pyrrolidine (2.75 mL, 32.72 mmol) and sodium triacetoxyborohydride (6.94 g, 32.72 mmol) in dichloromethane (45 mL) under stirring. The reaction mixture was stirred for 16 h at room temperature. Water (20 mL) and saturated K$_2$CO$_3$ (5 mL) were added, and the layers were separated. The water layer was subjected to extraction with CHCl$_3$ (2×50 mL). The combined organic layers were washed with water (30 mL), brine, dried with Na$_2$SO$_4$, and evaporated. The residue was purified by chromatography (silica gel, 63/100 μm, 50 g, CHCl$_3$/MeOH 100:0→80:20). Fractions containing the target compound were evaporated. The residue was crystallized from ether to furnish the title compound (4.7 g, 73%) as white crystals. LCMS data: 246 and 248 (M+H)$^+$ (calculated for $C_{11}H_{13}Cl_2NO$ 246.14). $^1$H NMR data (DMSO-d6): 10.47 (br.s, 1H, OH); 7.19 (d, 1H, J=9 Hz, Ar—H); 6.89 (d, 1H, J=9 Hz, Ar—H); 3.78 (s, 2H, CH$_2$Ar); 2.50-2.56 (m, 4H, CH$_2$NCH$_2$); 1.60-1.68 (m, 4H, CH$_2$CH$_2$).

EXAMPLE 376 tert-Butyl ({trans-3-[2,4-dichloro-3-(pyrrolidin-1-ylmethyl)phenoxy]cyclobutyl}methyl)methylcarbamate. To a mixture of intermediate 6, cis-3-{[(tert-butoxycarbonyl)(methyl)amino]-methyl}cyclobutyl methanesulfonate (1.59 g, 5.42 mmol), intermediate 23, 2,4-dichloro-3-(pyrrolidin-1-ylmethyl)phenol (2 g, 8.13 mmol), and Cs$_2$CO$_3$ (2.65 g, 8.13 mmol) in DMSO (30 mL) was heated at 90-95° C. for 2 h under vigorous stirring in a flow of argon, and then cooled. Water (20 mL) and ether (50 mL) were added, and the layers were separated. The water layer was subjected to extraction with ether (2×50 mL). The combined organic layers were washed with water (30 mL), brine, dried with Na$_2$SO$_4$, and evaporated. The residue was purified by chromatography (silica gel, 63/100 μm, 50 g, CHCl$_3$/hexane 20:80→100:0, CHCl$_3$/MeOH 100:0→80:20) to furnish the title compound (1.7 g, 70%). LC/MS data: 443.1, 444.1, 445.1 (M+H) (calculated for $C_{22}H_{32}Cl_2N_2O_3$ 443.42). $^1$H NMR-data (DMSO-d6): 7.35 (d, 1H, J=9 Hz, Ar—H); 6.86 (d, 1H, J=9 Hz, Ar—H); 4.81-4.90 (m, 1H); 3.82 (brs, 2H, CH$_2$); 3.33 (d, 2H, J=8 Hz, CH$_2$); 2.78 (s, 3H, NCH$_3$); 2.50-2.62 (m, 5H); 2.22-2.30 (m, 2H); 2.11-2.21 (m, 2H); 1.58-1.72 (m, 4H); 1.40 (brs, 9H, Boc).

EXAMPLE 377

({trans-3-[2,4-Dichloro-3-(pyrrolidin-1-ylmethyl)phenoxy]cyclobutyl}methyl)methyl-amine. 4M HCl in dioxane (3.5 mL) was added to a solution of example 376, tert-Butyl ({trans-3-[2,4-dichloro-3-(pyrrolidin-1-ylmethyl)phenoxy]cyclobutyl}methyl)methylcarbamate (1.65 g, 3.72 mmol) in 2 mL of dioxane. The mixture was stirred for 20 h and evaporated to dryness. Water (5 mL) was added to the residue, and the solution was subjected to extraction with CHCl$_3$ (2×5 mL). The organic layers were discarded. Saturated K$_2$CO$_3$ (5 mL) was added to the water layer. The water solution was subjected to extraction with CHCl$_3$ (3×10 mL). The combined extracts were dried with Na$_2$SO$_4$ and evaporated; the residue was dried in vacuo to give the title compound (850 mg, 67%) as a yellow oil. LC/MS data: 343.1, 344.1, 345.1 (M+H) (calculated for C$_{17}$H$_{24}$Cl$_2$N$_2$O 343.3). $^1$H NMR-data (DMSO-d6): 7.33 (d, 1H, J=9 Hz, Ar—H); 6.86 (d, 1H, J=9.0 Hz, Ar—H); 4.79-4.88 (m, 1H), 3.81 (s, 2H, CH$_2$); 2.57 (d, 2H, J=7.3 Hz, CH$_2$); 2.50-2.55 (m, 4H); 2.33-2.45 (m, 1H); 2.28 (s, 3H, NCH$_3$); 2.21-2.27 (m, 2H); 2.10-2.19 (m, 2H); 1.60-1.68 (m, 4H).

EXAMPLE 378

N-({trans-3-[2,4-Dichloro-3-(pyrrolidin-1-ylmethyl)phenoxy]cyclobutyl}methyl)-N-methylcyclobutanecarboxamide Hydrochloride. CDI (227 mg, 1.40 mmol) was added to a solution of cyclobutanecarboxylic acid (CAS 3721-95-7, 140 mg, 1.40 mmol) in THF (3 mL). The mixture was stirred for 30 min, and a solution of Example 377, ({trans-3-[2,4-Dichloro-3-(pyrrolidin-1-ylmethyl)phenoxy]cyclobutyl}methyl)methylamine (400 mg, 1.165 mmol) in THF (1 mL) was added. The reaction mixture was stirred for 16 h at room temperature and evaporated. CHCl$_3$ (5 mL), a saturated solution of K$_2$CO$_3$ (0.5 mL), and water (0.5 mL) were added to the residue under stirring. The layers were separated, and the aqueous one was subjected to extraction with chloroform. The combined extracts were dried and evaporated. The residue was purified by chromatography (silica gel, 63-100 µm, 1 g, CHCl$_3$/MeOH 100:0→80:10). Fractions containing the target product were evaporated. The residue was dissolved in ether (1 mL), and 4M HCl/dioxane (0.3 mL) was added under stirring. The obtained mixture was evaporated and dryed in vacuo to afford the title compound (455 mg, 84%) as a light-yellow amorphous solid. LCMS data: 424.1, 425.1, 426.1, 427.1 (M+H) (calculated for C$_{22}$H$_{30}$Cl$_2$N$_2$O$_2$ 425.4). $^1$H NMR-data (DMSO-d6): 10.5 (brs, 1H, NH$^+$), 7.54, 7.53 (2d, 1H, J=9 Hz, Ar—H); 7.12, 7.09 (2d, 1H, J=9 Hz, Ar—H); 4.89-5.06 (m, 1H); 4.59 (s, 2H, CH$_2$); 3.48-3.59 (m, 2H), 3.19-3.48 (m, 5H); 2.77, 2.86 (2s, 3H, NCH$_3$), 2.53-2.66 (m, 1H), 1.82-2.33 (m, 13H); 1.66-1.79 (m, 1H).

EXAMPLE 379

N-({trans-3-[2,4-dichloro-3-(pyrrolidin-1-ylmethyl)phenoxy]cyclobutyl}methyl)-N-methyltetrahydro-2H-pyran-4-carboxamide hydrochloride. CDI (227 mg, 1.40 mmol) was added to a solution of tetrahydropyran-4-yl-carboxylic acid (CAS 5337-03-1, 182 mg, 1.40 mmol) in THF (3 mL). The mixture was stirred for 30 min, and a solution of Example 377, ({trans-3-[2,4-Dichloro-3-(pyrrolidin-1-ylmethyl)phenoxy]cyclobutyl}methyl)methylamine (400 mg, 1.165 mmol) in THF (1 mL) was added. The reaction mixture was stirred for 16 h at room temperature and evaporated. CHCl$_3$ (5 mL), a saturated solution of K$_2$CO$_3$ (0.5 mL), and water (0.5 mL) were added to the residue under stirring. The layers were separated, and the aqueous one was subjected to extraction with chloroform. The combined extracts were dried and evaporated. The residue was purified by chromatography (silica gel, 63-100 µm, 10 g, CHCl$_3$/MeOH 100:0→80:10). Fractions containing the target product were evaporated. The residue was dissolved in ether (1 mL), and 4M HCl/dioxane (0.3 mL) was added under stirring. The obtained mixture was evaporated and dryed in vacuo to afford the title compound (490 mg, 85%) as a light-yellow amorphous solid. LCMS data: 455.1, 456.1, 457.1 (M+H) (calculated for C$_{23}$H$_{32}$Cl$_2$N$_2$O$_3$ 455.43). $^1$H NMR-data (DMSO-d6): 10.09 (brs, 1H, NH$^+$), 7.55, 7.57 (2d, 1H, J=9 Hz, Ar—H); 7.12, 7.09 (2d, 1H, J=9 Hz, Ar—H); 4.88-5.09 (m, 1H); 4.60, 4.61 (2s, 2H, CH$_2$); 3.74-3.90 (m, 2H), 3.23-3.58 (m, 8H); 2.80, 3.03 (2s, 3H, NCH$_3$), 2.81-2.92 (m, 1H), 2.54-2.69 (m, 1H), 1.85-2.35 (m, 8H); 1.45-1.69 (m, 4H).

Intermediate 24

2,5-Dichloro-4-hydroxybenzaldehyde. 2,5-Dichlorophenol (CAS 583-78-8) (10 g, 0.060 mol), calcium hydroxide (19.5 g, 0.260 mol), and sodium carbonate (22.76 g, 0.220 mol) were suspended in water (140 mL). Chloroform (14.6 g, 0.120 mol) was added for 30 min, and the mixture was refluxed under vigorous stirring for 2 h. The reaction mixture was cooled on ice bath. Concentrated HCl (80 mL) and chloroform (200 mL) were added. The aqueous layer was discarded. The organic one was dried with anhydrous Na$_2$SO$_4$ (10 g) and evaporated in vacuo. The residue was purified by chromatography (silica gel 63-100 µm, 150 g, CCl$_4$→CCl$_4$: EtOAc (60:40)). Fractions containing the product were combined, evaporated to give the title compound (0.88 g, 4.60 mmol, 8%) as yellow crystals. $^1$H NMR data (DMSO-d6): 11.95 (s, 1H, CO<u>H</u>); 10.09 (s, 1H, OH); 7.83 (s, 1H, Ar—H); 7.09 (s, 1H, Ar—H).

Intermediate 25

2,5-Dichloro-4-pyrrolidin-1-ylmethyl-phenol. Pyrrolidine (0.48 mL, 5.76 mmol) was added to a suspension of Intermediate 24, 2,5-Dichloro-4-hydroxybenzaldehyde (0.88 g, 4.6 mmol) in dichloromethane (10 mL). The reaction mixture was cooled with an ice bath. Sodium triacetoxyborohydride (1.22 g, 5.76 mmol) was added in portions under stirring. The reaction mixture was stirred for 12 h at room temperature. Water (20 mL) and dichloromethane (10 mL) were added. The reaction mixture was acidified with 5N NAHSO$_4$ to pH~2. The organic layer was separated. The aqueous one was subjected to extraction with CH$_2$Cl$_2$ (2×30 mL), and the extracts were discarded. The aqueous fraction was alkalized with a saturated solution of potassium carbonate to pH 9-10. The product was extracted with CH$_2$Cl$_2$ (3×20 mL). The organic layer was dried with anhydrous Na$_2$SO$_4$ (5 g). The solvent was evaporated in vacuo, and coevaporated with dioxane to give the title compound (0.89 g, 3.6 mmol, 79%) as pale-yellow crystals. LC/MS data: 248.0, 247.0 and 246.0 (M+H); 174.9 (M-pyrrolidine+H) (calculated for C$_{11}$H$_{13}$ClNO 246.1). $^1$H NMR data (DMSO-d6): 10.52 (br.s., 1H, OH); 7.38 (s, 1H, s Ar—H); 6.98 (s, 1H, Ar—H); 3.54 (s, 2H, C<u>H$_2$</u>Ar); 2.40-2.47 (m, 4H); 1.63-1.74 (m, 4H).

EXAMPLE 380 tert-butyl ({trans-3-[2,5-dichloro-4-(pyrrolidin-1-ylmethyl)phenoxy]cyclobutyl}methyl)methylcarbamate. A solution of Intermediate 25, 2,5-Dichloro-4-pyrrolidin-1-ylmethyl-phenol (1.8 g, 7.5 mmol) and potassium tert-butoxide (0.85 g, 7.5 mmol) in DMSO (20 mL) was heated to 100° C. under vigorous stirring in a flow of argon. The mixture was stirred at this temperature for 15 min. A solution of intermediate 6, cis-3-{[(tert-butoxycarbonyl)(methyl)amino] methyl}cyclobutyl methanesulfonate (1.1 g, 3.8 mmol) in DMSO (10 mL) and tetrabutylammonium bromide (0.36 g, 1.14 mmol) were added. The mixture was stirred at 100° C. for 1 h, cooled, and diluted with $Et_2O$ (50 mL). The solution was washed with water (50 mL), 1N NaOH (3×25 mL), brine, dried with $Na_2SO_4$, and evaporated. The residue was purified by chromatography (silica gel 63-100µ, 20 mL, hexane/ $CHCl_3$ (20:80→0:100), then $CHCl_3$/MeOH 100:0→80:20). The product containing fractions were collected and concentrated to give the title compound (0.93 g, 55%) as a yellow oil. $^1$H NMR-data (DMSO-d6): 7.49 (s, 1H, Ar—H); 6.95 (s, 1H); 4.85-5.00 (m, 1H); 3.60 (br.s, 2H); 3.35 (d, 2H, J=8. Hz); 2.78 (s, 3H, $NCH_3$); 2.52-2.62 (m, 1H); 2.41-2.53 (m, 4H+DMSO); 2.22-2.30 (m, 2H); 2.08-2.20 (m, 2H); 1.65-1.74 (m, 4H); 1.43 (s, 9H, Boc).

EXAMPLE 381

({trans-3-[2,5-dichloro-4-(pyrrolidin-1-ylmethyl)phenoxy]cyclobutyl}methyl)methylamine. 4M HCl in dioxane (2.1 ml) was added to a solution of example 380, tert-butyl ({trans-3-[2,5-dichloro-4-(pyrrolidin-1-ylmethyl)phenoxy] cyclobutyl}methyl)methylcarbamate (0.93 g, 2.1 mmol) in 1 ml of dioxane. The mixture was stirred for 20 h and evaporated to dryness. The residue was recrystallized from MeOH-$Et_2O$. The crystals were separated by filtration and dried, then $CH_2Cl_2$ (30 mL) and saturated 10N NaOH (pH 12) were added under stirring. The layers were separated; the water solution was extracted with $CH_2Cl_2$ (3×20 mL). The combined extracts were dried ($Na_2SO_4$) and evaporated; the residue was dried in vacuo to give the title compound 101826-039 (0.49 g, 68%) was obtained as a yellow oil. LC/MS data: 343.0 (M+H) (calculated for $C_{17}H_{24}Cl_2N_2O$ 343.3). $^1$H NMR-data (DMSO-d6): 7.47 (s, 1H, Ar—H); 6.95 (s, 1H, Ar—H); 4.83-4.93 (m, 1H), 3.58 (s, 2H); 2.57 (d, 2H, J=7.3 Hz); 2.43-2.48 (m, 4H); 2.34-2.42 (m, 1H); 2.22-2.30 (s, 5H); 2.08-2.20 (m, 2H); 1.66-1.72 (m, 4H).

EXAMPLE 382

N-({trans-3-[2,5-Dichloro-4-(pyrrolidin-1-ylmethyl)phenoxy]cyclobutyl}methyl)-N,1-dimethylcyclopropanecarboxamide hydrochloride. CDI (71 mg, 0.43 mmol) was added to a solution of 1-methylcyclopropanecarboxylic acid CAS 6914-76-7 (66 mg, 65 mmol) in THF (2 ml) at RT under stirring, the mixture was stirred at RT for 1 h. Example 381, ({trans-3-[2,5-dichloro-4-(pyrrolidin-1-ylmethyl)phenoxy] cyclobutyl}methyl)methylamine (150 mg, 0.43 mmol) was added to the mixture and the solution was stirred at RT for 20 h and evaporated. The residue was purified by chromatography (silica gel, 63-100 µm, 5 g, hexane/$CHCl_3$ 20:80→0:100, then $CHCl_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (65 mg, 32%) as beige crystals. LC/MS data: 425.1 (M+H) (calculated for $C_{22}H_{30}Cl_2N_2O_2$ 425.4). $^1$H NMR-data (DMSO-d6): 10.77 (br.s, 1H, $NH^+$); 8.01 (s, 1H, NH); 7.09 (s, 1H, Ar—H); 4.80-4.92 (m, 1H), 4.42-4.56 (m, 2H); 3.33-3.55 (m, 4H); 2.95-3.18 (m, 5H); 2.60-2.70 (m, 1H); 2.17-2.34 (m, 4H); 1.84-2.17 (m, 4H); 1.25 (s, 3H); 0.92-0.96 (m, 2H), 0.46-0.52 (m, 2H).

EXAMPLE 383

N-({trans-3-[2,5-Dichloro-4-(pyrrolidin-1-ylmethyl)phenoxy]cyclobutyl}methyl)-N,3,5-trimethylisoxazole-4-carboxamide hydrochloride. Example 381, ({trans-3-[2,5-dichloro-4-(pyrrolidin-1-ylmethyl)phenoxy] cyclobutyl}methyl)methylamine (100 mg, 0.29 mmol) and triethylamine (0.04 mL, 0.29 mmol) were dissolved in $CH_2Cl_2$ (2 mL). 3,5-Dimethylisoxazole-4-carbonyl chloride (47 mg, 0.29 mmol) was added dropwise under stirring. The mixture was stirred at RT for 3 h and sat. $K_2CO_3$ was added. The mixture was stirred at RT for 20 h, dried with $Na_2SO_4$, and evaporated. The residue was purified chromatographically (silica gel 40-63 µm, 5 ml, $CCl_4$/$CHCl_3$ 100:0→0:100, then $CHCl_3$/MeOH 100:0→95:5). The residue was dissolved in ether (1 mL). 4N HCl/dioxane (0.10 mL) was added, and the reaction mixture was evaporated to dryness, recrystallized from i-PrOH/$Et_2O$. The crystals were separated by filtration and dried in vacuo to give the title compound (86 mg, 59%) as yellow crystals. LC/MS data: 466.2 (M+H) (calculated for $C_{23}H_{29}Cl_2N_3O_3$ 466.41). $^1$H NMR-data (DMSO-d6): 10.646 (br.s, 1H, $NH^+$); 7.99 (s, 1H, NH); 6.83-7.24 (m, 1H, Ar—H); 4.66-5.17 (m, 1H), 4.32-4.44 (m, 2H); 3.37-3.72 (m, 4H); 3.03-3.16 (m, 2H); 2.91 (s, 3H); 2.64-2.79 (m, 1H); 2.31-2.43 (m, 4H); 2.11-2.66 (m, 6H); 1.97-2.07 (m, 2H); 1.83-1.94 (m, 2H).

EXAMPLE 384

N-({trans-3-[2,5-Dichloro-4-(pyrrolidin-1-ylmethyl)phenoxy]cyclobutyl}methyl)-N-methyltetrahydro-2H-pyran-4-carboxamide. CDI (71 mg, 0.43 mmol) was added to a solution of tetrahydropyran-4-yl-carboxylic acid CAS 5337-03-1 (57 mg, 0.43 mmol) in THF (2 ml) at RT under stirring, the mixture was stirred at RT for 1 h. Example 381, ({trans-3-[2, 5-dichloro-4-(pyrrolidin-1-ylmethyl)phenoxy] cyclobutyl}methyl)methylamine (100 mg, 0.29 mmol) was added to the mixture and the solution was stirred at RT for 20 h and evaporated. The residue was purified by chromatography (silica gel, 63-100 µm, 5 g, hexane/$CHCl_3$ 20:80→0:100, then $CHCl_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (70 mg, 50% yield). LC/MS data: 455.1 (M+H) (calculated for $C_{23}H_{32}Cl_2N_2O_3$ 455.43). $^1$H NMR-data (DMSO-d6): 10.64 (br. s, 1H, $NH^+$); 7.88-8.09 (m, 1H, Ar—H); 7.00-7.13 (m, 1H, Ar—H); 4.88-5.37 (m, 1H), 4.32-4.44 (m, 2H); 3.79-3.91 (m, 2H); 3.33-3.56 (m, 6H); 2.98-3.15 (m, 4H); 2.76-2.93 (m, 2H); 2.56-2.65 (m, 1H); 2.10-2.33 (m, 4H); 1.81-2.07 (m, 4H); 1.46-1.69 (m, 4H).

Intermediate 26

N-Benzyl-3-oxocyclobutanecarboxamide. CDI (10.2 g, 0.063 mol) was added to a solution of 3-oxo-cyclobutanecarboxylic acid (6 g, 0.052 mol) in THF (60 ml) at 0° C. under stirring, the mixture was stirred at RT for 1 h. Benzylamine (6.9 ml, 0.063 mol) was added to the mixture and the mixture was stirred at RT for 3 h and evaporated. The residue was purified by chromatography (silica gel, 63-100 µm, 300 g, $CHCl_3$/MeOH 100:0→95:5) to give the title compound (9.5 g, 89%) as white crystals. LC/MS data: 204.0, 205.1 (M+H) (calculated for $C_{12}H_{13}NO_2$ 203.24). $^1$H NMR data (DMSO-d6): 8.62 (br.s, 1H, NH); 7.21-7.36 (m, 5H, Ph); 4.32 (d, 2H, $CH_2$, J=6.1 Hz); 3.10-3.28 (m, 5H).

Intermediate 27 cis-3-[(Benzylamino)methyl]cyclobutanol. A solution of intermediate 26 N-Benzyl-3-oxocyclobutanecarboxamide (9.5 g, 0.046 mol) in absolute THF (50 mL) was added to a suspension of LiAlH$_4$ (3.55 g, 0.093 mol) in absolute THF (50 ml) under stirring in argon. The mixture was refluxed under stirring for 1 h and cooled. Then 10 N NaOH (10 mL) and water (5 mL) were added. The organic layer was decanted, and the aqueous one was extracted with THF (2×50 mL). The organic layers were evaporated to give the title compound (7.4 g, 83%) as a yellow oil. $^1$H NMR-data (DMSO-d6): 7.00-7.49 (m, 6H, NH, Ph); 4.80 (br.s, 1H, OH); 3.81-3.95 (m, 1H); 3.67 (s, 2H, CH$_2$); 2.48 (d, 2H, CH$_2$, J=6.8 Hz); 2.19-2.30 (m, 2H); 1.70-1.84 (m, 1H); 1.35-1.50 (m, 2H).

Intermediate 28 cis-3-(Aminomethyl)cyclobutanol. 5% Pd/C (0.75 g) was added to a solution of intermediate 27, cis-3-[(Benzylamino) methyl]cyclobutanol (7.4 g, 0.039 mol) in MeOH (100 mL). The mixture was stirred under H$_2$ for 24 h and filtered through Celite. The solid was washed on the filter with MeOH (2×50 mL). The filtrate was evaporated to yield the title compound. This material was used without additional purification.

Intermediate 29 tert-Butyl [(cis-3-Hydroxycyclobutyl)methyl]carbamate. (Boc)$_2$O (8.6 g, 0.039 mol) was added to a solution of intermediate 28, cis-3-(Aminomethyl)cyclobutanol (4 g, 0.039 mol) and Et$_3$N (11 mL, 0.077 mol) in 50 mL absolute THF under stirring. The mixture was stirred at room temperature for 1 h and evaporated. The residue was purified by chromatography (silica gel, 63-100µ, 100 g, CHCl$_3$/MeOH 100:0→95:5) to give the title compound (5.15 g) as white crystals. $^1$H NMR-data (DMSO-d6): 6.61-6.87 (m, 1H, NH); 4.85 (br.s, 1H, OH); 3.77-3.92 (m, 1H); 2.90 (t, 2H, CH$_2$, J=6.1 Hz); 2.10-2.22 (m, 2H); 1.67-1.80 (m, 1H); 1.21-1.51 (m, 11H, CH$_2$, Boc).

Intermediate 30 cis-3-{[(tert-Butoxycarbonyl)amino]methyl}cyclobutyl Methanesulfonate. Intermediate 29, tert-Butyl [(cis-3-Hydroxycyclobutyl)methyl]carbamate (5.15 g, 26 mmol) and triethylamine (8.9 mL, 61 mmol) were dissolved in CH$_2$Cl$_2$ (50 mL). MsCl (2.4 mL, 31 mmol) was added dropwise at −20° C. under stirring in argon. The temperature was brought to ambient within 1 h. Water (100 mL) was added, and the layers were separated. The organic one was washed with water, brine, dried with Na$_2$SO$_4$, and evaporated, to give the title compound (5 g, 70%) white crystals. This crude product was used for the next stage without additional purification. $^1$H NMR-data (DMSO-d6): 6.74-7.00 (m, 1H, NH); 4.73-4.86 (m, 1H); 3.10 (s, 3H, MS); 2.97 (t, 2H, CH$_2$, J=5.7 Hz); 2.32-2.42 (m, 2H); 1.80-2.43 (m, 3H); 1.38 (s, 9H, Boc).

EXAMPLE 385 tert-butyl ({trans-3-[2-Chloro-3-(pyrrolidin-1-ylmethyl) phenoxy]cyclobutyl}methyl) carbamate. A mixture of intermediate 30, cis-3-{[(tert-Butoxycarbonyl)amino]methyl}-cyclobutyl methanesulfonate (1.5 g, 5.4 mmol), intermediate 13, 2-Chloro-3-pyrrolidin-1-ylmethyl-phenol (2.27 g, 10.74 mmol) and Cs$_2$CO$_3$ (3.5 g, 10.74 mmol) in DMSO (20 mL) was heated at 90-95° C. for 4 h under vigorous stirring in a flow of argon, then cooled. Water (40 ml) and EtOAc (40 ml) were added, and the layers were separated. The water layer was extracted with ether (20 ml), the combined organic layers were washed with 1N NaOH (3×25 mL), brine, dried with Na$_2$SO$_4$, and evaporated to give the title compound (1.9 g, 90%) as a yellow oil. LC/MS data: 395.5 (M+H) (calculated for C$_{21}$H$_{31}$ClN$_2$O$_3$ 394.95). $^1$H NMR-data (DMSO-d6): 7.16-7.25 (m, 1H, Ar—H); 7.05-7.09 (m, 1H, Ar—H); 6.87-6.97 (m, 1H, NH); 6.75-6.80 (m, 1H, Ar—H); 4.75-4.85 (m, 1H); 3.66 (s, 2H); 3.07 (t, 2H, J=6.6 Hz); 2.43-2.53 (m, 4H+DMSO); 2.31-2.42 (m, 1H); 2.21-2.30 (m, 2H); 2.08-2.18 (m, 2H); 1.64-1.75 (m, 4H); 1.39 (s, 9H, Boc).

EXAMPLE 386

({trans-3-[2-Chloro-3-(pyrrolidin-1-ylmethyl)phenoxy] cyclobutyl}methyl) amine hydro-chloride. 4M HCl in dioxane (6.05 ml) was added to a solution of Example 385, tert-butyl ({trans-3-[2-Chloro-3-(pyrrolidin-1-ylmethyl) phenoxy]cyclobutyl}methyl) carbamate (1.9 g, 4.84 mmol) in 2 ml of dioxane. The mixture was stirred for 20 h and evaporated to dryness. The residue was recrystallized from MeOH-Et$_2$O. The crystals were separated by filtration and dried, then CH$_2$Cl$_2$ (30 mL) and saturated sat. K$_2$CO$_3$ (pH 10) were added under stirring. The layers were separated, the water solution was extracted with CH$_2$Cl$_2$ (3×20 mL). The combined extracts were dried (Na$_2$SO$_4$) and evaporated; the residue was dried in vacuo to give the title compound (0.89 g, 64%) as a yellow oil. LC/MS data: 295.1 (M+H) (calculated for C$_{16}$H$_{23}$ClN$_2$O 294.83). $^1$H NMR-data (DMSO-d6): 7.14-7.26 (m, 1H, Ar—H); 7.00-7.07 (m, 1H, Ar); 6.75-6.84 (m, 1H, Ar—H); 4.74-4.88 (m, 1H), 3.66 (s, 2H); 2.67 (d, 2H, J=6.6 Hz); 2.43-2.53 (m, 4H+DMSO); 2.22-2.32 (m, 2H); 2.05-2.19 (m, 2H); 1.64-1.75 (m, 4H).

EXAMPLE 387

N-({trans-3-[2-Chloro-3-(pyrrolidin-1-ylmethyl)phenoxy]cyclobutyl}methyl)-N,3,5-trimethylisoxazole-4-carboxamide hydrochloride. Example 386, ({trans-3-[2-Chloro-3-(pyrrolidin-1-ylmethyl)phenoxy]cyclobutyl}methyl) amine (200 mg, 0.7 mmol) and triethylamine (0.1 mL, 0.7 mmol) were dissolved in CH$_2$Cl$_2$ (2 mL). 3,5-Dimethylisoxazole-4-carbonyl chloride (109 mg, 0.7 mmol) was added dropwise under stirring. The mixture was stirred at RT for 3 h and sat. K$_2$CO$_3$ was added. The mixture was stirred at RT for 20 h, dried with Na$_2$SO$_4$, and evaporated. The residue was purified chromatographically (silica gel 40-63 µm, 3 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (170 mg, 55%) as yellow crystals. LC/MS data: 418.1 (M+H) (calculated for C$_{22}$H$_{28}$ClN$_3$O$_3$ 417.94). $^1$H NMR-data (DMSO-d6): 10.36 (br.s, 1H, NH$^+$); 7.87-8.40 (m, 1H, NH); 7.30-7.44 (m, 2H, Ar—H); 6.96-7.04 (m, 1H, Ar—H); 4.88-5.00 (m, 1H), 4.46-4.52 (m, 2H); 3.35-3.48 (m, 4H); 3.08-3.19 (m, 2H); 2.52-2.62 (m, 1H); 2.48 (s, 3H); 2.31-2.40 (m, 2H); 2.28 (s, 3H); 2.13-2.23 (m, 2H); 1.97-2.10 (m, 2H); 1.83-1.94 (m, 2H).

EXAMPLE 388

N-(((trans)-3-(2-chloro-3-((pyrrolidin-1-yl)methyl)phenoxy)cyclobutyl)methyl)-1-methylcyclopropanecarboxamide hydrochloride. CDI (110 mg, 0.70 mmol) was added to a solution of 1-methylcyclopropanecarboxylic acid CAS 6914-76-7 (102 mg, 1.0 mmol) in THF (2 ml) at RT under stirring, the mixture was stirred at RT for 1 h. Example 386, ({trans-3-[2-Chloro-3-(pyrrolidin-1-ylmethyl)phenoxy] cyclobutyl}methyl) amine (200 mg, 0.7 mmol) was added to the mixture and the solution was stirred at RT for 20 h and evaporated. The residue was purified by chromatography (silica gel, 63-100 µm, 5 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (135 mg, 48%) as beige crystals. LC/MS data: 377.1 (M+H) (calculated for $C_{21}H_{29}ClN_2O_2$ 376.93). $^1H$ NMR-data (DMSO-d6): 10.53 (br.s, 1H, NH$^+$); 7.49-7.78 (m, 1H, NH); 7.32-7.43 (m, 2H, Ar—H); 6.95-7.03 (m, 1H, Ar—H); 4.80-4.92 (m, 1H), 4.42-4.56 (m, 2H); 3.39-3.47 (m, 2H); 3.18-3.25 (m, 2H); 3.07-3.18 (m, 2H); 2.39-2.47 (m, 1H); 2.27-2.34 (m, 2H); 1.97-2.17 (m, 4H); 1.84-1.95 (m, 2H); 1.25 (s, 3H); 0.92-0.96 (m, 2H), 0.46-0.52 (m, 2H).

EXAMPLE 389

N-({trans-3-[2-Chloro-3-(pyrrolidin-1-ylmethyl)phenoxy]cyclobutyl}methyl)-N-methyltetrahydro-2H-pyran-4-carboxamide hydrochloride. CDI (110 mg, 0.70 mmol) was added to a solution of tetrahydropyran-4-yl-carboxylic acid CAS 5337-03-1 (132 mg, 1.0 mmol) in THF (2 ml) at RT under stirring, the mixture was stirred at RT for 1 h. Example 386, ({trans-3-[2-Chloro-3-(pyrrolidin-1-ylmethyl)phenoxy]cyclobutyl}methyl) amine (200 mg, 0.7 mmol) was added to the mixture and the solution was stirred at RT for 20 h and evaporated. The residue was purified by chromatography (silica gel, 63-100 μm, 5 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (162 mg, 53% yield). LC/MS data: 407.1 (M+H) (calculated for $C_{22}H_{31}ClN_2O_3$ 406.96). $^1H$ NMR-data (DMSO-d6): 10.31 (br. s, 1H, NH$^+$); 7.73-8.12 (m, 1H, NH); 7.30-7.44 (m, 2H, Ar—H); 6.94-7.04 (m, 1H, Ar—H); 4.78-4.95 (m, 1H), 4.42-4.58 (m, 2H); 3.79-3.91 (m, 2H); 3.41-3.49 (m, 2H+ H$_2$O); 3.25-3.34 (m, 2H); 3.09-3.24 (m, 4H); 2.24-2.45 (m, 4H); 1.98-2.19 (m, 4H); 1.83-1.94 (m, 2H); 1.83-1.94 (m, 4H).

Intermediate 31

1-(tert-Butyldimethylsilyl)oxy-2-fluorobenzene. To a solution of 2-fluorophenol CAS 367-12-4 (10 g, 89 mmol) and imidazole (13.4 g, 19.6 mmol) in DMF (100 mL) was added TBDMSCl (14.8 g, 98 mmol) at 0° C., and the mixture was stirred ar RT for 20 min. Water was added at 0° C., and aqueous layer was extracted with Et$_2$O. The organic layer was washed with 1M NaHSO$_4$, brine, dried over Na$_2$SO$_4$ and evaporated in vacuo. The residue was purified by chromatography (silica gel 63-100μ, 400 mL, Hex→Hex/EtOAc 93:7) to furnish compound 101826-053 (20.1 g, 99%, 89 mmol) as a colorless oil. 1H NMR data (dmso-d6): 7.15-7.23 (m, 1H, H—Ar), 6.91-7.09 (m, 3H, H—Ar), 0.97 (s, 9H, t-Bu), 0.18 (s, 6H, 2CH$_3$).

Intermediate 32

3-{[tert-butyl(dimethyl)silyl]oxy}-2-fluorobenzaldehyde. Sec-BuLi (1.3M solution in cyclohexane, 75 mL, 98 mmol) was added slowly at −78° C. to a solution of Intermediate 31, 1-(tert-Butyldimethylsilyl)oxy-2-fluorobenzene (20.1 g, 89 mmol) and TMEDA (14.8 mL, 98 mmol) in THF (200 mL) and the mixture was stirred at the same temperature for 30 min. DMF (7.5 mL, 98 mmol) was added to the mixture at −78° C., and the mixture was stirred at the same temperature for 1.5 h. Then 10% aqueous HCl was added to attain pH~4-5 (200 mL), and the reaction mixture was stirred at RT for 30 min. The organic layer was separated. Aqueous layer was extracted with EtOAc (200 mL). The organic layers was washed with sat. NaHCO$_3$, brine, dried with Na$_2$SO$_4$ and evaporated in vacuo to give the title compound (16.7 g, 74%, 66 mmol) as a yellow oil. 1H NMR data (dmso-d6): 10.21 (s, 1H, CHO), 7.39-7.45 (m, 1H, H—Ar), 7.32-7.38 (m, 1H, H—Ar), 7.22-7.28 (m, 1H, H—Ar), 0.97 (s, 9H, t-Bu), 0.20 (s, 6H, 2CH$_3$).

Intermediate 33

1-(3-{[tert-butyl(dimethyl)silyl]oxy}-2-fluorobenzyl) pyrrolidine. Pyrrolidine (6.8 mL, 82 mmol) was added to a solution of intermediate 32, 3-{[tert-butyl(dimethyl)silyl] oxy}-2-fluorobenzaldehyde (16.7 g, 66 mmol) in dichloromethane (200 mL). The reaction mixture was cooled on ice bath, and sodium triacetoxyborohydride (17.4 g, 82 mmol) was added in portions under stirring. The reaction mixture was intensively stirred for 12 h at RT. Water (100 mL) was added. The organic layer was separated. The aqueous one was extracted with CH$_2$Cl$_2$ (2×100 mL). The organic layer was washed with brine, dried over Na$_2$SO$_4$ and evaporated in vacuo to give the title compound (19 g, 94%, 60 mmol). $^1H$ NMR data (DMSO-d6): 6.92-7.03 (m, 2H, H—Ar), 6.83-6.91 (m, 1H, H—Ar), 3.58 (d, 2H, J=1.7 Hz, Ar—CH$_2$); 2.38-2.46 (m, 4H), 1.63-1.70 (m, 4H) 0.97 (s, 9H, t-Bu), 0.16 (s, 6H, 2CH$_3$).

Intermediate 34

2-fluoro-3-(pyrrolidin-1-ylmethyl)phenol. To a solution of intermediate 33, 1-(3-{[tert-butyl(dimethyl)silyl]oxy}-2-fluorobenzyl)pyrrolidine (19 g, 60 mmol) in MeOH (200 mL) was added KF (7.1 g, 120 mmol), and the mixture was stirred at RT for 1 h. The reaction mixture evaporated in vacuo. Water (100 mL) and concentrated HCl were added to attain pH~6. The organic layer was separated. The aqueous one was extracted with CH$_2$Cl$_2$ (2×100 mL). The organic layers were discarded. The aqueous fraction was alkalized with K$_2$CO$_3$ to pH~10, the aqueous one was extracted with CHCl$_3$. The organic layer was washed with brine, dried over Na$_2$SO$_4$ and evaporated in vacuo, recrystallized from Et$_2$O/hexane mixture (1:1) to give the title compound (9.3 g, 78%, 48 mmol) as a yellow crystals. LCMS data: 197.1 and 196.1 (M+H)$^+$ (calculated for $C_{11}H_{14}FNO$ 195.24). $^1H$ NMR data (DMSO-d6): 9.63 (s, 1H, OH), 6.87-6.96 (m, 1H, H—Ar), 6.71-6.85 (m, 2H, H—Ar), 3.58 (s, 2H, Ar—CH$_2$); 2.36-2.46 (m, 4H), 1.61-1.72 (m, 4H).

EXAMPLE 390 tert-butyl ({trans-3-[2-fluoro-3-(pyrrolidin-1-ylmethyl) phenoxy]cyclobutyl}methyl)-methylcarbamate. A mixture of intermediate 6, cis-3-{[(tert-butoxycarbonyl)(methyl) amino]-methyl}cyclobutyl methanesulfonate (1.5 g, 5.2 mmol), intermediate 34, 2-fluoro-3-(pyrrolidin-1-ylmethyl) phenol (2.02 g, 10.4 mmol) and Cs$_2$CO$_3$ (3.38 g, 10.4 mmol) in DMSO (20 mL) was heated at 90-95° C. for 4 h under vigorous stirring in a flow of argon, then cooled. Water (40 ml) and EtOAc (40 ml) were added, and the layers were separated. The water layer was extracted with ether (20 ml), the combined organic layers were washed with 1N NaOH (3×25 mL), brine, dried with Na$_2$SO$_4$, and evaporated. Compound 101826-057 (1.9 g, 94%) was obtained as a yellow oil. LC/MS data: 394.6, 393.6 (M+H) (calculated for $C_{22}H_{33}FN_2O_3$ 392.52). $^1H$ NMR-data (DMSO-d6): 7.00-7.07 (m, 1H, Ar—H); 6.91-6.97 (m, 1H, Ar—H); 6.79-6.86 (m, 1H, Ar—H); 4.79-4.87 (m, 1H); 3.63 (s, 2H, CH$_2$); 3.32 (d, 2H, J=8.1 Hz, CH$_2$); 2.78 (s, 3H, NCH$_3$); 2.52-2.62 (m, 1H); 2.38-2.50 (m, 4H); 2.11-2.30 (m, 4H); 1.58-1.73 (m, 4H); 1.41 (s, 9H, Boc).

EXAMPLE 391

({trans-3-[2-fluoro-3-(pyrrolidin-1-ylmethyl)phenoxy] cyclobutyl}methyl)methylamine. 4M HCl in dioxane (6.05 ml) was added to a solution of example 390, tert-butyl ({trans-3-[2-fluoro-3-(pyrrolidin-1-ylmethyl)phenoxy]cyclobutyl}methyl)methylcarbamate (1.9 g, 4.84 mmol) in 2 ml of dioxane. The mixture was stirred for 20 h and evaporated to dryness. The residue was recrystallized from MeOH-Et$_2$O. The crystals were separated by filtration and dried, then CH$_2$Cl$_2$ (30 mL) and saturated 10N NaOH (pH 12) were added under stirring. The layers were separated; the water solution was extracted with CH$_2$Cl$_2$ (3×20 mL). The combined extracts were dried (Na$_2$SO$_4$) and evaporated; the residue was dried in vacuo to give the title compound (1.1 g, 79%) as a yellow oil. LC/MS data: 294.4, 293.4 (M+H) (calculated for C$_{17}$H$_{25}$FN$_2$O 292.5). $^1$H NMR-data (DMSO-d6): 6.98-7.04 (m, 1H, Ar—H); 6.88-6.94 (m, 1H, Ar); 6.78-6.84 (m, 1H, Ar—H); 4.77-4.86 (m, 1H), 3.60 (s, 2H); 2.57 (d, 2H, J=7.4 Hz); 2.33-2.47 (m, 5H); 2.30 (s, 3H, NCH$_3$); 2.20-2.28 (m, 4H); 1.64-1.73 (m, 4H).

EXAMPLE 392

N-({trans-3-[2-Fluoro-3-(pyrrolidin-1-ylmethyl)phenoxy]cyclobutyl}methyl)-N,1-dimethylcyclopropanecarboxamide hydrochloride. CDI (111 mg, 0.70 mmol) was added to a solution of 1-methylcyclopropanecarboxylic acid CAS 6914-76-7 (103 mg, 1.0 mmol) in THF (2 ml) at RT under stirring, the mixture was stirred at RT for 1 h. Example 391, ({trans-3-[2-fluoro-3-(pyrrolidin-1-ylmethyl)phenoxy]cyclobutyl}methyl)methylamine (200 mg, 0.7 mmol) was added to the mixture and the solution was stirred at RT for 20 h and evaporated. The residue was purified by chromatography (silica gel, 63-100 μm, 3 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (144 mg, 51%) as yellow crystals. LC/MS data: 375.2 (M+H) (calculated for C$_{22}$H$_{31}$FN$_2$O$_2$ 374.5). $^1$H NMR-data (DMSO-d6): 10.67 (br.s, 1H, NH$^+$); 7.13-7.32 (m, 2H, Ar—H); 6.95-7.08 (m, 1H, Ar—H); 4.77-4.97 (m, 1H), 4.38 (s, 2H); 3.35-3.54 (m, 4H); 2.93-3.15 (m, 5H); 2.56-2.67 (m, 1H); 2.11-2.30 (m, 4H); 1.79-2.07 (m, 4H); 1.23 (s, 3H, CH$_3$); 0.74-0.83 (m, 2H), 0.53-0.59 (m, 2H).

EXAMPLE 393

N-({trans-3-[2-Fluoro-3-(pyrrolidin-1-ylmethyl)phenoxy]cyclobutyl}methyl)-N-methyltetrahydro-2H-pyran-4-carboxamide hydrochloride. CDI (111 mg, 0.70 mmol) was added to a solution of tetrahydropyran-4-yl-carboxylic acid CAS 5337-03-1 (133 mg, 1.0 mmol) in THF (2 ml) at RT under stirring, the mixture was stirred at RT for 1 h. Example 391, ({trans-3-[2-fluoro-3-(pyrrolidin-1-ylmethyl)phenoxy]cyclobutyl}methyl)methylamine (200 mg, 0.7 mmol) was added to the mixture and the solution was stirred at RT for 20 h and evaporated. The residue was purified by chromatography (silica gel, 63-100 μm, 3 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (185 mg, 61%). LC/MS data: 405.2 (M+H) (calculated for C$_{23}$H$_{33}$FN$_2$O$_3$ 404.53). $^1$H NMR-data (DMSO-d6): 10.34-10.87 (m, 1H, NH$^+$); 7.15-7.28 (m, 2H, Ar—H); 6.98-7.10 (m, 1H, Ar—H); 4.83-5.09 (m, 1H), 4.38 (s, 2H), 3.85 (d, 2H, J=11 Hz); 3.33-3.54 (m, 6H); 3.04-3.15 (m, 4H); 2.77-2.96 (m, 2H); 2.53-2.68 (m, 1H); 2.09-2.31 (m, 4H); 1.95-2.07 (m, 2H); 1.80-1.94 (m, 2H); 1.46-1.68 (m, 4H).

EXAMPLE 394

N-({trans-3-[2-Fluoro-3-(pyrrolidin-1-ylmethyl)phenoxy]cyclobutyl}methyl)-N,3,5-trimethylisoxazole-4-carboxamide hydrochloride. Example 391, ({trans-3-[2-fluoro-3-(pyrrolidin-1-ylmethyl)phenoxy]cyclobutyl}methyl)methylamine (200 mg, 0.7 mmol) and triethylamine (0.1 mL, 0.7 mmol) were dissolved in CH$_2$Cl$_2$ (2 mL). 3,5-Dimethylisoxazole-4-carbonyl chloride (109 mg, 0.7 mmol) was added dropwise under stirring. The mixture was stirred at RT for 3 h and sat. K$_2$CO$_3$ was added. The mixture was stirred at RT for 20 h, dried with Na$_2$SO$_4$, and evaporated. The residue was purified chromatographically (silica gel 40-63 μm, 3 g, hexane/CHCl$_3$ 20:80→0:100, then CHCl$_3$/MeOH 100:0→95:5). The residue was dissolved in ether (1 mL). 4N HCl/dioxane (0.20 mL) was added, and the reaction mixture was evaporated to dryness. The obtained crystals were washed with ether and dried in vacuo to give the title compound (160 mg, 52%) as yellow crystals. LC/MS data: 416.2 (M+H) (calculated for C$_{23}$H$_{30}$FN$_3$O$_3$ 415.51). $^1$H NMR-data (DMSO-d6): 10.64 (br.s, 1H, NH$^+$); 7.13-7.29 (m, 2H, Ar—H); 6.87-7.12 (m, 1H, Ar—H); 4.53-5.07 (m, 1H), 4.38 (br.s, 2H); 3.57-3.67 (m, 1H); 3.37-3.52 (m, 3H); 2.97-3.13 (m, 2H); 2.91 (s, 3H); 2.61-2.78 (m, 1H); 2.28-2.41 (m, 4H); 2.11-2.23 (m, 6H); 1.94-2.06 (m, 2H); 1.79-1.94 (m, 2H).

EXAMPLE 395 tert-Butyl ({trans-3-[4-(Pyrrolidin-1-ylmethyl)phenoxy]cyclobutyl}methyl)carbamate. A solution on intermediate 1,4-(pyrrolidin-1-ylmethyl)phenol (4.5 g, 25 mmol) and potassium tert-butoxide (2.85 g, 25 mmol) in DMSO (100 mL) was heated to 100° C. under vigorous stirring in a flow of argon. The mixture was stirred at this temperature for 15 min. A solution intermediate 30, cis-3-{[(tert-Butoxycarbonyl)amino]methyl}cyclobutyl Methane-sulfonate (3.5 g, 13 mmol) in DMSO (100 mL) and tetrabutylammonium bromide (1.23 g, 3.8 mmol) were added. The mixture was stirred at 100° C. for 1 h and cooled. The residue was dissolved in EtOAc (150 mL). The solution was washed with water (300 mL), 1 N NaOH (2×100 mL), brine, dried with Na$_2$SO$_4$, and evaporated. The residue was purified by chromatography (silica gel, 63/100 μm, 60 g, CHCl$_3$/hexane 20:80→100:0, CHCl$_3$/MeOH 100:0→80:20 to furnish the title compound (2.16 g, 47%). LCMS-data: M+H 361.2, 362.2, M-Boc+H 261.2, 262.2 (calc. 360.5). 1H NMR-data (DMSO-d6): 7.17 (d, 2H, Ph, J=8.6 Hz); 6.86-7.00 (m, 1H, NH); 6.72 (d, 2H, Ph, J=8.6 Hz); 4.65-4.76 (m, 1H); 3.47 (s, 3H, CH$_2$); 3.00 (t, 2H, CH$_2$, J=6.3 Hz); 2.30-2.44 (m, 5H); 2.18-2.28 (m, 2H); 2.00-2.13 (m, 2H); 1.60-1.72 (m, 4H); 1.4 (s, 9H, Boc).

EXAMPLE 396

({trans-3-[4-(Pyrrolidin-1-ylmethyl)phenoxy]cyclobutyl}methyl)amine. Trifluoroacetic acid (3.5 mL, 49 mmol) was added to a solution of example 395, tert-Butyl ({trans-3-[4-(Pyrrolidin-1-ylmethyl)phenoxy]cyclobutyl}methyl)carbamate (2.16 g, 6 mmol) in dichloromethane (20 mL). The reaction mass was stirred at room temperature for 2 h and evaporated in vacuo. The residue was diluted with water (50 mL), and the obtained solution was extracted with CH$_2$Cl$_2$. The organic layer was discarded. The aqueous one was alkalized with 10 N NaOH to pH 12 and extracted with CHCl$_3$ (3×50 mL). The combined extracts were dried and evaporated to afford compound 10 (aap327) (1.4 g, 91%) as a yellow oil. LCMS-data: M+H 261.2, 262.2 (calc 260.38). $^1$H NMR-data (DMSO-d6): 7.17 (d, 2H, Ph, J=8.6 Hz); 6.72 (d, 2H, Ph, J=8.6 Hz); 4.65-4.76 (m, 1H); 3.47 (s, 3H, CH$_2$); 2.63 (d, 2H, CH$_2$, J=6.6 Hz); 2.32-2.42 (m, 4H); 2.18-2.28 (m, 3H); 2.00-2.13 (m, 2H); 1.60-1.72 (m, 4H).

EXAMPLE 397

N-[3-(4-Pyrrolidin-1-ylmethyl-phenoxy)-cyclobutylmethyl]-nicotinamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 21 mg, HPLC purity ELSD=100%, retention time (min)= 1.146; LRMS m/z Calcd for C22H27N3O2, 365.5; obsd LRMS APCI (M+1) m/z 366.

EXAMPLE 398

2-Pyridin-4-yl-N-[3-(4-pyrrolidin-1-ylmethyl-phenoxy)-cyclobutylmethyl]-acetamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 26 mg, HPLC purity ELSD=99.0739%, retention time (min)=1.086; LRMS m/z Calcd for C23H29N3O2, 379.5; obsd LRMS APCI (M+1) m/z 381.

EXAMPLE 399

3-Methyl-N-[3-(4-pyrrolidin-1-ylmethyl-phenoxy)-cyclobutylmethyl]-butyramide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 20 mg, HPLC purity ELSD=99.0745%, retention time (min)=1.451; LRMS m/z Calcd for C21H32N2O2, 344.5; obsd LRMS APCI (M+1) m/z 346.

EXAMPLE 400

2-Methoxy-N-[3-(4-pyrrolidin-1-ylmethyl-phenoxy)-cyclobutylmethyl]-acetamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 22 mg, HPLC purity ELSD=95.995%, retention time (min)=1.047; C19H28N2O3, 332.4; obsd LRMS APCI (M+1) m/z 333.

EXAMPLE 401

N-[3-(4-Pyrrolidin-1-ylmethyl-phenoxy)-cyclobutylmethyl]-acetamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 21 mg, HPLC purity ELSD=100%, retention time (min)= 0.986; C18H26N2O2, 302.4; obsd LRMS APCI (M+1) m/z 303.

EXAMPLE 402

6-Methyl-N-[3-(4-pyrrolidin-1-ylmethyl-phenoxy)-cyclobutylmethyl]-nicotinamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 24 mg, HPLC purity ELSD=100%, retention time (min)=1.14; LRMS m/z Calcd for C23H29N3O2, 379.5; obsd LRMS APCI (M+1) m/z 381.

EXAMPLE 403

N-[3-(4-Pyrrolidin-1-ylmethyl-phenoxy)-cyclobutylmethyl]-isobutyramide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 20 mg, HPLC purity ELSD=99.5743%, retention time (min)= 1.129; LRMS m/z Calcd for C20H30N2O2, 330.5; obsd LRMS APCI (M+1) m/z 331.

EXAMPLE 404

6-Methyl-pyridine-2-carboxylic acid [3-(4-pyrrolidin-1-ylmethyl-phenoxy)-cyclobutylmethyl]-amide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 20 mg, HPLC purity ELSD=96.381%, retention time (min)=1.492; LRMS m/z Calcd for C23H29N3O2, 379.5; obsd LRMS APCI (M+1) m/z 381.

EXAMPLE 405

2-Methyl-2H-pyrazole-3-carboxylic acid [3-(4-pyrrolidin-1-ylmethyl-phenoxy)-cyclobutylmethyl]-amide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 16 mg, HPLC purity ELSD=98.7275%, retention time (min)=1.389; LRMS m/z Calcd for C21H28N4O2, 368.5; obsd LRMS APCI (M+1) m/z 369.

EXAMPLE 406

N-[3-(4-Pyrrolidin-1-ylmethyl-phenoxy)-cyclobutylmethyl]-propionamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 18 mg, HPLC purity ELSD=95.49%, retention time (min)= 1.288; LRMS m/z Calcd for C19H28N2O2, 316.4; obsd LRMS APCI (M+1) m/z 317.

EXAMPLE 407

N-[3-(4-Pyrrolidin-1-ylmethyl-phenoxy)-cyclobutylmethyl]-isonicotinamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 15 mg, HPLC purity ELSD=100%, retention time (min)=0.963; LRMS m/z Calcd for C22H27N3O2, 365.5; obsd LRMS APCI (M+1) m/z 366.

EXAMPLE 408

2-Methyl-N-[3-(4-pyrrolidin-1-ylmethyl-phenoxy)-cyclobutylmethyl]-nicotinamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 20 mg, HPLC purity ELSD=100%, retention time (min)=0.948; LRMS m/z Calcd for C23H29N3O2, 379.5; obsd LRMS APCI (M+1) m/z 381.

EXAMPLE 409

2-Cyclopentyl-N-[3-(4-pyrrolidin-1-ylmethyl-phenoxy)-cyclobutylmethyl]-acetamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 22 mg, HPLC purity ELSD=99.5%, retention time (min)=1.583; LRMS m/z Calcd for C23H34N2O2, 370.5; obsd LRMS APCI (M+1) m/z 372.

EXAMPLE 401

3-Methoxy-N-[3-(4-pyrrolidin-1-ylmethyl-phenoxy)-cyclobutylmethyl]-propionamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 21 mg, HPLC purity ELSD=97.4%, retention time (min)=1.031; LRMS m/z Calcd for C20H30N2O3, 346.5; obsd LRMS APCI (M+1) m/z 347.

EXAMPLE 411

2,5-Dimethyl-2H-pyrazole-3-carboxylic acid [3-(4-pyrrolidin-1-ylmethyl-phenoxy)-cyclobutylmethyl]-amide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 19 mg, HPLC purity ELSD=98.6%, retention time (min)=1.44; LRMS m/z Calcd for C22H30N4O2, 382.5; obsd LRMS APCI (M+1) m/z 384.

EXAMPLE 412

Pyrazine-2-carboxylic acid [3-(4-pyrrolidin-1-ylmethyl-phenoxy)-cyclobutylmethyl]-amide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 12 mg, HPLC purity ELSD=97.4%, retention time (min)=1.142; LRMS m/z Calcd for C21H26N4O2, 366.5; obsd LRMS APCI (M+1) m/z 367.

EXAMPLE 413

2-Pyridin-2-yl-N-[3-(4-pyrrolidin-1-ylmethyl-phenoxy)-cyclobutylmethyl]-acetamide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 26 mg, HPLC purity ELSD=99.2%, retention time (min)=1.099; LRMS m/z Calcd for C23H29N3O2, 379.5; obsd LRMS APCI (M+1) m/z 381.

EXAMPLE 414

Tetrahydro-pyran-4-carboxylic acid [3-(4-pyrrolidin-1-ylmethyl-phenoxy)-cyclobutylmethyl]-amide. Reaction was conducted using the conditions described in General Procedure C: Amide Coupling, using Example 396 as the starting amine and the appropriate acid. The product was purified by HPLC (Preparative Purification Method A) yielding the title compound as the TFA salt, 21 mg, HPLC purity ELSD=97.9%, retention time (min)=1.061; LRMS m/z Calcd for C22H32N2O3, 372.5; obsd LRMS APCI (M+1) m/z 374.

EXAMPLE 415

Ethanesulfonic acid [3-(4-pyrrolidin-1-ylmethyl-phenoxy)-cyclobutylmethyl]-amide. Reaction was conducted using the conditions described in General Procedure S: Sulfonamide Coupling, using Example 396 as the starting amine and the appropriate sulfonyl chloride. The product was purified by HPLC (Preparative Purification Method A) yielding the title compound as the TFA salt, 17 mg, HPLC purity ELSD=97.1%, retention time (min)=1.1; LRMS m/z Calcd for C18H28N2O3S, 352.5; obsd LRMS APCI (M+1) m/z 353.

EXAMPLE 416

Benzylsulfonic acid [3-(4-pyrrolidin-1-ylmethyl-phenoxy)-cyclobutylmethyl]-amide. Reaction was conducted using the conditions described in General Procedure S: Sulfonamide Coupling, using Example 396 as the starting amine and the appropriate sulfonyl chloride. The product was purified by HPLC (Preparative Purification Method A) yielding the title compound as the TFA salt, 13 mg, HPLC purity ELSD=95.6%, retention time (min)=1.6; LRMS m/z Calcd for C23H30N2O3S, 414.6; obsd LRMS APCI (M+1) m/z 416.

EXAMPLE 417

3-Fluoro-N[3-(4-pyrrolidin-1-ylmethyl-phenoxy)-cyclobutylmethyl]-benzenesulfonamide. Reaction was conducted using the conditions described in General Procedure S: Sulfonamide Coupling, using Example 396 as the starting amine and the appropriate sulfonyl chloride. The product was purified by HPLC (Preparative Purification Method A) yielding the title compound as the TFA salt, 7 mg, HPLC purity ELSD=98.6%, retention time (min)=1.6; LRMS m/z Calcd for C22H27FN2O3S, 418.5; obsd LRMS APCI (M+1) m/z 420.

EXAMPLE 418

N[3-(4-Pyrrolidin-1-ylmethyl-phenoxy)-cyclobutylmethyl]-methanesulfonamide. Reaction was conducted using the conditions described in General Procedure S: Sulfonamide Coupling, using Example 396 as the starting amine and the appropriate sulfonyl chloride. The product was purified by HPLC (Preparative Purification Method A) yielding the title compound as the TFA salt, 13 mg, HPLC purity ELSD=97.06%, retention time (min)=1.3; LRMS m/z Calcd for C17H26N2O3S, 338.5; obsd LRMS APCI (M+1) m/z 339.

EXAMPLE 419

Pyridine-3-sulfonic acid [3-(4-pyrrolidin-1-ylmethyl-phenoxy)-cyclobutylmethyl]-amide. Reaction was conducted using the conditions described in General Procedure S: Sulfonamide Coupling, using Example 396 as the starting amine and the appropriate sulfonyl chloride. The product was purified by HPLC (Preparative Purification Method A) yielding the title compound as the TFA salt, 13 mg, HPLC purity ELSD=95.1%, retention time (min)=1.2; LRMS m/z Calcd for C21H27N3O3S, 401.5; obsd LRMS APCI (M+1) m/z 403.

EXAMPLE 420

Piperidine-1-sulfonic acid [3-(4-pyrrolidin-1-ylmethyl-phenoxy)-cyclobutylmethyl]-amide. Reaction was conducted using the conditions described in General Procedure S: Sulfonamide Coupling, using Example 396 as the starting amine and the appropriate sulfonyl chloride. The product was purified by HPLC (Preparative Purification Method A) yielding the title compound as the TFA salt, 8 mg, HPLC purity ELSD=95.6%, retention time (min)=1.4; LRMS m/z Calcd for C21H33N3O3S, 407.6; obsd LRMS APCI (M+1) m/z 409.

Intermediate 35

1-(Methanesulphonyl)piperazine. Methanesulphonyl chloride (18.3 mL, 0.236 mol) was added dropwise to a solution of tert-butyl piperazine-1-carboxylate (40 g, 0.214 mol) and triethylamine (60 mL, 0.43 mol) in $CH_2Cl_2$ (300 mL) in argon under stirring at $-20°$ C. The mixture was stirred at room temperature for 1 h, and water (100 mL) was added. The layers were separated, and the water layer was extracted with chloroform (2×200 mL). The organic fraction were washed with the 1 N $NaHSO_4$ solution (100 mL), the saturated $NaHCO_3$ solution (100 mL), dried over $Na_2SO_4$, filtered through $SiO_2$ (50 g, 40-63 μm), and evaporated to dryness. The residue (white crystals) was dissolved in isopropanol (200 mL), concentrated HCl (35 mL) was added, and the mixture was refluxed for 1 h and evaporated. Chloroform (200 mL), the saturated $K_2CO_3$ solution (50 mL), and water (50 mL) were added to the residue under stirring. The organic layer was separated, and the water layer was extracted with chloroform (2×100 mL). The organic layers were dried over $Na_2SO_4$, filtered through $SiO_2$ (50 g, 40-63 μm), and evaporated to dryness. The residue (white crystals) was dried to give the title compound in 94% (33 g) yield. LCMS data: $M^+H$ 165.0 (Calculated for $C_5H_{12}N_2O_2S$ 164.23), 97.2%, r.t. 0.913 min. $^1$H-NMR data (dmso-d6): 2.99 (m, 4H), 2.83 (s, 3H), 2.74 (m, 4H).

Intermediate 36

3-{[4-(methylsulfonyl)piperazin-1-yl]carbonyl}cyclobutanone. BOP (4.43 g, 10 mmol) was poured some more to a solution of 3-oxo-cyclobutanecarboxylic acid (1.14 g, 10 mmol), intermediate 35, 1-(Methanesulphonyl) piperazine (1.64 g, 10 mmol), and triethylamine (4.1 mL, 30 mmol) in DMF (10 mL) in argon under stirring at 0° C. The mixture was stirred for 20 h, evaporated, and the residue was dried at 0.5 mmHg. The residue was subjected to chromatography on $SiO_2$ (200 g, 40-63 μm, $CHCl_3$/hexane 8:2, 9:1, 9.5:0.5→$CHCl_3$→$CHCl_3$/i-PrOH 99:1→95:5) to give the title compound as white crystals in 2.2 g yield. GCMS data: $M^+$ 260 (Calculated for $C_{10}H_{16}N_2O_4S$ 260.31), 93.5%, r.t. 14.64 min. $^1$H-NMR data (dmso-d6): 3.56-3.64 (m, 4H), 3.50 (ddd, 1H, J=7.1 Hz, J=9 Hz, J=15 Hz), 3.20-3.29 (m, 4H), 3.08-3.15 (m, 4H), 2.89 (s, 3H).

Intermediate 37 cis-3-{[4-(methylsulfonyl)piperazin-1-yl]methyl}cyclobutanol. $LiAlH_4$ (150 mg, 3.95 mmol) was poured some more to a solution of intermediate 36, 3-{[4-(methylsulfonyl)piperazin-1-yl]carbonyl}cyclobutanone (500 mg, 1.92 mol) in absolute THF (5 mL) in argon under stirring. The mixture was refluxed under stirring for 4 h, cooled, and 10 N NaOH (0.5 mL) and water (0.5 mL) were added. The organic layer was decanted, and the water layer was extracted with THF (2×5 mL). The residue was vacuum-dried and dissolved in $CH_2Cl_2$ (10 mL). Triethylamine (0.550 mL, 4 mmol) was added, and then methanesulphonyl chloride (0.163 mL, 2.11 mmol) was added in argon under stirring at 0° C. The mixture was stirred at room temperature for 20 h, and the saturated $NaHCO_3$ solution (5 mL) was added. The layers were separated, and the water layer was extracted with chloroform (2×5 mL). The organic layers were dried over $Na_2SO_4$, evaporated, and the residue was diluted on $SiO_2$ ((10 g, 40-63 μm, $CHCl_3$/hexane 8:2, 9:1, 9.5: 0.5→$CHCl_3$→$CHCl_3$/MeOH 99:1→90:10) to give compound 7 as white crystals in 70% (435 mg) yield. $^1$H-NMR data (dmso-d6): 4.84 (qw, 1H, J=7.6 Hz), 3.12 (s, 3H), 3.07 (m, 4H), 2.85 (s, 3H), 2.54 (d, 1H, J=9.5 Hz), 2.4-2.50 (m, 7H), 2.00-2.1 (m, 1H), 1.8-1.9 (m, 2H).

Intermediate 38

3-{[4-(methylsulfonyl)piperazin-1-yl]methyl}cyclobutyl methanesulfonate. Intermediate 37, cis-3-{[4-(methylsulfonyl)piperazin-1-yl]methyl}cyclobutanol and triethylamine were dissolved in $CH_2Cl_2$ (50 mL). MsCl was added dropwise at $-20°$ C. under stirring in argon. The temperature was brought to ambient within 1 h. Water (100 mL) was added, and the layers were separated. The organic one was washed with water, brine, dried with $Na_2SO_4$, and evaporated, to give the title compound. This crude product was used for the next stage without additional purification.

EXAMPLE 421

1-(Methylsulfonyl)-4-({trans-3-[4-(pyrrolidin-1-ylmethyl)phenoxy]cyclobutyl}methyl)-piperazine. t-BuOK (304 mg, 2.7 mmol) was added to a solution of intermediate 1,1-(4-hydroxybenzyl)pyrrolidine (480 mg, 2.7 mL) in DMSO (20 mL). The mixture was stirred in argon at 100° C. for 15 min, and a solution of intermediate 38, 3-{[4-(methylsulfonyl)piperazin-1-yl]methyl}cyclobutyl methanesulfonate (435 mg, 1.34 mmol) and TBAB (131 mg, 0.406 mmol) in DMSO (10 mL) was added. The mixture was stirred at 100° C. for 2 h, water (50 mL) was added, and the mixture was extracted with ethyl acetate (3×50 mL). The organic layers were washed with 1 N NaOH (3×20 mL) and the saturated NaCl solution, dried over $Na_2SO_4$, and evaporated. The residue was diluted on $SiO_2$ (200 g, 40-63 μm, $CHCl_3$/hexane 8:2, 9:1, 9.5:0.5→$CHCl_3$→$CHCl_3$/MeOH 99:1→90:30) to give the title compound as white crystals in 66% (360 mg) yield. LCMS data: $M^+H$ 408.2 (Calculated for C21H33N3O3S 407.58), 100%, r.t. 2.408 min. $^1$H-NMR data (dmso-d6): 7.18 (d, 2H, J=8.3 Hz), 6.73 (d, 2H), 4.77 (qt, 1H, J=6.3 Hz), 3.49 (s, 2H), 3.09 (m, 4H), 2.85 (s, 3H), 2.38-2.50 (m, 11H), 2.10-2.23 (m, 4H), 1.65-1.70 (m, 4H).

Intermediate 39

3-(Morpholin-4-ylcarbonyl)cyclobutanone. CDI (8.1 g, 50 mmol) was added to a solution of 3-oxo-cyclobutanecarboxylic acid (5 g, 44 mmol) under vigorous stirring and cooling with an ice bath at 0° C. for 5 min. The reaction mixture was heated to 25° C., stirred at this temperature for 1 h, cooled to ° C., and morpholine (4.5 mL, 50 mmol) was added. The reaction mixture was heated to 25° C., stirred at this temperature for 3 h, and evaporated in vacuo. The residue was subjected to chromatography on $SiO_2$ (600 mL, 40-63 μm, $CCl_4 \rightarrow CHCl_3 \rightarrow 5\%$ i-PrOH) to give compound 4 in (6.5 g, 81%) yield as a colorless oil solidifying in a refrigerator. LC MS-data: $M^+$ 184.1 and 185.1 (calculated for $C_{19}H_{13}NO_4$ 183.21). $^1$H-NMR (400 MHz)-data (dmso-d6): 3.54-3.60 (m, 4H), 3.43-3.52 (m, 5H), 3.16-3.32 (m, 4H).

Intermediate 40 cis-3-(Morpholin-4-ylmethyl)cyclobutanol. A solution of intermediate 39, 3-(Morpholin-4-ylcarbonyl)cyclobutanone (1.1 g, 6.1 mmol) in absolute THF (10 mL) was added dropwise to a solution of $LiAlH_4$ (0.46 g, 12 mmol) in absolute THF (10 mL) in argon under stirring. The mixture was refluxed under stirring for 1 h, cooled, and 10 N NaOH (0.5 mL) and water (2.5 mL) were added. The organic layer was decanted, and the water layer was extracted with THF (2×5 mL). The organic layers were evaporated to give the title compound as colorless oil in ~100% (1.1 g) yield. $^1$H-NMR (400 MHz)-data (dmso-d6): 4.8-4.95 (d, 1H, J=6.4 Hz, OH), 3.8 (ddddd, 4H, J=5.3 Hz, CHOH), 3.48-3.58 (m, 4H, CH2OCH2), 2.22-2.35 (m, 8H, (CH2)3N, cyclobutylCHH), 1.77-1.90 (m (ttt), 1H, CHCH2N), 1.36-1.47 (m, 2H, cyclobutylCHH).

Intermediate 41 cis-3-(Morpholin-4-ylmethyl)cyclobutyl Methanesulfonate. MsCl (0.27 mL, 3.5 mmol) was added dropwise to a solution of intermediate 40, cis-3-(Morpholin-4-ylmethyl)cyclobutanol (0.5 g, 2.9 mmol) and triethylamine (1 mL, 7.0 mmol) in $CH_2Cl_2$ (5 mL) in argon under stirring on an ice bath. The mixture was brought to room temperature for 1 h, water (10 mL) was added, and the layers were separated. The organic layer was washed with water. The water layer was washed with the saturated NaCl solution, dried over $Na_2SO_4$, and evaporated to give the title compound as a yellow oil in 99% (718 mg, 2.88 mmol) yield. This material was used without additional purification. $^1$H-NMR (400 MHz)-data (dmso-d6): 4.83 (dddd, 1H, J=7.5 Hz, CHOMs), 3.51-3.58 (m, 4H, CH2OCH2), 3.12 (s, 1H, Ms), 2.46-2.55 (m, 2H, cyclobutylCHH), 2.28-2.40 (m, 6H, (CH2)3N), 2.00-2.12 (m, 1H, CHCH2N), 1.80-1.89 (m, 2H, cyclobutylCHH).

EXAMPLE 422

4-({trans-3-[4-(Pyrrolidin-1-ylmethyl)phenoxy]cyclobutyl}methyl)morpholine. A solution of intermediate 1,1-(4-hydroxybenzyl)pyrrolidine (1.02 g, 5.76 mmol) and sodium tert-butylate (0.65 g, 5.76 mmol) in DMSO (20 mL) was heated to T=100° C. in a stream of argon under vigorous stirring. Then the solution was stirred at T=100° C. for 15 min, and a solution of intermediate 41, cis-3-(Morpholin-4-ylmethyl)cyclobutyl methanesulfonate (0.718 g, 2.88 mmol) in DMSO (10 mL) and TBAB (0.28 g, 0.86 mmol) were added. The mixture was stirred at T=100° C. for 1 h, cooled, and dissolved in EtOAc (50 mL). The solution was washed with water (100 mL), 1 N NaOH (2×50 mL), the saturated NaCl solution, dried over $Na_2SO_4$, and evaporated. The residue was subjected to chromatography on $SiO_2$ (20 g, 63/100 μm, $CHCl_3$/20% hexane→$CHCl_3$→$CHCl_3$/20% MeOH) to give the title compound in 46% (438 mg) yield. LC MS-data: $M^+$ 331.3, (calculated for $C_{20}H_{30}N_2O_2$ 330.47). $^1$H-NMR (400 MHz)-data (dmso-d6): 7.20 (d, 2H, J=8.3, Ar—H), 6.74 (d, 2H, J=8.3, Ar—H), 4.76 (dddd, 4H, J=6.2 Hz, CHOAr), 3.50-3.60 (m, 6H), 2.39-2.54 (m, 7H), 2.30-2.38 (m, 4H), 2.10-2.25 (m, 4H), 1.64-1.73 (m, 4H).

Intermediate 42

2-Methoxy-4-(pyrrolidin-1-ylmethyl)phenol. $NaB(OAc)_3$H (8.7 g, 0.041 mol) was added in portions for 30 min to a mixture of pyrrolidine (3.4 mL, 0.041 mol) and vanillin (5 g, 0.033 mol) in $CH_2Cl_2$ (50 mL) under vigorous stirring and cooling with an ice bath in an atmosphere of argon. The mixture was stirred for 2 h and cooled. Then 10 N NaOH (4.1 mL) and water (30 mL) were added. The organic layer was separated; the aqueous one was extracted with chloroform (2×50 mL). The organic fractions were evaporated. The residue was distributed between water and $CH_2Cl_2$. Concentrated HCl (2.98 mL) was added. The organic layer was separated and discarded. The aqueous one was alkalized with 10 N NaOH to pH 6 and extracted with chloroform (2×100 mL). The combined extracts were dried with $Na_2SO_4$, and evaporated to give the title compound (5.1 g, 75%) was obtained as white crystals. $^1$H-NMR (400 MHz)-data (dmso-d6): 8.72 (s, 1H ArOH), 6.81-6.84 (m, 1H, Ar—H), 6.64-6.70 (m, 2H, Ar—H), 3.74 (s, 3H, ArOCH3), 3.43 (s, 2H, ArCH2), 2.36-2.41 (m, 4H, pyrrolidine (CH2)2N), 1.64-1.70 (m, 4H, CH2CH2CH2).

EXAMPLE 423

4-({trans-3-[2-Methoxy-4-(pyrrolidin-1-ylmethyl)phenoxy]cyclobutyl}methyl)-morpholine. A solution of intermediate 42, 2-Methoxy-4-(pyrrolidin-1-ylmethyl)phenol (0.66 g, 32 mmol) and potassium tert-butoxide (0.36 g, 32 mmol) in DMSO (10 mL) was heated to 100° C. under vigorous stirring in a flow of argon. The solution was stirred at this temperature for 15 min. Then a solution of intermediate 41, cis-3-(Morpholin-4-ylmethyl)cyclobutyl methanesulfonate (0.4 g, 16 mmol) in DMSO (10 mL) and tetrabutylammonium bromide (0.16 g, 0.48 mmol) were added. The mixture was stirred at 100° C. for 1 h, cooled, diluted with EtOAc (50 mL), washed with water (50 mL), 1 N NaOH (3×25 mL), brine, dried with $Na_2SO_4$, and evaporated. The residue was purified by chromatography (silica gel 63-100 μm, 25 mL, $CHCl_3$/hexane 20:80→100:0, $CHCl_3$/MeOH 100:0% 80:20) to give the title compound (400 mg, 69%) as yellow crystals. LC MS-data: $M^+$ 361.2, (calculated for $C_{21}H_{32}N_2O_3$ 360.50). $^1$H-NMR (400 MHz, J, Hz)-data (dmso-d6): 6.87 (d, 1H, J=1.8, Ar—H), 6.75 (dd, 1H, $J_1$=8.1, $J_2$=1.8, Ar—H), 6.63 (d, 1H, J=8.1, Ar—H), 4.72 (dddd, 4H, J=6.3, CHOAr), 3.73 (s, 3H, ArOCH3), 3.53-3.57 (m, 4H), 3.46-3.49 (m, 2H), 2.38-2.52 (m, 7H), 2.31-2.36 (m, 4H), 2.10-2.20 (m, 4H), 1.64-1.74 (m, 4H).

Intermediate 43

3-Methoxy-4-(pyrrolidin-1-ylmethyl)phenol. $NaB(OAc)_3$H (8.7 g, 0.041 mol) was added in portions for 30 min to a mixture of pyrrolidine (3.4 mL, 0.0.41 mol) and 4-hydroxy-2-methoxybenzaldehyde (5 g, 0.033 mol) in $CH_2Cl_2$ (50 mL) under vigorous stirring and cooling with an ice bath in an atmosphere of argon. The mixture was stirred for 2 h and cooled. Then 10 N NaOH (4.1 mL) and water (30 mL) were added. The organic layer was separated, the aqueous one was extracted with chloroform (2×50 mL). The organic fractions were evaporated. The residue was distributed between water and $CH_2Cl_2$. Concentrated HCl (2.98 mL) was added. The organic layer was separated and discarded. The aqueous one was alkalized with 10 N NaOH to pH 6 and extracted with chloroform (2×50 mL). The combined extracts were dried with $Na_2SO_4$, and evaporated to give the title compound (3.37 g, 07%) as yellow crystals. $^1$H-NMR (400 MHz)-data (dmso-d6, j, Hz): 9.25 (s, 1H ArOH), 7.02 (d, 1H, J=8.3, Ar—H), 6.36 (d, 1H, J=2.2, Ar—H) 6.30 (dd, 1H, J$_1$=8.3, J$_2$=2.2, Ar—H), 3.70 (s, 3H, ArOC$\underline{H}$3), 3.44 (s, 2H, ArC$\underline{H}$2), 2.38-2.44 (m, 4H, pyrrolidine (CH2)2N), 1.62-1.68 (m, 4H, CH2C$\underline{H}$2C$\underline{H}$2CH2).

EXAMPLE 424

4-({trans-3-[3-Methoxy-4-(pyrrolidin-1-ylmethyl)phenoxy]cyclobutyl}methyl)-morpholine. A solution of intermediate 43, 3-Methoxy-4-(pyrrolidin-1-ylmethyl)phenol (0.66 g, 32 mmol) potassium tert-butoxide (0.36 g, 32 mmol) in DMSO (10 mL) was heated to 100° C. under vigorous stirring in a flow of argon. The solution was stirred at this temperature for 15 min. Then a solution of intermediate 41, cis-3-(Morpholin-4-ylmethyl)cyclobutyl methanesulfonate (0.4 g, 16 mmol) in DMSO (10 mL) and tetrabutylammonium bromide (0.16 g, 0.48 mmol) were added. The mixture was stirred at 100° C. for 1 h, cooled, diluted with EtOAc (50 mL), washed with water (50 mL), 1 N NaOH (3×25 mL), brine, dried with Na$_2$SO$_4$, evaporated. The residue was purified by chromatography (silica gel 63-100 μm, 25 mL, CHCl$_3$/hexane 20:80→100:0, CHCl$_3$/MeOH 100:0→80:20) to afford target compound 7 (aap331) (350 mg, 60%) as a yellow oil. LC MS-data: M+361.2, 404.2 (+CH3CN) (calculated for C$_{21}$H$_{32}$N$_2$O$_3$ 360.50). $^1$H-NMR (400 MHz, J, Hz)-data (dmso-d6): 7.13 (d, 1H, J=8.3, Ar—H), 6.41 (d, 1H, J=2.2, Ar—H) 6.31 (dd, 1H, J$_1$=8.3, J$_2$=2.2, Ar—H), 4.78 (dddd, 4H, J=6.3, C$\underline{H}$OAr), 3.73 (s, 3H, ArOC$\underline{H}$3), 3.48-3.59 (m, 6H), 2.40-2.52 (m, 7H), 2.31-2.37 (m, 4H), 2.10-2.24 (m, 4H), 1.63-1.71 (m, 4H).

Intermediate 44

4-(Pyrrolidin-1-ylmethyl)phenol. NaB(OAc)$_3$H (32 g, 0.15 mol) was added in portions for 15 min to a mixture of pyrrolidine (9.1 mL, 0.11 mol) and 4-hydroxybenzaldehyde (12.2 g, 0.1 mol) in CH$_2$Cl$_2$ (100 mL) under vigorous stirring and cooling with an ice bath in an atmosphere of argon Ar. The mixture was stirred for 20 h and cooled with an ice bath. Concentrated HCl (20 mL) was added. The organic layer was separated and discarded. The aqueous one was alkalized with K$_2$CO$_3$ to pH 9 (40 mL) and extracted with chloroform (3×100 mL). The combined extracts were dried with Na$_2$SO$_4$, and evaporated to give the title compound (17.4 g, 98%) was obtained as white crystals. LCMS-data: (M+H)$^+$ 178.1 and 179.1 (calculated for C$_{11}$H$_{15}$NO 177.0). $^1$H NMR (400Mz)-data (DMSO-d6, J, Hz): 9.19 (br s, 1H, OH); 7.03-7.11 (t, 1H, ArH, J=7.5 Hz); 6.66-6.73 (m, 1H, ArH); 6.34-6.59 (dd, 1H, ArH, J1=1.7 Hz, J2=6.4 Hz); 3.46 (s, 2H, CH2Ar); 2.37-2.43 (m, 4H, C$\underline{H}$2CH2CH2C$\underline{H}$2); 1.62-1.73 (m, 4H, CH2C$\underline{H}$2C$\underline{H}$2CH2).

EXAMPLE 425

4-({trans-3-[3-(pyrrolidin-1-ylmethyl)phenoxy]cyclobutyl}methyl)morpholine Dihydrochloride. A solution of intermediate 44, 4-(Pyrrolidin-1-ylmethyl)phenol (0.57 g, 3.2 mmol) and potassium tert-butoxide (0.36 g, 3.2 mmol) in DMSO (15 mL) was heated to 90° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 1.6 mmol) in DMSO (10 mL) and tetrabutylammonium bromide (1 g, 0.1 mmol) were added. The mixture was stirred at 90-100° C. for 2 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100μ, 8 mL, CHCl$_3$/MeOH 100:0→50:30). The obtained product was dissolved in ether, and 4M HCl/dioxane (0.40 mL) was added. The precipitate was separated by filtration, washed with ether, and dried in vacuo to give the title compound (200 mg, 38%) as white crystals. LCMS-data: LCMS-data: 331.2, and 332.2 (M+H)$^+$, 445.1, and 446.1 (M+TFA+H)$^+$ M (calculated for C$_{20}$H$_{30}$N$_2$O$_2$ 331). $^1$H NMR data (DMSO-d6): 11.10-11.30 (m, 2H, N+H2); 7.25-7.40 (m, 2H, Ar—H); 7.10-7.20 (d, 1H, Ar—H, J=7.1 Hz); 6.80-6.90 (d, 1H, Ar—H, J=7.3 Hz); 4.75-4.84 (m, 1H); 4.23-4.28 (m, 2H); 3.77-3.96 (m, 4H); 3.16-3.40 (m, 6H+H$_2$O); 2.83-3.06 (m, 5H); 2.20-2.52 (m, 4H); 1.84-2.05 (m, 4H).

Intermediate 45

2-Methoxy-6-chloro-4-(pyrrolidin-1-ylmethyl)phenol. NaB(OAc)$_3$H (12.5 g, 0.098 mol) was added in portions for 15 min to a mixture of pyrrolidine (5.41 mL, 0.087 mol) and 2-methoxy-5-chloro-4-hydroxybenzaldehyde (12.5 g, 0.089 mol) in CH$_2$Cl$_2$ (100 mL) under vigorous stirring and cooling with an ice bath in an atmosphere of argon Ar. The mixture was stirred for 20 h and cooled with an ice bath. Concentrated HCl (18 mL) was added. The organic layer was separated and discarded. The aqueous one was alkalized with 10 N NaOH to pH 9 (30 mL) and extracted with chloroform (2×100 mL). The combined extracts were dried with Na$_2$SO$_4$, and evaporated to give compound (5.1 g, 75%) was obtained as white crystals. LCMS-data: 242.0 (M+H)$^+$, (calculated for C$_{12}$H$_{16}$NOCl 241.5). 1H NMR (400 MHz)-data (DMSO-d6, J, Hz): 9.18 (br s, 1H, OH); 6.83 (s, 2H, ArH); 3.79 (s, 3H, CH3); 3.44 (s, 2H, CH2Ar); 2.36-2.44 (m, 4H, C$\underline{H}$2CH2CH2C$\underline{H}$2,); 1.65-1.72 (m, 4H, CH2C$\underline{H}$2C$\underline{H}$2CH2,).

EXAMPLE 426

4-({trans-3-[2-Methoxy-6-chloro-4-(pyrrolidin-1-ylmethyl)phenoxy]cyclobutyl}methyl)-morpholine Dihydrochloride. A solution of intermediate 45, 2-Methoxy-6-chloro-4-(pyrrolidin-1-ylmethyl)phenol (0.77 g, 3.2 mmol) and potassium tert-butoxide (0.36 g, 3.2 mmol) in DMSO (15 mL) was heated to 90° C. under vigorous stirring in a flow of argon. The mixture was stirred at this temperature for 15 min. A solution of intermediate 41, cis-3-(Morpholin-4-ylmethyl) cyclobutyl methanesulfonate (0.4 g, 1.6 mmol) in DMSO (10 mL) and tetrabutylammonium bromide (1 g, 0.1 mmol) were added. The mixture was stirred at 90-100° C. for 2 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100μ, 8 mL, CHCl$_3$/MeOH 100:0→50:30). The obtained product was dissolved in ether, and 4M HCl/dioxane (0.48 mL) was added. The precipitate was separated by filtration, washed with ether, and dried in vacuo to give the title compound (290 mg, 48%) was obtained as white crystals. LCMS-data: 395.2, and 397.1 (M+H), 509.1 and 511.1 (M+FTA+H), (calculated for C21H31N2O2Cl 394.95). $^1$H NMR data (DMSO-d6): 10.83-11.74 (m, 2H, N$^+$H2); 7.49 (s, 1H, Ar—H); 7.29 (s, 1H, Ar—H); 4.75-4.84 (m, 1H); 4.23-4.28 (m, 2H); 3.77-3.96 (m, 8H); 3.16-3.40 (m, 6H+H$_2$O); 2.83-3.06 (m, 5H); 2.20-2.42 (m, 4H); 1.84-2.05 (m, 4H).

Intermediate 46

3-Chloro-4-(pyrrolidin-1-ylmethyl)phenol. NaB(OAc)$_3$H (20 g, 0.094 mol) was added in portions for 15 min to a mixture of pyrrolidine (7.78 mL, 0.11 mol) and 3-chloro-4-hydroxybenzaldehyde (12.5 g, 0.079 mol) in CH$_2$Cl$_2$ (100 mL) under vigorous stirring and cooling with an ice bath in an atmosphere of argon Ar. The mixture was stirred for 20 h and cooled with an ice bath. Concentrated HCl (18 mL) was added. The organic layer was separated and discarded. The aqueous one was alkalized with 10 N NaOH to pH 9 (30 mL) and extracted with chloroform (3×100 mL). The combined extracts were dried with Na$_2$SO$_4$, and evaporated. The residue was purified by chromatography (silica gel 63-100μ, 8 mL, CHCl$_3$/5% i-PrOH to give the title compound (8.07 g, 52%) was obtained as white crystals. LCMS-data: 212 and 214 (M+H)$^+$, (calculated for C$_{11}$H$_{14}$NOCl 211.6); 1H NMR (400Mz)-data (DMSO-d6, J, Hz): 9.95 (br s, 1H, OH); 7.20 (d, 1H, Ar, J=2 Hz); 7.00 (dd, 1H, Ar, J1=2 Hz, J2=8.1 Hz); 6.89 (d, 1H, Ar, J=8.1); 3.43 (s, 2H, CH2); 2.35-2.40 (m, 4H); 1.63-1.69 (m, 4H).

EXAMPLE 427

4-({trans-3-[2-chloro-4-(pyrrolidin-1-ylmethyl)phenoxy] cyclobutyl}methyl)morpholine Dihydrochloride. A solution of intermediate 46, 3-Chloro-4-(pyrrolidin-1-ylmethyl)phenol (0.63 g, 3.2 mmol) and potassium tert-butoxide (0.36 g, 3.2 mmol) in DMSO (15 mL) was heated to 90° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 1.6 mmol) in DMSO (10 mL) and tetrabutylammonium bromide (1 g, 0.1 mmol) were added. The mixture was stirred at 90-100° C. for 2 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100μ, 8 mL, CHCl$_3$/MeOH 100:0→50:30). The obtained product was dissolved in ether, and 4M HCl/dioxane (0.30 mL) was added. The precipitate was separated by filtration, washed with ether, and dried in vacuo to give the title compound (148 mg, 25%) was obtained as white crystals. LCMS-data: LCMS-data: 365.1 and 367.1 and 368.1 (M+H)$^+$ 591.1 and 592.1, and 593.5 (M+TFA+H)$^+$, (calculated for C$_{21}$H$_{29}$N$_2$O$_2$Cl 364.9). 1H NMR data (DMSO-d6): 10.76-10.98 (m, 2H, N$^+$H2); 7.70-7.75 (s, 1H, Ar—H); 7.49-7.56 (d, 1H, Ar—H, J=2 Hz); 6.95-7.00 (d, 1H, Ar—H, J=2 Hz); 4.89-4.91 (m, 1H); 4.22-4.28 (m, 2H); 3.78-3.97 (m, 4H); 3.24-3.37 (m, 6H+H$_2$O); 2.96-3.12 (m, 5H); 2.84-2.94 (m, 1H); 2.25-2.36 (m, 2H); 1.81-2.05 (m, 4H).

Intermediate 47

2-Ethoxy-4-(pyrrolidin-1-ylmethyl)phenol. NaB(OAc)$_3$H (8 g, 0.038 mol) was added in portions for 30 min to a mixture of pyrrolidine (3.1 mL, 0.038 mol) and 3-ethoxy-4-hydroxybenzaldehyde (5 g, 0.03 mol) in CH$_2$Cl$_2$ (50 mL) under vigorous stirring and cooling with an ice bath in an atmosphere of argon Ar. The mixture was stirred for 12 h and cooled with an ice bath. 10N NaOH (3.8 mL) and water (30 mL) were added. The organic layer was separated. The aqueous one was extracted with chloroform (2×100 mL). The extracts were evaporated. The residue was purified by chromatography (silica gel 40-63μ, 100 g, CCl$_4$—CHCl$_3$, CHCl$_3$/MeOH 100:0→90:10) to give the title compound (4.8 g, 73%) was obtained as dark-yellow crystals. $^1$H NMR data (DMSO-d6): 8.65 (s, 1H ArOH), 6.81 (d, 1H, J=1.71, Ar—H), 6.70 (d, 1H, J=7.8, Ar—H); 6.65 (dd, 1H, J$_1$=7.8, J$_2$=1.7, Ar—H), 3.98 (q, 2H, CH$_2$CH$_3$), 3.42 (s, 2H, ArCH$_2$), 2.33-2.45 (m, 4H, pyrrolidine (CH$_2$)$_2$N), 1.59-1.73 (m, 4H, CH$_2$CH$_2$CH$_2$CH$_2$); 1.31 (t, 3H, J=6.9, CH$_2$CH$_3$).

EXAMPLE 428

4-({trans-3-[2-Ethoxy-4-(pyrrolidin-1-ylmethyl)phenoxy]cyclobutyl}methyl)morpholine Dihydrochloride. A solution of intermediate 47, 2-Ethoxy-4-(pyrrolidin-1-ylmethyl)phenol (0.71 g, 32 mmol) and potassium tert-butoxide (0.36 g, 32 mmol) in DMSO (10 mL) was heated to 100° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 16 mmol) in DMSO (10 mL) and tetrabutylammonium bromide (0.16 g, 0.48 mmol) were added. The mixture was stirred at 100° C. for 1 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100μ, 8 mL, CHCl$_3$/hexane 20:80→100:0; CHCl$_3$/MeOH 100:0→80:20). The obtained product was dissolved in ether, and 4M HCl/dioxane (0.4 mL) was added. The precipitate was separated by filtration, washed with ether, and dried in vacuo to give the title compound (285 mg, 40%) as white crystals. LC/MS-data: M$^+$ 376.2, and 375.2 (calculated for C$_{22}$H$_{34}$N$_2$O$_3$ 374). $^1$H NMR data (DMSO-d6): 11.74-10.83 (m, 2H, N$^+$H2); 7.32 (s, 1H, Ar—H); 7.03 (d, 1H, Ar—H); 6.76 (d, 1H, Ar—H); 5.09-4.52 (m, 1H); 3.76-4.26 (m, 8H); 3.20-3.43 (m, 6H+H$_2$O); 2.76-3.11 (m, 5H); 2.21-2.48 (m, 4H); 1.77-2.06 (m, 4H); 1.28-1.40 (m, 3H).

Intermediate 48

4-((pyrrolidin-1-yl)methyl)naphthalen-1-ol. NaB(OAc)$_3$H (6.4 g, 0.030 mol) was added in portions for 15 min to a mixture of pyrrolidine (2.1 mL, 0.025 mol) and 4-hydroxynaphthalene-1-carbaldehyde (3.40 g, 0.020 mol) in (C$_2$H$_5$)$_2$O (80 mL) under vigorous stirring and cooling with an ice bath in an atmosphere of argon Ar. The mixture was stirred for 20 h and cooled with an ice bath. Concentrated HCl (18 mL) was added. The organic layer was separated and discarded. The aqueous one was alkalized with 10 N NaOH to pH 9 (30 mL) and extracted with (2×100 mL) (C$_2$H$_5$)$_2$O. The combined extracts were dried with Na$_2$SO$_4$, and evaporated to give the title compound (5.1 g, 75%) was obtained as white crystals. LCMS-data: 228.1 and 229.1 (M+H)$^+$, (calculated for C$_{15}$H$_{17}$NO 227.13). 1H NMR (400 MHz)-data (DMSO-d6, J, Hz): 9.18 (br s, 1H, OH); 6.83 (s, 2H, ArH); 3.79 (s, 3H, CH$_3$); 3.44 (s, 2H, CH$_2$Ar); 2.36-2.44 (m, 4H, CH2CH2CH2 CH2,); 1.65-1.72 (m, 4H, CH2CH2CH2CH2,).

EXAMPLE 429

(4-[3-(4-Pyrrolidin-1-ylmethyl-naphthalen-1-yloxy)-cyclobutylmethyl]-morpholine Dihydrochloride. A solution of intermediate 48, 4-((pyrrolidin-1-yl)methyl)naphthalen-1-ol (0.77 g, 3.2 mmol) and potassium tert-butoxide (0.36 g, 3.2 mmol) in DMSO (15 mL) was heated to 90° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 1.6 mmol) in DMSO (10 mL) and tetrabutylammonium bromide (1 g, 0.1 mmol) were added. The mixture was stirred at 90-100° C. for 2 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100μ, 8 mL, CHCl$_3$/MeOH 100:0→50:30). The obtained product was dissolved in ether, and 4M HCl/dioxane (0.48 mL) was added. The precipitate was separated by filtration, washed with ether, and dried in vacuo to give the title compound (27 mg 3.7%) as red crystals. LCMS-data: 382.2, and 381.2 (M+H)$^+$ (calculated for C$_{23}$H$_{30}$N$_2$O 380.5). 1H NMR data (DMSO-d6): 10.83-11.74 (m, 2H, N$^+$H2); 8.38-8.42 (d, 1H, Ar—H, J=8.6 Hz); 8.13-8.19 (d, 1H, Ar—H, J=8.6 Hz); 7.68-7.75 (m, 3H, Ar—H); 6.46-6.65 (d, 1H, Ar—H, J=7.8 Hz); 5.07-5.14 (m, 1H); 4.02-4.11 (m, 2H); 3.78-3.89 (m, 2H);

3.49-3.52 (m, 6H+H$_2$O); 3.32-3.42 (m, 2H); 3.15-3.25 (m, 1H); 2.52-2.54 (m, 4H); 2.00-2.60 (m, 4H).

Intermediate 49

2-Isopropyl-5-Methyl-4-(pyrrolidin-1-ylmethyl)phenol. 4-Hydroxy-5-isopropyl-2-methyl-benzaldehyde (1.0 g, 5.6 mmol) was added in portions for 30 min to a mixture of pyrrolidine (0.58 mL, 7 mmol) and NaB(OAc)$_3$H (1.49 g, 7 mmol) in CH$_2$Cl$_2$ (10 mL) under vigorous stirring and cooling with an ice bath in an atmosphere of argon. The mixture was stirred for 12 h and cooled with an ice bath. Water (25 mL) and 5N NaHSO$_4$ (to pH 1) were added. The organic layer was separated and discarded. The aqueous one was alkalized with saturated K$_2$CO$_3$ to pH 6 and extracted with chloroform (2×25 mL). The combined extracts were dried with Na$_2$SO$_4$, and evaporated to give the title compound (1.0 g, 80%) was obtained as dark-yellow crystals. LCMS-data: (M+H)$^+$ 234.1 and 235.1 (calculated for C$_{15}$H$_{23}$NO 233.4). $^1$H NMR data (DMSO-d6): 8.88 (br. s, 1H ArOH), 6.90 (s, 1H, Ar—H), 6.54 (s, 1H, Ar—H); 3.40 (s, 2H, ArCH$_2$), 3.13 (m, 1H, CH(CH$_3$)$_2$), 2.33-2.45 (m, 4H, pyrrolidine (CH$_2$)$_2$N), 2.17 (s, 3H, CH$_3$), 1.60-1.70 (m, 4H, CH$_2$CH$_2$CH$_2$CH$_2$), 1.12 (d, 6H, J=6.9 Hz, CH(CH$_3$)$_2$).

EXAMPLE 430

4-({trans-3-[2-Isopropyl-5-Methyl-4-(pyrrolidin-1-ylmethyl)phenoxy]cyclobutyl}methyl)-morpholine Dihydrochloride. A solution of intermediate 49, 2-Isopropyl-5-Methyl-4-(pyrrolidin-1-ylmethyl)phenol (0.75 g, 32 mmol) and potassium tert-butoxide (0.36 g, 32 mmol) in DMSO (10 mL) was heated to 100° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 16 mmol) in DMSO (10 mL) and tetrabutylammonium bromide (0.16 g, 0.48 mmol) were added. The mixture was stirred at 100° C. for 1 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100µ, 15 mL, ether/Mix (MeOH 150 ml, iPOH 75 ml, CHCl$_3$ 225, NH$_3$ 50 ml, TFA 1.55 ml) 99:1→0:100). The obtained product was washed with saturated K$_2$CO$_3$, dried with Na$_2$SO$_4$, and evaporated. The obtained product was dissolved in ether, and 4M HCl/dioxane (0.21 mL) was added. The reaction mixture was evaporated, the residue was recrystallized from MeOH-Et$_2$O, separated by filtration, washed with ether, and dried in vacuo to give the title compound (280 mg, 37%) as white crystals. LCMS-data: (M+H)$^+$ 387.2, and 388.2 (calculated for C$_{24}$H$_{38}$N$_2$O$_2$ 386.5). 1H NMR data (DMSO-d6): 11.15 (m, 1H, N$^+$H); 10.55 (m, 1H, N$^+$H); 7.43 (s, 1H, Ar—H); 6.60 (s, 1H, Ar—H); 4.61-5.05 (m, 1H); 4.10-4.37 (m, 2H); 3.73-4.00 (m, 4H); 3.43-3.12 (m, 7H+H$_2$O); 3.10-2.77 (m, 5H); 2.17-2.59 (m, 2H+DMSO); 2.37 (s, 3H, CH$_3$); 2.20-2.30 (m, 2H); 1.83-2.06 (m, 4H); 1.19 (d, 6H, J=6.9 Hz).

Intermediate 50

3-Methyl-4-(pyrrolidin-1-ylmethyl)phenol. 4-Hydroxy-2-methylbenzaldehyde (1.1 g, 8 mmol) was added in portions for 30 min to a mixture of pyrrolidine (0.84 mL, 10 mmol) and NaB(OAc)$_3$H (2.14 g, 10 mmol) in CH$_2$Cl$_2$ (10 mL) under vigorous stirring and cooling with an ice bath in an atmosphere of argon. The mixture was stirred for 12 h and cooled with an ice bath. Water (20 mL) and 5N NaHSO$_4$ (to pH 1) were added. The organic layer was separated and discarded. The aqueous one was alkalized with saturated K$_2$CO$_3$ to pH 6 and extracted with chloroform (2×25 mL). The combined extracts were dried with Na$_2$SO$_4$, and evaporated to give the title compound (1.45 g, 94%) was obtained as dark-yellow crystals. LCMS-data: (M+H)$^+$ 193.1 and 192.1 (calculated for C$_{12}$H$_{17}$NO 191.3). 1H NMR data (DMSO-d6): 9.08 (br. s, 1H ArOH), 6.97 (d, 1H, J=8.1 Hz, Ar—H), 6.54 (d, 1H, J=2.4 Hz, Ar—H); 6.49 (dd, 1H, J$_1$=2.4 Hz, J$_2$=8.1 Hz, Ar—H), 3.40 (s, 2H, ArCH2), 2.33-2.45 (m, 4H, pyrrolidine (CH$_2$)$_2$N),), 2.21 (s, 3H, OCH$_3$), 1.60-1.68 (m, 4H, CH$_2$CH$_2$CH$_2$CH$_2$).

EXAMPLE 431

4-({trans-3-[3-Methyl-4-(pyrrolidin-1-ylmethyl)phenoxy]cyclobutyl}methyl)morpholine Dihydrochloride. A solution of intermediate 50, 3-Methyl-4-(pyrrolidin-1-ylmethyl)phenol (0.61 g, 32 mmol) and potassium tert-butoxide (0.36 g, 32 mmol) in DMSO (10 mL) was heated to 100° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 16 mmol) in DMSO (10 mL) and tetrabutylammonium bromide (0.16 g, 0.48 mmol) were added. The mixture was stirred at 100° C. for 1 h, cooled, and diluted with Et$_2$O (50 mL). The solution was washed with water (50 mL), 1N NaOH (3×25 mL), brine, dried with Na$_2$SO$_4$, and evaporated. The obtained product was dissolved in ether, and 4M HCl/dioxane (0.46 mL) was added. The reaction mixture was evaporated, the residue was recrystallized from MeOH-Et$_2$O, separated by filtration, washed with ether, and dried in vacuo to give the title compound (450 mg, 67%) as white crystals. LCMS-data: (M+H)$^+$ 345.2, and 346.2 (calculated for C$_{21}$H$_{32}$N$_2$O$_2$ 344.5). 1H NMR data (DMSO-d6): 11.28 (br.s, 1H, N$^+$H); 10.65 (br.s, 1H, N$^+$H); 7.51 (d, 1H, Ar—H, J=8.3 Hz); 6.67-6.78 (m, 2H, Ar—H); 4.71-4.94 (m, 1H,); 4.25 (d, 2H, J=5.6 Hz); 3.78-4.00 (m, 4H); 3.20-3.38 (m, 6H+H$_2$O); 2.97-3.13 (m, 4H); 2.76-2.95 (m, 1H); 2.41-2.52 (m, 2H+DMSO); 2.4 (s, 3H, CH$_3$); 2.17-2.31 (m, 2H); 1.83-2.08 (m, 4H).

Intermediate 51

2-Chloro-3-(pyrrolidin-1-ylmethyl)phenol. 2-Chloro-3-hydroxybenzaldehyde (4.5 g, 0.03 mol) was added in portions for 30 min to a mixture of pyrrolidine (3. mL, 0.036 mol) and NaB(OAc)$_3$H (7.6 g, 0.036 mol) in CH$_2$Cl$_2$ (50 mL) under vigorous stirring and cooling with an ice bath in an atmosphere of argon. The mixture was stirred for 3 h and cooled with an ice bath. Water (50 mL) and 5N NaHSO$_4$ (to pH 1) were added. The organic layer was separated and discarded. The aqueous one was alkalized with saturated K$_2$CO$_3$ to pH 6 and extracted with chloroform (2×50 mL). The combined extracts were dried with Na$_2$SO$_4$, and evaporated to give the title compound (5.76 g, 95%) as white crystals. LCMS-data: (M+H)$^+$ 214.0 and 212.0 (calculated for C$_{11}$H$_{14}$ClNO 211.7). $^1$H NMR data (DMSO-d6): 9.95 (br. s, 1H, ArOH), 7.07 (t, 1H, J$_1$=7.8 Hz, J$_2$=15.7, Ar—H), 6.90 (dd, 1H, J$_1$=1.5 Hz, J$_2$=7.6 Hz, Ar—H); 6.85 (dd, 1H, J$_1$=1.5, J$_2$=9.5, Ar—H), 3.63 (s, 2H, ArCH$_2$), 2.43-2.50 (m, 4H, pyrrolidine (CH$_2$)$_2$N), 1.63-1.73 (m, 4H, CH$_2$CH$_2$CH$_2$CH$_2$).

EXAMPLE 432

4-({trans-3-[2-Chloro-3-(pyrrolidin-1-ylmethyl)phenoxy]cyclobutyl}methyl)morpholine Dihydrochloride. A solution of intermediate 51, 2-Chloro-3-(pyrrolidin-1-ylmethyl)phenol (0.68 g, 32 mmol) and potassium tert-butoxide (0.40 g, 32 mmol) in DMSO (10 mL) was heated to 100° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 16 mmol) in DMSO (10 mL) and tetrabutylammonium bromide (0.16 g, 0.48 mmol) were added. The mixture was stirred at 100° C. for 1 h, cooled, and diluted with Et$_2$O (50 mL). The solution was washed with water (50 mL), 1N NaOH (3×50 mL), brine, dried with Na$_2$SO$_4$, and evaporated. The obtained product was dissolved in ether, and 4M HCl/dioxane (0.7 mL) was added. The reaction mixture was evaporated, the residue was recrystallized from iPOH-Et$_2$O, separated by filtration, washed with ether, and dried in vacuo to give the title compound (208 mg, 36%) as white crystals. LCMS-data: 365.1, 367.1 and 368.1 (M+H)$^+$, 479.1 (M+TFA+H)$^+$ (calculated for C$_{20}$H$_{28}$N$_2$O$_2$Cl 364.92). 1H NMR data (DMSO-d6): 10.70-11.45 (m, 2H, N$^+$H2); 7.33-7.52 (m, 2H, Ar—H); 7.00 (d, 1H, Ar—H, J=8 Hz); 4.87-4.96 (m, 1H); 4.50 (d, 2H, J=5 Hz); 3.81-3.96 (m, 4H); 3.24-3.49 (m, masked); 2.84-3.16 (m, 5H); 2.25-2.41 (m, 2H); 1.83-2.10 (m, 4H).

Intermediate 52

2-Methoxy-5-(pyrrolidin-1-ylmethyl)phenol. NaB(OAc)$_3$H (32 g, 0.15 mol) was added in portions for 15 min to a mixture of pyrrolidine (9.1 mL, 0.11 mol) and 4-methoxy-5-hydroxybenzaldehyde (15.2 g, 0.1 mol) in CH$_2$Cl$_2$ (100 mL) under vigorous stirring and cooling with an ice bath in an atmosphere of argon Ar. The mixture was stirred for 20 h and cooled with an ice bath. Concentrated HCl (21 mL) was added. The organic layer was separated and discarded. The aqueous one was alkalized with K$_2$CO$_3$ to pH 9 (60 mL) and extracted with chloroform (3×100 mL). The combined extracts were dried with Na$_2$SO$_4$, and evaporated to give the title compounds (17.6 g, 85%) as white crystals. LCMS-data: 208.1 and 209.1 (M+H)$^+$, (calculated for C$_{12}$H$_{17}$NO$_2$ 207.1). 1H NMR (400 MHz)-data (DMSO-d6, J, Hz): 8.81 (br s, 1H, OH); 6.80 (d, 1H, ArH, J=8.3 Hz); 6.73 (d, 1H, ArH, J=2 Hz); 6.65 (dd, 1H, ArH, J1=2 Hz, J2=8 Hz); 3.72 (s, 3H, OCH$_3$); 3.40 (s, 2H, CH$_2$Ar); 2.41-2.33 (m, 4H, CH$_2$CH$_2$CH$_2$CH$_2$); 1.70-1.62 (m, 4H, CH$_2$CH$_2$CH$_2$CH$_2$,).

EXAMPLE 433

4-({trans-3-[2-Methoxy-5-(pyrrolidin-1-ylmethyl)phenoxy]cyclobutyl}methyl)morpholine Dihydrochloride. A solution of intermediate 52, 2-Methoxy-5-(pyrrolidin-1-ylmethyl)phenol (0.66 g, 3.2 mmol) and potassium tert-butoxide (0.39 g, 3.2 mmol) in DMSO (15 mL) was heated to 90° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 1.6 mmol) in DMSO (10 mL) and tetrabutylammonium bromide (0.16 g, 0.48 mmol) were added. The mixture was stirred at 90-100° C. for 2 h, cooled, and diluted with Et$_2$O (100 mL). The solution was washed with water (50 mL), 1N NaOH (3×50 mL), brine, dried with Na$_2$SO$_4$, and evaporated. The residue was purified by chromatography (silica gel 63-100µ, 8 mL, CHCl$_3$/MeOH 100:0→60:40). The obtained product was dissolved in ether, and 4M HCl/dioxane (0.47 mL) was added. The reaction mixture was evaporated, the residue was recrystallized from MeOH-Et$_2$O, separated by filtration, washed with ether, and dried in vacuo to give the title compound (200 mg, 36%) as white crystals. LCMS-data: 361.2 (M+H)$^+$, 475.2 and 476.2 (M+TFA+H)$^+$, (calculated for C$_{21}$H$_{32}$N$_2$O$_3$ 360.5). $^1$H NMR data (DMSO-d6): 10.82-11.24 (m, 2H, N$^+$H2); 7.28 (s, 1H, Ar—H); 6.94-7.08 (m, Ar—H); 4.79-4.88 (m, 1H); 4.17-4.27 (m, 2H); 3.71-3.99 (m, masked); 2.80 (br.s, 1H); 2.22-2.34 (m, 2H); 1.82-2.22 (m, 4H).

Intermediate 53

4-Methoxy-5-(pyrrolidin-1-ylmethyl)phenol. 5-Hydroxy-2-methoxybenzaldehyde (4.5 g, 0.03 mol) was added in portions for 30 min to a mixture of pyrrolidine (3.1 mL, 0.037 mol) and NaB(OAc)$_3$H (7.8 g, 0.037 mol) in CH$_2$Cl$_2$ (50 mL) under vigorous stirring and cooling with an ice bath in an atmosphere of argon. The mixture was stirred for 12 h and cooled with an ice bath. Water (50 mL) and 5N NaHSO$_4$ (to pH 1) were added. The organic layer was separated and discarded. The aqueous one was alkalized with saturated K$_2$CO$_3$ to pH 6 and extracted with chloroform (2×50 mL). The combined extracts were dried with Na$_2$SO$_4$, and evaporated to give the title compound (5.42 g, 89%) was obtained as brown crystals. LCMS-data: (M+H)$^+$ 208.1 and 209.1 (calculated for C$_{12}$H$_{17}$NO$_2$ 207.3). 1H NMR data (DMSO-d6): 8.79 (br. s, 1H ArOH), 6.81 (d, 1H, J=8.1 Hz, Ar—H), 6.74 (d, 1H, J=4.9 Hz, Ar—H); 6.64 (dd, 1H, J$_1$=1.9, J$_2$=8.1, Ar—H), 3.73 (s, 2H, OCH$_3$), 3.42 (s, 2H, ArCH$_2$), 2.33-2.45 (m, 4H, pyrrolidine (CH$_2$)$_2$N), 1.59-1.73 (m, 4H, CH$_2$CH$_2$CH$_2$CH$_2$).

EXAMPLE 434

4-({trans-3-[4-Methoxy-3-(pyrrolidin-1-ylmethyl)phenoxy]cyclobutyl}methyl)morpholine Dihydrochloride. A solution of intermediate 53, 4-Methoxy-5-(pyrrolidin-1-ylmethyl)phenol (0.66 g, 32 mmol) and potassium tert-butoxide (0.36 g, 32 mmol) in DMSO (10 mL) was heated to 100° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 16 mmol) in DMSO (10 mL) and tetrabutylammonium bromide (0.16 g, 0.48 mmol) were added. The mixture was stirred at 100° C. for 1 h, cooled, and diluted with Et$_2$O (50 mL). The solution was washed with water (50 mL), 1N NaOH (3×25 mL), brine, dried with Na$_2$SO$_4$, and evaporated. The obtained product was dissolved in ether, and 4M HCl/dioxane (0.4 mL) was added. The reaction mixture was evaporated, the residue was recrystallized from iPOH-Et$_2$O, separated by filtration, washed with ether, and dried in vacuo to give the title compound (464 mg, 80%) as white crystals. LCMS-data: 361.2 (M+H)$^+$, 475.2 and 476.2 (M+TFA+H)$^+$, (calculated for C$_{20}$H$_{30}$N$_2$O$_2$ 358.53). 1H NMR data (DMSO-d6): 10.96-11.34 (m, 2H, N$^+$H$_2$); 7.26-7.30 (m, 1H, Ar—H); 6.94-7.03 (m, 2H, Ar—H); 4.80-4.88 (m, 1H); 4.18-4.26 (m, 2H); 3.72-3.98 (m, 8H+H$_2$O); 3.23-3.39 (m, masked); 2.93-3.14 (m, 4H); 2.77-2.89 (m, 1H); 2.23-2.32 (m, 2H); 1.83-2.05 (m, 4H).

Intermediate 54

2,6-Dimethyl-4-(pyrrolidin-1-ylmethyl)phenol. NaB(OAc)$_3$H (22.1 g, 0.104 mol) was added in portions for 15 min to a mixture of pyrrolidine (8.1 mL, 0.098 mol) and 3,5-dimethyl-4-hydroxybenzaldehyde (12.5 g, 0.083 mol) in CH$_2$Cl$_2$ (100 mL) under vigorous stirring and cooling with an ice bath in an atmosphere of argon Ar. The mixture was stirred for 20 h and cooled with an ice bath. Concentrated HCl (19 mL) was added. The organic layer was separated and discarded. The aqueous one was alkalized with 10 N NaOH to pH 9 (30 mL) and extracted with chloroform (2×100 mL). The combined extracts were dried with Na$_2$SO$_4$, and evaporated to give the title compound (14 g, 82%) was obtained as white crystals. LCMS-data: 206.1 and 207.1 (M+H)$^+$ (calculated for C$_{13}$H$_{19}$NO 205.1). 1H NMR (400 MHz)-data (DMSO-d6, J, Hz): 7.99 (br s, 1H, OH); 6.80 (s, 2H, ArH);

3.36 (s, 2H, CH2); 2.32-2.41 (m, 4H, C$\underline{\text{H}}$2CH2CH2C$\underline{\text{H}}$2); 2.13 (s, 6H, (CH3)2); 1.61-1.70 (m, 4H, CH2C$\underline{\text{H}}$2CH2CH2).

EXAMPLE 435

4-({trans-3-[2,6-dimethyl-4-(pyrrolidin-1-ylmethyl)phenoxy]cyclobutyl}methyl)-morpholine Dihydrochloride. A solution of intermediate 54, 2,6-Dimethyl-4-(pyrrolidin-1-ylmethyl)phenol (1.31 g, 3.2 mmol) and potassium tert-butoxide (0.36 g, 3.2 mmol) in DMSO (15 mL) was heated to 90° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 1.6 mmol) in DMSO (10 mL) and tetrabutylammonium bromide (1 g, 0.1 mmol) were added. The mixture was stirred at 90-100° C. for 2 h, cooled, and diluted with CHCl$_3$ (100 mL). The solution was washed with water (100 mL), 1N NaOH (3×25 mL), brine, dried with Na$_2$SO$_4$, and evaporated. The residue was purified by chromatography (silica gel 63-100µ, 8 mL, CHCl$_3$/MeOH 100: 0→70:30). The obtained product was dissolved in ether, and 4M HCl/dioxane (0.75 mL) was added. The precipitate was separated by filtration, washed with ether, and dried in vacuo to give the title compound (75 mg, 23%) as white crystals. LCMS-data: 359.2 and 360.2 (M+H)$^+$, 474.2 and 473.2 (M+H+FTA)$^+$, (calculated for C$_{22}$H$_{34}$N$_2$O$_2$ 358.3). 1H NMR data (DMSO-d6): 10.70-11.21 (m, 2H, N$^+$H2); 7.28 (s, 2H, Ar—H); 4.36-4.51 (m, 1H); 4.09-4.29 (m, 2H); 3.76-4.02 (m, 4H); 3.14-3.46 (m, masked); 2.92-3.10 (m, 4H); 2.68-2.84 (m, 1H); 2.31-2.45 (m, masked); 1.76-2.08 (m, 4H).

Intermediate 55

2-Methyl-4-(pyrrolidin-1-ylmethyl)phenol. NaB(OAc)$_3$H (11.8 g, 0.056 mol) was added in portions for 15 min to a mixture of pyrrolidine (3.3 mL, 0.041 mol) and 2-methyl-4-hydroxybenzaldehyde (5 g, 0.037 mol) in CH$_2$Cl$_2$ (100 mL) under vigorous stirring and cooling with an ice bath in an atmosphere of argon Ar. The mixture was stirred for 20 h and cooled with an ice bath. Concentrated HCl (10 mL) was added. The organic layer was separated and discarded. The aqueous one was alkalized with K$_2$CO$_3$ to pH 9 (30 mL) and extracted with EtOAc (4×100 mL). The combined extracts were dried with Na$_2$SO$_4$, and evaporated to give the title compound (6.06 g, 86%) was obtained as white crystals. H-NMR (400 MHz)-data (DMSO-d6, J, Hz): 9.18 (br s, 1H, OH); 6.83 (s, 2H, ArH); 3.79 (s, 3H, CH3); 3.44 (s, 2H, CH2Ar); 2.36-2.44 (m, 4H, C$\underline{\text{H}}$2CH2CH2C$\underline{\text{H}}$2,); 1.65-1.72 (m, 4H, CH2C$\underline{\text{H}}$2CH2CH2).

EXAMPLE 436

4-({trans-3-[2-Methil-4-(pyrrolidin-1-ylmethyl)phenoxy]cyclobutyl}methyl)morpholine Dihydrochloride. A solution of intermediate 55, 2-Methyl-4-(pyrrolidin-1-ylmethyl)phenol (0.61 g, 3.2 mmol) and potassium tert-butoxide (0.31 g, 3.2 mmol) in DMSO (15 mL) was heated to 90° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 1.6 mmol) in DMSO (10 mL) and tetrabutylammonium bromide (0.16 g, 0.48 mmol) were added. The mixture was stirred at 90-100° C. for 2 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100µ, 8 mL, CHCl$_3$/MeOH 100:0→60:40). The obtained product was dissolved in ether, and 4M HCl/dioxane (0.27 mL) was added. The reaction mixture was evaporated, the residue was recrystallized from iPOH-Et$_2$O, separated by filtration, washed with ether, and dried in vacuo to give the title compound (228 mg, 43%) was obtained as white crystals. LCMS-data: 345.2 and 346.2 (M+H)$^+$, (calculated for C$_{21}$H$_{30}$N$_2$O$_3$ 344.50). $^1$H NMR data (DMSO-d6): 10.76-11.36 (m, 2H, N$^+$H2); 7.32 (s, 1H, Ar—H); 6.70-6.78 (m, 1H, Ar—H); 4.79-4.88 (m, 1H); 4.20 (d, 2H, J=4.6); 3.81-3.96 (m, 4H); 2.84-3.11 (m, 5H); 2.22-3.33 (m, 2H); 1.80-2.04 (m, 4H).

Intermediate 56

2,5-Dimethoxyphenyl Acetate. CH$_3$COONa (0.7 g, 0.009 mol) was added under stirring to a solution of 2',5'-dimethoxyacetophenone (CAS 1201-38-3, 45 g, 0.25 mol) in acetic acid (50 mL). A 50% solution of H$_2$O$_2$ in H$_2$O (43 g, 0.62 mol) was added dropwise at 40° C. The reaction mixture was stirred at 40° C. for 144 h. Then it was cooled, diluted with ether (150 mL) and H$_2$O (100 mL), and alkalized to pH 6 with a saturated solution of K$_2$CO$_3$. The layers were separated. The organic one was washed with water (2×100 mL), brine, dried, and evaporated. The residue was recrystallized from ether to give the title compound (13.9 g, 28%) as white crystals. LCMS data: 197.0 (M+H)$^+$ and 155.1, 156.1 (M-Ac+H) (calculated for C$_{10}$H$_{12}$O$_4$ 196.2). $^1$H NMR data (DMSO-d6): 7.04 (d, 1H, J=9.0 Hz, Ar—H), 6.80 (dd, 1H, J$_1$=3.2 Hz, J$_2$=9.0 Hz, Ar—$\underline{\text{H}}$), 6.72 (d, 1H, J=2.9 Hz, Ar—$\underline{\text{H}}$), 3.70 (s, 3H, —OC$\underline{\text{H}}_3$), 3.69 (s, 3H, —OCH$_3$), 2.24 (s, 3H, —COC$\underline{\text{H}}_3$).

Intermediate 57

2,5-Dimethoxyphenol. A mixture of intermediate 56, 2,5-Dimethoxyphenyl Acetate (13.9 g, 0.07 mol) and NaOH (4.26 g, 0.11 mol) in MeOH (150 mL) was stirred for 12 h in a flow of argon. A 5 M solution of NaHSO$_4$ (21 mL) was added, and the mixture was evaporated. The residue was distributed between CH$_2$Cl$_2$ and H$_2$O (300 mL, 1:1). The aqueous layer was separated, and the product was extracted with CH$_2$Cl$_2$ (2×100 mL). The combined extracts were dried and evaporated to give the title compound (10.8 g, 99%). LCMS data: 156.0 and 155.1 (M+H)$^+$ (calculated for C$_8$H$_{10}$O$_3$ 154.1). 1H NMR data (DMSO-d6): 8.96 (s, 1H, Ar—O$\underline{\text{H}}$), 6.80 (d, 1H, J=8.8 Hz, Ar—$\underline{\text{H}}$), 6.39 (d, 1H, J=2.9 Hz, Ar—$\underline{\text{H}}$), 6.39 (dd, 1H, J$_1$=2.9 Hz, J$_2$=8.8 Hz, Ar—$\underline{\text{H}}$), 3.70 (s, 3H, —OC$\underline{\text{H}}_3$), 3.64 (s, 3H, —OCH$_3$).

Intermediate 58

4-Hydroxy-2,5-dimethoxybenzaldehyde. POCl$_3$ was added dropwise (T<20° C.) to a solution of intermediate 57, 2,5-Dimethoxyphenol (10.8 g, 0.07 mol) in DMF (22 mL, 0.28 mol) under vigorous stirring and cooling with an ice bath. The reaction mixture was stirred at room temperature for 72 h, then at 50° C. for 48 h, cooled, and diluted with H$_2$O and ether (50 mL each). The solution was alkalized to pH 6 with a 10 N solution of NaOH. The aqueous layer was separated and subjected to extraction with ether. The combined extracts were dried and evaporated. The residue was recrystallized from ether. The obtained crystals were dissolved under argon in MeOH (20 mL). NaOH (0.5 g, 12 mmol) was added, and the mixture was stirred for 12 h. Then pH was brought to 6 with a 5 M solution of NaHSO$_4$ (2.4 mL), and the mixture was evaporated. The residue was dissolved in CHCl$_3$. The solution was washed with H$_2$O, dried, and evaporated to give the title compound (1.2 g, 10%) as yellow crystals. $^1$H NMR data (DMSO-d6): 10.37 (s, 1H, —CO$\underline{\text{H}}$), 10.14 (s, 1H, Ar—O$\underline{\text{H}}$), 7.17 (s, 1H, Ar—$\underline{\text{H}}$), 6.60 (s, 1H, Ar—$\underline{\text{H}}$), 3.81 (s, 3H, —OC$\underline{\text{H}}_3$), 3.76 (s, 3H, —OC$\underline{\text{H}}_3$).

Intermediate 59

2,5-Dimethoxy-4-(pyrrolidin-1-ylmethyl)phenol. Intermediate 58, 4-Hydroxy-2,5-dimethoxybenzaldehyde (1.2 g, 6.6 mmol) was added in portions for 30 min to a mixture of pyrrolidine (0.7 mL, 8.2 mmol) and NaB(OAc)$_3$H (1.75 g, 8.2 mmol) in CH$_2$Cl$_2$ (20 mL) under vigorous stirring and cooling with an ice bath in an atmosphere of argon. The mixture was stirred for 12 h and cooled with an ice bath. Water (30 mL) and a 5 N solution of NaHSO$_4$ were added to pH 1. The organic layer was separated and discarded. The aqueous one was alkalized with a saturated solution of K$_2$CO$_3$ to pH 6 and subjected to extraction with chloroform (2×50 mL). The combined extracts were dried with Na$_2$SO$_4$ and evaporated to give the title compound (0.9 g, 58%) as a yellow oil. LCMS data: 238.1 (M+H)$^+$ and 168.0, 167.0 (M-pyrrolidine+H) (calculated for C$_{15}$H$_{23}$NO 237.3). $^1$H NMR data (DMSO-d6): 8.88 (br. s, 1H ArOH), 6.84 (s, 1H, Ar—H), 6.45 (s, 1H, Ar—H); 3.69 (s, 3H, —OCH$_3$), 3.659 (s, 3H, —OCH$_3$), 3.47 (s, 2H, —CH$_2$—), 2.37-2.49 (m, 4H, pyrrolidine (CH$_2$)$_2$N), 1.60-1.73 (m, 4H, CH$_2$CH$_2$CH$_2$CH$_2$).

EXAMPLE 437

4-(((Trans)-3-(2,5-dimethoxy-4-((pyrrolidin-1-yl)methyl) phenoxy)cyclobutyl)methyl)-morpholine Dihydrochloride. A solution of intermediate 59, 2,5-Dimethoxy-4-(pyrrolidin-1-ylmethyl)phenol (0.76 g, 3.2 mmol) and potassium tert-butoxide (0.36 g, 3.2 mmol) in DMSO (10 mL) was heated to 100° C. under vigorous stirring in a flow of argon. The mixture was stirred at this temperature for 15 min. A solution of intermediate 41, cis-3-(Morpholin-4-ylmethyl)cyclobutyl methanesulfonate (0.4 g, 1.6 mmol) in DMSO (10 mL) and tetrabutylammonium bromide (0.16 g, 0.48 mmol) were added. The mixture was stirred at 100° C. for 1 h, cooled, and diluted with Et$_2$O (50 mL). The solution was washed with water (50 mL), 1N NaOH (3×25 mL), brine, dried with Na$_2$SO$_4$, and evaporated. The residue was purified by chromatography (silica gel 63-100µ, 10 mL, CCl$_4$→CHCl$_3$, CHCl$_3$/i-PrOH 100:0→80:20). The obtained product was washed with saturated K$_2$CO$_3$, dried with Na$_2$SO$_4$, and evaporated. The obtained product was dissolved in ether, and 4M HCl/dioxane (0.26 mL) was added. The reaction mixture was evaporated, the residue was recrystallized from MeOH-Et$_2$O, separated by filtration, washed with ether, and dried in vacuo to give the title compound (160 mg, 22%) as yellow crystals. LCMS-data: 392.2, and 391.2 (M+H)$^+$ (calculated for C$_{22}$H$_{34}$N$_2$O$_2$ 390.5). 1H NMR data (DMSO-d6): 11.21 (br.s, 1H, N$^+$H); 10.45 (br.s, 1H, N+H); 7.27 (s, 1H, Ar—H); 6.51 (s, 1H, Ar—H); 4.77-4.99 (m, 1H); 4.10-4.27 (m, 2H); 3.67-4.00 (m, 4H); 3.81 (s, 3H, —OCH$_3$), 3.75 (s, 3H, —OCH$_3$), 3.20-3.45 (m, H+H$_2$O); 2.95-3.13 (m, 4H); 2.75-2.93 (m, 1H), 2.40-2.66 (m, H+DMSO); 2.22-2.38 (m, 2H); 1.80-2.06 (m, 4H).

Intermediate 60

3,5-dimethyl-4-(pyrrolidin-1-ylmethyl)phenol. To a stirring solution of 2,6-dimethyl-4-hydroxybenzaldehyde (8.2 g, 52.1 mmol) in methylene chloride (80 mL) at 0 C (ice/water bath) was added pyrrolidine (6.5 mL, 78.1 mmol) followed by Na(Oac)3BH and then the reaction was warmed to rt. After 2 hr the reaction was quenched with 1 N NaOH and extracted with methylene chloride. The combined organic layers were dried over MgSO$_4$, filtered and concentrated. This material was triterated with diethyl ether and filtered. The filtrate was concentrated and chromatographed by flash column chromatography using a 330 g ISCO column, eluting with a gradient of 10%, 20%, 30%, 50% MeOH/CHCl3. The product containing fractions were collected and concentrated to give the title compound (3.5 g, 33% yield) as a yellow solid. LCMS-data: 392.2, and 206.3 (M+H)$^+$ (calculated for C$_{13}$H19NO 205.3). $^1$H NMR data (CDCl3): 7.52 (bs, 1H), 6.17 (s, 2H), 3.57 (s, 2H), 2.67-2.61 (m, 4H), 2.25 (s, 6H), 1.82-1.72 (m, 4H); C13 NMR δ 155.2, 139.0, 127.4, 116.2, 54.8, 53.0, 23.4, 20.5.

EXAMPLE 438

4-(((trans)-3-(3,5-dimethyl-4-((pyrrolidin-1-yl)methyl) phenoxy)cyclobutyl)methyl) morpholine. A solution intermediate 60, 3,5-dimethyl-4-(pyrrolidin-1-ylmethyl)phenol (0.62 g, 3.0 mmol) and potassium tert-butoxide (3 mL, 1M THF, 3.0 mmol) in DMSO (10 mL) was heated to 100° C. under vigorous stirring. The mixture was stirred at this temperature for 10 min. A solution of intermediate 41, cis-3-(Morpholin-4-ylmethyl)cyclobutyl methanesulfonate (0.3 g, 1.2 mmol) in DMSO (10 mL) and tetrabutylammonium bromide (0.16 g, 0.48 mmol) were added. The mixture was stirred at 100° C. overnight, cooled, and diluted with Et$_2$O (50 mL). The solution was washed with water (50 mL), 1N NaOH (3×25 mL), brine, dried with Na$_2$SO$_4$, and evaporated. The residue was purified by chromatography using a 40 g ISCO column eluting with a gradient of 5%, 10% MeOH:CHCl3 with 0.2% NH4OH. The product containing fractions were collected and concentrate to give the title compound (282 mg, 66% yield) as an oil. LCMS-data: 359.2 (M+H)$^+$ (calculated for C$_{22}$H$_{34}$N$_2$O$_2$ 358.5). 1H NMR data (CDCl3) 6.43 (s, 2H), 4.71-4.68 (m, 1H), 3.71-3.69 (m, 4H), 3.54 (s, 2H), 2.62-218 (m, 21H), 1.63-1.80 (m, 4H); C13 NMR (CDCl3) d 156.1, 139.2, 114.6, 70.7, 67.2, 65.1, 54.2, 54.0, 52.9, 34.3, 26.4, 23.8, 20.7.

Determination of Biological Activity

The in vitro affinity of the compounds in the present invention at the rat or human histamine H3 receptors can be determined according to the following procedure. Frozen rat frontal brain or frozen human post-mortem frontal brain is homogenized in 20 volumes of cold 50 mM Tris HCl containing 2 mM MgCl$_2$ (pH to 7.4 at 4 degrees C.). The homogenate is then centrifuged at 45,000 G for 10 minutes. The supernatant is decanted and the membrane pellet re-suspended by Polytron in cold 50 mM Tris HCl containing 2 mM MgCl$_2$ (pH to 7.4 at 4 degrees C.) and centrifuged again. The final pellet is re-suspended in 50 mM Tris HCl containing 2 mM MgCl$_2$ (pH to 7.4 at 25 degrees C.) at a concentration of 12 mg/mL. Dilutions of compounds are made in 10% DMSO/50 mM Tris buffer (pH 7.4) (at 10× final concentration, so that the final DMSO concentration is 1%). Incubations are initiated by the addition of membranes (200 microliters) to 96 well V-bottom polypropylene plates containing 25 microliters of drug dilutions and 25 microliters of radioligand (1 nM final concentration $^3$H—N-methylhistamine). After a 1 hour incubation, assay samples are rapidly filtered through Whatman GF/B filters and rinsed with ice-cold 50 mM Tris buffer (pH 7.4) using a Skatron cell harvester. Radioactivity is quantified using a BetaPlate scintillation counter. The percent inhibition of specific binding can then be determined for each dose of the compound, and an IC50 or Ki value can be calculated from these results.

The invention claimed is:
1. A compound of formula Ia or Ib

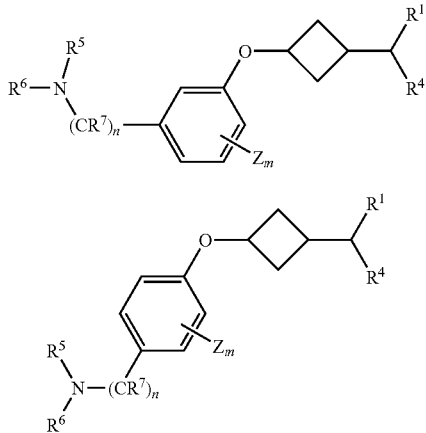

or a pharmaceutically acceptable salt thereof, or cis isomer, or trans isomer, or a mixture of cis and trans isomer, wherein:
$R^1$ is selected from the group consisting of $OR^4$, and $NR^2R^3$;
$R^2$ and $R^3$ are each independently selected from the group consisting of hydrogen;
$C_1$-$C_8$ alkyl optionally substituted with 1 to 4 halogens;
$C_1$-$C_4$ alkyl group optionally substituted with a substituent selected from the group consisting of OH, one to four $C_1$-$C_4$ alkyl, $C_3$-$C_7$ cycloalkyl, $C_1$-$C_4$ dialkylamino, $C_6$-$C_{14}$ aryl optionally substituted with a halogen or $C_6$-$C_{10}$ aryloxy optionally substituted with one to two halogens, and 5-10-membered heteroaryl optionally substituted with a $C_6$-$C_{10}$ aryl group and optionally substituted with one to three $C_1$-$C_4$ alkyl groups;
$C_3$-$C_7$ cycloalkyl;
$C_6$-$C_{14}$ aryl;
3-8-membered heterocycloalkyl optionally substituted with one or more $C_1$-$C_4$ alkyl-carbonyl group;
$C_6$-$C_{10}$ arylsulfonyl optionally substituted with one or more $C_1$-$C_2$ alkyl;
5-10-membered heteroaryl;
$C_6$-$C_{14}$ aryl-O—$C_0$-$C_4$ alkylene-O—$C_0$-$C_4$ alkyl, wherein each $C_0$-$C_4$ alkyl and each $C_0$-$C_4$ alkylene is optionally substituted with one to four $C_1$-$C_4$ alkyl;
—C(=O)$R^{3'}$, —S(O)$_2R^{3'}$; wherein $R^{3'}$ is selected from the group consisting of hydrogen, ($C_1$-$C_4$)alkyl, ($C_1$-$C_4$) alkenyl, aryl, heteroaryl, ($C_3$-$C_7$)cycloalkyl, ($C_3$-$C_7$)cycloheteroalky, and wherein each hydrogen in $R^{3'}$ may independently optionally be substituted with halo, ($C_1$-$C_4$)alkyl, ($C_2$-$C_4$)alkenyl, and —S(O)$_2$CH$_3$;
wherein $R^3$ can be further selected from the group consisting of
$C_6$-$C_{14}$ arylcarbonyl-$C_6$-$C_{14}$ aryl; $C_6$-$C_{14}$ arylcarbonyl-3-8-membered heterocycloalkyl; $C_3$-$C_8$ cycloalkylcarbonyl-$C_6$-$C_{14}$ aryl; $C_3$-$C_8$ cycloalkylcarbonyl-3-8-membered heterocycloalkyl; 3-8-membered heterocycloalkylcarbonyl-$C_8$-$C_{14}$ aryl; and 3-8-membered heterocycloalkylcarbonyl-3-8-membered heterocycloalkyl;
or $R^3$ and $R^2$ together with the nitrogen of the $NR^2R^3$ group form a first 5-, 6-, or 7-membered aliphatic ring, wherein one of the carbons in the first 5-, 6-, or 7-membered aliphatic ring is optionally replaced by O, S, $NR^{2'}$, or CO, and the first 5-, 6-, or 7-membered aliphatic ring is optionally fused to a $C_6$-$C_{10}$ arylene and is optionally substituted at a ring carbon with a substituent selected from the group consisting of
5-10-membered heteroaryl optionally substituted with one or more halogens and optionally substituted with one or more $C_1$-$C_2$ alkyl,
$C_1$-$C_4$ alkoxy optionally substituted with one or more $C_1$-$C_2$ alkoxy and optionally substituted with one or more $C_1$-$C_4$ dialkylaminocarbonyl, and
one or two $C_1$-$C_4$ alkyl optionally and independently substituted with one or more $C_1$-$C_2$ alkoxy;
wherein $R^{2'}$ is
hydrogen;
$C_1$-$C_8$ alkyl optionally substituted with 1 to 4 halogens;
5-10-membered heteroaryl optionally substituted with a substituent selected from the group consisting of halogen, $C_1$-$C_4$ alkyl, $C_1$-$C_2$ alkoxy, $C_6$-$C_{10}$ aryl, $C_1$-$C_4$ alkylaminocarbonyl, and cyano;
$C_1$-$C_4$ alkyl group optionally substituted with a substituent selected from the group consisting of $C_1$-$C_2$ alkoxycarbonyl, 5-10-membered heteroaryl optionally substituted with one or more $C_1$-$C_2$ alkyl, one to four $C_1$-$C_4$ alkyl, $C_3$-$C_7$ cycloalkyl, and $C_6$-$C_{14}$ aryl;
$C_6$-$C_{10}$ aryl optionally substituted with one or two $C_1$-$C_2$ alkyl; $C_1$-$C_4$ alkylcarbonyl; or $C_6$-$C_{14}$ aryl-$C_0$-$C_4$ alkylene-O—$C_0$-$C_4$ alkyl, wherein each $C_0$-$C_4$ alkyl and each $C_0$-$C_4$ alkylene is optionally substituted with one to four $C_1$-$C_4$ alkyl; C1-C4 alkylsulfonyl
$R^4$ is hydrogen or methyl;
$R^5$ and $R^6$ are each independently selected from the group consisting of hydrogen; $C_1$-$C_4$ alkyl group optionally substituted with a substituent selected from the group consisting of OH, $C_1$-$C_3$ alkyl, $C_1$-$C_3$ alkoxy;
or $R^5$ and $R^6$ together with the nitrogen together to which they are attached form a 3-7-membered cyclic amine optionally substituted with one or more $C_1$-$C_4$ alkyl;
$R^7$ is independently hydrogen or methyl;
n is 1, 2, or 3;
m is 1, 2, or 3;
Z is independently selected from the group consisting of hydrogen, halogen, $C_1$-$C_4$ alkyl, $C_1$-$C_4$ alkoxy, and —C(H)=CH$_2$; or wherein, when m is 2 and both Z's are —C(H)=CH$_2$, both Z's together with 2 adjacent carbons of the phenyl ring of formula I form a 6 membered aromatic ring fused to said phenyl ring.

2. The compound of claim 1 wherein
$R^1$ is $NR^2R^3$ and
$R^2$ is hydrogen or methyl and $R^3$ is selected from the group consisting of —C(=O)$R^{3'}$, —S(O)$_2R^{3'}$;
wherein $R^{3'}$ is selected from the group consisting of hydrogen, ($C_1$-$C_4$)alkyl, ($C_1$-$C_4$)alkenyl, aryl, heteroaryl, ($C_3$-$C_7$)cycloalkyl, ($C_3$-$C_7$)cycloheteroalky, and wherein each hydrogen in $R^{3'}$ may independently optionally be substituted with halo, ($C_1$-$C_4$)alkyl, ($C_2$-$C_4$)alkenyl, and —S(O)$_2$CH$_3$;
or $R^3$ and $R^2$ together with the nitrogen of the $NR^2R^3$ group form a 5-, 6-, or 7-membered aliphatic ring, wherein one of the carbons of said 5-, 6-, or 7-membered aliphatic ring is optionally replaced by oxygen;
$R^4$ is hydrogen;
n is 1 or 2;
m is 1 or 2;
Z is independantly selected from the group consisting of hydrogen, halogen, $C_1$-$C_4$ alkyl, and $C_1$-$C_4$ alkoxy;

and R⁵ and R⁶ together with the nitrogen to which they are attached form a 3-7-membered cyclic amine optionally substituted with one or more $C_1$-$C_4$ alkyl.

3. The compound of claim 2 wherein R² is hydrogen or methyl and R³ is selected from the group consisting of —C(=O)R³', —S(O)₂R³'; wherein R³' is selected from the group consisting of hydrogen, ($C_1$-$C_4$)alkyl, ($C_1$-$C_4$)alkenyl, aryl, heteroaryl, ($C_3$-$C_7$)cycloalkyl, ($C_3$-$C_7$)cycloheteroalky, and wherein each hydrogen in R³' may independently optionally be substituted with halo, ($C_1$-$C_4$)alkyl, ($C_2$-$C_4$)alkenyl, and —S(O)₂CH₃.

4. The compound of claim 2 wherein R³ and R² together with the nitrogen of the NR²R³ group form a 5-, 6-, or 7-membered aliphatic ring, wherein one of the carbons of said 5-, 6-, or 7-membered aliphatic ring is optionally replaced by oxygen.

5. The compound of claim 1 selected from the group consisting of:

Dimethyl-[4-(3-pyrrolidin-1-ylmethyl-cyclobutoxy)-benzyl]-amine;
Dimethyl-[4-(3-pyrrolidin-1-ylmethyl-cyclobutoxy)-benzyl]-amine;
4-[3-(4-Pyrrolidin-1-ylmethyl-phenoxy)-cyclobutylmethyl]-morpholine;
4-[3-(3-Methoxy-4-pyrrolidin-1-ylmethyl-phenoxy)-cyclobutylmethyl]-morpholine;
4-[3-(3,5-Dimethyl-4-pyrrolidin-1-ylmethyl-phenoxy)-cyclobutylmethyl]-morpholine;
4-[3-(3-Chloro-4-pyrrolidin-1-ylmethyl-phenoxy)-cyclobutylmethyl]-morpholine;
4-[3-(2-Chloro-4-pyrrolidin-1-ylmethyl-phenoxy)-cyclobutylmethyl]-morpholine;
4-[3-(2-Isopropyl-5-methyl-4-pyrrolidin-1-ylmethyl-phenoxy)-cyclobutylmethyl]-morpholine;
4-[3-(3-Methyl-4-pyrrolidin-1-ylmethyl-phenoxy)-cyclobutylmethyl]-morpholine;
4-[3-(2-Chloro-3-pyrrolidin-1-ylmethyl-phenoxy)-cyclobutylmethyl]-morpholine;
4-[3-(2-Methyl-4-pyrrolidin-1-ylmethyl-phenoxy)-cyclobutylmethyl]-morpholine;
4-{3-[3-Chloro-4-((S)-1-pyrrolidin-1-yl-ethyl)-phenoxy]-cyclobutylmethyl}-morpholine;
4-{3-[3-Chloro-4-((R)-2-methyl-pyrrolidin-1-ylmethyl)-phenoxy]-cyclobutylmethyl}-morpholine;
Cyclobutanecarboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2-cyclopropyl-N-methyl-acetamide;
3,5-Dimethyl-isoxazole-4-carboxylic acid [3-(2-chloro-3-pyrrolidin-1-ylmethyl-phenoxy)-cyclobutylmethyl]-methyl-amide;
1-Ethyl-1-H-pyrazole-4-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-isonicotinamide;
N-[3-(3-Chloro-4-pyrrolidin-1-ylmethyl-phenoxy)-cyclobutylmethyl]-3,4,N-trimethyl-benzamide;
N-{3-[3-Chloro-4-((S)-2-methyl-pyrrolidin-1-ylmethyl)-phenoxy]-cyclobutylmethyl}-N-methyl-benzamide;
[3-(2,5-Dichloro-4-pyrrolidin-1-ylmethyl-phenoxy)-cyclobutylmethyl]-methyl-amine;
3,5-Dimethyl-isoxazole-4-carboxylic acid [3-(2-chloro-3-pyrrolidin-1-ylmethyl-phenoxy)-cyclobutylmethyl]-amide;
C-[3-(2-Chloro-3-pyrrolidin-1-ylmethyl-phenoxy)-cyclobutyl]-methylamine;
1-Methyl-cyclopropanecarboxylic acid [3-(2-chloro-3-pyrrolidin-1-ylmethyl-phenoxy)-cyclobutylmethyl]-amide;
1-Methyl-cyclopropanecarboxylic acid [3-(3-chloro-5-fluoro-4-pyrrolidin-1-ylmethyl-phenoxy)-cyclobutylmethyl]-methyl-amide;
1-Methyl-cyclopropanecarboxylic acid [3-(3,5-difluoro-4-pyrrolidin-1-ylmethyl-phenoxy)-cyclobutylmethyl]-methyl-amide;
[3-(3,5-Difluoro-4-pyrrolidin-1-ylmethyl-phenoxy)-cyclobutylmethyl]-methyl-amine;
3,5-Dimethyl-isoxazole-4-carboxylic acid [3-(3-chloro-5-fluoro-4-pyrrolidin-1-ylmethyl-phenoxy)-cyclobutylmethyl]-methyl-amide;
[3-(3-Chloro-5-fluoro-4-pyrrolidin-1-ylmethyl-phenoxy)-cyclobutylmethyl]-methyl-amine;
3,5-Dimethyl-isoxazole-4-carboxylic acid [3-(2-methoxy-3-pyrrolidin-1-ylmethyl-phenoxy)-cyclobutylmethyl]-methyl-amide;
[3-(2-Methoxy-3-pyrrolidin-1-ylmethyl-phenoxy)-cyclobutylmethyl]-methyl-carbamic acid tert-butyl ester;
6-Methyl-pyridine-2-carboxylic acid {3-[3-chloro-4-((S)-2-methyl-pyrrolidin-1-ylmethyl)-phenoxy]-cyclobutylmethyl}-methyl-amide;
N-{3-[3-Chloro-4-((S)-2-methyl-pyrrolidin-1-ylmethyl)-phenoxy]-cyclobutylmethyl}-3,N-dimethyl-butyramide;
N-[3-(3-Chloro-4-pyrrolidin-1-ylmethyl-phenoxy)-cyclobutylmethyl]-N-methyl-C-phenyl-methanesulfonamide;
1-[3-(3-Chloro-4-pyrrolidin-1-ylmethyl-phenoxy)-cyclobutylmethyl]-3-(4-fluoro-phenyl)-1-methyl-urea;
N-[3-(3-Chloro-4-pyrrolidin-1-ylmethyl-phenoxy)-cyclobutylmethyl]-N-methyl-propionamide;
N-[3-(3-Chloro-4-pyrrolidin-1-ylmethyl-phenoxy)-cyclobutylmethyl]-2,4,N-trimethyl-benzamide;
2,6-Dimethyl-pyrimidine-4-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-2-pyridin-4-yl-acetamide;
3,5-Dimethyl-isoxazole-4-carboxylic acid [3-(3-chloro-4-pyrrolidin-1-ylmethyl-phenoxy)-cyclobutylmethyl]-methyl-amide;
Cyclopropanecarboxylic acid [3-(3-chloro-4-pyrrolidin-1-ylmethyl-phenoxy)-cyclobutylmethyl]-methyl-amide;
1-Methyl-cyclopropanecarboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2-fluoro-N-methyl-benzamide;
1-[3-(3-Chloro-4-pyrrolidin-1-ylmethyl-phenoxy)-cyclobutylmethyl]-3-(3-methoxy-phenyl)-1-methyl-urea;
N-[3-(3-Chloro-4-pyrrolidin-1-ylmethyl-phenoxy)-cyclobutylmethyl]-N-methyl-nicotinamide;
3-(4-Chloro-phenyl)-1-[3-(3-chloro-4-pyrrolidin-1-ylmethyl-phenoxy)-cyclobutylmethyl]-1-methyl-urea;
3-(2-Chloro-phenyl)-1-[3-(3-chloro-4-pyrrolidin-1-ylmethyl-phenoxy)-cyclobutylmethyl]-1-methyl-urea;
1-[3-(3-Chloro-4-pyrrolidin-1-ylmethyl-phenoxy)-cyclobutylmethyl]-1-methyl-3-phenyl-urea;
1-[3-(3-Chloro-4-pyrrolidin-1-ylmethyl-phenoxy)-cyclobutylmethyl]-3-(3-fluoro-phenyl)-1-methyl-urea;
4-Methyl-oxazole-5-carboxylic acid [3-(3-chloro-4-pyrrolidin-1-ylmethyl-phenoxy)-cyclobutylmethyl]-methyl-amide;

Pyridine-2-carboxylic acid [3-(3-chloro-4-pyrrolidin-1-ylmethyl-phenoxy)-cyclobutylmethyl]-methyl-amide;
1-[3-(3-Chloro-4-pyrrolidin-1-ylmethyl-phenoxy)-cyclobutylmethyl]-1-methyl-3-p-tolyl-urea;
5-Ethyl-isoxazole-3-carboxylic acid [3-(3-chloro-4-pyrrolidin-1-ylmethyl-phenoxy)-cyclobutylmethyl]-methyl-amide;
3-(3-Acetyl-phenyl)-1-[3-(3-chloro-4-pyrrolidin-1-ylmethyl-phenoxy)-cyclobutylmethyl]-1-methyl-urea;
2-Ethyl-5-methyl-2H-pyrazole-3-carboxylic acid [3-(3-chloro-4-pyrrolidin-1-ylmethyl-phenoxy)-cyclobutylmethyl]-methyl-amide;
5-Isopropyl-isoxazole-3-carboxylic acid [3-(3-chloro-4-pyrrolidin-1-ylmethyl-phenoxy)-cyclobutylmethyl]-methyl-amide;
1-[3-(3-Chloro-4-pyrrolidin-1-ylmethyl-phenoxy)-cyclobutylmethyl]-3-(4-methoxy-2-methyl-phenyl)-1-methyl-urea;
N-[3-(3-Chloro-4-pyrrolidin-1-ylmethyl-phenoxy)-cyclobutylmethyl]-4,N-dimethyl-benzamide;
1-[3-(3-Chloro-4-pyrrolidin-1-ylmethyl-phenoxy)-cyclobutylmethyl]-3-(3,5-dimethyl-phenyl)-1-methyl-urea;
3-(5-Chloro-2-methyl-phenyl)-1-[3-(3-chloro-4-pyrrolidin-1-ylmethyl-phenoxy)-cyclobutylmethyl]-1-methyl-urea;
1-[3-(3-Chloro-4-pyrrolidin-1-ylmethyl-phenoxy)-cyclobutylmethyl]-3-(2,6-dimethyl-phenyl)-1-methyl-urea;
N-[3-(3-Chloro-4-pyrrolidin-1-ylmethyl-phenoxy)-cyclobutylmethyl]-3,5-difluoro-N-methyl-benzamide;
N-[3-(3-Chloro-4-pyrrolidin-1-ylmethyl-phenoxy)-cyclobutylmethyl]-2,3-difluoro-N-methyl-benzamide;
1-[3-(3-Chloro-4-pyrrolidin-1-ylmethyl-phenoxy)-cyclobutylmethyl]-3-(2-methoxy-5-methyl-phenyl)-1-methyl-urea;
N-[3-(3-Chloro-4-pyrrolidin-1-ylmethyl-phenoxy)-cyclobutylmethyl]-2,5,N-trimethyl-benzamide;
N-[3-(3-Chloro-4-pyrrolidin-1-ylmethyl-phenoxy)-cyclobutylmethyl]-2-(2-fluoro-phenyl)-N-methyl-acetamide;
N-[3-(3-Chloro-4-pyrrolidin-1-ylmethyl-phenoxy)-cyclobutylmethyl]-2,4-difluoro-N-methyl-benzamide;
1-[3-(3-Chloro-4-pyrrolidin-1-ylmethyl-phenoxy)-cyclobutylmethyl]-3-(2-methoxy-phenyl)-1-methyl-urea;
4-Methyl-furazan-3-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2-(3-fluoro-phenyl)-N-methyl-acetamide;
3-Isopropyl-isoxazole-5-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2,4,N-trimethyl-benzenesulfonamide;
3-(4-Chloro-2-methyl-phenyl)-1-[3-(3-chloro-4-pyrrolidin-1-yl-methyl-phenoxy)-cyclobutylmethyl]-1-methyl-urea;
5-Cyclopropyl-isoxazole-3-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-benzamide;
N-[3-(3-Chloro-4-pyrrolidin-1-ylmethyl-phenoxy)-cyclobutylmethyl]-2-methoxy-N-methyl-nicotinamide;
N-[3-(3-Chloro-4-pyrrolidin-1-ylmethyl-phenoxy)-cyclobutylmethyl]-3,N-dimethyl-butyramide;
5-Cyclopropyl-oxazole-4-carboxylic acid [3-(3-chloro-4-pyrrolidin-1-ylmethyl-phenoxy)-cyclobutylmethyl]-methyl-amide;
2-Ethyl-4-methyl-oxazole-5-carboxylic acid [3-(3-chloro-4-pyrrolidin-1-ylmethyl-phenoxy)-cyclobutylmethyl]-methyl-amide;
1,5-Dimethyl-1H-pyrazole-3-carboxylic acid [3-(3-chloro-4-pyrrolidin-1-ylmethyl-phenoxy)-cyclobutylmethyl]-methyl-amide;
6-Methyl-pyridine-2-carboxylic acid [3-(3-chloro-4-pyrrolidin-1-ylmethyl-phenoxy)-cyclobutylmethyl]-methyl-amide;
1-Isopropyl-1H-pyrazole-4-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2,N-dimethyl-nicotinamide;
3-(3-Chloro-phenyl)-1-[3-(3-chloro-4-pyrrolidin-1-ylmethyl-phenoxy)-cyclobutylmethyl]-1-methyl-urea;
N-[3-(3-Chloro-4-pyrrolidin-1-ylmethyl-phenoxy)-cyclobutylmethyl]-3-fluoro-N-methyl-benzamide;
1-[3-(3-Chloro-4-pyrrolidin-1-ylmethyl-phenoxy)-cyclobutylmethyl]-3-(4-methoxy-phenyl)-1-methyl-urea;
1-[3-(3-Chloro-4-pyrrolidin-1-ylmethyl-phenoxy)-cyclobutylmethyl]-3-(2,4-difluoro-phenyl)-1-methyl-urea;
Propane-2-sulfonic acid [3-(3-chloro-4-pyrrolidin-1-ylmethyl-phenoxy)-cyclobutylmethyl]-methyl-amide;
4-Chloro-N-[3-(3-chloro-4-pyrrolidin-1-ylmethyl-phenoxy)-cyclobutylmethyl]-N-methyl-benzamide;
1-[3-(3-Chloro-4-pyrrolidin-1-ylmethyl-phenoxy)-cyclobutylmethyl]-3-(3,4-dimethyl-phenyl)-1-methyl-urea;
1-[3-(3-Chloro-4-pyrrolidin-1-ylmethyl-phenoxy)-cyclobutylmethyl]-3-(2-ethyl-phenyl)-1-methyl-urea;
Pyridine-3-sulfonic acid [3-(3-chloro-4-pyrrolidin-1-ylmethyl-phenoxy)-cyclobutylmethyl]-methyl-amide;
1-[3-(3-Chloro-4-pyrrolidin-1-ylmethyl-phenoxy)-cyclobutylmethyl]-1-methyl-3-o-tolyl-urea;
3-(3-Chloro-4-methyl-phenyl)-1-[3-(3-chloro-4-pyrrolidin-1-ylmethyl-phenoxy)-cyclobutylmethyl]-1-methyl-urea;
1-{[3-(3-Chloro-4-pyrrolidin-1-ylmethyl-phenoxy)-cyclobutyl]methyl}-1-methyl-3-(2-trifluoromethyl-phenyl)-urea;
1-[3-(3-Chloro-4-pyrrolidin-1-ylmethyl-phenoxy)-cyclobutylmethyl]-3-ethyl-1-methyl-urea;
3-Ethyl-5-methyl-isoxazole-4-carboxylic acid [3-(3-chloro-4-pyrrolidin-1-ylmethyl-phenoxy)-cyclobutylmethyl]-methyl-amide;
3-Chloro-N-[3-(3-chloro-4-pyrrolidin-1-ylmethyl-phenoxy)-cyclobutylmethyl]-N-methyl-benzamide;
5-Cyclopropyl-2H-pyrazole-3-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-4-fluoro-N-methyl-benzamide;
3-(3-Chloro-2-methyl-phenyl)-1-[3-(3-chloro-4-pyrrolidin-1-ylmethyl-phenoxy)-cyclobutylmethyl]-1-methyl-urea;
N-[3-(3-Chloro-4-pyrrolidin-1-ylmethyl-phenoxy)-cyclobutylmethyl]-3,4-difluoro-N-methyl-benzamide;
1-[3-(3-Chloro-4-pyrrolidin-1-ylmethyl-phenoxy)-cyclobutylmethyl]-1-methyl-3-m-tolyl-urea;

1-[3-(3-Chloro-4-pyrrolidin-1-ylmethyl-phenoxy)-cyclobutylmethyl]-3-(2,5-dimethyl-phenyl)-1-methyl-urea;

3-(2-Chloro-6-methyl-phenyl)-1-[3-(3-chloro-4-pyrrolidin-1-ylmethyl-phenoxy)-cyclobutylmethyl]-1-methyl-urea;

N-[3-(3-Chloro-4-pyrrolidin-1-ylmethyl-phenoxy)-cyclobutylmethyl]-N-methyl-acetamide;

5-Ethyl-2-methyl-2H-pyrazole-3-carboxylic acid [3-(3-chloro-4-pyrrolidin-1-ylmethyl-phenoxy)-cyclobutylmethyl]-methyl-amide;

5-Methyl-isoxazole-3-carboxylic acid [3-(3-chloro-4-pyrrolidin-1-ylmethyl-phenoxy)-cyclobutylmethyl]-methyl-amide;

Prop-2-ene-1-sulfonic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2-methoxy-N-methyl-acetamide;

N-[3-(3-Chloro-4-pyrrolidin-1-ylmethyl-phenoxy)-cyclobutylmethyl]-6,N-dimethyl-nicotinamide;

1-[3-(3-Chloro-4-pyrrolidin-1-ylmethyl-phenoxy)-cyclobutylmethyl]-3-isopropyl-1-methyl-urea;

N-[3-(3-Chloro-4-pyrrolidin-1-ylmethyl-phenoxy)-cyclobutylmethyl]-N-methyl-isobutyramide;

Cyclobutanecarboxylic acid [3-(3-chloro-4-pyrrolidin-1-ylmethyl-phenoxy)-cyclobutylmethyl]-methyl-amide;

3-Ethyl-isoxazole-5-carboxylic acid [3-(3-chloro-4-pyrrolidin-1-ylmethyl-phenoxy)-cyclobutylmethyl]-methyl-amide;

N-[3-(3-Chloro-4-pyrrolidin-1-ylmethyl-phenoxy)-cyclobutylmethyl]-2,5-difluoro-N-methyl-benzamide;

1-{[3-(3-Chloro-4-pyrrolidin-1-ylmethyl-phenoxy)-cyclobutyl]methyl}-1-methyl-3-(4-trifluoromethyl-phenyl)-urea;

3-(5-Chloro-2-methoxy-phenyl)-1-[3-(3-chloro-4-pyrrolidin-1-ylmethyl-phenoxy)-cyclobutylmethyl]-1-methyl-urea;

3-Benzyl-1-[3-(3-chloro-4-pyrrolidin-1-ylmethyl-phenoxy)-cyclobutylmethyl]-1-methyl-urea;

Pyrazine-2-carboxylic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2,4-difluoro-N-methyl-benzenesulfonamide;

1-[3-(2-Chloro-3-pyrrolidin-1-ylmethyl-phenoxy)-cyclobutylmethyl]-3-isopropyl-1-methyl-urea;

4-Chloro-N-[3-(2-chloro-3-pyrrolidin-1-ylmethyl-phenoxy)-cyclobutylmethyl]-N-methyl-benzamide;

N-[3-(2-Chloro-3-pyrrolidin-1-ylmethyl-phenoxy)-cyclobutylmethyl]-3,4-difluoro-N-methyl-benzamide;

3-Benzyl-1-[3-(2-chloro-3-pyrrolidin-1-ylmethyl-phenoxy)-cyclobutylmethyl]-1-methyl-urea;

3,5-Dimethyl-isoxazole-4-sulfonic acid [3-(2-chloro-3-pyrrolidin-1-ylmethyl-phenoxy)-cyclobutylmethyl]-methyl-amide;

1-Methyl-cyclopropanecarboxylic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2,4-difluoro-N-methyl-benzamide;

N-[3-(2-Chloro-3-pyrrolidin-1-ylmethyl-phenoxy)-cyclobutylmethyl]-2,5-difluoro-N-methyl-benzamide;

3-Chloro-N-[3-(2-chloro-3-pyrrolidin-1-ylmethyl-phenoxy)-cyclobutylmethyl]-2,N-dimethyl-benzenesulfonamide;

5-Ethyl-isoxazole-3-carboxylic acid [3-(2-chloro-3-pyrrolidin-1-ylmethyl-phenoxy)-cyclobutylmethyl]-methyl-amide;

3,5-Dimethyl-isoxazole-4-carboxylic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-3,5-difluoro-N-methyl-benzamide;

N-[3-(2-Chloro-3-pyrrolidin-1-ylmethyl-phenoxy)-cyclobutylmethyl]-N-methyl-2-pyridin-2-yl-acetamide;

3-tert-Butyl-1-[3-(2-chloro-3-pyrrolidin-1-ylmethyl-phenoxy)-cyclobutylmethyl]-1-methyl-urea;

N-[3-(2-Chloro-3-pyrrolidin-1-ylmethyl-phenoxy)-cyclobutylmethyl]-2,N-dimethyl-nicotinamide;

1-[3-(2-Chloro-3-pyrrolidin-1-ylmethyl-phenoxy)-cyclobutylmethyl]-3-(2-fluoro-phenyl)-1-methyl-urea;

N-[3-(2-Chloro-3-pyrrolidin-1-ylmethyl-phenoxy)-cyclobutylmethyl]-6,N-dimethyl-nicotinamide;

Propane-1-sulfonic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-2-fluoro-N-methyl-benzamide;

N-[3-(2-Chloro-3-pyrrolidin-1-ylmethyl-phenoxy)-cyclobutylmethyl]-N-methyl-benzamide;

1-[3-(2-Chloro-3-pyrrolidin-1-ylmethyl-phenoxy)-cyclobutylmethyl]-3-(4-methoxy-phenyl)-1-methyl-urea;

3-(5-Chloro-2-methyl-phenyl)-1-[3-(2-chloro-3-pyrrolidin-1-ylmethyl-phenoxy)-cyclobutylmethyl]-1-methyl-urea;

Thiophene-3-sulfonic acid [3-(2-chloro-3-pyrrolidin-1-ylmethyl-phenoxy)-cyclobutylmethyl]-methyl-amide;

4-Methyl-pentanoic acid [3-(2-chloro-3-pyrrolidin-1-ylmethyl-phenoxy)-cyclobutylmethyl]-methyl-amide;

4-Chloro-N-[3-(2-chloro-3-pyrrolidin-1-ylmethyl-phenoxy)-cyclobutylmethyl]-N-methyl-benzenesulfonamide;

(S)—N-[3-(2-Chloro-3-pyrrolidin-1-ylmethyl-phenoxy)-cyclobutylmethyl]-2-hydroxy-N-methyl-2-phenyl-acetamide;

1,5-Dimethyl-1H-pyrazole-3-carboxylic acid [3-(2-chloro-3-pyrrolidin-1-ylmethyl-phenoxy)-cyclobutylmethyl]-methyl-amide;

1-[3-(2-Chloro-3-pyrrolidin-1-ylmethyl-phenoxy)-cyclobutylmethyl]-1-methyl-3-m-tolyl-urea;

N-[3-(2-Chloro-3-pyrrolidin-1-ylmethyl-phenoxy)-cyclobutylmethyl]-2,3-difluoro-N-methyl-benzamide;

4-Methyl-oxazole-5-carboxylic acid [3-(2-chloro-3-pyrrolidin-1-ylmethyl-phenoxy)-cyclobutylmethyl]-methyl-amide;

N-[3-(2-Chloro-3-pyrrolidin-1-ylmethyl-phenoxy)-cyclobutylmethyl]-4-fluoro-N-methyl-benzenesulfonamide;

2-Chloro-N-[3-(2-chloro-3-pyrrolidin-1-ylmethyl-phenoxy)-cyclobutylmethyl]-N-methyl-benzenesulfonamide;

1-[3-(2-Chloro-3-pyrrolidin-1-ylmethyl-phenoxy)-cyclobutylmethyl]-3-ethyl-1-methyl-urea;

1-Isopropyl-1H-pyrazole-4-carboxylic acid [3-(2-chloro-3-pyrrolidin-1-ylmethyl-phenoxy)-cyclobutylmethyl]-methyl-amide;

3-(3-Acetyl-phenyl)-1-[3-(2-chloro-3-pyrrolidin-1-ylmethyl-phenoxy)-cyclobutylmethyl]-1-methyl-urea;

5-Methyl-isoxazole-3-carboxylic acid [3-(2-chloro-3-pyrrolidin-1-ylmethyl-Phenoxy)-cyclobutylmethyl]-methyl-amide;

2-Ethyl-4-methyl-oxazole-5-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-3-fluoro-N-methyl-benzamide;
N-[3-(2-Chloro-3-pyrrolidin-1-ylmethyl-phenoxy)-cyclobutylmethyl]-N-methyl-2-pyridin-4-yl-acetamide;
5-Ethyl-2-methyl-2H-pyrazole-3-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-N-methyl-2-pyrazol-1-yl-acetamide;
Cyclopropanecarboxylic acid [3-(2-chloro-3-pyrrolidin-1-ylmethyl-phenoxy)-cyclobutylmethyl]-methyl-amide;
3-Chloro-N-[3-(2-chloro-3-pyrrolidin-1-ylmethyl-phenoxy)-cyclobutylmethyl]-N-methyl-benzenesulfonamide;
1-[3-(2-Chloro-3-pyrrolidin-1-ylmethyl-phenoxy)-cyclobutylmethyl]-3-(2-ethyl-phenyl)-1-methyl-urea;
N-[3-(2-Chloro-3-pyrrolidin-1-ylmethyl-phenoxy)-cyclobutylmethyl]-2-(2-fluoro-phenyl)-N-methyl-acetamide;
N-[3-(2-Chloro-3-pyrrolidin-1-ylmethyl-phenoxy)-cyclobutylmethyl]-N-methyl-C-phenyl-methanesulfonamide;
N-[3-(2-Chloro-3-pyrrolidin-1-ylmethyl-phenoxy)-cyclobutylmethyl]-4-fluoro-N-methyl-benzamide;
N-[3-(2-Chloro-3-pyrrolidin-1-ylmethyl-phenoxy)-cyclobutylmethyl]-N-methyl-benzenesulfonamide;
1-{[3-(2-Chloro-3-pyrrolidin-1-ylmethyl-phenoxy)-cyclobutyl]methyl}-1-methyl-3-(2-trifluoromethyl-phenyl)-urea;
N-[3-(2-Chloro-3-pyrrolidin-1-ylmethyl-phenoxy)-cyclobutylmethyl]-2-cyclopentyl-N-methyl-acetamide;
N-[3-(2-Chloro-3-pyrrolidin-1-ylmethyl-phenoxy)-cyclobutylmethyl]-N-methyl-acetamide;
N-[3-(2-Chloro-3-pyrrolidin-1-ylmethyl-phenoxy)-cyclobutylmethyl]-N-methyl-isonicotinamide;
Cyclopentanecarboxylic acid [3-(2-chloro-3-pyrrolidin-1-ylmethyl-phenoxy)-cyclobutylmethyl]-methyl-amide;
Benzo[1,2,5]thiadiazole-4-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-3,4-difluoro-N-methyl-benzenesulfonamide;
1-[3-(2-Chloro-3-pyrrolidin-1-ylmethyl-phenoxy)-cyclobutylmethyl]-1-methyl-3-o-tolyl-urea;
3-Chloro-N-[3-(2-chloro-3-pyrrolidin-1-ylmethyl-phenoxy)-cyclobutylmethyl]-N-methyl-benzamide;
5-Cyclopropyl-2H-pyrazole-3-carboxylic acid [3-(2-chloro-3-pyrrolidin-1-ylmethyl-phenoxy)-cyclobutylmethyl]-methyl-amide;
3-(4-Chloro-phenyl)-1-[3-(2-chloro-3-pyrrolidin-1-ylmethyl-phenoxy)-cyclobutylmethyl]-1-methyl-urea;
Piperidine-1-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-N-methyl-2-(3-methyl-pyrazol-1-yl)-acetamide;
1-[3-(2-Chloro-3-pyrrolidin-1-ylmethyl-phenoxy)-cyclobutylmethyl]-1-methyl-3-p-tolyl-urea;
N-[3-(2-Chloro-3-pyrrolidin-1-ylmethyl-phenoxy)-cyclobutylmethyl]-4,4,4-trifluoro-N-methyl-butyramide;
Morpholine-4-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2-(3,5-dimethyl-Isoxazol-4-yl)—N-methyl-acetamide;
N-[3-(2-Chloro-3-pyrrolidin-1-ylmethyl-phenoxy)-cyclobutylmethyl]-3,N-dimethyl-butyramide;
Tetrahydro-pyran-4-carboxylic acid [3-(2-chloro-3-pyrrolidin-1-ylmethyl-phenoxy)-cyclobutylmethyl]-methyl-amide;
3-(3-Chloro-2-methyl-phenyl)-1-[3-(2-chloro-3-pyrrolidin-1-yl-methyl-phenoxy)-cyclobutylmethyl]-1-methyl-urea;
Propane-2-sulfonic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-3-(2-methoxy-phenyl)-1-methyl-urea;
3-(2-Chloro-phenyl)-1-[3-(2-chloro-3-pyrrolidin-1-ylmethyl-phenoxy)-cyclobutylmethyl]-1-methyl-urea;
1-[3-(2-Chloro-3-pyrrolidin-1-ylmethyl-phenoxy)-cyclobutylmethyl]-3-(2,5-dimethyl-phenyl)-1-methyl-urea;
4-Methyl-furazan-3-carboxylic acid [3-(2-chloro-3-pyrrolidin-1-ylmethyl-phenoxy)-cyclobutylmethyl]-methyl-amide;
N-({trans-3-[3-(2-chloro-pyrrolidiylmethyl)phenoxy]cyclobutyl}methyl)-N,N,N'-trimethylsulfamide;
N-[3-(2-Chloro-3-pyrrolidin-1-ylmethyl-phenoxy)-cyclobutylmethyl]-2,4-dimethoxy-N-methyl-benzenesulfonamide;
2,5-Dimethyl-thiophene-3-sulfonic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-1-methyl-3-phenyl-urea;
N-[3-(2-Chloro-3-pyrrolidin-1-ylmethyl-phenoxy)-cyclobutylmethyl]-N-methyl-isobutyramide;
1-[3-(2-Chloro-3-pyrrolidin-1-ylmethyl-phenoxy)-cyclobutylmethyl]-3-(2,4-difluoro-phenyl)-1-methyl-urea;
6-Methyl-pyridine-2-carboxylic acid [3-(2-chloro-3-pyrrolidin-1-ylmethyl-phenoxy)-cyclobutylmethyl]-methyl-amide;
3-(3-Chloro-phenyl)-1-[3-(2-chloro-3-pyrrolidin-1-ylmethyl-phenoxy)-cyclobutylmethyl]-1-methyl-urea;
N-[3-(2-Chloro-3-pyrrolidin-1-ylmethyl-phenoxy)-cyclobutylmethyl]-N-methyl-nicotinamide;
N-[3-(2-Chloro-3-pyrrolidin-1-ylmethyl-phenoxy)-cyclobutylmethyl]-2-(3-fluoro-phenyl)-N-methyl-acetamide;
1-[3-(2-Chloro-3-pyrrolidin-1-ylmethyl-phenoxy)-cyclobutylmethyl]-3-(3-methoxy-phenyl)-1-methyl-urea;
N-[3-(2-Chloro-3-pyrrolidin-1-ylmethyl-phenoxy)-cyclobutylmethyl]-2,5,N-trimethyl-benzamide;
N-[3-(2-Chloro-3-pyrrolidin-1-ylmethyl-phenoxy)-cyclobutylmethyl]-2-cyclopropyl-N-methyl-acetamide;
N-[3-(2-Chloro-3-pyrrolidin-1-ylmethyl-phenoxy)-cyclobutylmethyl]-N-methyl-propionamide;
N-[3-(2-Chloro-3-pyrrolidin-1-ylmethyl-phenoxy)-cyclobutylmethyl]-2-methoxy-N-methyl-nicotinamide;
N-[3-(2-Chloro-3-pyrrolidin-1-ylmethyl-phenoxy)-cyclobutylmethyl]-2,6-difluoro-N-methyl-benzamide;
1-{[3-(2-Chloro-3-pyrrolidin-1-ylmethyl-phenoxy)-cyclobutyl]methyl}-1-methyl-3-(3-trifluoromethyl-phenyl)-urea;
N-[3-(2-Chloro-3-pyrrolidin-1-ylmethyl-phenoxy)-cyclobutylmethyl]-2-methoxy-N-methyl-acetamide;
N-[3-(2-Chloro-3-pyrrolidin-1-ylmethyl-phenoxy)-cyclobutylmethyl]-3-methoxy-N-methyl-propionamide;

N-[3-(2-Chloro-3-pyrrolidin-1-ylmethyl-phenoxy)-cyclobutylmethyl]-2,3,N-trimethyl-benzamide;
N-[3-(2-Chloro-3-pyrrolidin-1-ylmethyl-phenoxy)-cyclobutylmethyl]-N-methyl-2-pyridin-3-yl-acetamide;
N-[3-(2-Chloro-3-pyrrolidin-1-ylmethyl-phenoxy)-cyclobutylmethyl]-3-fluoro-N-methyl-benzenesulfonamide;
N-[3-(2-Chloro-3-pyrrolidin-1-ylmethyl-phenoxy)-cyclobutylmethyl]-2,2,N-trimethyl-propionamide;
1-Ethyl-1H-pyrazole-4-carboxylic acid [3-(2-chloro-3-pyrrolidin-1-ylmethyl-phenoxy)-cyclobutylmethyl]-methyl-amide;
Pyridine-2-carboxylic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-3-(2,6-dimethyl-phenyl)-1-methyl-urea;
N-[3-(2-Chloro-3-pyrrolidin-1-ylmethyl-phenoxy)-cyclobutylmethyl]-3,3,N-trimethyl-butyramide;
4-[3-(2-Fluoro-4-pyrrolidin-1-ylmethyl-phenoxy)-cyclobutylmethyl]-morpholine;
4-{3-[2-Fluoro-4-(2-pyrrolidin-1-yl-ethyl)-phenoxy]-cyclobutylmethyl}-morpholine;
Pyridine-3-sulfonic acid [3-(4-pyrrolidin-1-ylmethyl-phenoxy)-cyclobutylmethyl]-amide;
2,5-Dimethyl-2H-pyrazole-3-carboxylic acid [3-(4-pyrrolidin-1-ylmethyl-phenoxy)-cyclobutylmethyl]-amide;
N-[3-(4-Pyrrolidin-1-ylmethyl-phenoxy)-cyclobutylmethyl]-isonicotinamide;
2-Methyl-2H-pyrazole-3-carboxylic acid [3-(4-pyrrolidin-1-ylmethyl-phenoxy)-cyclobutylmethyl]-amide;
6-Methyl-N-[3-(4-pyrrolidin-1-ylmethyl-phenoxy)-cyclobutylmethyl]-nicotinamide;
C-Phenyl-N-[3-(4-pyrrolidin-1-ylmethyl-phenoxy)-cyclobutylmethyl]-methanesulfonamide;
Ethanesulfonic acid [3-(4-pyrrolidin-1-ylmethyl-phenoxy)-cyclobutylmethyl]-amide;
4-{3-[4-(1-Pyrrolidin-1-yl-ethyl)-phenoxy]-cyclobutylmethyl}-morpholine;
4-[3-(2,5-Dimethoxy-4-pyrrolidin-1-ylmethyl-phenoxy)-cyclobutylmethyl]-morpholine;
4-[3-(2,6-Dimethyl-4-pyrrolidin-1-ylmethyl-phenoxy)-cyclobutylmethyl]-morpholine;
4-{3-[3-Chloro-4-(1-pyrrolidin-1-yl-ethyl)-phenoxy]-cyclobutylmethyl}-morpholine;
4-[3-(4-Pyrrolidin-1-ylmethyl-naphthalen-1-yloxy)-cyclobutylmethyl]-morpholine;
4-[3-(2-Ethoxy-4-pyrrolidin-1-ylmethyl-phenoxy)-cyclobutylmethyl]-morpholine;
4-[3-(2-Chloro-6-methoxy-4-pyrrolidin-1-ylmethyl-phenoxy)-cyclobutylmethyl]-morpholine;
4-[3-(3-Pyrrolidin-1-ylmethyl-phenoxy)-cyclobutylmethyl]-morpholine;
4-[3-(2-Methoxy-4-pyrrolidin-1-ylmethyl-phenoxy)-cyclobutylmethyl]-morpholine;
3,4-Difluoro-N-methyl-N-[3-(4-pyrrolidin-1-ylmethyl-phenoxy)-cyclobutylmethyl]-benzenesulfonamide;
Pyridine-3-sulfonic acid methyl-[3-(4-pyrrolidin-1-ylmethyl-phenoxy)-cyclobutylmethyl]-amide;
2-Methoxy-N-methyl-N-[3-(4-pyrrolidin-1-ylmethyl-phenoxy)-cyclobutylmethyl]-acetamide;
2,5-Dimethyl-2H-pyrazole-3-carboxylic acid methyl-[3-(4-pyrrolidin-1-ylmethyl-phenoxy)-cyclobutylmethyl]-amide;
1-Methanesulfonyl-4-[3-(4-pyrrolidin-1-ylmethyl-phenoxy)-cyclobutylmethyl]-piperazine;
Ethanesulfonic acid methyl-[3-(4-pyrrolidin-1-ylmethyl-phenoxy)-cyclobutylmethyl]-amide;
1,3,5-Trimethyl-1H-pyrazole-4-sulfonic acid methyl-[3-(4-pyrrolidin-1-ylmethyl-phenoxy)-cyclobutylmethyl]-amide;
N-Methyl-2-pyridin-3-yl-N-[3-(4-pyrrolidin-1-ylmethyl-phenoxy)-cyclobutylmethyl]-acetamide;
N-Methyl-N-[3-(4-pyrrolidin-1-ylmethyl-phenoxy)-cyclobutylmethyl]-nicotinamide;
2-Chloro-4-fluoro-N-methyl-N-[3-(4-pyrrolidin-1-ylmethyl-phenoxy)-cyclobutylmethyl]-benzenesulfonamide;
3-Methoxy-N-methyl-N-[3-(4-pyrrolidin-1-ylmethyl-phenoxy)-cyclobutylmethyl]-propionamide;
2,N-Dimethyl-N-[3-(4-pyrrolidin-1-ylmethyl-phenoxy)-cyclobutylmethyl]-nicotinamide;
2-Methyl-2H-pyrazole-3-carboxylic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-isobutyramide;
5-Ethyl-isoxazole-3-carboxylic acid methyl-[3-(4-pyrrolidin-1-ylmethyl-phenoxy)-cyclobutylmethyl]-amide;
2-Cyclopentyl-N-methyl-N-[3-(4-pyrrolidin-1-ylmethyl-phenoxy)-cyclobutylmethyl]-acetamide;
N-Methyl-N-[3-(4-pyrrolidin-1-ylmethyl-phenoxy)-cyclobutylmethyl]-methanesulfonamide;
4-Acetyl-N-methyl-N-[3-(4-pyrrolidin-1-ylmethyl-phenoxy)-cyclobutylmethyl]-benzenesulfonamide;
6,N-Dimethyl-N-[3-(4-pyrrolidin-1-ylmethyl-phenoxy)-cyclobutylmethyl]-nicotinamide;
6-Methyl-pyridine-2-carboxylic acid methyl-[3-(4-pyrrolidin-1-ylmethyl-phenoxy)-cyclobutylmethyl]-amide;
Pyridine-2-carboxylic acid methyl-[3-(4-pyrrolidin-1-ylmethyl-phenoxy)-cyclobutylmethyl]-amide;
Tetrahydro-pyran-4-carboxylic acid methyl-[3-(4-pyrrolidin-1-ylmethyl-phenoxy)-cyclobutylmethyl]-amide;
N-Methyl-2-pyridin-4-yl-N-[3-(4-pyrrolidin-1-ylmethyl-phenoxy)-cyclobutylmethyl]-acetamide;
3,N-Dimethyl-N-[3-(4-pyrrolidin-1-ylmethyl-phenoxy)-cyclobutylmethyl]-butyramide;
Propane-2-sulfonic acid methyl-[3-(4-pyrrolidin-1-ylmethyl-phenoxy)-cyclobutylmethyl]-amide;
4-Chloro-N-methyl-N-[3-(4-pyrrolidin-1-yl-methyl-phenoxy)-cyclobutylmethyl]-benzenesulfonamide;
3-Methyl-1H-pyrazole-4-carboxylic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-propionamide;
N-Methyl-2-pyridin-2-yl-N-[3-(4-pyrrolidin-1-ylmethyl-phenoxy)-cyclobutylmethyl]-acetamide;
N-Methyl-C-phenyl-N-[3-(4-pyrrolidin-1-ylmethyl-phenoxy)-cyclobutylmethyl]-methanesulfonamide;
2,2,2-Trifluoro-ethanesulfonic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-acetamide;
Piperidine-1-sulfonic acid methyl-[3-(4-pyrrolidin-1-ylmethyl-phenoxy)-cyclobutylmethyl]-amide;
Pyrrolidine-1-sulfonic acid methyl-[3-(4-pyrrolidin-1-ylmethyl-phenoxy)-cyclobutylmethyl]-amide;
N-Methyl-N-[3-(4-pyrrolidin-1-ylmethyl-phenoxy)-cyclobutylmethyl]-isonicotinamide;
Pyrazine-2-carboxylic acid methyl-[3-(4-pyrrolidin-1-ylmethyl-phenoxy)-cyclobutylmethyl]-amide;

4-[3-(2,6-Dimethoxy-4-pyrrolidin-1-ylmethyl-phenoxy)-cyclobutylmethyl]-morpholine;
4-[3-(2-Methoxy-5-pyrrolidin-1-ylmethyl-phenoxy)-cyclobutylmethyl]-morpholine;
4-[3-(4-Methoxy-3-pyrrolidin-1-ylmethyl-phenoxy)-cyclobutylmethyl]-morpholine;
4-{3-[3-Chloro-4-((R)-1-pyrrolidin-1-yl-ethyl)-phenoxy]-cyclobutylmethyl}-morpholine;
4-[3-(3-Methyl-5-pyrrolidin-1-ylmethyl-phenoxy)-cyclobutylmethyl]-morpholine;
N-[3-(4-Pyrrolidin-1-ylmethyl-phenoxy)-cyclobutylmethyl]-nicotinamide;
2-Pyridin-4-yl-N-[3-(4-pyrrolidin-1-ylmethyl-phenoxy)-cyclobutylmethyl]-acetamide;
3-Methyl-N-[3-(4-pyrrolidin-1-ylmethyl-phenoxy)-cyclobutylmethyl]-butyramide;
2-Methoxy-N-[3-(4-pyrrolidin-1-ylmethyl-phenoxy)-cyclobutylmethyl]-acetamide;
N-[3-(4-Pyrrolidin-1-ylmethyl-phenoxy)-cyclobutylmethyl]-acetamide;
N-[3-(4-Pyrrolidin-1-ylmethyl-phenoxy)-cyclobutylmethyl]-isobutyramide;
N-[3-(4-Pyrrolidin-1-ylmethyl-phenoxy)-cyclobutylmethyl]-propionamide;
N-[3-(4-Pyrrolidin-1-ylmethyl-phenoxy)-cyclobutylmethyl]-methanesulfonamide;
2-Cyclopentyl-N-[3-(4-pyrrolidin-1-ylmethyl-phenoxy)-cyclobutylmethyl]-acetamide;
3-Methoxy-N-[3-(4-pyrrolidin-1-ylmethyl-phenoxy)-cyclobutylmethyl]-propionamide;
2-Pyridin-2-yl-N-[3-(4-pyrrolidin-1-ylmethyl-phenoxy)-cyclobutylmethyl]-acetamide;
Piperidine-1-sulfonic acid [3-(4-pyrrolidin-1-ylmethyl-phenoxy)-cyclobutylmethyl]-amide;
N-[3-(2-Chloro-3-pyrrolidin-1-ylmethyl-phenoxy)-cyclobutylmethyl]-2,6-difluoro-N-methyl-benzenesulfonamide;
N-[3-(2-Chloro-3-pyrrolidin-1-ylmethyl-phenoxy)-cyclobutylmethyl]-4,N-dimethyl-benzamide;
1-[3-(2-Chloro-3-pyrrolidin-1-ylmethyl-phenoxy)-cyclobutylmethyl]-3-(3-fluoro-phenyl)-1-methyl-urea;
2-Oxo-2,3-dihydro-benzooxazole-6-sulfonic acid [3-(2-chloro-3-pyrrolidin-1-ylmethyl-phenoxy)-cyclobutylmethyl]-methyl-amide;
1-[3-(2-Chloro-3-pyrrolidin-1-ylmethyl-phenoxy)-cyclobutylmethyl]-3-(3,5-dimethyl-phenyl)-1-methyl-urea;
4-Methyl-thiophene-2-sulfonic acid [3-(2-chloro-3-pyrrolidin-1-ylmethyl-phenoxy)-cyclobutylmethyl]-methyl-amide;
3-(5-Chloro-2-methoxy-phenyl)-1-[3-(2-chloro-3-pyrrolidin-1-ylmethyl-phenoxy)-cyclobutylmethyl]-1-methyl-urea;
2-Ethyl-5-methyl-2H-pyrazole-3-carboxylic acid [3-(2-chloro-3-pyrrolidin-1-ylmethyl-phenoxy)-cyclobutylmethyl]-methyl-amide;
4-Acetyl-N-[3-(2-chloro-3-pyrrolidin-1-ylmethyl-phenoxy)-cyclobutylmethyl]-N-methyl-benzenesulfonamide;
Pyrrolidine-1-sulfonic acid [3-(2-chloro-3-pyrrolidin-1-ylmethyl-phenoxy)-cyclobutylmethyl]-methyl-amide;
Cyclohexanecarboxylic acid [3-(2-chloro-3-pyrrolidin-1-ylmethyl-phenoxy)-cyclobutylmethyl]-methyl-amide;
2-Chloro-N-[3-(2-chloro-3-pyrrolidin-1-ylmethyl-phenoxy)-cyclobutylmethyl]-N-methyl-benzamide;
4-tert-Butyl-N-[3-(2-chloro-3-pyrrolidin-1-ylmethyl-phenoxy)-cyclobutylmethyl]-N-methyl-benzenesulfonamide;
3-Chloro-N-[3-(2-chloro-3-pyrrolidin-1-ylmethyl-phenoxy)-cyclobutylmethyl]-4-fluoro-N-methyl-benzenesulfonamide;
2,3-Dihydro-benzo[1,4]dioxine-6-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-5-fluoro-2,N-dimethyl-benzenesulfonamide;
Furazan-3-carboxylic acid [3-(2-chloro-3-pyrrolidin-1-ylmethyl-phenoxy)-cyclobutylmethyl]-methyl-amide;
2,6-Dimethyl-pyrimidine-4-carboxylic acid [3-(2-chloro-3-pyrrolidin-1-ylmethyl-phenoxy)-cyclobutylmethyl]-methyl-amide;
5-Chloro-thiophene-2-sulfonic acid [3-(2-chloro-3-pyrrolidin-1-ylmethyl-phenoxy)-cyclobutylmethyl]-methyl-amide;
4-Chloro-N-[3-(2-chloro-3-pyrrolidin-1-ylmethyl-phenoxy)-cyclobutylmethyl]-2,5,N-trimethyl-benzenesulfonamide;
5-Isopropyl-isoxazole-3-carboxylic acid [3-(2-chloro-3-pyrrolidin-1-ylmethyl-phenoxy)-cyclobutylmethyl]-methyl-amide;
3-(2-Chloro-6-methyl-phenyl)-1-(3-(2-chloro-3-pyrrolidin-1-ylmethyl-phenoxy)-cyclobutylmethyl]-1-methyl-urea;
N-[3-(2-Chloro-3-pyrrolidin-1-ylmethyl-phenoxy)-cyclobutylmethyl]-4-ethyl-N-methyl-benzenesulfonamide;
N-[3-(2-Chloro-3-pyrrolidin-1-ylmethyl-phenoxy)-cyclobutylmethyl]-3,N-dimethyl-benzenesulfonamide;
N-[3-(2-Chloro-3-pyrrolidin-1-ylmethyl-phenoxy)-cyclobutylmethyl]-2-methoxy-5,N-dimethyl-benzenesulfonamide;
1-[3-(2-Chloro-3-pyrrolidin-1-ylmethyl-phenoxy)-cyclobutylmethyl]-3-(2-methoxy-5-methyl-phenyl)-1-methyl-urea;
N-[3-(2-Chloro-3-pyrrolidin-1-ylmethyl-phenoxy)-cyclobutylmethyl]-4,N-dimethyl-benzenesulfonamide;
Prop-2-ene-1-sulfonic acid [3-(2-chloro-3-pyrrolidin-1-ylmethyl-phenoxy)-cyclobutylmethyl]-methyl-amide;
Thiophene-2-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2,5-dimethoxy-N-methyl-benzenesulfonamide;
(E)-2-Phenyl-ethenesulfonic acid [3-(2-chloro-3-pyrrolidin-1-ylmethyl-phenoxy)-cyclobutylmethyl]-methyl-amide;
2-{[3-(2-Chloro-3-pyrrolidin-1-ylmethyl-phenoxy)-cyclobutylmethyl]-methyl-sulfamoyl}-benzoic acid methyl ester;
1,3,5-Trimethyl-1H-pyrazole-4-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2-(3,5-dimethyl-pyrazol-1-yl)—N-methyl-acetamide;
1-[3-(2-Chloro-3-pyrrolidin-1-ylmethyl-phenoxy)-cyclobutylmethyl]-3-(3,4-dimethyl-phenyl)-1-methyl-urea;
1-{[3-(2-Chloro-3-pyrrolidin-1-ylmethyl-phenoxy)-cyclobutyl]methyl}-1-methyl-3-(4-trifluoromethyl-phenyl)-urea;

Pyridine-3-sulfonic acid [3-(2-chloro-3-pyrrolidin-1-ylmethyl-phenoxy)-cyclobutylmethyl]-methyl-amide;
5-Methyl-thiophene-2-sulfonic acid [3-(2-chloro-3-pyrrolidin-1-ylmethyl-phenoxy)-cyclobutylmethyl]-methyl-amide;
5-Methyl-pyrazine-2-carboxylic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2,4,N-trimethyl-benzamide;
N-(4-{[3-(2-Chloro-3-pyrrolidin-1-ylmethyl-phenoxy)-cyclobutylmethyl]-methyl-sulfamoyl}-phenyl)-acetamide;
N-[3-(2-Chloro-3-pyrrolidin-1-ylmethyl-phenoxy)-cyclobutylmethyl]-N-methyl-methanesulfonamide;
N-[3-(2-Chloro-3-pyrrolidin-1-ylmethyl-phenoxy)-cyclobutylmethyl]-3,4-dimethoxy-N-methyl-benzenesulfonamide;
N-[3-(2-Chloro-3-pyrrolidin-1-ylmethyl-phenoxy)-cyclobutylmethyl]-2,4,N-trimethyl-benzenesulfonamide;
N-[3-(2-Chloro-3-pyrrolidin-1-ylmethyl-phenoxy)-cyclobutylmethyl]-N-methyl-4-trifluoromethyl-benzenesulfonamide;
5-Chloro-N-[3-(2-chloro-3-pyrrolidin-1-ylmethyl-phenoxy)-cyclobutylmethyl]-2-methoxy-N-methyl-benzenesulfonamide;
3-(3-Chloro-4-methyl-phenyl)-1-[3-(2-chloro-3-pyrrolidin-1-ylmethyl-phenoxy)-cyclobutylmethyl]-1-methyl-urea;
Quinoline-8-sulfonic acid [3-(2-chloro-3-pyrrolidin-1-ylmethyl-phenoxy)-cyclobutylmethyl]-methyl-amide;
Ethanesulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2,4,5-trifluoro-N-methyl-benzenesulfonamide;
N-[3-(2-Chloro-3-pyrrolidin-1-ylmethyl-phenoxy)-cyclobutylmethyl]-N-methyl-2-trifluoromethyl-benzenesulfonamide;
Benzo[b]thiophene-2-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2-fluoro-N-methyl-benzenesulfonamide;
N-[3-(2-Chloro-3-pyrrolidin-1-ylmethyl-phenoxy)-cyclobutylmethyl]-4-methoxy-N-methyl-benzenesulfonamide;
1-[3-(2-Chloro-3-pyrrolidin-1-ylmethyl-phenoxy)-cyclobutylmethyl]-3-(4-fluoro-phenyl)-1-methyl-urea;
Naphthalene-1-sulfonic acid [3-(2-chloro-3-pyrrolidin-1-ylmethyl-phenoxy)-cyclobutylmethyl]-methyl-amide;
N-(3-{[3-(2-Chloro-3-pyrrolidin-1-ylmethyl-phenoxy)-cyclobutylmethyl]-methyl-sulfamoyl}-phenyl)-acetamide;
5-Ethyl-thiophene-2-sulfonic acid [3-(2-chloro-3-pyrrolidin-1-ylmethyl-phenoxy)-cyclobutylmethyl]-methyl-amide;
3-(4-Chloro-2-methyl-phenyl)-1-[3-(2-chloro-3-pyrrolidin-1-ylmethyl-phenoxy)-cyclobutylmethyl]-1-methyl-urea;
Naphthalene-2-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-3,4,N-trimethyl-benzamide;
5-Chloro-1,3-dimethyl-1H-pyrazole-4-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-2,5,N-trimethyl-benzenesulfonamide;
3-Methyl-thiophene-2-sulfonic acid [3-(2-chloro-3-pyrrolidin-1-ylmethyl-phenoxy)-cyclobutylmethyl]-methyl-amide;
N-[3-(2-Chloro-3-pyrrolidin-1-ylmethyl-phenoxy)-cyclobutylmethyl]-N-methyl-3-trifluoromethyl-benzenesulfonamide;
Pyrazine-2-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-2-pyridin-2-yl-acetamide;
5-Methyl-pyrazine-2-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2,5-dimethoxy-N-methyl-benzenesulfonamide;
N-[3-(3-Chloro-4-pyrrolidin-1-ylmethyl-phenoxy)-cyclobutylmethyl]-2,4-difluoro-N-methyl-benzenesulfonamide;
Cyclohexanecarboxylic acid [3-(3-chloro-4-pyrrolidin-1-ylmethyl-phenoxy)-cyclobutylmethyl]-methyl-amide;
Cyclopentanecarboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2-cyclopropyl-N-methyl-acetamide;
N-(3-{[3-(3-Chloro-4-pyrrolidin-1-ylmethyl-phenoxy)-cyclobutylmethyl]-methyl-sulfamoyl}-phenyl)-acetamide;
N-[3-(3-Chloro-4-pyrrolidin-1-ylmethyl-phenoxy)-cyclobutylmethyl]-3,4-dimethoxy-N-methyl-benzenesulfonamide;
N-[3-(3-Chloro-4-pyrrolidin-1-ylmethyl-phenoxy)-cyclobutylmethyl]-2-(3,5-dimethyl-pyrazol-1-yl)—N-methyl-acetamide;
3-Chloro-N-[3-(3-chloro-4-pyrrolidin-1-ylmethyl-phenoxy)-cyclobutylmethyl]-2,N-dimethyl-benzenesulfonamide;
N-[3-(3-Chloro-4-pyrrolidin-1-ylmethyl-phenoxy)-cyclobutylmethyl]-2,5,N-trimethyl-benzenesulfonamide;
(S)—N-[3-(3-Chloro-4-pyrrolidin-1-ylmethyl-phenoxy)-cyclobutylmethyl]-2-hydroxy-N-methyl-2-phenyl-acetamide;
Naphthalene-1-sulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2,6-difluoro-N-methyl-benzenesulfonamide;
Piperidine-1-sulfonic acid [3-(3-chloro-4-pyrrolidin-1-ylmethyl-phenoxy)-cyclobutylmethyl]-methyl-amide;
3,5-Dimethyl-isoxazole-4-sulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-3-methoxy-N-methyl-propionamide;
N-[3-(3-Chloro-4-pyrrolidin-1-ylmethyl-phenoxy)-cyclobutylmethyl]-N-methyl-methanesulfonamide;
4-Chloro-N-[3-(3-chloro-4-pyrrolidin-1-ylmethyl-phenoxy)-cyclobutylmethyl]-2,5,N-trimethyl-benzenesulfonamide;
2-Methoxy-pyrimidine-5-carboxylic acid [3-(3-chloro-4-pyrrolidin-1-ylmethyl-phenoxy)-cyclobutylmethyl]-methyl-amide;

1-[3-(3-Chloro-4-pyrrolidin-1-ylmethyl-phenoxy)-cyclobutylmethyl]-3-(2-fluoro-phenyl)-1-methyl-urea;
N-[3-(3-Chloro-4-pyrrolidin-1-ylmethyl-phenoxy)-cyclobutylmethyl]-2,4-dimethoxy-N-methyl-benzenesulfonamide;
N-[3-(3-Chloro-4-pyrrolidin-1-ylmethyl-phenoxy)-cyclobutylmethyl]-3,3,N-trimethyl-butyramide;
1,3,5-Trimethyl-1H-pyrazole-4-sulfonic acid [3-(3-chloro-4-pyrrolidin-1-ylmethyl-phenoxy)-cyclobutylmethyl]-methyl-amide;
Morpholine-4-sulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-4-methoxy-N-methyl-benzenesulfonamide;
N-[3-(3-Chloro-4-pyrrolidin-1-ylmethyl-phenoxy)-cyclobutylmethyl]-2,4,5-trifluoro-N-methyl-benzenesulfonamide;
3-tert-Butyl-1-[(3-(3-chloro-4-pyrrolidin-1-ylmethyl-phenoxy)-cyclobutylmethyl]-1-methyl-urea;
2,3-Dihydro-benzo[1,4]dioxine-6-sulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-benzenesulfonamide;
2-Oxo-2,3-dihydro-benzooxazole-6-sulfonic acid [3-(3-chloro-4-pyrrolidin-1-ylmethyl-phenoxy)-cyclobutylmethyl]-methyl-amide;
2-Chloro-N-[3-(3-chloro-4-pyrrolidin-1-ylmethyl-phenoxy)-cyclobutylmethyl]-N-methyl-benzenesulfonamide;
N-[3-(3-Chloro-4-pyrrolidin-1-ylmethyl-phenoxy)-cyclobutylmethyl]-5-fluoro-2,N-dimethyl-benzenesulfonamide;
2-[([3-(3-Chloro-4-pyrrolidin-1-ylmethyl-phenoxy)-cyclobutylmethyl]-methyl-sulfamoyl]-benzoic acid methyl ester;
4-tert-Butyl-N-[3-(3-chloro-4-pyrrolidin-1-ylmethyl-phenoxy)-cyclobutylmethyl]-N-methyl-benzenesulfonamide;
N-[3-(3-Chloro-4-pyrrolidin-1-ylmethyl-phenoxy)-cyclobutylmethyl]-N-methyl-2-(3-methyl-pyrazol-1-yl)-acetamide;
N-[3-(3-Chloro-4-pyrrolidin-1-ylmethyl-phenoxy)-cyclobutylmethyl]-2-methoxy-5,N-dimethyl-benzenesulfonamide;
Ethanesulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-3,4-difluoro-N-methyl-benzenesulfonamide;
N-[3-(3-Chloro-4-pyrrolidin-1-ylmethyl-phenoxy)-cyclobutylmethyl]-N-methyl-2-(4-methyl-furazan-3-yl)-acetamide;
N-[3-(3-Chloro-4-pyrrolidin-1-ylmethyl-phenoxy)-cyclobutylmethyl]-4,4,4-trifluoro-N-methyl-butyramide;
N-[3-(3-Chloro-4-pyrrolidin-1-ylmethyl-phenoxy)-cyclobutylmethyl]-N-methyl-2-trifluoromethyl-benzenesulfonamide;
2,5-Dimethyl-thiophene-3-sulfonic acid [3-(3-chloro-4-pyrrolidin-1-ylmethyl-phenoxy)-cyclobutylmethyl]-methyl-amide;
Benzo[1,2,5]thiadiazole-4-sulfonic acid [3-(3-chloro-4-pyrrolidin-1-ylmethyl-phenoxy)-cyclobutylmethyl]-methyl-amide;
Quinoline-8-sulfonic acid [3-(3-chloro-4-pyrrolidin-1-ylmethyl-phenoxy)-cyclobutylmethyl]-methyl-amide;
4-Acetyl-N-[3-(3-chloro-4-pyrrolidin-1-ylmethyl-phenoxy)-cyclobutylmethyl]-N-methyl-benzenesulfonamide;
Furazan-3-carboxylic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-3-trifluoromethyl-benzenesulfonamide;
Pyrrolidine-1-sulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-N-methyl-2-pyridin-3-yl-acetamide;
(E)-2-Phenyl-ethenesulfonic acid [3-(3-chloro-4-pyrrolidin-1-ylmethyl-phenoxy)-cyclobutylmethyl]-methyl-amide;
N-[3-(3-Chloro-4-pyrrolidin-1-ylmethyl-phenoxy)-cyclobutylmethyl]-2,2,N-trimethyl-propionamide;
N-[3-(3-Chloro-4-pyrrolidin-1-ylmethyl-phenoxy)-cyclobutylmethyl]-2-cyclopentyl-N-methyl-acetamide;
N-[3-(3-Chloro-4-pyrrolidin-1-ylmethyl-phenoxy)-cyclobutylmethyl]-2-(3,5-dimethyl-isoxazol-4-yl)—N-methyl-acetamide;
N-[3-(3-Chloro-4-pyrrolidin-1-ylmethyl-phenoxy)-cyclobutylmethyl]-3-fluoro-N-methyl-benzenesulfonamide;
Tetrahydro-pyran-4-carboxylic acid [3-(3-chloro-4-pyrrolidin-1-ylmethyl-phenoxy)-cyclobutylmethyl]-methyl-amide;
2-Chloro-N-[3-(3-chloro-4-pyrrolidin-1-ylmethyl-phenoxy)-cyclobutylmethyl]-4-fluoro-N-methyl-benzenesulfonamide;
N-[3-(3-Chloro-4-pyrrolidin-1-ylmethyl-phenoxy)-cyclobutylmethyl]-N-methyl-2-pyrazol-1-yl-acetamide;
N-(4-{[3-(3-Chloro-4-pyrrolidin-1-ylmethyl-phenoxy)-cyclobutylmethyl]-methyl-sulfamoyl}-phenyl)-acetamide;
4-Methyl-pentanoic acid [3-(3-chloro-4-pyrrolidin-1-ylmethyl-phenoxy)-cyclobutylmethyl]-methyl-amide;
5-Chloro-N-[3-(3-chloro-4-pyrrolidin-1-ylmethyl-phenoxy)-cyclobutylmethyl]-2-methoxy-N-methyl-benzenesulfonamide;
1-{[3-(3-Chloro-4-pyrrolidin-1-ylmethyl-phenoxy)-cyclobutyl]methyl}-1-methyl-3-(3-trifluoromethyl-phenyl)-urea;
4-[3-(3-Chloro-5-pyrrolidin-1-ylmethyl-phenoxy)-cyclobutylmethyl]-morpholine;
Tetrahydro-pyran-4-carboxylic acid [3-(2-methoxy-3-pyrrolidin-1-ylmethyl-phenoxy)-cyclobutylmethyl]-methyl-amide;
Tetrahydro-pyran-4-carboxylic acid [3-(3-chloro-5-fluoro-4-pyrrolidin-1-ylmethyl-phenoxy)-cyclobutylmethyl]-methyl-amide;
3,5-Dimethyl-isoxazole-4-carboxylic acid [3-(3,5-difluoro-4-pyrrolidin-1-ylmethyl-phenoxy)-cyclobutylmethyl]-methyl-amide;
1-Methyl-cyclopropanecarboxylic acid [3-(2-fluoro-3-pyrrolidin-1-ylmethyl-phenoxy)-cyclobutylmethyl]-methyl-amide;
Tetrahydro-pyran-4-carboxylic acid [3-(2-fluoro-3-pyrrolidin-1-ylmethyl-phenoxy)-cyclobutylmethyl]-methyl-amide;
3,5-Dimethyl-isoxazole-4-carboxylic acid [3-(2-fluoro-3-pyrrolidin-1-ylmethyl-phenoxy)-cyclobutylmethyl]-methyl-amide;
Tetrahydro-pyran-4-carboxylic acid [3-(3,5-difluoro-4-pyrrolidin-1-ylmethyl-phenoxy)-cyclobutylmethyl]-methyl-amide;

[3-(2-Fluoro-3-pyrrolidin-1-ylmethyl-phenoxy)-cyclobutylmethyl]-methyl-amine;

Tetrahydro-pyran-4-carboxylic acid [3-(2-chloro-3-pyrrolidin-1-ylmethyl-phenoxy)-cyclobutylmethyl]-amide;

Tetrahydro-pyran-4-carboxylic acid [3-(2,5-dichloro-4-pyrrolidin-1-ylmethyl-phenoxy)-cyclobutylmethyl]-methyl-amide;

3,5-Dimethyl-isoxazole-4-carboxylic acid [3-(2,5-dichloro-4-pyrrolidin-1-ylmethyl-phenoxy)-cyclobutylmethyl]-methyl-amide;

1-Methyl-cyclopropanecarboxylic acid [3-(2,5-dichloro-4-pyrrolidin-1-ylmethyl-phenoxy)-cyclobutylmethyl]-methyl-amide;

[3-(2,4-Dichloro-3-pyrrolidin-1-ylmethyl-phenoxy)-cyclobutylmethyl]-methyl-amine;

Tetrahydro-pyran-4-carboxylic acid [3-(2,4-dichloro-3-pyrrolidin-1-ylmethyl-phenoxy)-cyclobutylmethyl]-methyl-amide; and Cyclobutanecarboxylic acid [3-(2,4-dichloro-3-pyrrolidin-1-ylmethyl-phenoxy)-cyclobutylmethyl]-methyl-amide.

6. A method of treating a disorder or condition in a mammal in need thereof, the method comprising administering to the mammal a compound of claim 1, or a pharmaceutically acceptable salt thereof, or cis isomer, or trans isomer, or a mixture of cis and trans isomer, said disorder or condition being selected from depression, schizophrenia, Alzheimer's disease, attention-deficit hyperactivity disorder (ADHD), obesity, dizziness, epilepsy, motion sickness, enemy, allergy-induced airway responses, allergic rhinitis, nasal congestion, allergic congestion, congestion, hypotension, hyper and hypo motility and acidic secretion of the gastrointestinal tract, adult respiratory distress syndrome, acute respiratory distress syndrome, bronchitis, chronic bronchitis, chronic obstructive pulmonary disease, cystic fibrosis, asthma, emphysema, rhinitis and chronic sinusitis.

7. A pharmaceutical composition comprising a compound of claim 1 or a pharmaceutically acceptable salt thereof, or cis isomer, or trans isomer, or a mixture of cis and trans isomer, and optionally a pharmaceutically acceptable carrier.

8. The method of claim 6 wherein said disorder or condition is selected from depression, schizophrenia, Alzheimer's disease, attention-deficit hyperactivity disorder (ADHD), obesity, dizziness, epilepsy, motion sickness, allergy, allergy-induced airway responses, allergic rhinitis, nasal congestion, allergic congestion, congestion, hypotension, or hyper and hypo motility and acidic secretion of the gastro-intestinal tract.

9. The method of claim 8 wherein the disorder or condition is selected from attention-deficit hyperactivity disorder and obesity.

10. The method of claim 8 wherein the disorder or condition is selected from adult respiratory distress syndrome, acute respiratory distress syndrome, bronchitis, chronic bronchitis, chronic obstructive pulmonary disease, cystic fibrosis, asthma, emphysema, rhinitis and chronic sinusitis.

11. A pharmaceutical composition comprising
(a) an H3 receptor antagonist compound of formula 1; or a pharmaceutically acceptable salt thereof;
(b) an H1 receptor antagonist or a pharmaceutically acceptable salt thereof; and
(c) a pharmaceutically acceptable carrier.

12. The composition according to claim 11 wherein the H3 receptor antagonist and the H1 receptor antagonist are given simultaneously.

13. The pharmaceutical composition of claim 11, wherein the H1 receptor antagonist is cetirizine.

14. A method of treating allergic rhinitis, nasal congestion or allergic congestion in a mammal in need thereof, said method comprising administering to said mammal a pharmaceutical composition of claim 11 wherein said H1 receptor antagonist or pharmaceutically acceptable salt thereof and said H3 receptor antagonist or pharmaceutically acceptable salt thereof are present in amounts that render the composition effective in treating allergic rhinitis, nasal congestion or allergic congestion in said mammal.

15. 3-(3-Acetyl-phenyl)-1-[3-(3-chloro-4-pyrrolidin-1-ylmethyl-phenoxy)-cyclobutylmethyl]-1-methyl-urea or a pharmaceutically acceptable salt thereof.

16. 5-Cyclopropyl-2H-pyrazole-3-carboxylic acid [3-(3-chloro-4-pyrrolidin-1-ylmethyl-phenoxy)-cyclobutylmethyl]-methyl-amide or a pharmaceutically acceptable salt thereof.

17. 3-(3-Acetyl-phenyl)-1-[3-(2-chloro-3-pyrrolidin-1-ylmethyl-phenoxy)-cyclobutylmethyl]-1-methyl-urea or a pharmaceutically acceptable salt thereof.

18. 5-Cyclopropyl-2H-pyrazole-3-carboxylic acid [3-(2-chloro-3-pyrrolidin-1-ylmethyl-phenoxy)-cyclobutylmethyl]-methyl-amide or a pharmaceutically acceptable salt thereof.

19. Furazan-3-carboxylic acid [3-(2-chloro-3-pyrrolidin-1-ylmethyl-phenoxy)-cyclobutylmethyl]-methyl-amide or a pharmaceutically acceptable salt thereof.

20. 2-Oxo-2,3-dihydro-benzooxazole-6-sulfonic acid [3-(3-chloro-4-pyrrolidin-1-ylmethyl-phenoxy)-cyclobutylmethyl]-methyl-amide or a pharmaceutically acceptable salt thereof.

* * * * *